(12) United States Patent
Suslov

(10) Patent No.: US 12,058,801 B2
(45) Date of Patent: *Aug. 6, 2024

(54) SYSTEMS, METHODS, AND DEVICES FOR GENERATING PREDOMINANTLY RADIALLY EXPANDED PLASMA FLOW

(71) Applicant: PLASMA SURGICAL, INC., Roswell, GA (US)

(72) Inventor: Nikolay Suslov, Roswell, GA (US)

(73) Assignee: Plasma Surgical, Inc., Roswell, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/538,270

(22) Filed: Dec. 13, 2023

(65) Prior Publication Data

US 2024/0147599 A1 May 2, 2024

Related U.S. Application Data

(63) Continuation of application No. 18/114,023, filed on Feb. 24, 2023, now Pat. No. 11,882,643, which is a
(Continued)

(51) Int. Cl.
*H05H 1/46* (2006.01)
*H05H 1/02* (2006.01)
*H05H 1/54* (2006.01)

(52) U.S. Cl.
CPC ............... *H05H 1/46* (2013.01); *H05H 1/02* (2013.01); *H05H 1/54* (2013.01); *H05H 2242/22* (2021.05)

(58) Field of Classification Search
None
See application file for complete search history.

(56) References Cited

U.S. PATENT DOCUMENTS 3,077,108 A 2/1963 Gage et al.
3,082,314 A 3/1963 Yoshiaki et al.
(Continued)

FOREIGN PATENT DOCUMENTS

AU 2000250426 B2 6/2005
AU 2006252145 A1 1/2007
(Continued)

OTHER PUBLICATIONS

510(k) Notification (21 CFR 807.90(e)) for the Plasma Surgical Ltd. PlasmaJet® Neutral Plasma Surgery System, Section 10—Executive Summary, dated Jan. 25, 2008—K080197, 2 pages.
(Continued)

*Primary Examiner* — Srinivas Sathiraju
(74) *Attorney, Agent, or Firm* — COOLEY LLP

(57) ABSTRACT

Systems, devices, and methods generating a plasma flow are disclosed. A method may include applying energy that alternates between being at a base level for a first duration and at a pulse level for a second duration according to a controlled pattern, generating a plasma flow having a directional axis, and discharging the plasma flow alternating between a base configuration and a pulse configuration according to the controlled pattern. The plasma flow in the base configuration may have (1) a first temperature at the outlet and (2) a first flow front that advances along the directional axis. The plasma flow in the pulse configuration may have (1) a second temperature at the outlet that is greater than the first temperature and (2) a second flow front that advances along the directional axis at a speed greater than the first flow front.

20 Claims, 87 Drawing Sheets

Related U.S. Application Data continuation of application No. PCT/US2021/048052, filed on Aug. 27, 2021.

(60) Provisional application No. 63/071,787, filed on Aug. 28, 2020.

(56) References Cited

U.S. PATENT DOCUMENTS

| | | |
|---|---|---|
| 3,100,489 A | 8/1963 | Bagley |
| 3,145,287 A | 8/1964 | Siebein et al. |
| 3,153,133 A | 10/1964 | Ducati |
| 3,270,745 A | 9/1966 | Charle |
| 3,360,988 A | 1/1968 | Stine et al. |
| 3,396,882 A | 8/1968 | Abe |
| 3,413,509 A | 11/1968 | Cann et al. |
| 3,433,991 A | 3/1969 | Whyman |
| 3,434,476 A * | 3/1969 | Shaw .................. A61B 18/042 606/22 |
| 3,534,388 A | 10/1970 | Ito et al. |
| 3,534,739 A * | 10/1970 | Bryne .................. A61B 18/02 222/394 |
| 3,628,079 A | 12/1971 | Dobbs et al. |
| 3,676,638 A | 7/1972 | Stand |
| 3,775,825 A | 12/1973 | Samuels et al. |
| 3,803,380 A | 4/1974 | Ragaller |
| 3,838,242 A | 9/1974 | Goucher |
| 3,851,140 A | 11/1974 | Coucher |
| 3,866,089 A | 2/1975 | Hengartner |
| 3,903,891 A | 9/1975 | Brayshaw |
| 3,914,573 A | 10/1975 | Muehlberger |
| 3,938,525 A | 2/1976 | Coucher |
| 3,991,764 A | 11/1976 | Incropera et al. |
| 3,995,138 A | 11/1976 | Kalev et al. |
| 4,029,930 A | 6/1977 | Sagara et al. |
| 4,035,684 A | 7/1977 | Svoboda et al. |
| 4,041,952 A | 8/1977 | Morrison, Jr. et al. |
| 4,201,314 A | 5/1980 | Samuels et al. |
| 4,256,779 A | 3/1981 | Sokol et al. |
| 4,317,984 A | 3/1982 | Fridlyand |
| 4,397,312 A | 8/1983 | Molko |
| 4,445,021 A | 4/1984 | Irons et al. |
| 4,620,080 A | 10/1986 | Arata et al. |
| 4,661,682 A | 4/1987 | Gruner et al. |
| 4,672,163 A | 6/1987 | Matsui et al. |
| 4,674,683 A | 6/1987 | Fabel |
| 4,682,598 A | 7/1987 | Beraha |
| 4,696,855 A | 9/1987 | Pettit, Jr. et al. |
| 4,711,627 A | 12/1987 | Oeschsle et al. |
| 4,713,170 A | 12/1987 | Saibic |
| 4,743,734 A | 5/1988 | Garlanov et al. |
| 4,764,656 A | 8/1988 | Browning |
| 4,777,949 A | 10/1988 | Perlin |
| 4,780,591 A | 10/1988 | Bernecki et al. |
| 4,781,175 A | 11/1988 | McGreevy et al. |
| 4,784,321 A | 11/1988 | Delaplace |
| 4,785,220 A | 11/1988 | Brown et al. |
| 4,839,492 A | 6/1989 | Bouchier et al. |
| 4,841,114 A | 6/1989 | Browning |
| 4,853,515 A | 8/1989 | Willen et al. |
| 4,855,563 A | 8/1989 | Beresnev et al. |
| 4,866,240 A | 9/1989 | Webber |
| 4,869,936 A | 9/1989 | Moskowitz et al. |
| 4,874,988 A | 10/1989 | English et al. |
| 4,877,937 A | 10/1989 | Muller |
| 4,916,273 A | 4/1990 | Browning |
| 4,924,059 A | 5/1990 | Rotolico et al. |
| 5,008,511 A | 4/1991 | Ross |
| 5,013,883 A | 5/1991 | Fuimefreddo et al. |
| 5,079,403 A | 1/1992 | Sturges et al. |
| 5,100,402 A | 3/1992 | Fan |
| 5,144,110 A | 9/1992 | Marantz et al. |
| 5,151,102 A | 9/1992 | Kamiyama et al. |
| 5,155,547 A * | 10/1992 | Casper .............. H01J 37/32165 356/316 |
| 5,201,900 A | 4/1993 | Nardella |
| 5,207,691 A | 5/1993 | Nardella |
| 5,211,646 A | 5/1993 | Alperovich et al. |
| 5,217,460 A | 6/1993 | Knoepfler |
| 5,225,652 A | 7/1993 | Landes |
| 5,227,603 A | 7/1993 | Doolette et al. |
| 5,261,905 A | 11/1993 | Doresey, III |
| 5,285,967 A | 2/1994 | Weidman |
| 5,330,606 A * | 7/1994 | Kubota .............. H01J 37/32165 204/298.34 |
| 5,332,885 A | 7/1994 | Landes |
| 5,352,219 A | 10/1994 | Reddy |
| 5,403,312 A | 4/1995 | Yates et al. |
| 5,406,046 A | 4/1995 | Landes |
| 5,408,066 A | 4/1995 | Trapani et al. |
| 5,412,173 A | 5/1995 | Muehlberger |
| 5,445,638 A | 8/1995 | Rydell et al. |
| 5,452,854 A | 9/1995 | Keller |
| 5,460,629 A | 10/1995 | Shlain et al. |
| 5,485,721 A | 1/1996 | Steenborg |
| 5,514,848 A | 5/1996 | Ross et al. |
| 5,519,183 A | 5/1996 | Mueller |
| 5,527,313 A | 6/1996 | Scott et al. |
| 5,571,366 A * | 11/1996 | Ishii .................. H01J 37/3299 216/60 |
| 5,573,682 A | 11/1996 | Beason, Jr. et al. |
| 5,582,611 A | 12/1996 | Tsuruta et al. |
| 5,620,616 A | 4/1997 | Anderson et al. |
| 5,629,585 A | 5/1997 | Altmann et al. |
| 5,637,242 A | 6/1997 | Muehlberger |
| 5,640,843 A | 6/1997 | Aston |
| 5,662,680 A | 9/1997 | Desai |
| 5,665,085 A | 9/1997 | Nardella |
| 5,679,167 A | 10/1997 | Muehlberger |
| 5,680,014 A | 10/1997 | Miyamoto et al. |
| 5,688,270 A | 11/1997 | Yates et al. |
| 5,697,281 A | 12/1997 | Eggers et al. |
| 5,697,882 A | 12/1997 | Eggers et al. |
| 5,702,390 A | 12/1997 | Austin et al. |
| 5,720,745 A | 2/1998 | Farin et al. |
| 5,733,662 A | 3/1998 | Bogachek |
| 5,797,941 A | 8/1998 | Schulze et al. |
| 5,827,271 A | 10/1998 | Buysse et al. |
| 5,833,690 A | 11/1998 | Yates et al. |
| 5,837,959 A | 11/1998 | Muehlberger et al. |
| 5,843,079 A | 12/1998 | Suslov |
| 5,858,469 A | 1/1999 | Sahoo et al. |
| 5,858,470 A | 1/1999 | Bernecki et al. |
| 5,897,059 A | 4/1999 | Muller |
| 5,906,757 A | 5/1999 | Kong et al. |
| 5,932,293 A | 8/1999 | Belashchenko et al. |
| 6,033,788 A | 3/2000 | Cawley et al. |
| 6,042,019 A | 3/2000 | Rusch |
| 6,099,523 A | 8/2000 | Kim et al. |
| 6,114,649 A | 9/2000 | Delcea |
| 6,135,998 A | 10/2000 | Palanker |
| 6,137,078 A | 10/2000 | Keller |
| 6,137,231 A | 10/2000 | Anders et al. |
| 6,162,220 A | 12/2000 | Nezhat |
| 6,169,370 B1 | 1/2001 | Platzer |
| 6,181,053 B1 | 1/2001 | Roberts |
| 6,202,939 B1 | 3/2001 | Delcea |
| 6,209,878 B1 | 4/2001 | Munro |
| 6,273,789 B1 | 8/2001 | LaSalle et al. |
| 6,283,386 B1 | 9/2001 | Van Steenkiste et al. |
| 6,329,628 B1 | 12/2001 | Kuo et al. |
| 6,352,533 B1 | 3/2002 | Ellman et al. |
| 6,386,140 B1 | 5/2002 | Müller et al. |
| 6,392,189 B1 | 5/2002 | Delcea |
| 6,443,948 B1 | 9/2002 | Suslov |
| 6,475,215 B1 | 11/2002 | Tanrisever |
| 6,514,252 B2 | 2/2003 | Nezhat et al. |
| 6,515,252 B1 | 2/2003 | Girold |
| 6,528,947 B1 | 3/2003 | Chen et al. |
| 6,548,817 B1 | 4/2003 | Anders et al. |
| 6,558,383 B2 | 5/2003 | Cunningham et al. |
| 6,562,037 B2 | 5/2003 | Paton et al. |
| 6,629,974 B2 | 10/2003 | Penny et al. |
| 6,657,152 B2 | 12/2003 | Shimazu |

(56) References Cited

U.S. PATENT DOCUMENTS

| | | | |
|---|---|---|---|
| 6,669,106 B2 | 12/2003 | Delcea | |
| 6,676,655 B2 | 1/2004 | McDaniel | |
| 6,780,184 B2 | 8/2004 | Tanrisever | |
| 6,845,929 B2 | 1/2005 | Dolatabadi et al. | |
| 6,886,757 B2 | 5/2005 | Byrnes et al. | |
| 6,958,063 B1 | 10/2005 | Soll et al. | |
| 6,972,138 B2 | 12/2005 | Heinrich et al. | |
| 6,986,471 B1 | 1/2006 | Kowalsky et al. | |
| 7,025,764 B2 | 4/2006 | Paton et al. | |
| 7,030,336 B1 | 4/2006 | Hawley | |
| 7,118,570 B2 | 10/2006 | Tetzlaff et al. | |
| 7,223,676 B2 * | 5/2007 | Hanawa | H01J 37/32174 438/513 |
| 7,361,175 B2 * | 4/2008 | Suslov | A61B 18/042 606/49 |
| 7,589,473 B2 | 9/2009 | Suslov | |
| 8,030,849 B2 * | 10/2011 | Suslov | A61B 18/042 315/111.21 |
| 8,043,286 B2 | 10/2011 | Palanker et al. | |
| 8,105,325 B2 * | 1/2012 | Suslov | H05H 1/34 606/45 |
| 8,226,644 B2 | 7/2012 | Sartor et al. | |
| 8,465,487 B2 * | 6/2013 | Suslov | H05H 1/34 606/45 |
| 8,613,742 B2 * | 12/2013 | Suslov | A61B 18/04 606/41 |
| 8,735,766 B2 * | 5/2014 | Suslov | H05H 1/34 315/111.21 |
| 8,876,746 B2 * | 11/2014 | Davison | A61B 18/1402 606/41 |
| 9,089,319 B2 * | 7/2015 | Suslov | H05H 1/34 |
| 9,168,087 B2 * | 10/2015 | Davison | A61B 18/1402 |
| 9,254,167 B2 * | 2/2016 | Davison | A61B 18/1402 |
| 9,640,368 B2 * | 5/2017 | Umehara | H01J 37/32935 |
| 9,801,678 B2 * | 10/2017 | Cox | A61B 18/1492 |
| 9,913,358 B2 * | 3/2018 | Suslov | H05H 1/28 |
| 10,201,067 B2 * | 2/2019 | Suslov | H05H 1/341 |
| 10,463,418 B2 * | 11/2019 | Suslov | A61B 18/042 |
| 10,492,845 B2 * | 12/2019 | Suslov | H05H 1/34 |
| 10,631,911 B2 * | 4/2020 | Suslov | H05H 1/34 |
| 10,648,728 B2 * | 5/2020 | Piel | H05B 6/62 |
| 10,991,554 B2 * | 4/2021 | Zhao | H01J 37/32128 |
| 11,232,931 B2 * | 1/2022 | Huh | H01J 37/32165 |
| 11,621,587 B1 * | 4/2023 | Yanovitz | H02J 50/12 307/104 |
| 11,882,643 B2 * | 1/2024 | Suslov | H05H 1/3494 |
| 2001/0021422 A1 * | 9/2001 | Yamakoshi | H01J 37/32082 315/169.3 |
| 2001/0041227 A1 | 11/2001 | Hislop | |
| 2002/0013583 A1 | 1/2002 | Camran et al. | |
| 2002/0071906 A1 | 6/2002 | Rusch | |
| 2002/0091385 A1 | 7/2002 | Paton et al. | |
| 2002/0097767 A1 | 7/2002 | Krasnov | |
| 2003/0030014 A1 | 2/2003 | Wieland et al. | |
| 2003/0040744 A1 | 2/2003 | Latterell et al. | |
| 2003/0075618 A1 | 4/2003 | Shimazu | |
| 2003/0114845 A1 | 6/2003 | Paton et al. | |
| 2003/0125728 A1 | 7/2003 | Nezhat et al. | |
| 2003/0178511 A1 | 9/2003 | Dolatabadi et al. | |
| 2003/0190414 A1 | 10/2003 | Van Steenkiste | |
| 2004/0018317 A1 | 1/2004 | Heinrich et al. | |
| 2004/0064139 A1 | 4/2004 | Yossepowitch | |
| 2004/0068304 A1 | 4/2004 | Paton et al. | |
| 2004/0116918 A1 | 6/2004 | Konesky | |
| 2004/0124256 A1 | 7/2004 | Itsukaichi et al. | |
| 2004/0129222 A1 | 7/2004 | Nylen et al. | |
| 2004/0195219 A1 | 10/2004 | Conway et al. | |
| 2004/0200417 A1 * | 10/2004 | Hanawa | H01L 21/2236 118/723 I |
| 2005/0082395 A1 | 4/2005 | Gardega | |
| 2005/0120957 A1 | 6/2005 | Kowalsky et al. | |
| 2005/0192610 A1 | 9/2005 | Houser et al. | |
| 2005/0192611 A1 | 9/2005 | Houser | |
| 2005/0192612 A1 | 9/2005 | Houser et al. | |
| 2005/0234447 A1 | 10/2005 | Paton et al. | |
| 2005/0255255 A1 * | 11/2005 | Kawamura | H01J 37/32082 118/723 E |
| 2005/0255419 A1 | 11/2005 | Belashchenko et al. | |
| 2006/0004354 A1 | 1/2006 | Suslov | |
| 2006/0037533 A1 | 2/2006 | Belashchenko et al. | |
| 2006/0049149 A1 | 3/2006 | Shimazu | |
| 2006/0090699 A1 | 5/2006 | Muller | |
| 2006/0091116 A1 | 5/2006 | Suslov | |
| 2006/0091117 A1 | 5/2006 | Blankenship et al. | |
| 2006/0091119 A1 | 5/2006 | Zajchowski et al. | |
| 2006/0108332 A1 | 5/2006 | Belashchenko | |
| 2006/0124613 A1 * | 6/2006 | Kumar | H05H 1/46 219/121.43 |
| 2006/0189976 A1 | 8/2006 | Karni et al. | |
| 2006/0217706 A1 | 9/2006 | Lau et al. | |
| 2006/0266735 A1 * | 11/2006 | Shannon | H01J 37/32082 216/59 |
| 2006/0287651 A1 | 12/2006 | Bayat | |
| 2007/0021747 A1 * | 1/2007 | Suslov | H05H 1/34 606/49 |
| 2007/0021748 A1 | 1/2007 | Suslov | |
| 2007/0029292 A1 | 2/2007 | Suslov et al. | |
| 2007/0038214 A1 | 2/2007 | Morley et al. | |
| 2007/0138147 A1 | 6/2007 | Molz et al. | |
| 2007/0173871 A1 | 7/2007 | Houser et al. | |
| 2007/0173872 A1 | 7/2007 | Neuenfeldt | |
| 2007/0191828 A1 | 8/2007 | Houser et al. | |
| 2008/0015566 A1 | 1/2008 | Livneh | |
| 2008/0071206 A1 | 3/2008 | Peters | |
| 2008/0114352 A1 | 5/2008 | Long et al. | |
| 2008/0185366 A1 | 8/2008 | Suslov | |
| 2008/0246385 A1 | 10/2008 | Schamiloglu et al. | |
| 2009/0039789 A1 | 2/2009 | Nikolay | |
| 2009/0039790 A1 | 2/2009 | Suslov | |
| 2010/0089742 A1 | 4/2010 | Suslov | |
| 2011/0190752 A1 | 8/2011 | Suslov | |
| 2011/0203543 A1 * | 8/2011 | Agneray | F02P 23/04 315/111.21 |
| 2012/0022522 A1 | 1/2012 | Suslov | |
| 2013/0313227 A1 * | 11/2013 | Katagiri | G21F 9/308 156/345.38 |
| 2014/0345802 A1 * | 11/2014 | Umehara | H01J 37/32568 156/345.28 |
| 2014/0377966 A1 * | 12/2014 | Funk | H01J 37/32192 438/795 |
| 2015/0126046 A1 * | 5/2015 | Funk | H01J 37/32229 118/723 AN |
| 2015/0327906 A1 * | 11/2015 | Suslov | A61B 18/042 606/34 |
| 2015/0371876 A1 * | 12/2015 | Terauchi | H01L 21/32136 156/345.28 |
| 2016/0008051 A1 * | 1/2016 | Suslov | A61B 18/042 252/372 |
| 2016/0051311 A1 * | 2/2016 | Suslov | A61B 18/1206 604/23 |
| 2017/0339775 A1 * | 11/2017 | Cheung | H01J 37/321 |
| 2018/0168022 A1 * | 6/2018 | Suslov | H05H 1/34 |
| 2019/0148113 A1 * | 5/2019 | Zhao | H01J 37/32146 427/569 |
| 2020/0253660 A1 * | 8/2020 | Suslov | H05H 1/34 |
| 2021/0118649 A1 * | 4/2021 | Huh | H01J 37/32183 |
| 2021/0373054 A1 * | 12/2021 | Fisk, II | H01J 37/32091 |
| 2021/0407771 A1 * | 12/2021 | Funk | H01J 37/3299 |
| 2022/0102116 A1 * | 3/2022 | Huh | H01J 37/32183 |
| 2023/0225041 A1 | 7/2023 | Suslov | |

FOREIGN PATENT DOCUMENTS

| | | |
|---|---|---|
| CA | 983586 A | 2/1976 |
| CA | 1144104 A | 4/1983 |
| CA | 1308772 C | 10/1992 |
| CA | 2594515 A1 | 7/2006 |
| CN | 85107499 B | 9/1987 |
| CN | 1331836 A | 1/2002 |
| CN | 1557731 A | 12/2004 |
| CN | 1682578 A | 10/2005 |
| DE | 2033072 A1 | 2/1971 |

(56) References Cited

FOREIGN PATENT DOCUMENTS

| | | |
|---|---|---|
| DE | 4209005 A1 | 9/1993 |
| DE | 10127261 A1 | 12/2002 |
| DE | 102007040434 A1 | 3/2009 |
| EP | 0282677 A1 | 9/1988 |
| EP | 0411170 A1 | 2/1991 |
| EP | 0748149 A1 | 12/1996 |
| EP | 0851040 A1 | 7/1998 |
| EP | 1293169 A1 | 3/2003 |
| EP | 1570798 A2 | 9/2005 |
| ES | 2026344 A6 | 4/1992 |
| FR | 2193299 A1 | 2/1974 |
| FR | 2567747 A1 | 1/1986 |
| GB | 751735 A | 7/1956 |
| GB | 921016 A | 3/1963 |
| GB | 1125806 A | 9/1968 |
| GB | 1176333 A | 1/1970 |
| GB | 1268843 A | 3/1972 |
| GB | 2407050 A | 4/2005 |
| JP | S479252 A | 3/1972 |
| JP | S52117255 A | 10/1977 |
| JP | S54120545 U | 8/1979 |
| JP | 57001580 A | 1/1982 |
| JP | 57068269 A | 4/1982 |
| JP | S6113600 A | 1/1986 |
| JP | S61193783 A | 8/1986 |
| JP | S61286075 A | 12/1986 |
| JP | S62123004 A | 6/1987 |
| JP | H01198539 A | 8/1989 |
| JP | H01319297 A | 12/1989 |
| JP | 3043678 A | 2/1991 |
| JP | H06262367 A | 9/1994 |
| JP | H09299380 A | 11/1997 |
| JP | H1024050 A | 1/1998 |
| JP | H10504751 A | 5/1998 |
| JP | H10234744 A | 9/1998 |
| JP | 2002541902 A | 12/2002 |
| JP | 2008036001 A | 2/2008 |
| JP | 2008284580 A | 11/2008 |
| JP | 2009541902 A | 11/2009 |
| MX | PA04010281 A | 6/2005 |
| RU | 2178684 C2 | 1/2002 |
| RU | 2183480 C2 | 6/2002 |
| RU | 2183946 C2 | 6/2002 |
| WO | WO-9007395 A1 | 7/1990 |
| WO | WO-9219166 A1 | 11/1992 |
| WO | WO-9606572 A1 | 3/1996 |
| WO | WO-9711647 A1 | 4/1997 |
| WO | WO-0162169 A2 | 8/2001 |
| WO | WO-0230308 A1 | 4/2002 |
| WO | WO-03028805 A1 | 4/2003 |
| WO | WO-2004028221 A1 | 4/2004 |
| WO | WO-2004030551 A1 | 4/2004 |
| WO | WO-2004105450 A1 | 12/2004 |
| WO | WO-2005099595 A1 | 10/2005 |
| WO | WO-2006012165 A2 | 2/2006 |
| WO | WO-2007003157 A2 | 1/2007 |
| WO | WO-2007006516 A2 | 1/2007 |
| WO | WO-2007006517 A2 | 1/2007 |
| WO | WO-2007040702 A2 | 4/2007 |
| WO | WO-2009018837 A1 | 2/2009 |
| WO | WO-2012010207 A1 | 1/2012 |
| WO | WO-2022047227 A2 * 3/2022 ............... H05H 1/02 |

OTHER PUBLICATIONS

510(k) Summary, dated Jun. 2, 2008, 3 pages.
510(k) Summary, dated Oct. 30, 2003, 2 pages.
Aptekman, 2007, "Spectroscopic analysis of the PlasmaJet® argon plasma with 5 mm-0.5 coag-cut handpieces," Document PSSRP-106—K080197, 14 pages.
Asawanonda et al., "308-nm excimer laser for the treatment of psoriasis: a dose- response study", Arch Dermatol. May 2000; 136(5): 619-24.
Branson, M. D., 2005, "Preliminary experience with neutral plasma, a new coagulation technology, in plastic surgery," Fayetteville, NY, 2 pages.
Canadian Office Action for Application No. 2,695,650, dated Jun. 18, 2013, 3 pages.
Canadian Office Action for Application No. 2,695,902, dated Jun. 12, 2013, 2 pages.
Charpentier et al., 2008, "Multicentric medical registry on the use of the Plasma Surgical PlasmaJet® System in thoracic surgery," Club Thorax, 3 pages.
Chen et al., "What do we know about long laminar plasma jets?", Pure Appl Chem, Jun. 2006, 78(6): 1253-1264.
Cheng et al., "Comparison of laminar and turbulent thermal plasma jet characteristics—a modeling study", Jun. 2006, Plasma Chemistry and Plasma Processing 26(3): 211-235.
Chinese Office Action for Application No. 200780052471.5, dated Dec. 5, 2012, 7 pages.
Chinese Office Action for Application No. 200780052471.5, dated May 25, 2012, with translation, 13 pages.
Chinese Office Action for Application No. 200780100857.9, dated May 25, 2012, with translation, 17 pages.
Chinese Office Action for Application No. 200780100857.9, dated May 30, 2013, with translation, 18 pages.
Chinese Office Action for Application No. 200780100858.3, dated Apr. 27, 2012, with translation, 10 pages.
Chinese Office Action for Application No. 200780100857.9, dated Nov. 28, 2011, with translation, 17 pages.
Chinese Office Action of application No. 200780100858.3, dated Aug. 29, 2012, 6 pages.
Chinese Office Action of application No. 2007801008583, dated Oct. 19, 2011 (with translation), 10 pages.
Chinese Office Action of Chinese Appl. No. 2012220800745680, dated Nov. 13, 2012, 16 pages.
Chinese Office Action (translated) for Chinese Application No. 200680030194.3, dated Jan. 31, 2011, 9 pages.
Chinese Office Action (translated) for Chinese Application No. 200680030216.6, dated Oct. 26, 2010, 8 pages.
Chinese Office Action (translated) for Chinese Application No. 200680030225.5, dated Jun. 11, 2010, 9 pages.
Chinese Office Action (translation) of application No. 200680030225.5, dated Mar. 9, 2011, 6 pages.
CoagSafe ™ Neutral Plasma Coagulator Operator Manual, Part No. OMC-2100-1, Revision 1.1, dated Mar. 2003—Appendix 1 of K030819, 22 pages.
Coven et al., "PUVA-induced lymphocyte apoptosis: mechanism of action in psoriasis", Feb. 1999, Photodermatol Photoimmunol Photomed. 15(1): 22-7.
Dabringhausen et al., "Determination of HID electrode falls in a model lamp I", Jul. 2002, Journal of Physics D Applied Physics 35(14):1621-1630.
DAVIS (Ed.), 2004, ASM thermal Spray society, Handbook of Thermal Spray Technology, U.S. 42-168.
Deb et al., "Histological quantification of the tissue damage caused in vivo y neutral PlasmaJet™ Coagulator", Nottingham University Hospitals, Queen's Medical Centre, Nottingham NG7 2UH—Poster, dated Oct. 2009, 1 page.
Electrosurgical Generators Force FX™ Electrosurgical Generators by ValleyLab—K080197, dated Sep. 2002, 4 pages.
ERBE APC 300 Argon Plasma Coagulation Unit for Endoscopic Applications, Brochure 1997—Appendix 4 of K030819, 7 pages.
European Office Action for European Application No. EP 07786583.0-1226, dated Jun. 29, 2010, 7 pages.
European Office Action of Appl. No. 07/786 582.2-1551, dated Mar. 11, 2015, 6 pages.
European Office Action of Appl. No. 10/ 734 147.1-1551, dated Oct. 28, 2015, 4 pages.
Examiner's Answer to Applicant's Appeal Brief in U.S. Appl. No. 11/482,580, dated Jun. 18, 2013, 10 pages.
Extended European Search Report mailed Aug. 8, 2017 for European Application No. EP 16 20 3010, 5 pages.
Extended European Search Report mailed Oct. 2, 2019 for European Application No. EP 19175795.4, 8 pages.

(56) References Cited

OTHER PUBLICATIONS

Feldman et al., "Efficacy of the 308-nm excimer laser for treatment of psoriasis: results of a multicenter study," J Am Acad Dermatol. Jun. 2002; 46(6): 900-6.
Final Office Action for U.S. Appl. No. 12/696,411, dated Jun. 10, 2013, 10 pages.
Final Office Action mailed Jan. 16, 2015 for U.S. Appl. No. 12/841,361, 11 pages.
Final Office Action mailed May 3, 2019 for U.S. Appl. No. 14/810,032, 7 pages.
FORCE Argon TM II System, Improved precision and control in electrosurgery, by Valleylab, 2006—K080197, 2 pages.
Gerber et al., "Ultraviolet B 308-nm excimer laser treatment of psoriasis: a new phototherapeutic approach," Dec. 2003, Br. J. Dermatol., 149:12580-1258.
Gugenheim et al., 2006, "Open, multicentric, clinical evaluation of the technical efficacy, reliability, safety, and clinical tolerance of the plasma surgical PlasmaJet™ system for intra-operative coagulation in open and laparoscopic general surgery," Department of Digestive Surgery, University Hospital, Nice, France, 1 page.
Haemmerich et al., 2003, "Hepatic radiofrequency ablation with internally cooled probes: effect of coolant temperature on lesion size," IEEE Transactions of Biomedical Engineering, 50(4):493-500.
Haines et al., "Argon neutral plasma energy for laparoscopy and open surgery recommended power settings and applications," Royal Surrey county Hospital, Guildford, Surry, UK. Dated Oct. 2009, 1 page.
Honigsman, 2001, "Phototherapy for psoriasis," Clin. Exp. Dermatol, 26:343-350, 8 pages.
Huang et al., 2008, "Laminar/turbulent plasma jets generated at reduced pressure," IEEE Transaction on Plasma Science, 36(4):1052-1053.
Iannelli et al., 2005, "Neutral plasma coagulation (NPC)—A preliminary report on a new technique for post-bariatric corrective abdominoplasty," Department of Digestive Surgery, University Hospital, Nice, France, 1 page.
International Preliminary Report on Patentability for International Application No. PCT/EP2007/006939, dated Feb. 9, 2010, 8 pages.
International Preliminary Report on Patentability for International Application No. PCT/EP2007/006940, dated Feb. 9, 2010, 7 pages.
International Preliminary Report on Patentability for International Application No. PCT/US2021/048052 dated Feb. 28, 2023, 10 pages.
International Search Report and Written Opinion for Application No. PCT/US2021/048052, mailed Feb. 28, 2022, 18 pages.
International Search Report for International Application No. PCT/EP2010/060641, dated Apr. 14, 2011, 5 pages.
International Search Report of International application No. PCT/EP2010/051130, dated Sep. 27, 2010, 7 pages.
International-type Search Report dated Jan. 18, 2006 for Swedish Application No. 0501602-7, 6 pages.
International-type Search Report dated Jan. 18, 2006 for Swedish Application No. 0501603-5, 6 pages.
International-type Search Report dated Jan. 18, 2006 for Swedish Application No. 0501604-3, 7 pages.
Invitation to Pay for International PCT Application No. PCT/US2021/048052, mailed Jan. 5, 2022, 11 pages.
Japanese Office Action for Application No. 2009-547536, dated Feb. 15, 2012, 5 pages.
Japanese Office Action for Application No. 2010-519339, dated Apr. 3, 2012, with translation, 14 pages.
Japanese Office Action for Application No. 2010-519340, dated Mar. 13, 2012, with translation, 4 pages.
Japanese Office Action (translation) of application No. 2008-519873, dated Jun. 10, 2011, 4 pages.
Letter to FDA re: 501(k) Notification (21 CFR 807 90(e)) for the PlasmaJet® Neutral Plasma Surgery System, dated Jun. 2, 2008—K080197, 3 pages.
Lichtenberg et al., 2002, "Observation of different modes of cathodic arc attachment to HID electrodes in a model lamp," J. Phys. D. appl. Phys. 35:1648-1656.
Marino, M. D., "A new option for patients facing liver resection surgery," Thomas Jefferson University Hospital, dated Mar. 24, 2005, 1 page.
McClurken et al., 2001, "Collagen shrinkage and vessel sealing," TissueLink Medical, Inc., Dover, NH; Technical Brief #300, 2 pages.
McClurken et al., 2002 "Histologic characteristics of the TissueLink Floating Ball device coagulation on porcine liver," TissueLink Medical, Inc., Dover, NH; Pre-Clinical Study #204, 4 pages.
Merloz, 2007, "Clinical evaluation of the Plasma Surgical PlasmaJet tissue sealing system in orthopedic surgery - Early report," Orthopedic Surgery Department, University Hospital, Grenoble, France, 1 page.
News Release and Video—2009, New Surgical Technology Offers Better Outcomes for Women's Reproductive Disorders: Stanford First in Bay Area to Offer PlasmaJet, Stanford Hospital and Clinics, 2 pages.
Nezhat et al., 2009, "Use of neutral argon plasma in the laparoscopic treatment of endometriosis," Journal of the Society of Laparoendoscopic Surgeons, pp. 1-5.
Non-Final Office Action for U.S. Appl. No. 18/114,023 dated May 24, 2023, 10 pages.
Non-Final Office Action mailed Apr. 9, 2014 for U.S. Appl. No. 12/841,361, 14 pages.
Non-Final Office Action mailed Feb. 8, 2018 for U.S. Appl. No. 14/809,865, 9 pages.
Non-Final Office Action mailed Feb. 8, 2018 for U.S. Appl. No. 14/810,032, 9 pages.
Non-Final Office Action mailed Jan. 3, 2018 for U.S. Appl. No. 14/810,102, 8 pages.
Notice of Allowance and Fees Due for U.S. Appl. No. 12/557,645, dated May 26, 2011, 5 pages.
Notice of Allowance and Fees Due for U.S. Appl. No. 12/696,411, dated Aug. 12, 2013, 4 pages.
Notice of Allowance and Fees Due for U.S. Appl. No. 13/357,895, dated Feb. 21, 2013, 9 pages.
Notice of Allowance and Fees Due of U.S. Appl. No. 11/482,581, filed Oct. 28, 2011, 10 pages.
Notice of Allowance and Fees Due of U.S. Appl. No. 11/482,582, filed Sep. 23, 2011, 10 pages.
Notice of Allowance and Fees Due of U.S. Appl. No. 13/358,934, dated Sept. 5, 2012, 22 pages.
Notice of Allowance dated May 15, 2009 for U.S. Appl. No. 11/890,938, 7 pages.
Notice of Allowance for U.S. Appl. No. 16/599,532 dated Feb. 20, 2024, 10 pages.
Notice of Allowance for U.S. Appl. No. 18/114,023 dated Sep. 6, 2023, 10 pages.
Notice of Allowance of U.S. Appl. No. 11/701,911, dated Dec. 6, 2010, 5 pages.
Office Action dated Apr. 17, 2008 for U.S. Appl. No. 11/701,911, 7 pages.
Office Action dated Apr. 2, 2010 for U.S. Appl. No. 11/701,911, 20 pages.
Office Action dated Apr. 9, 2010 for U.S. Appl. No. 11/890,937, 15 pages.
Office Action dated Feb. 1, 2008 for U.S. Appl. No. 11/482,580, 13 pages.
Office Action dated Jun. 23, 2010 for U.S. Appl. No. 11/482,582, 40 pages.
Office Action dated Jun. 24, 2010 for U.S. Appl. No. 11/482,581, 42 pages.
Office Action dated Mar. 13, 2009 for U.S. Appl. No. 11/701,911, 6 pages.
Office Action dated Mar. 19, 2009 for U.S. Appl. No. 11/482,580, 14 pages.
Office Action dated Oct. 18, 2007 for U.S. Appl. No. 11/701,911, 12 pages.
Office Action dated Oct. 19, 2009 for U.S. Appl. No. 11/482,580, 18 pages.

(56) References Cited

OTHER PUBLICATIONS

Office Action dated Sep. 17, 2009 for U.S. Appl. No. 11/890,937, 19 pages.
Office Action dated Sep. 29, 2009 for U.S. Appl. No. 11/701,911, 8 pages.
Office Action for U.S. Appl. No. 11/482,580, dated Apr. 11, 2012, 14 pages.
Office Action for U.S. Appl. No. 11/482,582, dated May 23, 2011, 15 pages.
Office Action for U.S. Appl. No. 11/701,911 dated Jul. 19, 2010, 7 pages.
Office Action for U.S. Appl. No. 11/890,937, dated Apr. 3, 2013, 7 pages.
Office Action for U.S. Appl. No. 12/696,411, dated Dec. 5, 2012, 10 pages.
Office Action for U.S. Appl. No. 13/357,895, dated Mar. 29, 2012, 25 pages.
Office Action for U.S. Appl. No. 13/358,934, dated Apr. 24, 2012, 13 pages.
Office Action of U.S. Appl. No. 12/557,645, dated Nov. 26, 2010, 26 pages.
Office Action of U.S. Appl. No. 13/357,895, dated Sept. 7, 2012, 26 pages.
Office Action of U.S. Appl. No. 11/482,581, dated Dec. 8, 2010, 23 pages.
Office Action of U.S. Appl. No. 11/482,582, dated Dec. 6, 2010, 14 pages.
Office Action U.S. Appl. No. 11/482,580, dated Oct. 24, 2012, 14 pages.
Palanker et al., "Electrosurgery with cellular precision," IEEE Transactions of Biomedical Engineering, Feb. 2008, 55(2): 838-841.
Pan et al., "Characteristics of argon laminar DC PlasmaJet at atmospheric pressure," Jun. 2002, Plasma Chem and Plasma Proc, 22(2): 271-283.
Pan et al., "Generation of long, laminar plasma jets at atmospheric pressure and effects of low turbulence," Mar. 2001, Plasma Chem Plasma Process, 21(1):23-35.
PCT International Preliminary Report on Patentability and Written Opinion dated Aug. 4, 2009 for International Application No. PCT/EP2007/000919, 8 pages.
PCT International Search Report dated Feb. 14, 2007 for International Application No. PCT/EP2006/006688, 4 pages.
PCT International Search Report dated Feb. 22, 2007 for International Application No. PCT/EP2006/006689, 4 pages.
PCT International Search Report dated Feb. 22, 2007 for International Application No. PCT/EP2006/006690, 4 pages.
PCT International Search Report dated Oct. 23, 2007 for International Application No. PCT/EP2007/000919, 4 pages.
PCT International Search Report for PCT/EP2007/006939, dated May 26, 2008, 13 pages.
PCT International Search Report for PCT/EP2007/006940, dated Jul. 11, 2008, 5 pages.
PCT Invitation to Pay Additional Fees for PCT/EP2007/006940, dated May 20, 2008, 21 pages.
PCT Written Opinion dated Feb. 14, 2007 for International Application No. PCT/EP2006/006688, 10 pages.
PCT Written Opinion dated Feb. 22, 2007 for International Application No. PCT/EP2006/006689, 6 pages.
PCT Written Opinion dated Feb. 22, 2007 for International Application No. PCT/EP2006/006690, 6 pages.
PCT Written Opinion for PCT/EP2007/006939, dated May 26, 2008, 24 pages.
PCT Written Opinion for PCT/EP2007/006940, Jul. 11, 2008, 6 pages.
Plasma Surgery: A Patient Safety Solution (Study Guide 002), dated Feb. 25, 2010, pp. 1-19.
Plasma Surgical Headlines Article: Atlanta, Feb. 2, 2010—"New Facilities Open in UK and US", 2 pages.
Plasma Surgical Headlines Article: Atlanta, Feb. 2, 2010—"PlasmaJet to be Featured in Live Case at Endometriosis 2010 in Milan, Italy", 4 pages.
Plasma Surgical Headlines Article: Chicago, Sep. 17, 2008—"PlasmaJet Named Innovation of the Year by the Society of Laparoendoscopic Surgeons", pp. 1-3.
PlasmaJet English brochure, dated Feb. 2010, 111 pages.
PLASMAJET Neutral Plasma Coagulator Brochure mpb 2100—K080197, dated Oct. 2006, 4 pages.
PLASMAJET Neutral Plasma Coagulator Operator Manual, Part No. OMC-2100-1 (Revision 1.7, dated May 2004)—K030819, pp. 1-22.
PLASMAJET Operator Manual Part No. OMC-2130-EN (Revision 3.1/Draft) dated May 2008—K080197, pp. 1-25.
Premarket Notification 510(k) Submission, Plasma Surgical Ltd.—CoagSafe ™, Section 4 Device Description—K030819, Mar. 14, 2003, 4 pages.
Premarket Notification 510(k) Submission, Plasma Surgical Ltd.—PlasmaJet™ (formerly CoagSafe TM) Neutral Plasma Coagulator, additional information provided in response to the e-mail request dated Jul. 14, 2004—K030819, pp. 1-13.
Premarket Notification 510(k) Submission, Plasma Surgical Ltd. CoagSafe™, Section 5 Substantial Equivalence—K030819, Mar. 14, 2003, 4 pages.
Premarket Notification 510(k) Submission, Plasma Surgical Ltd. PlasmaJet™, Section 11 Device Description, K080197, Jan. 2, 2008, 6 pages.
Report on the comparative analysis of morphological changes in tissue from different organs after using the PlasmaJet version 3 (including cutting handpieces), Aug. 2007—K080197, 32 pages.
SCHMITZ & RIEMANN, "Analysis of the cathode region of atmospheric pressure discharges," Jul. 4, 2002, J. Phys. D. Appl. Phys. 35:1727-1735.
Severtsev et al. 1997, "Polycystic liver disease: sclerotherapy, surgery and sealing of cysts with fibrin sealant", European Congress of the International Hepatobiliary Association, Hamburg, Germany Jun. 8-12; p. 259-263.
Severtsev et al., "Comparison of different equipment for final haemostasis of the wound surface of the liver following resection," Dept. of Surgery, Postgraduate and Research Centre, Medical Centre of the Directorate of Presidential Affairs of the Russian Federation, Moscow, Russia—K030819, Jun. 1997, 8 pages.
Sonoda et al., "Pathologic analysis of ex-vivo plasma energy tumor destruction in patients with ovarian or peritoneal cancer," Gynecology Service, Department of Surgery—Memorial Sloan-Kettering Cancer Center, New York, NY—Poster, 2010, 1 page.
Supplemental Notice of Allowability of U.S. Appl. No. 11/482,582, filed Oct. 12, 2011, 4 pages.
Supplemental Notice of Allowability of U.S. Appl. No. 11/482,582, filed Oct. 25, 2011, 5 pages.
The Edge in Electrosurgery From Birtcher, 1991, Brochure - Appendix 4 of K030819, 2 pages.
The Valleylab FORCE GSU System, Brochure—Appendix 4 of K030819, dated Jan. 1991, 2 pages.
Treat, "A new thermal device for sealing and dividing blood vessels", Dept. of Surgery, Columbia University. New York, NY, Jun. 29, 2005, 2 pages.
Trehan & Taylor, 2002, "Medium-dose 308-mm excimer laser for the treatment of psoriasis," J. Am. Acad. Dermatol. 47:701-8.
U.S. Appl. No. 12/557,645, Suslov, Sep. 11, 2009, 46 pages.
White Paper—A Tissue Study using the PlasmaJet for coagulation: A tissue study comparing the PlasmaJet with argon enhanced electrosurgery and fluid coupled electrosurgery, Oct. 23, 2007, 11 pages.
White Paper—Plasma Technology and its Clinical Application: An introduction to Plasma Surgery and the PlasmaJet—a new surgical technology, Oct. 23, 2010, pp. 1-7.
Written Opinion for International Application No. PCT/EP2010/060641, dated Apr. 14, 2011, 10 pages.
Written Opinion of International application No. PCT/EP2010/051130, dated Sep. 27, 2010, 8 pages.

(56) References Cited

OTHER PUBLICATIONS

Zenker, 2008, "Argon plasma coagulation," German Medical Science, 3(1):1-5.

* cited by examiner

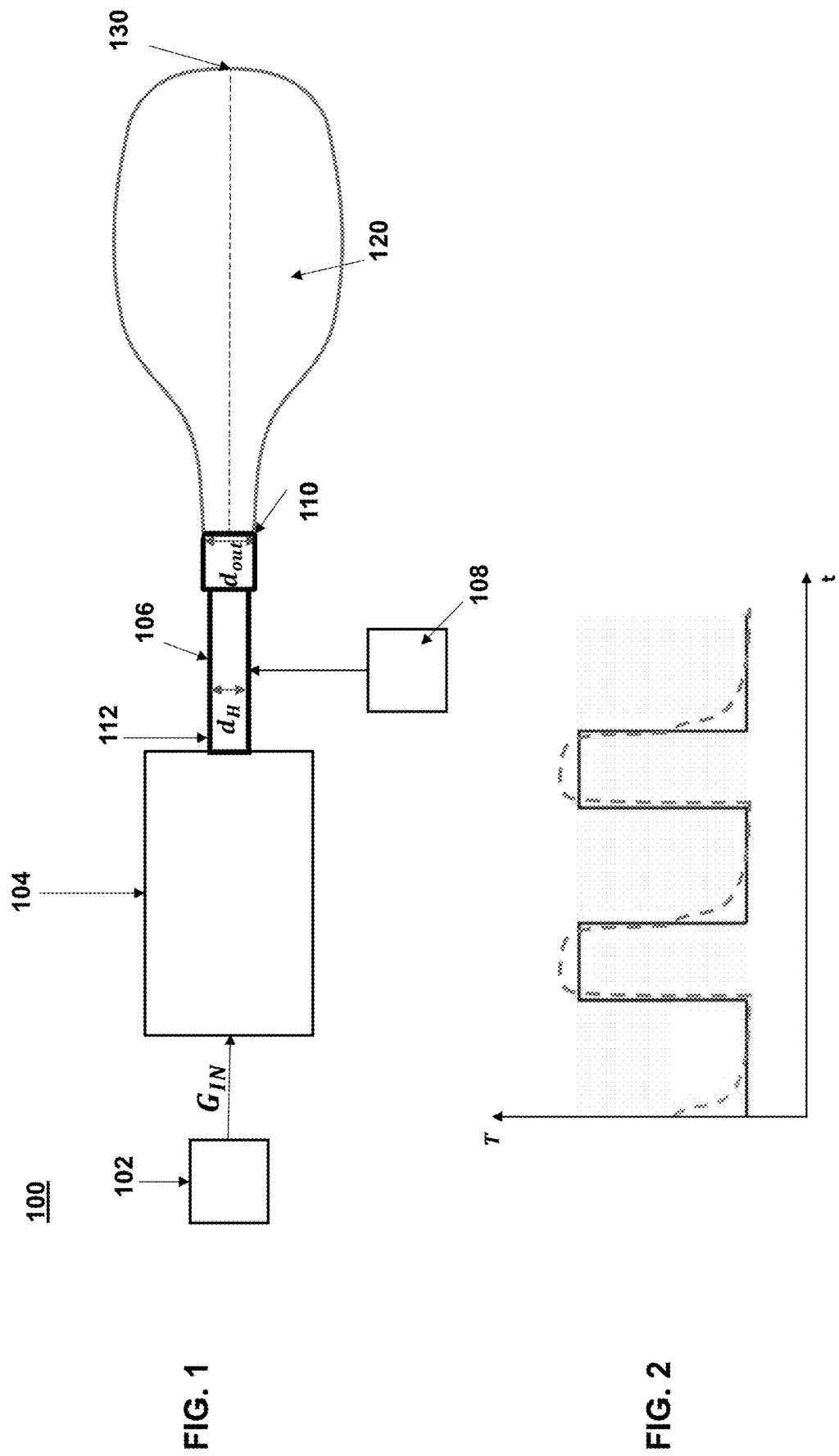

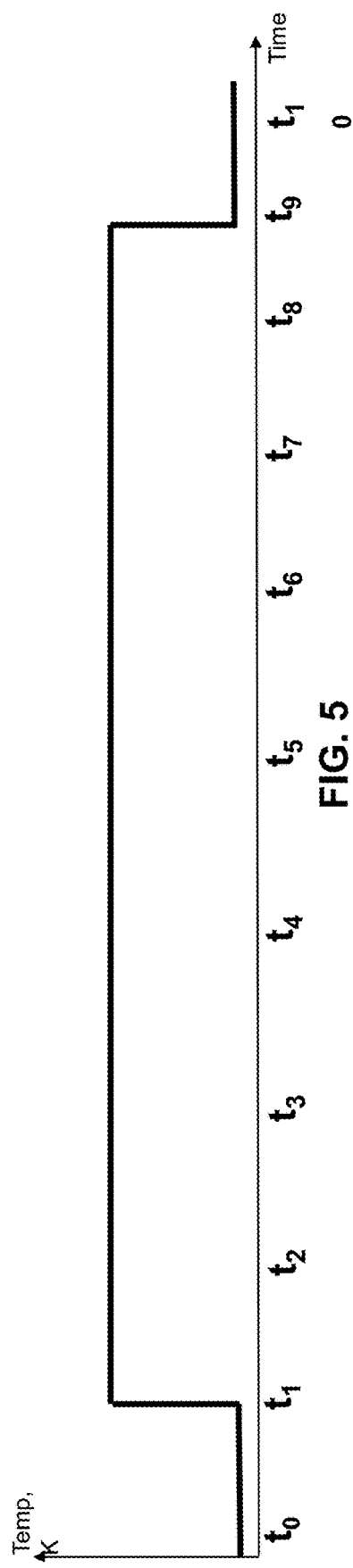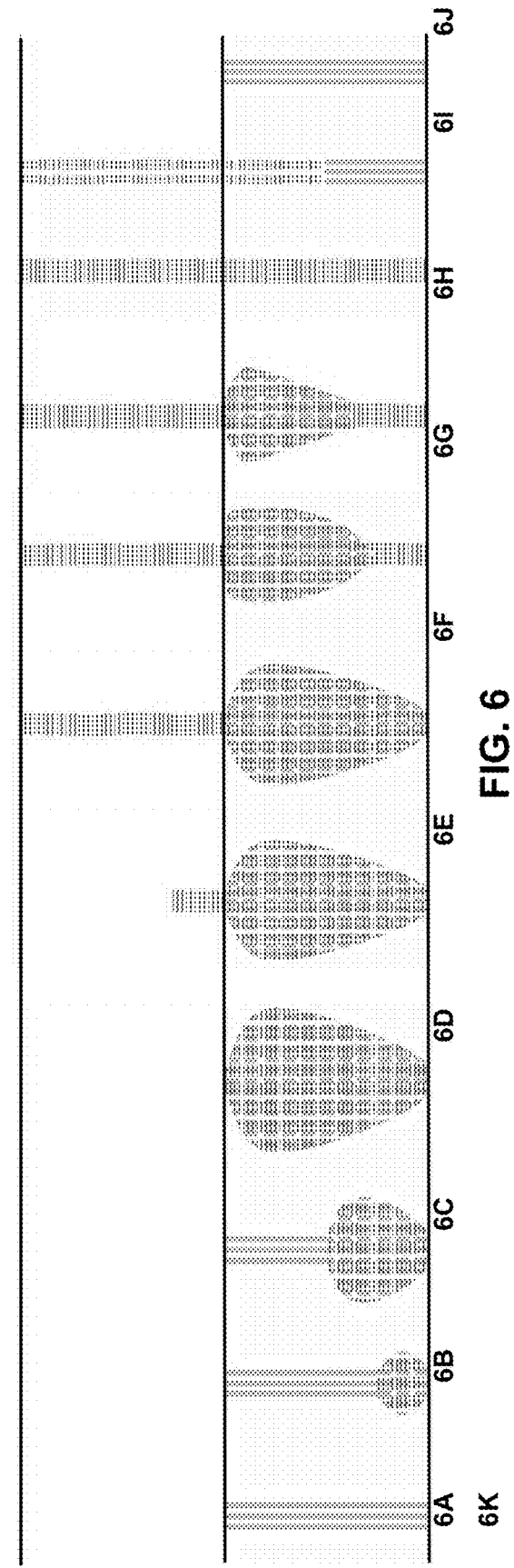

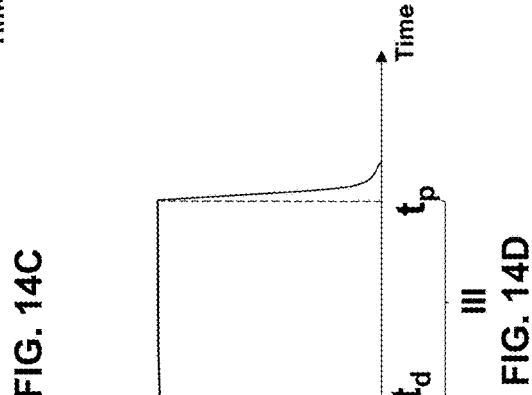
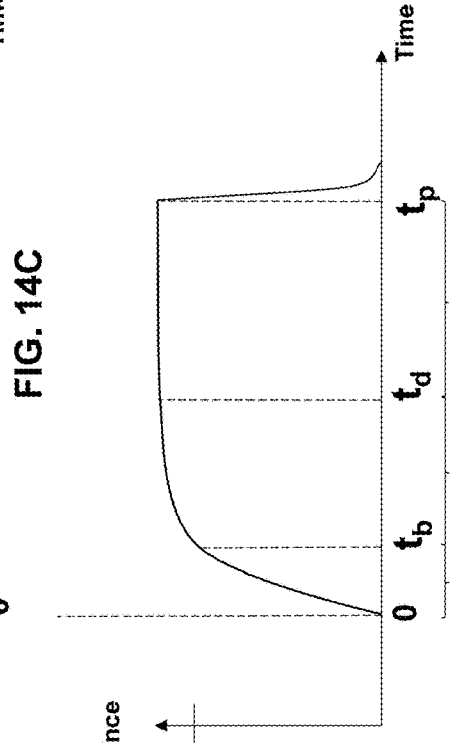
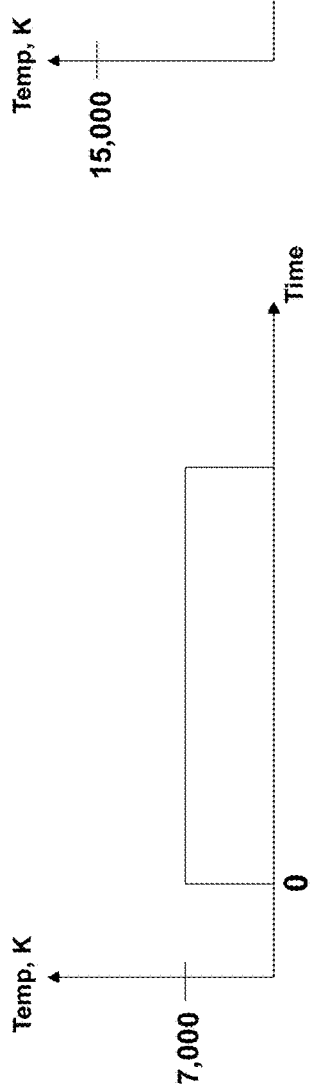
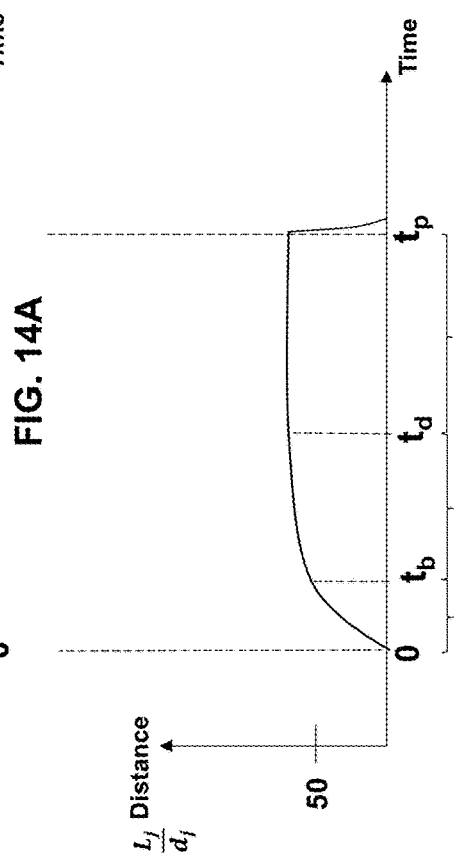

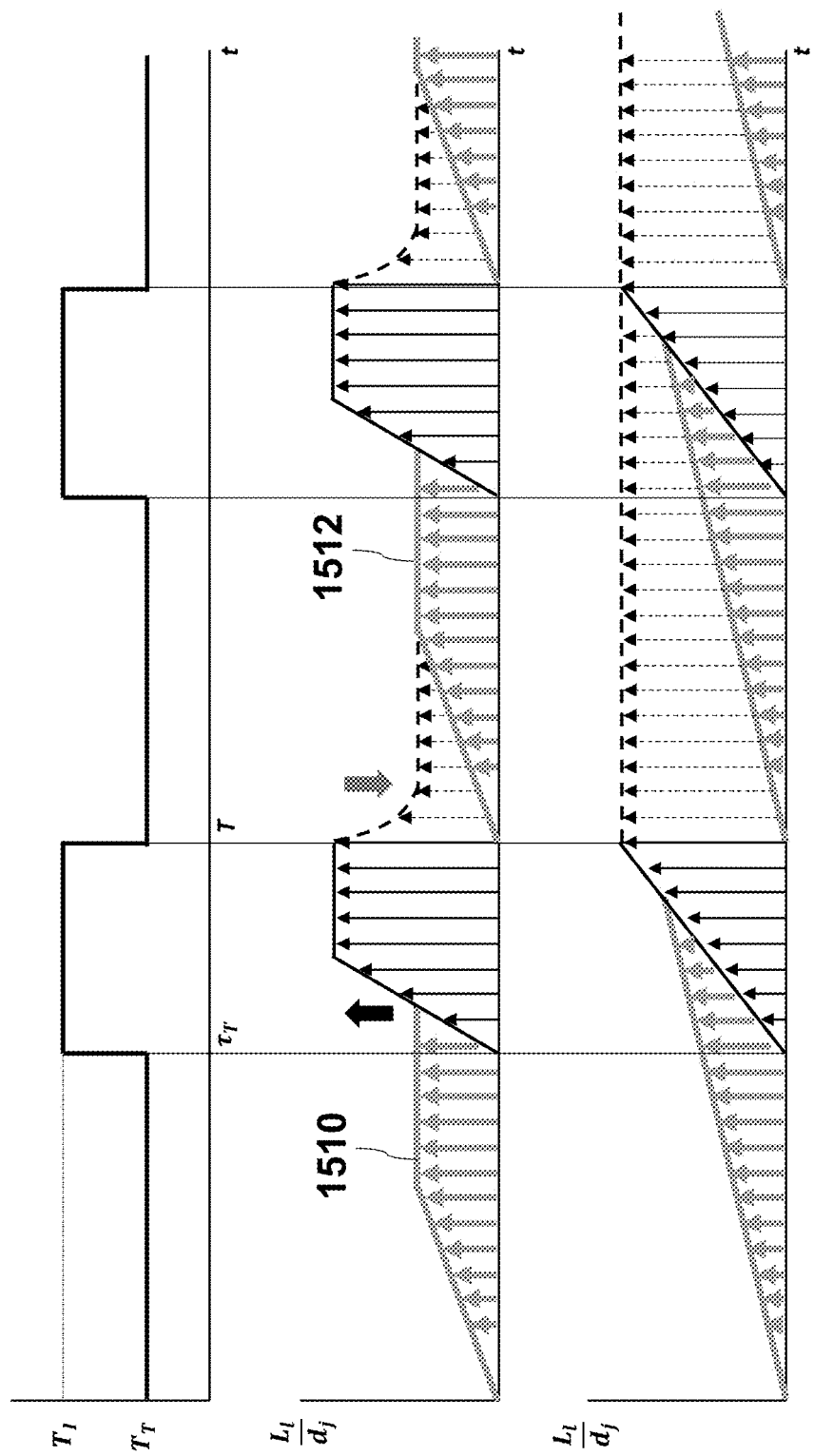

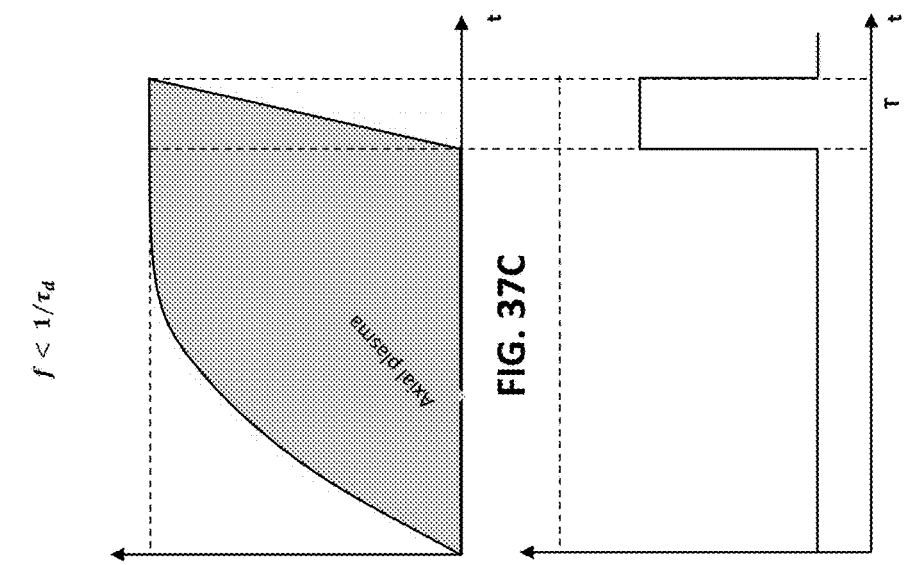
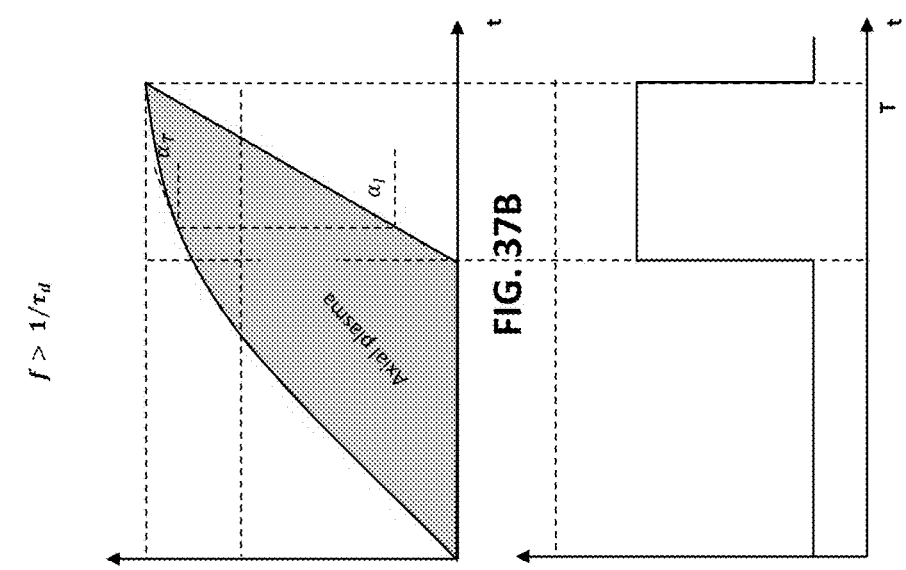
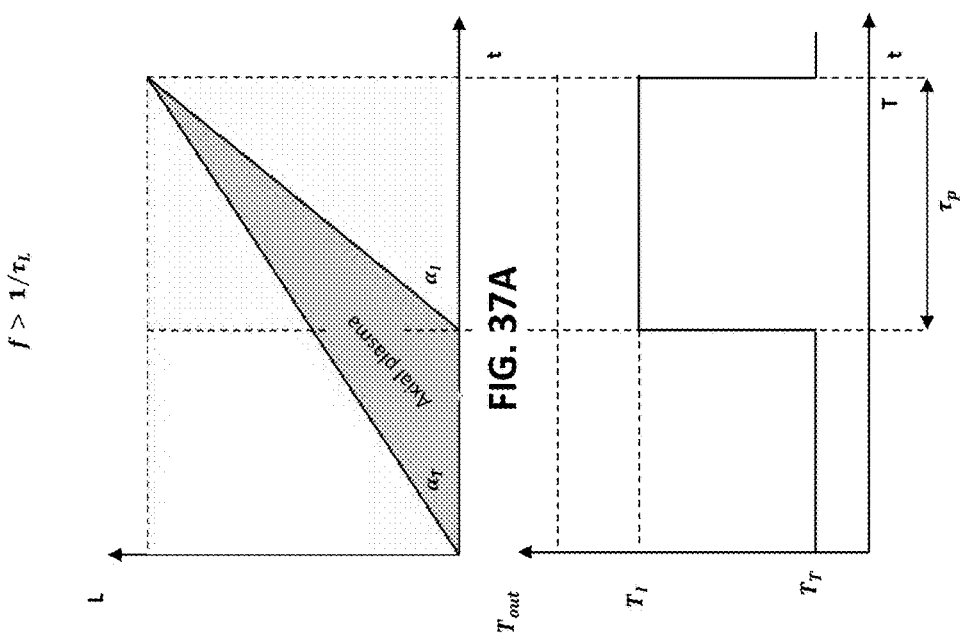

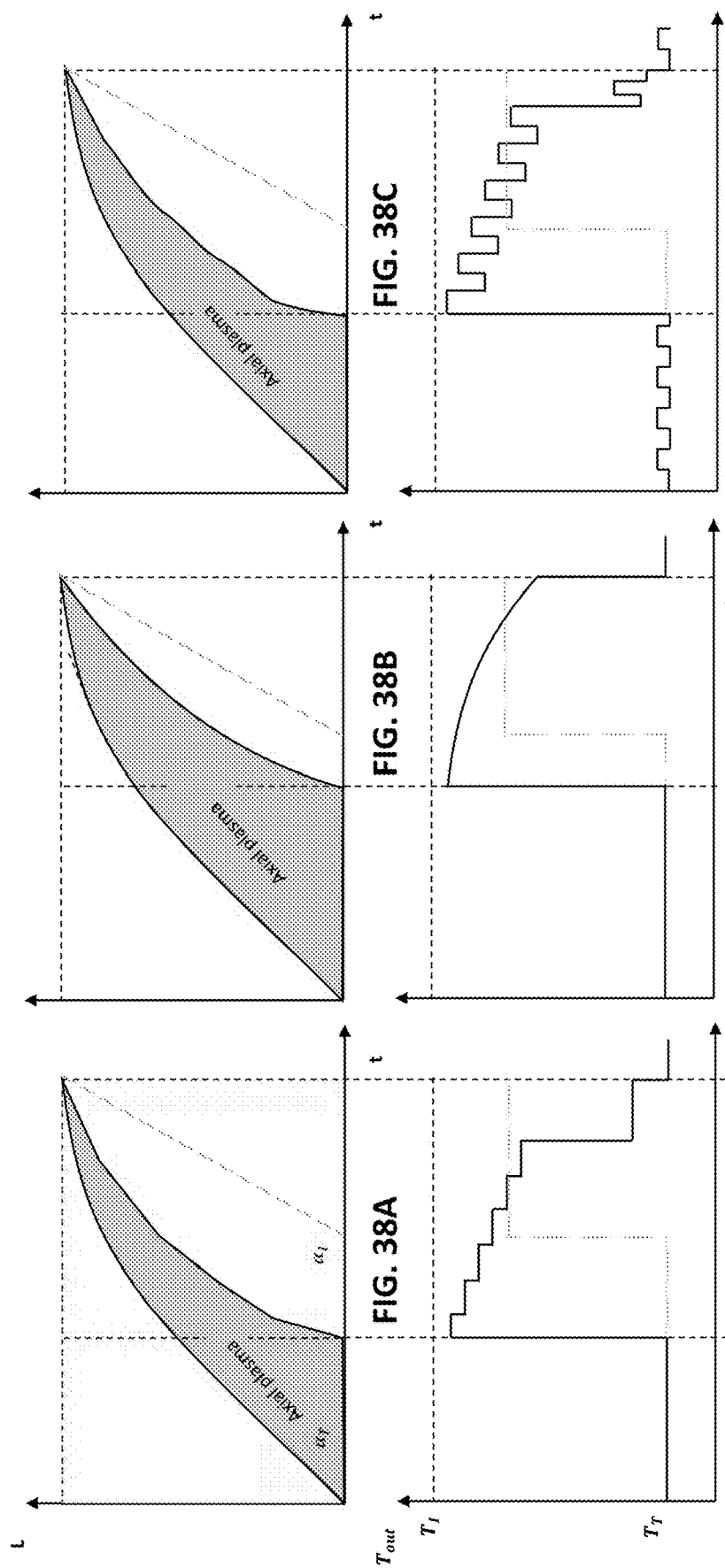

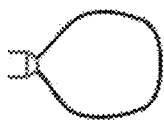

FIG. 42F $G_{IN} = 0.5 \frac{L}{min}$
$d_H = 0.4mm$
$d_{OUT} = \mathbf{0.6mm}$
$T_T = 3000K$
$T_I = 13400K$
$D = 0.5$
$T = 25\mu s$

FIG. 42G $G_{IN} = 0.5 \frac{L}{min}$
$d_H = 0.4mm$
$d_{OUT} = 0.5mm$
$T_T = 3000K$
$T_I = \mathbf{16000K}$
$\mathbf{D = 0.4}$
$T = 25\mu s$

FIG. 42H $G_{IN} = 0.5 \frac{L}{min}$
$d_H = 0.4mm$
$d_{OUT} = 0.5mm$
$T_T = 3000K$
$T_I = \mathbf{11200K}$
$\mathbf{D = 0.6}$
$T_t = 3000K$
$T = 25\mu s$

FIG. 42I $G_{IN} = 0.5 \frac{L}{min}$
$d_H = 0.4mm$
$d_{OUT} = 0.5mm$
$T_T = \mathbf{10000K}$
$T_I = \mathbf{21500K}$
$D = 0.5$
$T_t = 3000K$
$T = 25\mu s$

FIG. 42J $G_{IN} = 0.5 \frac{L}{min}$
$d_H = 0.4mm$
$d_{OUT} = 0.5mm$
$T_T = 3000K$
$T_I = \mathbf{16000K}$
$\mathbf{D_{eff} = 0.6}$
$T_t = 3000K$
$T = 25\mu s$

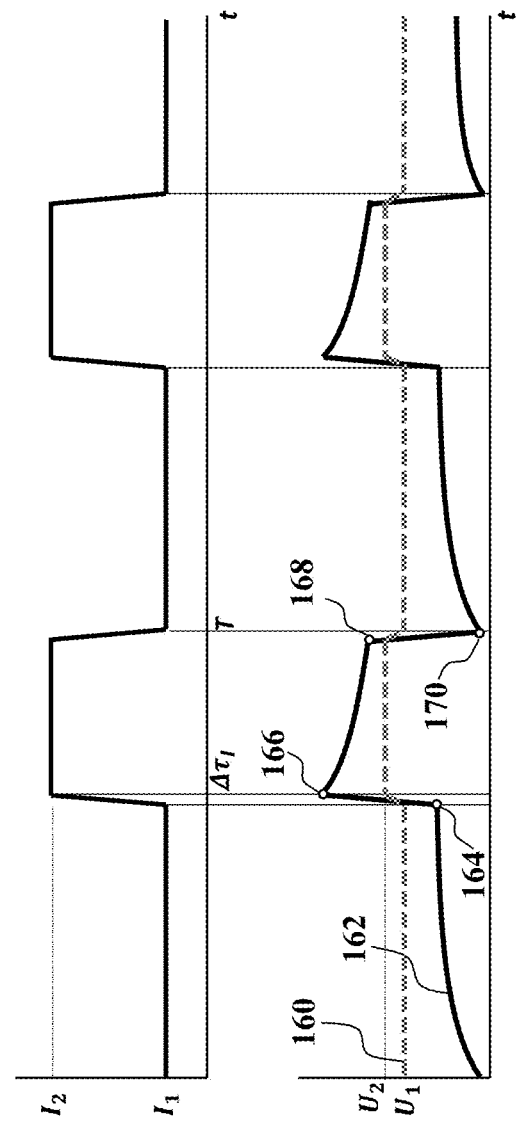

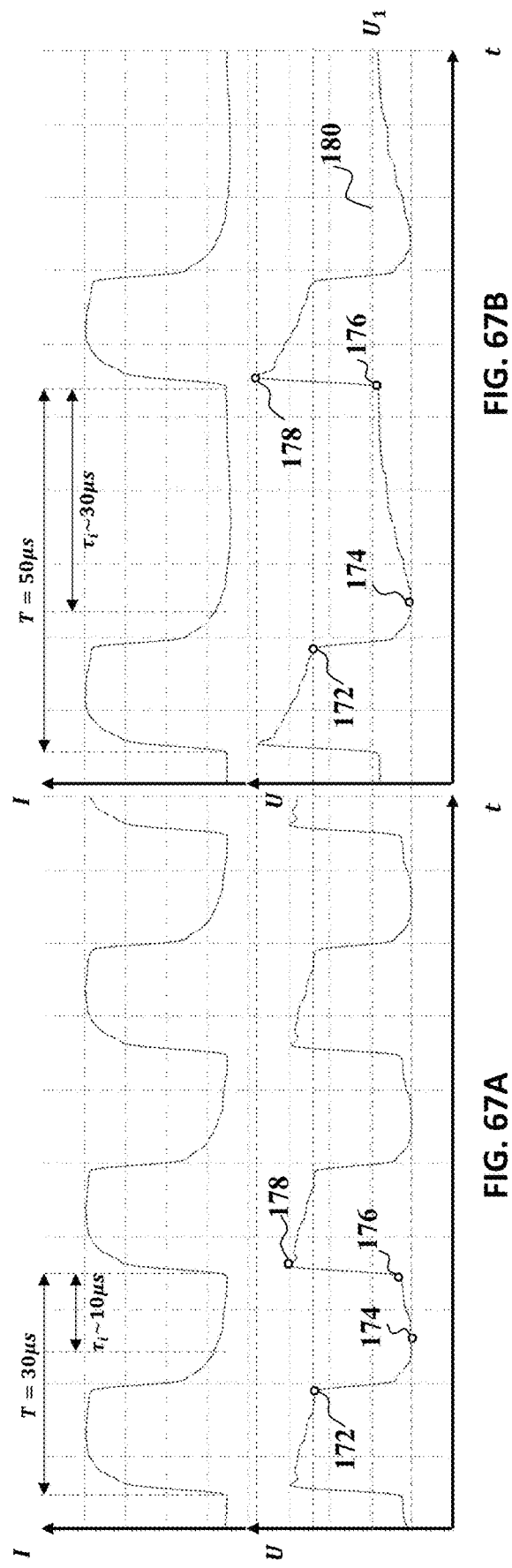

SYSTEMS, METHODS, AND DEVICES FOR GENERATING PREDOMINANTLY RADIALLY EXPANDED PLASMA FLOW

CROSS-REFERENCE TO RELATED APPLICATIONS

The application is a continuation of U.S. patent application Ser. No. 18/114,023, filed Feb. 24, 2023, entitled "Systems, Methods, and Devices for Generating Predominantly Radially Expanded Plasma Flow," which is a continuation of International Patent Application No. PCT/US2021/048052, filed Aug. 27, 2021, entitled "Systems, Methods, and Devices for Generating Predominantly Radially Expanded Plasma Flow," which claims priority to U.S. Provisional Application No. 63/071,787, filed Aug. 28, 2020, entitled "Systems, Methods, and Devices for Generating Predominantly Radially Expanded Plasma Flow," the contents of each of which is hereby incorporated by reference in their entirety.

TECHNICAL FIELD

Devices, systems, and methods herein relate to generation of plasma flow, and specifically to the generation of radially expanded plasma flows and to practical applications of radially expanded plasma flows.

BACKGROUND

Plasma generating devices play an important role in many areas. Plasma is a phase of matter in which a non-negligible number of particles are ionized. Plasma can be generated from a fluid, which is typically a gas at room temperature, referred to as plasma-generating gas. Plasma may be generated by means of applying energy to the plasma-generating gas flowing through a plasma-generating device. The application of energy results in a substantial temperature increase of the plasma-generating gas, which in turn, results in ionization of the plasma-generating gas particles.

Plasma flows with different characteristics may have applications in industrial, cosmetic, spraying, medical, and other fields. Plasma flow may be generated with predetermined properties (e.g., continuous, intermittent) based on the particular application of the plasma flow. Application of energy that is substantially constant, such as a constant direct current (DC), can result in the generation of a continuous plasma flow, with properties that do not substantially change over time in operation. These properties include the shape of the flow, the temperature distribution, and the static and dynamic pressure of the flow. It has been observed, however, that, while such continuous flows may be optimal for some applications, they are not well suited for many other applications.

Various systems and methods for changing the properties of a plasma flow in operation have been proposed. For example, U.S. Pat. No. 7,589,473 discloses systems and methods for generating pulsed plasma or an intermittent plasma flow in which the flow of plasma periodically ceases during operation. U.S. Pat. No. 9,089,319 discloses systems and methods for the generation of volumetrically oscillating plasma flows. U.S. Pat. No. 9,089,319 further discloses various uses and benefits of volumetrically oscillating plasma flows in medical and non-medical fields. Volumetrically oscillating plasma flows, however, may not be optimal for some medical applications. For example, due to the changes in the volumetrically oscillating plasma flow's active zone, the effect on the treated surface can be unpredictable. Moreover, changes in the device's position with respect to the treated surface can produce uncertain and often undesirable results. Additionally, certain conditions for generating volumetrically oscillating plasma flows are not optimal for certain applications, including medical applications, and can introduce unnecessary requirements on a plasma-generating device.

Existing and previously used power supply systems, as well as plasma generating devices, may not be adequate to meet the requirements for generation of useful and stable plasma flows. For example, existing power supply systems may not be capable of generating energy patterns necessary for generations of certain plasma flows. Generation of certain plasma flows can also cause the rapid destruction of internal components, rendering existing devices unsuitable for real-life applications, especially in the medical field.

Accordingly, there exists a need for systems and methods that generate plasma flows that exhibit substantially uniform, or homogeneous, characteristics over a substantial distance range from the outlet of the device.

SUMMARY

Described herein are devices, systems, and methods for generating a predominantly radially expanded plasma flow. These devices and systems may generate plasma flows that exhibit substantially uniform, or homogeneous, characteristics over a predetermined distance.

In some embodiments, a method may comprise supplying a plasma-generating gas to a plasma generating device having an outlet, applying energy to the plasma-generating gas according to a predetermined energy pattern, and discharging, in response to applying the energy, a plasma flow from the outlet of the plasma generating device, the plasma flow having a periodic pattern including a base plasma flow and a pulse plasma flow. The base plasma flow having a first temperature at the outlet of the device, and the pulse plasma flow having a second temperature at the outlet of the device that is greater than the first temperature. The base plasma having a first density at the first temperature, and the pulse plasma having a second density at the second temperature, the first density being at least two times the second density. The base plasma flow having a first speed of sound, and the pulse plasma flow having a second speed of sound that is at most about four times greater than the first speed of sound.

In some embodiments, the pattern may include alternating between discharging the base plasma flow for a base duration and discharging the pulse plasma flow for a pulse duration, the pulse duration being less than the base duration.

In some embodiments, the plasma-generating gas may be supplied at a predetermined flow rate, and the sum of the base duration and the pulse duration may be based at least in part on the flow rate. In some embodiments, the sum of the base duration and the pulse duration may be further based on the second temperature. In some embodiments, the second temperature may be less than or equal to 15,000 K, a ratio of the predetermined flow rate G (L/min) of the plasma-generating gas to a diameter d (mm) of the outlet may be less than or equal to 100, and the sum of the base duration and the pulse duration may be less than $$100{,}000 * \frac{d^4}{G^2}.$$

In some embodiments, the second temperature may be less than or equal to 15,000 K, a ratio of the predetermined flow rate G (L/min) of the plasma-generating gas to a diameter d (mm) of the outlet may be greater than 100, and the sum of the base duration and the pulse duration may be less than 5 ms. In some embodiments, the second temperature may be greater than 15,000 K, a ratio of the predetermined flow rate G (L/min) of the plasma-generating gas to a diameter d (mm) of the outlet may be less than or equal to 100, and the sum of the base duration and the pulse duration may be less than $$5,000 * \frac{d^4}{G^2}.$$

In some embodiments, the second temperature may be greater than 15,000 K, a ratio of the predetermined flow rate G (L/min) of the plasma-generating gas to a diameter d (mm) of the outlet may be greater than 100, and the sum of the base duration and the pulse duration may be less than 500 μs. In some embodiments, a frequency of the alternating between the base plasma flow and the pulse plasma flow may be greater than about 1 kHz. In some embodiments, a diameter of the outlet may be less than about 140 mm when the second temperature is less than or equal to about 10,000 K. In some embodiments, the plasma-generating gas may be supplied at a predetermined flow rate that is directly proportional to a diameter of the outlet.

In some embodiments, if the diameter of the outlet is about 0.5 mm, the predetermined flow rate may be between about 0.5 l/min and about 4 l/min, if the diameter of the outlet is about 5 mm, the predetermined flow rate may be between about 5 l/min and about 40 l/min, and if the diameter of the outlet is about 10 mm, the predetermined flow rate may be between about 10 l/min and about 80 l/min.

In some embodiments, the plasma flow may have an outlet temperature-time profile that includes a repeated set of regions, the repeated set of regions including a first region in which the plasma flow has an outlet temperature maintained at the first temperature, a second region in which the outlet temperature of the plasma flow rises to the second temperature, a third region in which the outlet temperature of the plasma flow reduces at a first rate to a third temperature, a fourth region in which the outlet temperature of the plasma flow reduces at a second rate to a fourth temperature, and a fifth region in which the outlet temperature of the plasma flow reduces at a third rate to the first temperature. In some embodiments, the second rate may be greater than the first and third rates. In some embodiments, the outlet temperature may rise to the second temperature in the second region during a time interval of about 0.01 to about 0.1 times the total duration of the set of regions. In some embodiments, the outlet temperature may reduce to the fourth temperature in the fourth region during a time interval of about 0.01 to about 0.1 times the total duration of the set of regions. In some embodiments, the outlet temperature may reduce to the first temperature in the fifth region during a time interval of about 0.2 to about 0.4 times the total duration of the set of regions. In some embodiments, the fourth temperature may be an intermediate temperature between the first and third temperatures, the fourth temperature being equal to about 0.2 to about 0.4 times a difference between the first and third temperatures. In some embodiments, the total duration of the set of regions may be between about 10 and about 50 μs. In some embodiments, the first temperature may be between about 2,000 K and about 4,000 K.

In some embodiments, a system may comprise a current control generator configured to supply current having a current pattern to a plasma-generating device such that the plasma-generating device can generate a radially expanded plasma flow, the current pattern including: a first set of oscillations between a first base level and a second base level, the second base level being greater than the first base level, the first set of oscillations having a first frequency, and a second set of oscillations between a first pulse level and a second pulse level. The second pulse level being greater than the first pulse level and the first and second base levels. The second set of oscillations having a second frequency greater than the first frequency. The first and second sets of oscillations being synchronized such that the first base level is paired with the first pulse level for generating the radially expanded plasma flow and the second base level is paired with the second pulse level for generating the radially expanded plasma flow.

In some embodiments, the first set of oscillations may have a current pulse resolution between about 0.1 ms to about 0.2 ms. In some embodiments, the second set of oscillations may have a current pulse resolution between about 0.1 μs and 1 μs. In some embodiments, a root mean square of the current having the current pattern is between about 12 A and about 15 A.

In some embodiments, the second set of oscillations may include a repeated set of regions, the repeated set of regions including: a first region in which the current maintained at the first base level or the second base level, a second region in which the current rises to a first top pulse level from the first base level or a second top pulse level from the second base level, a third region in which the current reduces to a first bottom pulse level from the first top pulse level or a second bottom pulse level from the second top pulse level, a fourth region in which the current reduces to a first intermediate level from the first bottom pulse level or a second intermediate level from the second bottom pulse level, and a fifth region in which the current reduces to the first base level from the first intermediate level or the second base level from the second intermediate level.

In some embodiments, the current may reduce to the first bottom pulse level or the second bottom pulse level at a first rate, and the current may reduce to the first intermediate level or the second intermediate level at a second rate, the second rate being greater than the first rate.

In some embodiments, the current may reduce to the first bottom pulse level or the second bottom pulse level at a first rate, the current may reduce to the first intermediate level or the second intermediate level at a second rate, and the current may reduce to the first base level or the second base level at a third rate, the second rate being greater than the first and third rates.

In some embodiments, the current may rise to the first top pulse level or the second top pulse level in the second region during a time interval of about 0.01 to about 0.1 times the total duration of the set of regions. In some embodiments, the current may reduce to the first intermediate level or the second intermediate level in the fourth region during a time interval of about 0.01 to about 0.1 times the total duration of the set of regions.

In some embodiments, the current may reduce to the first base level or the second base level in the fifth region during a time interval of about 0.2 to about 0.4 times the total duration of the set of regions. In some embodiments, the first intermediate level may be about 0.2 to about 0.4 times a difference between the first bottom pulse level and the first base level, and the second intermediate level may be about 0.2 to about 0.4 times a difference between the second bottom pulse level and the second base level. In some embodiments, the first frequency of the first set of oscillations may be between about 100 Hz and about 2000 Hz.

In some embodiments, a plasma-generating device may be configured to heat, in response to receiving the current, a plasma-generating gas, and discharge, in response to heating the plasma-generating gas, the radially expanded plasma flow alternating between a low intensity plasma flow and a high intensity plasma flow from an outlet. The low intensity plasma flow being associated with the first base level and the high intensity plasma flow being associated with the second base level.

In some embodiments, the plasma-generating device may be configured to discharge the low intensity plasma flow to heat a treated specimen. In some embodiments, the plasma-generating device may be configured to discharge the high intensity plasma flow to vaporize or sublimate a treated specimen. In some embodiments, the low intensity plasma flow has a first degree of radial expansion, and the high intensity plasma flow has a second degree of radial expansion that is different than the first degree of radial expansion. In some embodiments, the first degree of radial expansion may be greater than the second degree of radial expansion. In some embodiments, the plasma flow may include an active zone defined by plasma having a temperature above 1,000 K, the active zone having a diameter that is at least ten times greater than a diameter of the outlet.

In some embodiments, a plasma-generating device may comprise a cathode including a tapered distal portion, an anode disposed downstream from the cathode and being electrically insulated from the cathode, the anode defining an opening therethrough. A plurality of intermediate electrodes may be disposed between the cathode and the anode, the plurality of intermediate electrodes electrically insulated from each other and from the anode and the cathode, each intermediate electrode from the plurality of intermediate electrodes defining an opening therethrough such that the openings in the plurality of intermediate electrodes and the anode collectively define a plasma channel for discharging a plasma flow, the plasma channel including: a first portion having a first cross-sectional diameter; and a second portion having a second cross-sectional diameter, the first cross-sectional diameter being at least four times the second cross-sectional diameter; an insulator sleeve extending along a surrounding a portion of the cathode.

In some embodiments, a distance from a distal end of the cathode to the second portion of the plasma channel may be at least 1.25 times the second cross-sectional diameter. In some embodiments, a ratio of a length of a portion of the cathode protruding beyond a distal edge of the insulator sleeve to a maximum diameter of the catheter being between about 1.0 and about 1.6. In some embodiments, a ratio of a length of the tapered distal portion of the cathode to a maximum diameter of the cathode may be between about 1.5 and about 2.0. In some embodiments, the second cross-sectional diameter may have between about 0.4 mm and about 1.0 mm. In some embodiments, the anode may form an anode portion of the plasma channel, and a ratio of a length of the anode portion to a diameter of the anode portion may be between about 2 and about 4.

In some embodiments, the anode portion may have an outlet diameter of between about 0.3 mm and about 0.6 mm. In some embodiments, the opening in the anode may have a cross-sectional diameter at a proximal end of the anode that is less than a cross-sectional diameter at a distal end of the anode. In some embodiments, an outer sleeve may be coupled to the anode; and a divider disposed between the outer sleeve and the plurality of intermediate electrodes, the divider with outside surfaces of the plurality of intermediate electrode, an outside surface of the anode, and an inside surface of the outer sleeve collectively defining a cooling channel for cooling the plasma channel. In some embodiments, the cathode may be disposed in a cathode chamber having a diameter $d_{CC}$, the diameter $d_{CC}$ being at least four times the second cross-sectional diameter. In some embodiments, a length of the anode may be between about two times to about eight times a diameter of the anode. In some embodiments, the anode may have a shape of an adaptive nozzle.

BRIEF DESCRIPTION OF THE DRAWINGS

FIG. 1 is a schematic diagram of a plasma-generating device, according to an embodiment.

FIG. 2 is a plot of plasma flow temperature and time, according to an embodiment.

FIG. 5 is a plot of plasma flow temperature and time, according to an embodiment.

FIGS. 6A-6K are schematic diagrams of plasma flow volumes corresponding to the temperature and time plot of FIG. 5, according to an embodiment.

FIGS. 14A and 14C are plots of plasma flow temperature and time for a single pulse of constant outlet temperature. FIGS. 14B and 14D are plots of temperature and distance corresponding to respective FIGS. 14A and 14C, according to an embodiment.

FIG. 15A is a plot of temperature and time of a pulsed plasma flow, according to an embodiment. FIGS. 15B and 15C are plots of temperature and distance of the pulsed plasma flow corresponding to FIG. 15A, according to an embodiment.

FIGS. 37A-37C are plots of length and time corresponding to front propagation dynamics for target and initiator plasma flows depending on the frequency of outlet temperature oscillations, according to an embodiment.

FIGS. 37D-37F are plots of temperature and time of outlet temperature oscillations corresponding to respective FIGS. 37A-37C, according to an embodiment.

FIGS. 38A-38C are plots of length and time corresponding to front propagation dynamics for target and initiator plasma flows depending on the shape of outlet temperature oscillations, according to an embodiment.

FIGS. 38D-38F are plots of temperature and time of outlet temperature oscillations corresponding to respective FIGS. 38A-38C, according to an embodiment.

FIGS. 42A-42J are schematic diagrams of plasma jet shapes depending on an input and outlet temperature-time profile, according to an embodiment.

FIGS. 66A-66B are plots of a time scan of $U_{C-E1}$ for relatively low and relatively high frequency, according to an embodiment.

FIGS. 67A-67B are plots of a time scan of $U_{C-E1}$ for a set of pulse intervals, according to an embodiment.

DETAILED DESCRIPTION

Figure 3:
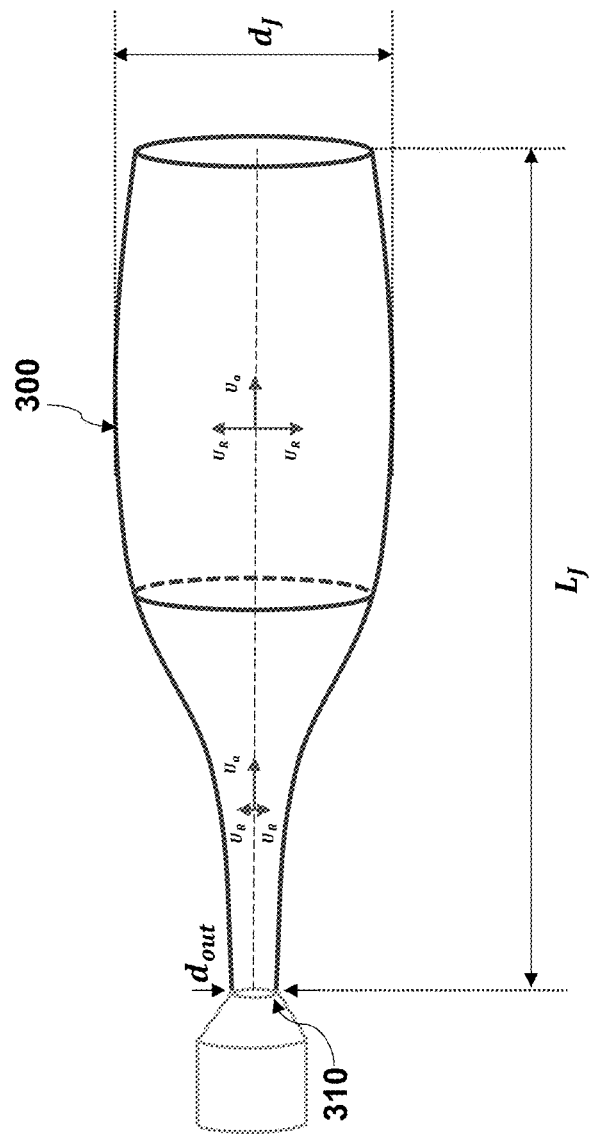
FIG. 3 is a schematic diagram of generated plasma, according to an embodiment.

1. Overview of Radially Expanded Plasma Flows

Plasma flows with different characteristics can be used for various applications, such as industrial, cosmetic, spraying, medical, and others. A plasma flow is a stream of gas particles in which a non-negligible number of gas particles are ionized. Plasma is generated from a fluid, which is typically a gas at room temperature, referred to as plasma-generating gas. Plasma may be generated by means of applying energy to the plasma-generating gas flowing through a plasma-generating device. The application of energy results in a substantial temperature increase of the plasma-generating gas, which in turn, results in ionization of the plasma-generating gas particles. In some embodiments, plasma flow may be generated by heating a stream of plasma-generating gas to a predetermined temperature to ionize a substantial portion of the gas particles.

Various systems and methods can be used to change the properties or characteristics of a plasma flow. These properties include the shape of the flow, the temperature distribution, and the static and dynamic pressure of the flow. For example, U.S. Pat. No. 7,589,473 discloses systems and methods for generating pulsed plasma or an intermittent plasma flow in which the flow of plasma periodically ceases during operation. As another example, embodiments for generating volumetrically oscillating plasma flows are described in U.S. Pat. No. 9,089,319, filed Jul. 22, 2010, and titled "VOLUMETRICALLY OSCILLATING PLASMA FLOWS," U.S. Pat. No. 8,613,742, filed Jan. 29, 2010, and titled "METHODS OF SEALING VESSELS USING PLASMA," the contents of each of which are hereby incorporated by reference in their entirety. Such embodiments can change a shape, temperature distribution, or other properties of a plasma flow. In some applications, however, such embodiments can cause significant differences in treatment in response to deviations in device positioning or operating conditions. Additionally, such embodiments can produce volumetrically oscillating plasma flows with low intensity plasma having a temperature at the device outlet of at least 10,000 K and high intensity plasma having a temperature exceeding the low intensity plasma temperature by at least 10,000 K. In some applications including medical applications, however, such temperatures are not suitable and can introduce unnecessary requirements on the plasma-generating device. Devices and methods described in U.S. Pat. Nos. 9,089,319 and 8,613,742 can also be improved to extend the life of various device components. Systems, devices, and methods described herein can generate plasma flows that exhibit substantially uniform or homogenous characteristics over a substantial distance from an outlet of a plasma-generating device without certain drawbacks.

FIG. 1 is a schematic diagram of a plasma-generating device 100 (e.g., plasma generating device). A plasma-generating device 100 may include a controller 102 (e.g., gas flow controller). The controller 102 may be configured to supply a gas for plasma generation at a constant predetermined rate of $G_{IN}$ (e.g., about 0.5 L/min) to expansion chamber 104. The controller 102 may be configured to supply the plasma-generating gas into expansion chamber 104, which is used to reduce the effect of inlet pressure $P_{IN}$ deviations in response to varying energy that is used to heat plasma-generating gas downstream. From the expansion chamber 104, the plasma-generating gas may flow into a channel 106 (e.g., active chamber, heating channel). The channel 106 may be configured to heat the plasma-generating gas using energy provided (e.g., applied, supplied) from power source 108. In some embodiments, the heating channel may comprise a diameter $d_H$. Energy may be applied to the plasma-generating gas inside the channel 106 to increase the gas temperature to thereby generate particle ionization. In some embodiments, the energy may be in the form of one or more of electromagnetic energy, electric energy, combinations thereof, and the like. As a result of this heating, plasma flow 120 may be discharged from outlet 110 of channel 106. In some embodiments, the outlet 110 can have a diameter $d_{OUT}$.

FIG. 2 is a plot of the temperature of plasma flow 120 generated as a result of heating a plasma-generating gas according to a predetermined pattern (e.g., controlled pattern, a series of current pulses). As shown in FIG. 1, the plasma flow 120 can define an axis 130, which represents a center line of the plasma flow extending in the direction of the plasma flow 120. The plasma flow 120 can include an active zone or volume of active plasma, which includes plasma having a temperature above a predetermined threshold. For example, the predetermined threshold temperature may be about 1,000 K. In some embodiments, the active zone may expand and contract volumetrically over time according to a controlled pattern such as, for example, a controlled pattern associated with a pattern of current or power density delivered to the plasma-generating device. In some embodiments, the active plasma can occupy a space as a volume of the plasma. The plasma flow 120 can be characterized by a length or a distance between an outlet of a plasma-generating device (e.g., outlet 110) and a point along axis 130 where the plasma comprises a threshold temperature. Alternatively or additionally, the plasma flow 120 can be characterized by a width at different points along the axis 130. Width with respect to the plasma flow in a predetermined plane transverse to the plasma flow axis can be the diameter of the active plasma in the predetermined plane. Additionally, width can generally refer to a maximum width or maximum lateral dimension of the plasma flow.

In some embodiments, the plasma flow 120 can be characterized by temperature and, specifically, a temperature at the outlet 110 of the plasma-generating device. Unless specifically stated otherwise, the term "temperature" with respect to a plasma flow refers to the temperature of the plasma flow at an outlet of a plasma-generating device or when the plasma first exits a plasma-generating device. For example, a generated plasma flow having a temperature of about 8,000 K corresponds to a plasma flow having a temperature of about 8,000 K at the outlet of the plasma-generating device 100. In some embodiments, the temperature may not be uniform along the axis 130 and may decrease as a function of distance from the outlet 110 along the axis 130 and as a function of distance in a direction transverse to the axis 130. In some embodiments, the plasma flow can be continuous and have properties (e.g., shape of the flow, temperature distribution, static and dynamic pressure of the flow) that do not substantially change over time during operation of a plasma-generating device. For example, a constant direct current (DC) (e.g., application of substantially constant energy) may generate a continuous plasma flow. Additionally or alternatively, the plasma flow can be intermittent or periodically cease during operation. While continuous flows can be useful for certain applications, in other applications, intermittent flows may be more suitable.

In some embodiments, under a first set of conditions, the plasma flow 120 remains laminar. A laminar flow may be characterized by fluid flowing in lamina or layers with substantially no exchange of fluid (e.g., mixing) between the neighboring lamina. Laminar flow may occur when viscous forces of a fluid are comparable to inertial forces. In some embodiments, under a second set of conditions, the plasma flow 120 can be a turbulent flow. Turbulent flow may occur when the inertial forces of plasma predominate over the viscous forces. A turbulent flow may be characterized by a rapid and chaotic variation of pressure and velocity in space and time. When a plasma flow is turbulent, the plasma flow may mix with the surrounding air. This mixing process may produce a rapid drop in temperature as the plasma flow propagates, thus forming unpredictable turbulent flow. Systems, methods, and devices described herein can be configured to generate plasma flows that are laminar plasma flows, which can avoid drawbacks associated with turbulent flows.

In some embodiments, systems, devices, and methods disclosed herein can generate radially expanded flows by using controlled repeated radial expansion with a number of predetermined parameters, as described herein. The radially expanded flows can be laminar plasma flows. Such repeated radial expansion of a plasma flow increases the flow's width, which can cause the flow's volume to assume a bottle-like shape. FIG. 3 depicts a radially expanded flow, where generated plasma 300 takes on a bottle-like shape. In some embodiments, repeated (e.g., periodic, intermittent) application of energy to generate a plasma flow may increase the width of a plasma flow hundreds or even thousands of times per second. Such radial expansion can cause the plasma flow to have a volume that assumes the generally bottle-like shape 300. Such plasma flows, referred to as predominantly radially expanded plasma flows, can have a width that becomes substantially larger than a diameter of an outlet (e.g., outlet 310) of a plasma-generating device. Continuous plasma flows, on the other hand, are unable to generate the bottle-like shape 300 and have such radial expansion.

Figure 4E:
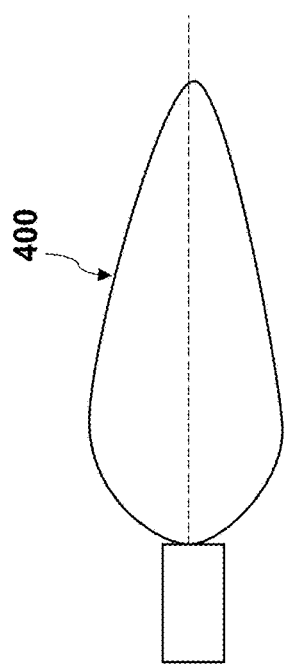
FIGS. 4A-4F are schematic diagrams of continuous plasma and predominantly radially expanded plasma, according to an embodiment.
Figure 4F:
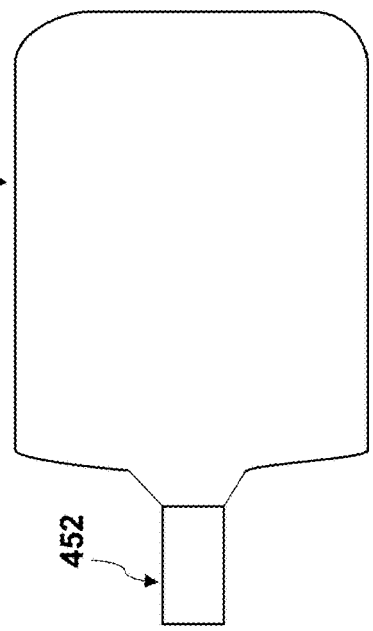
Figure 4C:
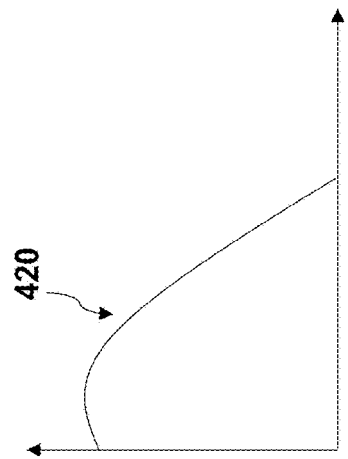
Figure 4D:
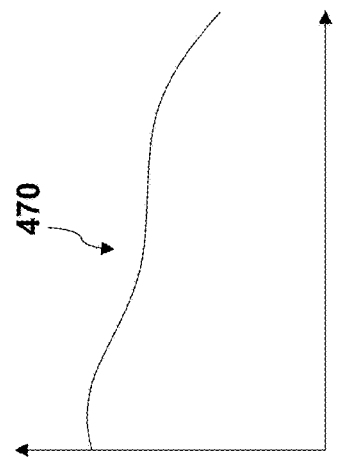
Figure 4A:
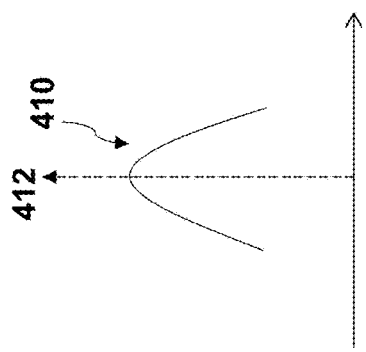
Figure 4B:
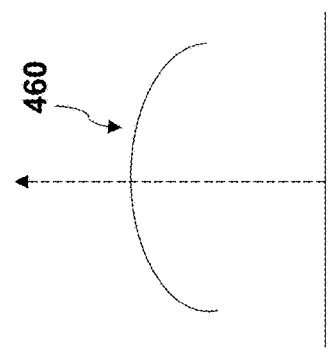

For illustrative purposes, and to provide context for understanding the benefits of predominantly radially expanded plasma flows, the properties of such flows can be compared to those of continuous plasma flows, as depicted in the following figures. FIGS. 4A-4F facilitate comparison between the properties of predominantly radially expanded flows 450 to those of continuous flows 400. FIG. 4E depicts a continuous plasma flow 400 having a corresponding radial temperature distribution 410 depicted in FIG. 4A. For example, the temperature distribution 410 of a continuous plasma flow 400 may be substantially parabolic. That is, the temperature of the plasma flow may be the highest at the axis 412 and may drop rapidly toward the periphery. Also, as shown in FIG. 4C, such a continuous plasma flow 400 may exhibit a substantial temperature 420 decrease as a function of a distance traversed with respect to an outlet of a plasma-generating device. FIG. 4F depicts a predominantly radially expanded plasma flow 450 having a corresponding temperature distribution 460 depicted in FIG. 4B. The volume of flow 450 depicted in FIG. 4F may be similar to that depicted in FIG. 3. For example, the volume of plasma flow 450 may have a shape resembling a bottle with its neck facing outlet 452. As depicted in FIGS. 4B and 4D, the radial and axial distribution of temperature, respectively shown, may vary less within a predetermined volume. In some embodiments, the temperature distributions can be substantially uniform or constant over a certain distance radially out from the center axis of the plasma flow or a certain distance axially out from the outlet of the plasma-generating device.

In some embodiments, a plasma flow having a generally bottle-shaped volume and associated temperature profiles can provide an increased margin for error for an operator performing a treatment procedure using such a plasma flow, thus potentially reducing adverse effects of plasma treatment due to human error and inexperience. For example, continuous plasma flows, including some volumetrically oscillating plasma flows, can require an operator to hold a plasma-generating device at a predetermined distance from and at a predetermined angle relative to a treatment surface. Deviations from a predetermined position of the plasma-generating device with respect to the surface being treated may result in detrimental and often irreversible damage to a patient. By contrast, predominantly radially expanded plasma flows may provide more uniform (e.g., substantially uniform) plasma properties in the active zone to increase the predetermined distances and angles relative to the treatment surface used by an operator.

In some embodiments, the volume of a plasma flow may comprise a predetermined shape based on relatively rapid changes in the energy applied to the plasma-generating gas. For example, for a plasma-generating device (e.g., plasma-generating device 100) configured to apply energy to a plasma-generating gas passing through it, a substantial portion of the plasma-generating gas particles may be ionized by the applied energy and converted to plasma discharged from an outlet of the plasma-generating device.

Radially oscillating plasma flows may be the result of collisions of a combination of relatively fast moving particles of a high intensity, high temperature, and low density plasma flow with relatively slow moving particles of a low intensity, low temperature, and high density plasma flow. As used herein, high and low, and fast and slow are relative terms used to characterize the different plasma flows relative to one another. For example, an 8,000 K plasma flow may be high intensity compared to a 3,000 K plasma flow and low intensity compared to a 15,000 K plasma flow. As used herein, low intensity plasma flow can also be referred to as a base plasma flow and high intensity flow can also be referred to as a pulse plasma flow. Base plasma flow may generally be generated using the base energy, and pulse plasma flow may generally be generated using a pulse of energy.

FIGS. 5-8E illustrate the interactions between base plasma flow and pulse plasma flow, and how timing of pulsing can impact the resulting shape of the plasma flow. FIGS. 5 and 6A-6K depict generation of an embodiment of plasma flow where the base plasma flow and the pulse plasma flow are fully allowed to develop. FIG. 5 is a plot of temperature and time where a base plasma temperature has been established at an outlet of the plasma-generating device at time $t_0$. At time $t_1$, the plasma temperature at an outlet of the plasma-generating device is increased to a pulse plasma temperature and maintained until time $t_9$, at which point the temperature is decreased back to the base plasma temperature and is maintained at that temperature through time $t_{10}$.

As depicted in FIGS. 5 and 6A-6K, the base plasma flow and the pulse plasma flow may both have an effect on a treated surface with the pulse plasma flow having a substantially greater effect. FIGS. 6A-6K are schematic diagrams of volumes of plasma flow corresponding to the temperature and time plot of FIG. 5. As shown, the radial expansion depicted in FIGS. 6B-6H may be temporary and unstable. FIG. 6A depicts a shape (e.g., volume) of plasma flow corresponding to time $t_0$ where plasma is heated to a base temperature at the outlet. FIG. 6B depicts a shape of the plasma flow corresponding to time $t_1$ where pulse plasma flow is generated at the outlet and where relatively fast moving particles begin to collide with the relatively slow moving particles of the base plasma flow in front of them. FIG. 6C depicts a shape of the plasma flow corresponding to time $t_2$ where the relatively fast moving particles of the pulse plasma flow propagate further (relative to FIG. 6B) to generate the radial expansion over about half the length of the base plasma flow. FIG. 6D depicts a shape of the plasma flow corresponding to time $t_3$ where the relatively fast moving particles of the pulse plasma flow propagate even further (relative to FIGS. 6B and 6C) to cover radial expansion over the entire length of the base plasma flow.

As depicted in FIGS. 6A-6K, the radial expansion of the plasma flow may be greatest at a distance almost equal to the length of the base plasma flow. This is because the ratio of densities of the base plasma flow to pulse plasma flow may be largest at the distal end of the plasma flow. At the distance equal to the length of the base plasma flow, the base plasma flow may have cooled off and become denser while the pulse plasma flow may not have significantly cooled off. FIG. 6E depicts a shape of the plasma flow corresponding to time $t_4$ where the radially expanded plasma flow exists but the pulse plasma flow has overshot the length of the base plasma flow and extends further from the outlet than the base plasma flow. This process continues in FIG. 6F that depicts a shape of the plasma flow corresponding to time $t_5$ where the pulse plasma flow reaches its maximum length while the radially expanded flow still exists. FIG. 6G depicts a shape of the plasma flow corresponding to time $t_6$ where the pulse plasma flow is maintained but the radially expanded plume shape begins to dissipate starting from the locations closest to the outlet. FIG. 6H depicts a shape of the plasma flow corresponding to time $t_7$ where the radially expanded plume shape is near the location corresponding to the length of the base plasma flow. FIG. 6I depicts a shape of the plasma flow corresponding to time $t_8$ where the radially expanded plume shape has dissipated to leave the pulse plasma. FIG. 6J depicts a shape of the plasma flow corresponding to time $t_9$ where the temperature drops to the base plasma temperature, the device again generates the base plasma flow, which replaces the pulse plasma over the partial length of the base plasma flow. FIG. 6K depicts a shape of the plasma flow corresponding to time $t_{10}$ where the base plasma flow is developed over its length and the pulse plasma has dissipated, similar to FIG. 6A.

As observed in FIGS. 6A-6K, if the base plasma flow and the pulse plasma flow are allowed to become fully developed, then both flows may have an effect on a treated surface, with pulse plasma flow having a substantially greater effect. When both flows are allowed to develop, the radial expansion of the plasma flow, as depicted in FIGS. 6B-6H, may be temporary and unstable.

Figure 7:
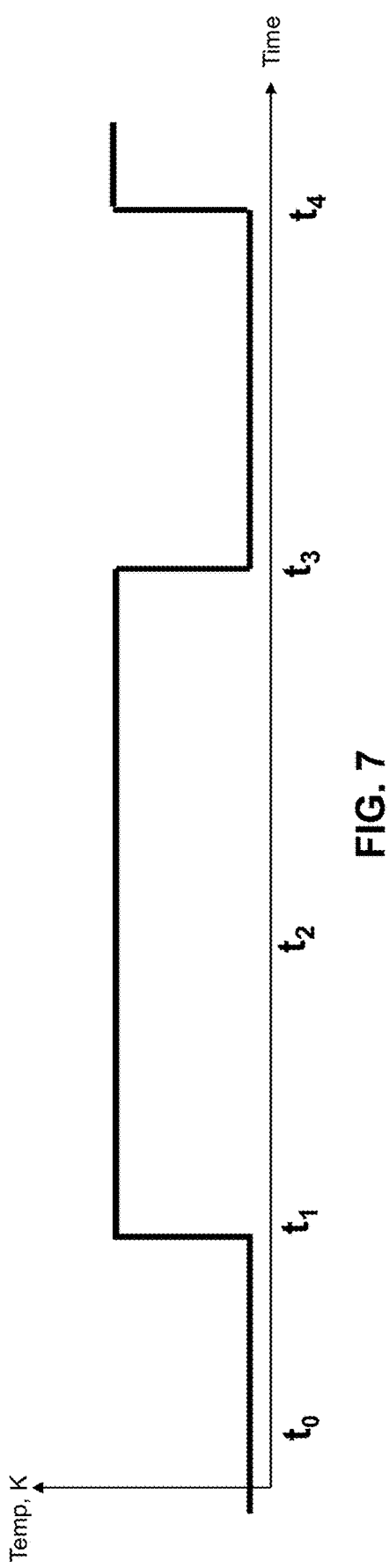
FIG. 7 is a plot of plasma flow temperature and time, according to an embodiment.
Figure 8:
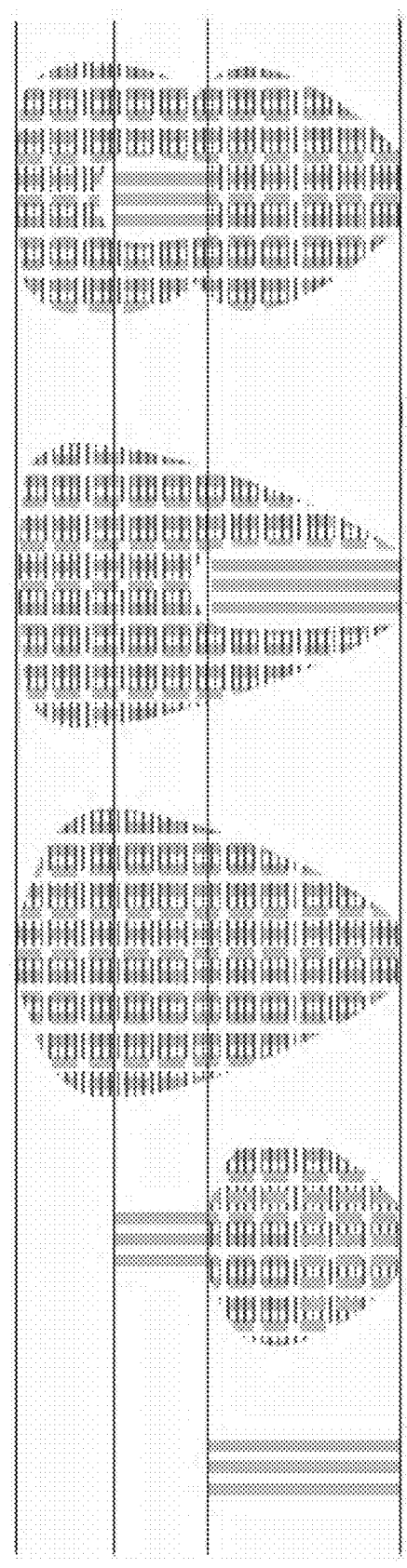
FIGS. 8A-8E are schematic diagrams of plasma flow corresponding to the temperature and time plot of FIG. 7, according to an embodiment.

In contrast to FIGS. 5 and 6A-6K, FIGS. 7 and 8A-8E depict generation of an embodiment of radially expanded plasma flow. FIG. 7 is a plot of temperature and time of a predominantly radially expanded plasma flow and FIGS. 8A-8E are schematic diagrams of the predominantly radially expanded plasma flow corresponding to the temperature and time plot of FIG. 7. FIG. 7 is a plot of temperature and time where a base plasma temperature has been established at an outlet of a plasma-generating device at time $t_0$. At time $t_1$, the plasma temperature at an outlet of the plasma-generating device is increased to a pulse plasma temperature and maintained until time $t_3$, at which point the temperature is decreased back to the base plasma temperature until it is raised again at time $t_4$. FIG. 8A depicts a shape (e.g., volume of plasma flow) corresponding to time $t_0$ where plasma is heated to a base temperature at the outlet.

FIG. 8B depicts a shape of plasma flow corresponding to time $t_1$ where pulse plasma flow begins to develop. As a pulse plasma flow front propagates, the pulse plasma particles can collide with slower base plasma flow particles to generate the radial expansion depicted in FIG. 8B to form in the proximity of the outlet of a plasma-generating device. FIG. 8C depicts a shape of plasma flow corresponding to time $t_2$ where the pulse plasma flow propagates along a length of the base plasma flow length so as to create the radial expansion over the length of the base plasma flow. FIG. 8D depicts a shape of plasma flow corresponding to time $t_3$ where the base plasma flow begins to form once again with the radially expanded flow from the previous collisions still present. FIG. 8E depicts a shape of plasma flow corresponding to time $t_4$ where the pulse plasma flow is formed again with pulse plasma particles that propagate downstream and collide with the particles of the base plasma flow to generate the radial expansion in the proximity of the outlet. The radially expanded plume extends along the length of the base plasma flow even at time $t_4$. In some embodiments, repeating this process may generate a predominantly radially expanded plasma flow.

For some applications, a predominantly radially expanded plasma flow may have advantages over a continuous plasma flow. For example, a continuous plasma flow may have a width (e.g., radial expansion) that is about two times to about four times a diameter of an outlet of a plasma-generating device, while a width (e.g., radial expansion) of a predominantly radially expanded plasma flow may be greater than that of a continuous plasma flow, e.g., greater than about four times the diameter of the outlet to about twenty times the diameter of the outlet, including all subranges and values therebetween. Furthermore, a temperature distribution along the length of the plasma flow may be more uniform (e.g., may have less variations) for a predominantly radially expanded plasma flow than a continuous plasma flow. These attributes of predominantly radially expanded plasma flows may help reduce adverse effects caused by operator errors due to skill and/or inexperience. Additionally or alternatively, the plasma flows described herein may be used in applications where continuous plasma flows are unsuitable.

In some embodiments, predominantly radially expanded plasma flows may be generated as a result of interactions of at least two plasma flow (e.g., a base plasma flow and a pulse plasma flow). Each of the base plasma flow and the pulse plasma flow in isolation may lack certain desirable qualities associated with predominantly radially expanded flows, but together they can generate a predominantly radially expanded flow with such desirable qualities. In some embodiments, a predominantly radially expanded plasma flow may be generated by optimizing one or more parameters of a base plasma flow and pulse plasma flow. First, for example, a duration of the high energy flow (e.g., a duration of energy above a predetermined threshold) can be selected to allow the plasma flow to undergo substantially radial expansion over an entire length or duration of the base plasma flow (e.g., time $t_3$ shown in FIG. 6D) without transitioning into the axial expansion (e.g., time $t_4$-$t_8$ shown in FIGS. 6E-6I). For a given base plasma temperature, decreasing the pulse plasma temperature and increasing the duty cycle may satisfy this first condition. More specifically, for a predetermined base plasma temperature, the pulse plasma temperature may be selected such the ratio of the speed of sound of the plasma at the pulse temperature to the speed of sound of the plasma at the base temperature is at most about four, which results in at least a duty cycle of about 0.25. This first condition can provide an upper boundary of the pulse plasma temperature.

Second, for example, given a base plasma temperature at the outlet, the pulse plasma temperature may be selected such that the density ratio of the two plasmas is at least about two. This second condition can provide a lower boundary condition of the pulse plasma temperature and can ensure a predetermined scattering effect of plasma particles when the dense and slow-moving base plasma particles are bombarded by the sparse and fast-moving pulse plasma particles.

Third, for example, a base energy duration may be configured such that the pulse plasma "catches up" to (e.g., reaches and/or interacts with) the base plasma at a distance about equal to the length of the base plasma flow. This can reduce the effect of the base plasma flow on a surface being treated and ensure that the surface is treated predominantly or only by the radially expanded plasma flow. In some applications, base plasma flow may be generally undesirable and may be reduced or minimized by configuring a base plasma-pulse plasma cycle period. In some embodiments, the base plasma-pulse plasma cycle period may be up to about 1 ms.

Figure 9:
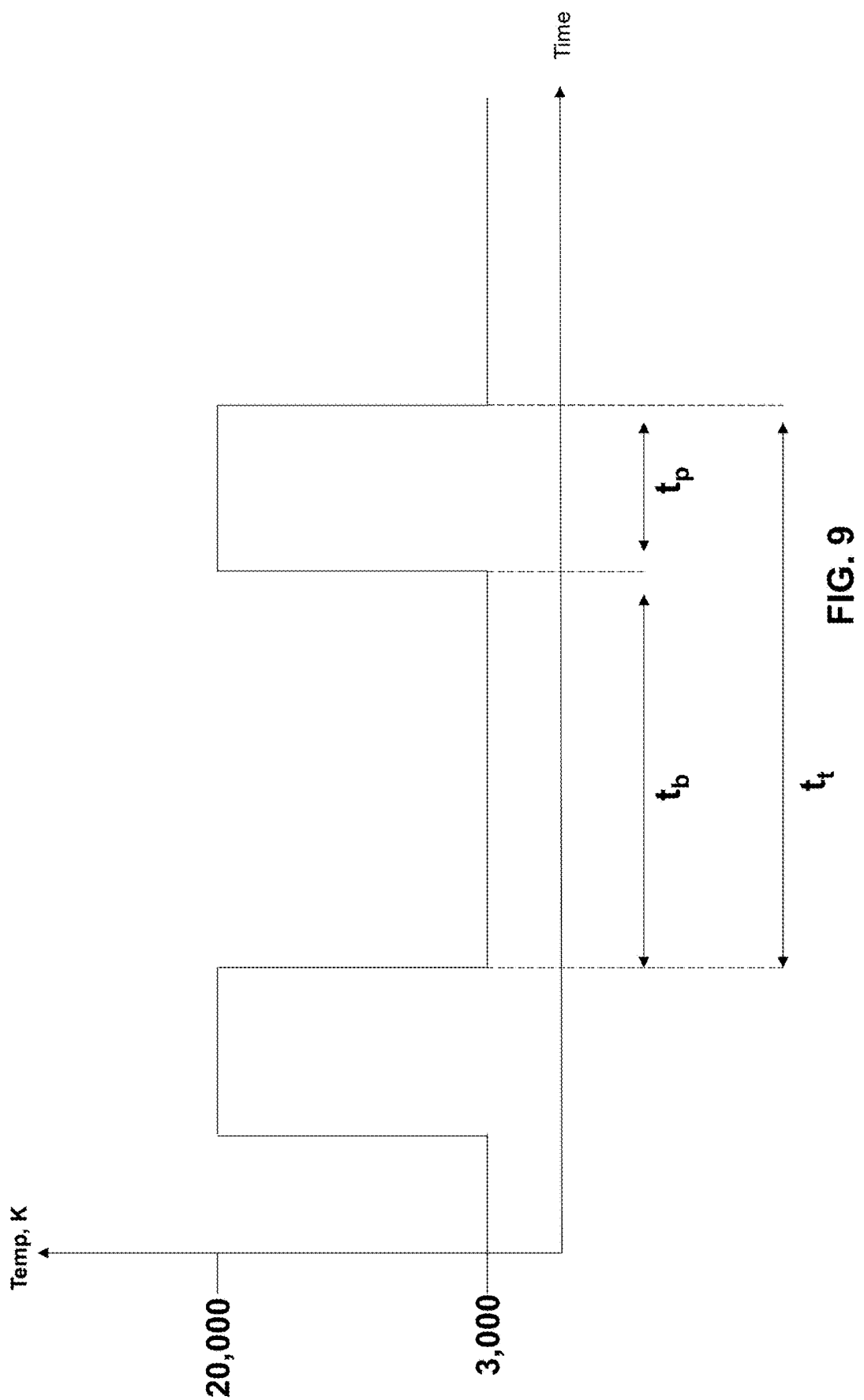
FIG. 9 is a plot of temperature and time of a rectangular pulse, according to an embodiment.

When pulses of the temperature of the plasma flow at the outlet of a pulse-generating device take the form of a rectangular waveform, such as that depicted in FIG. 9, a predominantly radially expanded flow satisfying the above three conditions can be generated for a given base plasma temperature by setting certain pulse plasma temperature and timing parameters. For example, FIG. 9 depicts a rectangular pulse including a predetermined base plasma temperature of about 3,000 K. The pulse plasma temperature may be set to about 20,000 K to satisfy the speed and density ratios relationships given the base plasma temperature, as described above. Furthermore, a pulse duration $t_p$ and off duration or base duration $t_b$ may be set to establish a period $t_r$ and duty cycle D. The period $t_r$ may be equal to the sum of pulse duration $t_p$ and off duration $t_b$. The duty cycle D may be equal to the pulse duration divided by the period, or $t_p/t_r$. Therefore, a substantially radially expanded plasma flow may be generated for a predetermined base plasma temperature when the plasma temperature falls into a range with a set of predetermined boundary conditions. The remaining timing parameters may be calculated based on the temperature values, as further described in detail below.

In some embodiments, a method may include applying, to a plasma-generating gas supplied to a plasma-generating device, energy that alternates between being at a base level for a first duration and at a pulse level for a second duration according to a predetermined (e.g., controlled) pattern. In response to applying the energy, a plasma flow having a directional axis may be generated. In some embodiments, the plasma flow alternating between a base configuration (or a base plasma flow) and a pulse configuration (or a pulse plasma flow) may be discharged from the outlet of the plasma-generating device according to the controlled pattern. In some embodiments, the plasma flow in the base configuration (or base plasma flow) may have (1) a first temperature at the outlet and (2) a first flow front that advances along the directional axis. In some embodiments, the plasma flow in the pulse configuration (or pulse plasma flow) may have (1) a second temperature at the outlet that is greater than the first temperature and (2) a second flow front that advances along the directional axis at a speed greater than the first flow front such that a distance traversed by the second flow front during the second duration is substantially the same as a distance traversed by the first flow front during the first duration and the second duration.

In some embodiments, the plasma flow in the base configuration may include plasma having a first density at the first temperature. The plasma flow in the pulse configuration may include plasma having a second density at the second temperature. The first density may be at least twice the second density.

In some embodiments, the plasma flow in the base configuration may include plasma having a first speed of sound at the first temperature. In some embodiments, the plasma flow in the pulse configuration may include plasma having a second speed of sound at the second temperature. In some embodiments, the second speed of sound may be at most four times the first speed of sound.

In some embodiments, the first temperature may be between about 2,000 K and about 4,000 K. In some embodiments, the second temperature may be less than or equal to about 15,000 K. In such embodiments, if a ratio of a flow rate G (L/min) of the plasma-generating gas to a diameter d (mm) of the outlet is less than or equal to 100, then a sum of the first and second durations may be less than $$100{,}000 * \frac{d^4}{G^2}.$$

Alternatively, if the ratio of the flow rate G (L/min) of the plasma-generating gas to a diameter d (mm) of the outlet is greater than 100, then a sum of the first and second durations may be less than 5 ms.

In some embodiments, the second temperature may be greater than 15,000 K. In such embodiments, if a ratio of the flow rate G (L/min) of the plasma-generating gas to a diameter d (mm) of the outlet is less than or equal to 100, then a sum of the first and second durations may be less than about $$5{,}000 * \frac{d^4}{G^2}.$$

Alternatively, in such embodiments, if the ratio of the flow rate G (L/min) of the plasma-generating gas to a diameter d (mm) of the outlet is greater than about 100, then a sum of the first and second durations may be less than about 500 μs.

In some embodiments, a length $L_J$ and a diameter $d_J$ of a radially expanded volume of plasma flow (e.g., shown in FIGS. 1 and 3) may be defined by a set of plasma-generating device parameters including inlet gas flow $G_{IN}$, diameter of heating channel $d_H$, outlet diameter $d_{OUT}$, and temperature and time profile of outlet plasma flow $T_{OUT}(t)$. In particular, the generation of a plasma jet or flow with predominant radial expansion can require a specific or predetermined temperature and time profile of outlet plasma flow $T_{OUT}(t)$, which may include one or more of a predetermined frequency of temperature oscillation, base plasma temperature, pulse temperature amplitude, pulse shape, duration, etc. In general, plasma flow refers to moving particles of gas and can include flow embodied as a plasma jet. A plasma jet refers outlet plasma flow from a device (e.g., a plasma-generating device, such as those described herein). In some embodiments, parameters such as inlet gas flow and outlet diameter may be constrained by requirements of a specific application of a plasma-generating device. Therefore, for each application, a plasma jet power needs to be regulated to achieve a desired effect. In some embodiments, the plasma jet power can be estimated as $P_J=G_{IN}*h(T)$, where $G_{IN}$ is the inlet gas flow and h(T) is an average enthalpy of the plasma flow. When the outlet temperature and time profile is fixed, the plasma jet power can be regulated by adjusting gas flow $G_{IN}$. Other device parameters that can affect the plasma jet power can be the outlet diameter $d_{OUT}$ or the heating channel diameter $d_H$. The outlet diameter $d_{OUT}$ can provide adjustment of heat flux, and the heating channel diameter $d_H$ when decreased can result in a higher level of inlet pressure, thus increasing the length of a radially expanded plasma flow. Configuration of such device parameters such as $G_{IN}$, $d_H$ and $d_{OUT}$ may be selected to be within a predetermined range and relationship in order to generate predominantly radial expansion of plasma flow.

In some embodiments, the plasma-generating gas for generating predominantly radially expanded plasma flows may be argon or other insert gases such as neon, krypton, xenon, radon, combinations thereof, and the like. Depending on the plasma-generating gas used, the different thermal properties of those gases can impact the different parameters calculated herein (e.g., sound speed of gas, ratio of sound speed of the gas to density), which in turn can impact the flow profile of the plasma flow generated, as described in further detail the following sections.

2. Parameters for Generating Radially Expanded Plasma Flows

Figure 10:
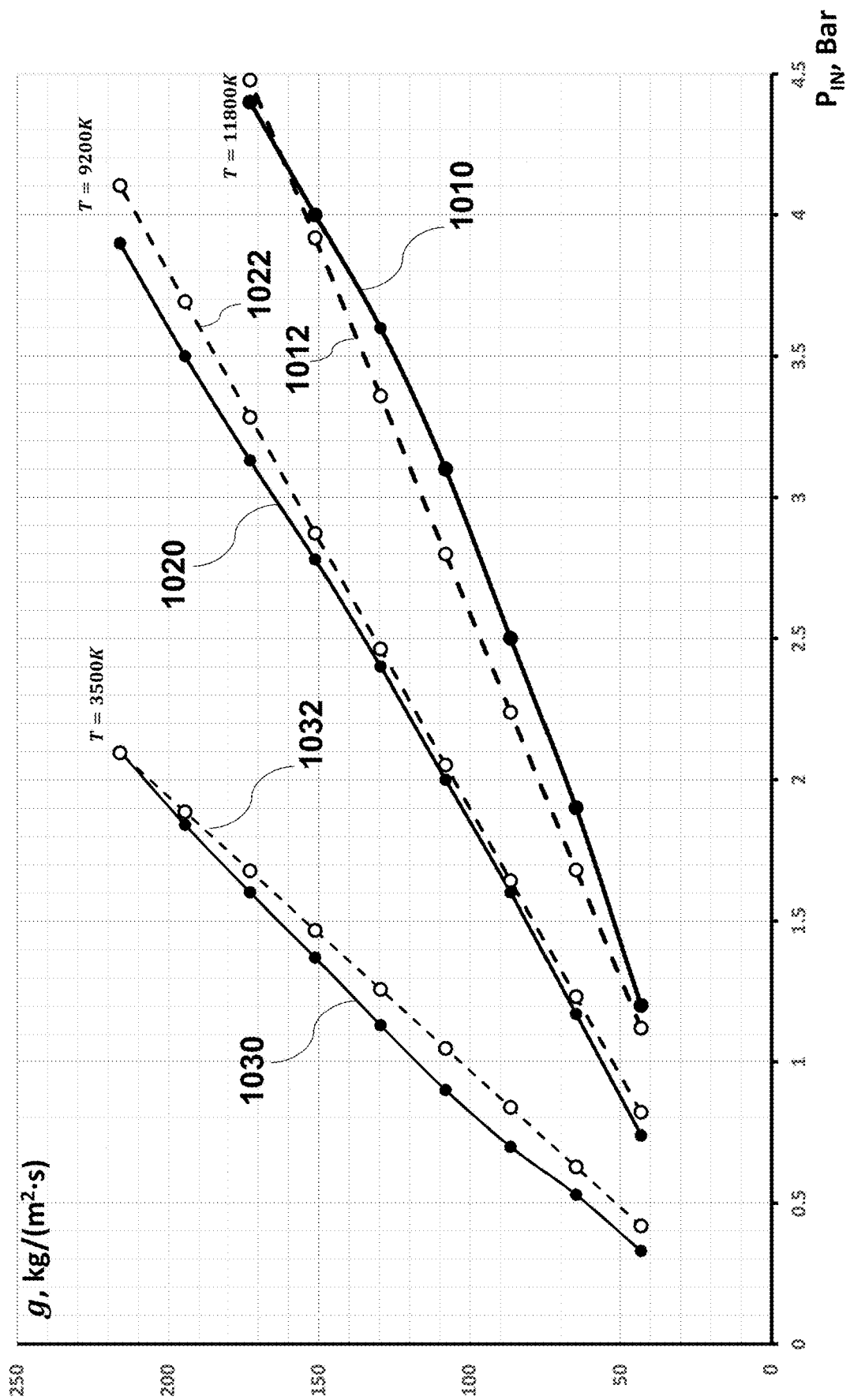
FIG. 10 is a plot of inlet pressure and argon mass flux dependence for steady laminar flow, according to an embodiment.

Predominantly radial expanded plasma flow may be characterized using theoretical and experimental relations between input device parameters, such as inlet gas flow $G_{IN}$, diameter of heating channel $d_H$, and outlet diameter $d_{OUT}$, and outlet jet parameters $T_{OUT}=T_{OUT}(t)$. FIG. 10 is a plot of inlet pressure and argon mass flux dependence for steady laminar flow. In particular, FIG. 10 provides a comparison between the theoretical models for the argon mass flux as a function of inlet pressure and their practical counterparts for different temperatures. For a cylindrical heating channel, the mass flux and the amount of heat added may correspond to the pressure of the plasma-generating gas at an active chamber inlet 112 (FIG. 1). For a constant heating channel diameter $d_H$, the flow parameters may be related by the following equations that include conservation of mass, momentum, energy, and equation of state, respectively:

$$\frac{d\rho}{\rho} + \frac{dU}{U} = 0 \qquad (1)$$

$$dP + \frac{1}{2}\rho U^2 \frac{f}{d_H} dx + \rho U dU = 0 \qquad (2)$$

$$gd\left(h + \frac{1}{2}U^2\right) = q \qquad (3)$$

where ρ is density, U is plasma flow velocity, P is pressure, f is a Moody friction factor in friction losses of pressure, g is mass flux, h is plasma enthalpy, q is added heat, Z is a compressibility factor to correct ideal gas equation, R is a gas constant for the plasma-generating gas, and T is the temperature of the plasma-generating gas.

The solid lines (1010, 1020, 1030) in FIG. 10 correspond to experimentally measured inlet pressures with controlled gas flow for an argon plasma-generating device, and the dotted lines (1012, 1022, 1032) correspond to calculated inlet pressures. For example, line 1010 corresponds to the experimentally measured inlet pressures associated with plasma flow at 11,800 K and line 1012 corresponds to the calculated inlet pressures associated with plasma flow at 11,800 K plasma flow; line 1020 corresponds to the experimentally measured inlet pressures associated with plasma flow at 9,200 K and line 1022 corresponds to the calculated inlet pressures associated with plasma flow at 9,200 K plasma flow; and line 1030 corresponds to the experimentally measured inlet pressures associated with plasma flow at 3,500 K and line 1032 corresponds to the calculated inlet pressures associated with plasma flow at 3,500 K plasma flow. Accordingly, as depicted in FIG. 10, for a wide range of temperatures, the experimental values track the expected values based on the equations described herein.

Figure 11:
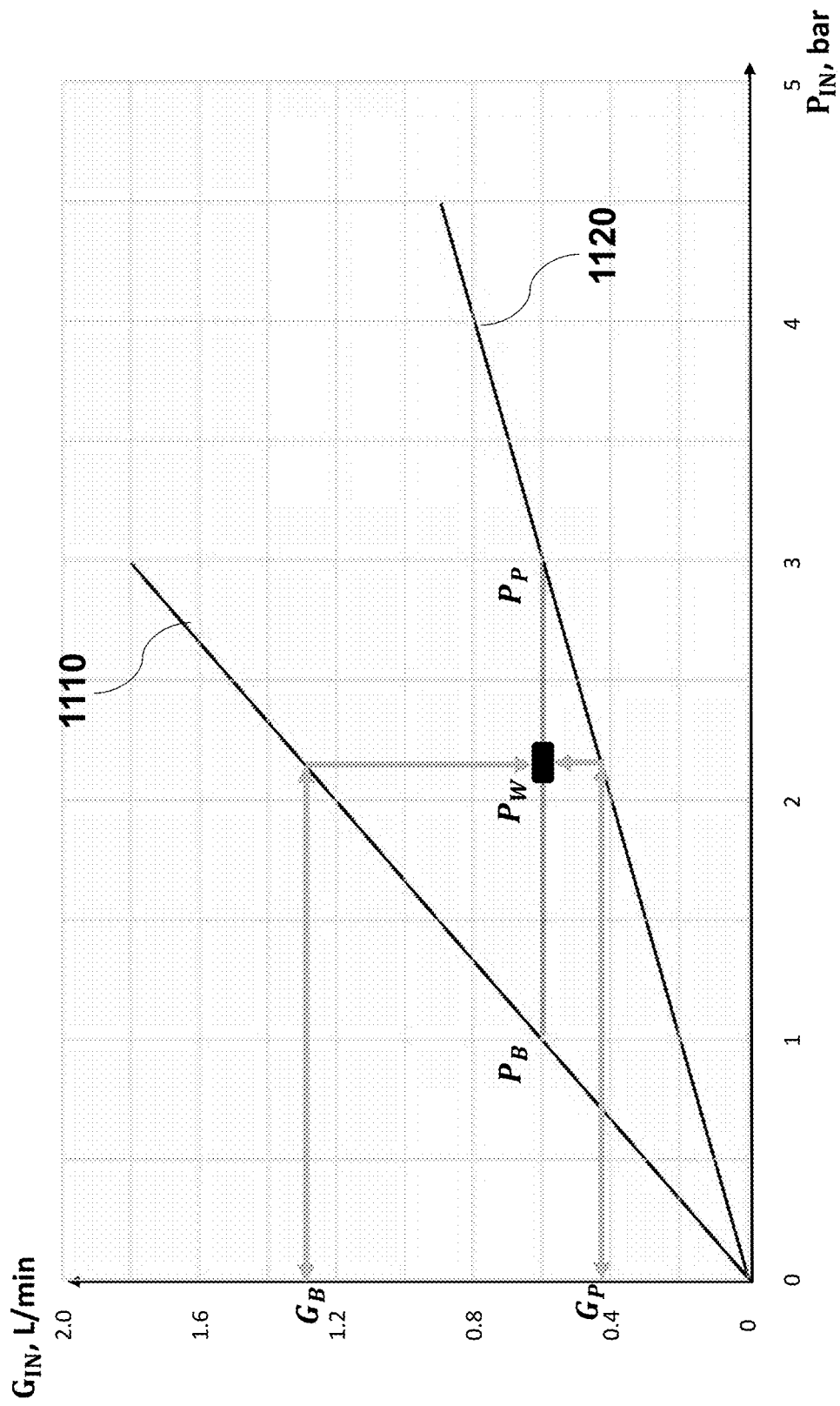
FIG. 11 is a plot of gas flow and inlet pressure dependence on oscillating outlet temperature, according to an embodiment.

FIG. 11 depicts a relationship between active chamber inlet pressure and plasma flux at different plasma flow temperatures. In FIG. 11, the base temperature 1110 is set to about 3,000 K and the pulse temperature 1120 is set to about 15,000 K. For example, a gas flow controller (e.g., controller 102 depicted in FIG. 1) may be configured to supply plasma generating gas with a substantially constant flow rate of about 0.6 L/min. Under these conditions, generation of about 3,000 K plasma flow would require about 1 Bar of pressure. For the same flow rate, generation of about 15,000 K plasma flow would require about 3 Bars of pressure. However, when the pulse plasma flow and the base plasma flow alternate with a duty cycle (e.g., of about 0.6), a pressure $P_W$ of about 2.2 Bar may be required. Projecting this pressure onto the corresponding 3,000 K base plasma flow graph 1110 and 15,000 K pulse plasma flow graph 1120 shows that during the base plasma flow, the gas flow rate can be about 1.32 L/min, and during the pulses the gas flow rate can be about 0.42 L/min. However, the gas flow can on average be about 0.6 L/min, and increasing the temperature can result in increased pressure. The subsequent decrease in temperature can result in a decrease or release of pressure. In some embodiments, $P_W$ may be represented by the following equation:

$$P_W = P_B + D \times (P_P - P_B) \tag{5}$$

where D is a duty cycle of pulses, $P_B$ and $P_P$ are the pressure at the active chamber inlet when generating the about 3,000 K base plasma flow and about 15,000 K constant current steady plasma flow, respectively. $P_W$ corresponds to working pressure that denotes the resulting inlet pressure in an active chamber of the plasma-generating device when the plasma flow is generated with oscillated outlet temperature with the duty cycle. While the duty cycle in this example is 0.6, it can be appreciated that other values for duty cycle can be used in accordance with the conditions described herein. If the working pressure $P_W$ is a constant and is between $P_B$ and $P_P$, then the relation between duty cycle D and gas flow may be calculated from the following expression:

$$G_{IN} \times T = G_P \times D \times T + G_B (T - D \times T) \tag{6}$$

$$D = \frac{G_B - G_{IN}}{G_B - G_P} \tag{7}$$

where $G_{IN}$ is inlet gas flow, T is a period of temperature oscillation, and $G_B$ and $G_P$ are the resulting outlet gas flows for base and pulse outlet temperature, respectively. FIG. 11 depicts these relationships.

Experimental data confirms the relationship shown in equation (5) for temperature oscillations having a frequency range between about 10 Hz and about 50 kHz. Thus, in certain applications, given predetermined base and pulse temperatures, the working pressure may be tuned by changing the pulse duty cycle. Accordingly, the temperature oscillation profile (defined by the base temperature, the pulse temperature, and the duty cycle) can affect the working pressure and can shift resulting pressure towards a predetermined value.

Choking Conditions

Figure 12:
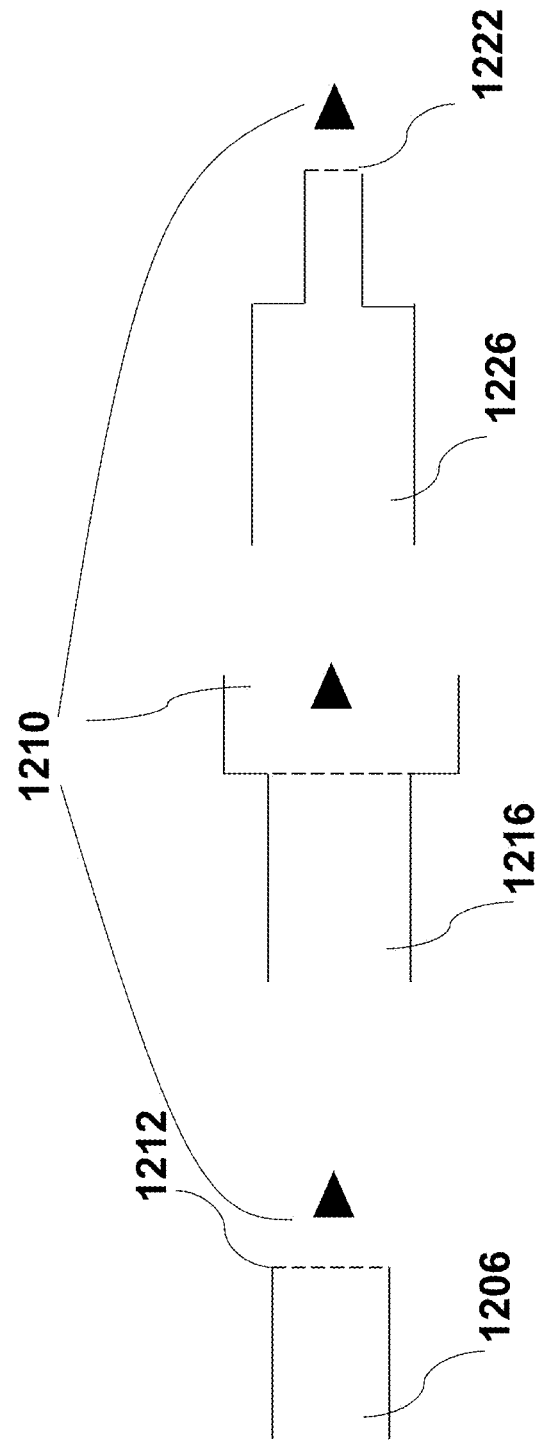
FIGS. 12A-12C are schematic diagrams of choking conditions for illustrative outlets, according to an embodiment.

In some embodiments, a sufficiently high working pressure level may cause a choking condition in the heating channel where the flow may choke at a position of the active chamber depending on a shape of the active chamber and its relationship to the outlet. Oftentimes, the choking condition occurs at an expansion point. FIGS. 12A-12C are schematic diagrams of choking conditions for example outlets. In FIGS. 12A-12C, location 1210 identifies a choking condition location (e.g., choke point). FIG. 12A depicts an active chamber 1206 having a constant diameter where the choking condition occurs as the plasma flow is discharged from the outlet 1212. In FIG. 12A, outlet 1212 serves as an expansion causing choking condition 1210. In FIG. 12B, the active chamber 1216 expands upstream of the outlet such that the choking condition 1210 occurs at the point of expansion. In FIG. 12C, the active chamber 1226 constricts upstream of the outlet such that the choking condition 1210 occurs at the outlet 1222. A corresponding choked velocity (e.g., sonic speed) may be established if the pressure drop $\Delta P$ in the heating portion of active chamber 1206, 1216, 1226 has the following relationship with atmospheric or ambient pressure, $P_a$:

$$\frac{\Delta P + P_a}{P_a} \geq \left(\frac{\gamma + 1}{2}\right)^{\frac{\gamma}{\gamma+1}} \tag{8}$$

$$P_{CH} = \Delta P + P_a \tag{9}$$

where $\gamma$ is an adiabatic index, and $P_{CH}$ is absolute inlet pressure if equation (8) is met. Equation (8) may be used to calculate the critical static pressure at the sonic speed.

Gas Flow Rate

In some embodiments, a plasma-generating device may include a relatively short channel configured to heat plasma-generating gas. For these embodiments, friction may be negligible and need not be considered in calculating the inlet pressure. For the choked condition, the corresponding equation for mass flow rate G (kg/s) and mass flux g (kg/(m²×s)) may be expressed as follows:

$$g = 4 \times \frac{G}{\pi d_{CH}^2} = P_{CH} \times \sqrt{\left(\frac{\gamma \times \mu}{Z \times R \times T_{CH}}\right) \times \left(\frac{2}{\gamma + 1}\right)^{\frac{\gamma+1}{\gamma-1}}} \tag{10}$$

where Z is a gas compressibility factor, and $P_{CH}$ and $T_{CH}$ stand for the inlet pressure and temperature of the choked plasma flow, respectively.

Considering the adiabatic index as a weak function of temperature, a flow rate ratio of pulse plasma flow to base plasma flow may be estimated based on Eq. 10 as follows:

$$\frac{G_P}{G_B} = \frac{g_P}{g_B} = \sqrt{\frac{T_B}{T_P}} \quad (11)$$

where $T_B$ and $T_P$ are base temperature and pulse temperature, respectively. Using Eq. 6, the base pulse flow rate and pulse flow rate may be evaluated as follows:

$$G_P = \frac{G_{IN}}{D + \sqrt{\frac{T_B}{T_P}} + (1-D)} \quad (12)$$

$$G_P = \frac{G_{IN}}{D\sqrt{\frac{T_B}{T_P}} + (1-D)} \quad (13)$$

Pulse gas flow rate $G_P$ can be less than base gas flow rate $G_B$ while inlet gas flow rate $G_{IN}$ is maintained constant. Thus, during oscillation of outlet temperature, the plasma-generating device can be analogized to a rapid valve that is open for base plasma flow and partially closed for pulse plasma flow. For example, if base and pulse temperatures are about 3000 K and about 11000K, respectively, and duty cycle is about 0.5, the pulse gas flow can be about $G_P = 0.69 \cdot G_{IN}$ and base gas flow can be about $G_B = 1.31 \cdot G_{IN}$. The pulse gas flow may be less than inlet gas flow and the base gas flow may be more than inlet gas flow. As a result, base plasma flow may drain the plasma-generating gas for the base duration and act as a pressure drain, and pulse plasma flow may build up pressure in the system for the pulse duration. For proper operation, the inlet pressure can be maintained constant. To achieve this, various parameters can be selected such that a predetermined amount of gas is stored in the expansion chamber and therefore pressure does not drop when the base plasma flow drains the gas. In some embodiments, the gas may be calculated as a product of base gas flow rate $G_B$ and base duration $T(1-D)$. In some embodiments, the volume of expansion chamber may be $V_{EXP} = N \cdot G_B \cdot T(1-D)$ where factor N may be a number that is about equal to at least 2 to 5 to maintain the inlet pressure.

Figure 13:
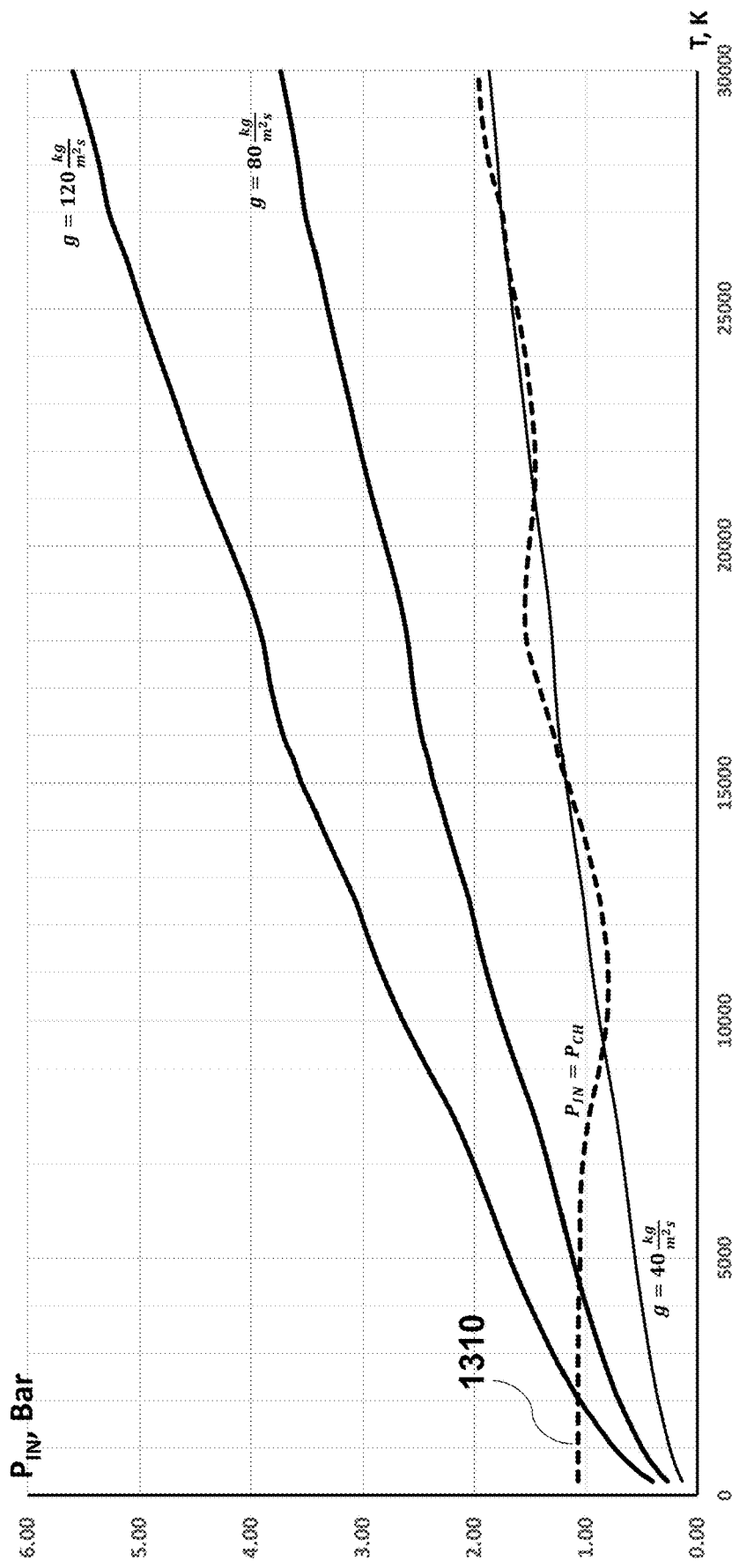
FIG. 13 is a plot of measured argon plasma flows with fixed mass flow rates, according to an embodiment.

FIG. 13 is a plot of measured argon plasma flows with fixed mass flux. The dash line 1310 corresponds to the calculated inlet pressure $P_{CH}$ according to equation (10). The obtained data reveals that for the values of mass flux, g, greater than about 40 kg/(m²s), the inlet pressure is higher than the critical value. A relatively high outlet static pressure may correspond to undesirable effects such as gas embolism for medical applications. Therefore, in some embodiments, the nozzle design depicted in FIG. 12B can be used, which is configured to prevent undesirably high outlet static pressure.

Mach Number

In some embodiments, an adaptive nozzle design may be used to avoid the excessive outlet static pressure and increase the outlet velocity of plasma flow. The maximum possible flow velocity that can be achieved without expansion of the nozzle is the speed of sound at a given or set temperature of the plasma-generating gas. When a working pressure is higher than a critical pressure, the outlet flow velocity may achieve a Mach number of more than unity (M>1) with an adaptive outlet nozzle. The Mach number can represent the ratio of flow velocity past a boundary to the local speed of sound, or $M = U_j/a$. At the boundary with choking conditions, the Mach number may be equal to unity, i.e., $M = 1$. In some embodiments, nozzle expansion may correspond to an increase of Mach number that results in an increase of flow velocity and decrease of outlet static pressure.

The Mach number that can be achieved for a given inlet pressure $P_{CH}$ can be evaluated using the following models. In some embodiments, inlet pressure or static pressure can be equal to stagnation pressure (e.g., associated with total energy) when there is a relatively cold gas flow that has a low speed. Stated differently, inlet pressure can be equal to stagnation pressure minus dynamic pressure. In particular, the relation between pressure ratio (i.e., $P_{CH}/P_a$) and the Mach number for isothermal and isentropic flow models may correspond to Eq. 14 and Eq. 15, respectively:

$$\frac{P_{CH}}{P_a} = \exp\left(\frac{M^2}{\gamma}\right) \quad (14)$$

$$\frac{P_{CH}}{P_a} = \left(1 + \frac{\gamma-1}{2}M^2\right)^{\frac{\gamma}{\gamma-1}} \quad (15)$$

These equations show an estimate for the maximum Mach number that can be achieved for a fixed value of working pressure. For example, for a working pressure of about 5 bar and plasma flow temperature of about 7,000 K, the Mach number can be calculated to be about 1.6. Accordingly, an outlet velocity of an adaptive nozzle may be about 1.6 times higher than the velocity at the boundary with choking conditions. The corresponding outlet diameter to achieve the maximum outlet jet velocity and level of static pressure with a given ambient pressure may be calculated based on the following area-Mach number function:

$$f(M) = \frac{A_{out}}{A_{ch}} = \frac{d_{OUT}^2}{d_H^2} = \left(\frac{\gamma+1}{2}\right)^{\frac{\gamma+1}{2(\gamma-1)}} \frac{M}{\left(1 + \frac{\gamma-1}{2}M^2\right)^{\frac{\gamma+1}{2(\gamma-1)}}} \quad (16)$$

where $A_{out}$ and $A_{ch}$ are outlet area and area of the boundary with choking conditions, respectively. Static pressure in the outlet plasma flow may depend on a number of factors, including, for example, inlet pressure, outlet mass flux, and nozzle geometry. Depending on these factors, the static pressure of the outlet plasma flow or the plasma jet can be above, equal to, or below ambient pressure.

Velocity

A radial velocity profile may be derived based on a radial temperature profile and known outlet Mach number as shown in the following equation:

$$U_j(r) = M \cdot a(T_{OUT}(r)) \quad (17)$$

In embodiments described herein, a high pulse temperature of plasma flow may be achieved using electric arc discharge for the heating source by having a high ratio of pulse power density. In some embodiments, a relatively small cross-section of a heating channel may be configured for a relatively high ratio of pulse power density. In some embodiments such as surgical instruments, the size of a plasma-generating device may be limited and therefore the size of the heating channel $d_H$ may be constrained. Such conditions may require a higher mass flux to provide a predetermined plasma jet power. In embodiments having size constrictions, the choke condition is typically realized in a wide range of working parameters of the plasma-generating device. Thus, equations for rocket engine design may be used to calculate outlet parameters of plasma flow that depend on conditions in the heating channel.

In some embodiments, the outlet velocity of a plasma flow is a parameter that can also be configured to generate a predominantly radially expanded plasma flow. In some embodiments, the outlet velocity of a plasma flow may depend on, but is not limited to, the plasma-generating gas flow rate, active chamber working pressure, plasma flow temperature, active chamber geometry and structure, and outlet nozzle design.

Based on the outlet thermodynamic parameters described herein, an outlet plasma velocity may correspond to a temperature of the plasma flow in the active chamber and a ratio between ambient pressure and active chamber pressure. For example, if the plasma flow temperature is in the range of between about 3,000 K and about 7,000 K, and the working pressure is in the range of between about 2 Bar and about 5 Bar, then the maximum plasma flow outlet speed may be calculated using the following equation:

$$U_J = \sqrt{2 \times h(T_B) \times \left[1 - (P_a/P_{CH})^{\frac{\gamma-1}{\gamma}}\right]} \quad (18)$$

where $h(T_B)$ is enthalpy of plasma flow, $T_B$ is base temperature, $P_a$ is ambient chamber pressure, and $P_{CH}$ is an active chamber inlet pressure, and $\gamma$ is an adiabatic index.

In embodiments described herein, collision of plasma particles are used to achieve radial expansion of a plasma flow. The higher the probability of such collisions, the more significant the radial expansion. In some embodiments, the volume where particles collide defines the resulting active zone or the plasma flow volume. Several kinematic criteria contribute to the formation of the optimal conditions for generating predominantly radially expanded plasma including the velocity ratio of colliding particles, the density ratio of colliding particles, the interaction zone, characteristic frequencies of temperature and time profiles, and the like.

In some embodiments, a "slower" plasma flow comprised of relatively slow-moving particles may be exposed to "faster" plasma flow comprised of relatively fast-moving particles to generate predominantly radial expansion. While the actual plasma flow speed changes along the axis, the slower plasma is slower than the faster plasma in the zone of interaction. As described above, base plasma flow may refer to a relatively low intensity flow (e.g., low speed with high density). Pulse plasma flow may refer to a relatively high intensity flow (e.g., high speed with low density) that catches up and collides with the base plasma flow.

Plasma Flow Temperature

As used herein, the term "temperature-time profile" may refer to the relationship of the outlet plasma flow temperature to time such as the temperature and time plots described herein. The temperature-time profile reflects the changes in outlet plasma temperature over time. The term "temperature-distance profile" may refer to the relationship of the plasma flow temperature to distance from the nozzle along the axis. While the temperature-time profile may be characterized by the temperature changes at an output of the plasma-generating device, the temperature-distance profile may be characterized by a dimensional temperature distribution at a predetermined time.

FIGS. 14A and 14C are plots of temperature and time of plasma flow (i.e., a temperature-time profile of the plasma flow) at a low temperature (about 7,000 K) and a high temperature (about 15,000 K). FIGS. 14B and 14D are plots of distance and time corresponding to respective FIGS. 14A and 14C. In particular, FIGS. 14B and 14D show the dynamics of plasma flow development corresponding to the temperature-time profiles depicted in FIGS. 14A and 14C, respectively. For example, FIG. 14B depicts the development of laminar flow length for a plasma flow that develops as a result of the temperature-profile pulse shown in FIG. 14A. As shown in FIG. 14B, the pulse duration is r, and the plasma flow length increases until reaching a plateau at $t=\tau_d$ (which may be different for different temperatures). The plasma flow fades when the pulse finishes ($t=\tau_p$). For a fixed nozzle diameter $d_j$, the plasma flow length $L_j$ may increase with higher temperatures. FIG. 14B depicts three distinct stages (e.g., I, II, III) of plasma flow propagation (e.g., development) as the derivative corresponding to speed, which in the context of a plasma flow relates to the plasma temperature. In stage I of FIG. 14B, plasma temperature and speed has an insignificant decrease and are almost constant as plasma flow propagates away from the outlet in the time range (0, $\tau_L$). In stage II, the plasma flow has a substantial decrease in temperature and speed in the time range ($\tau_L$, $\tau_d$). In stage III, plasma flow corresponds to an essentially flat (e.g., horizontal) line, and the temperature drops to the surrounding temperature with no significant speed associated with the plasma flow particles. Stage III corresponds to the time range ($\tau_d$, $\tau_p$). After the pulse terminates, the plasma flow rapidly fades. FIG. 14D has three stages similar to FIG. 14C with similar plasma flow duration.

FIG. 15A is a plot of temperature and time of a pulsed plasma flow. FIGS. 15B and 15C are plots of temperature and distance of the pulsed plasma flow corresponding to FIG. 15A. In particular, FIG. 15A depicts an oscillating temperature-time profile with base temperature $T_T$ and rectangular pulses $T_I$. FIGS. 15B and 15C depict two temperature-distance profiles corresponding to the plasma flow of FIG. 15A. At a low frequency, as depicted in FIG. 15B, base plasma pulses may reach the maximum jet length and form steady laminar flows 1510 and 1512. At time $\tau_T$, pulse plasma begins to form at the outlet and interact with the base plasma flow. Under the low frequency conditions of FIG. 15B, the pulse plasma flow may also form a steady laminar flow reaching its maximum length. Under such conditions, the plasma flow may correspond to predominantly axial expansion with minor (e.g., insignificant) periods of radial expansion. FIG. 15C depicts a high frequency condition where the pulses do not have enough time to reach the maximum length. In this case, the time of interaction between base plasma flow and pulse plasma flow may increase, thus generating more favorable conditions for radial expansion.

In some embodiments, at low frequencies, the particles of the pulse plasma flow collide with the particles of the base plasma flow at stage III of a base plasma flow front propagation, as shown in FIG. 14B and FIG. 15B. If the frequency is increased, the available time for the plasma flow development may decrease and eventually the pulse plasma flow can collide with base plasma flow at stage II ($f > 1/\tau_d$). If the frequency increases to even higher values, then the interaction may occur at stage I ($f > 1/\tau_L$). In this case, the speed of both base plasma flow and pulse plasma flow may be assumed to be constant. The validity of this assumption as well as frequency relationships is demonstrated by the temperature-distance profile of a steady laminar plasma flow, applicable to both the base and pulse plasma flows shown in FIG. 16.

Figure 16:
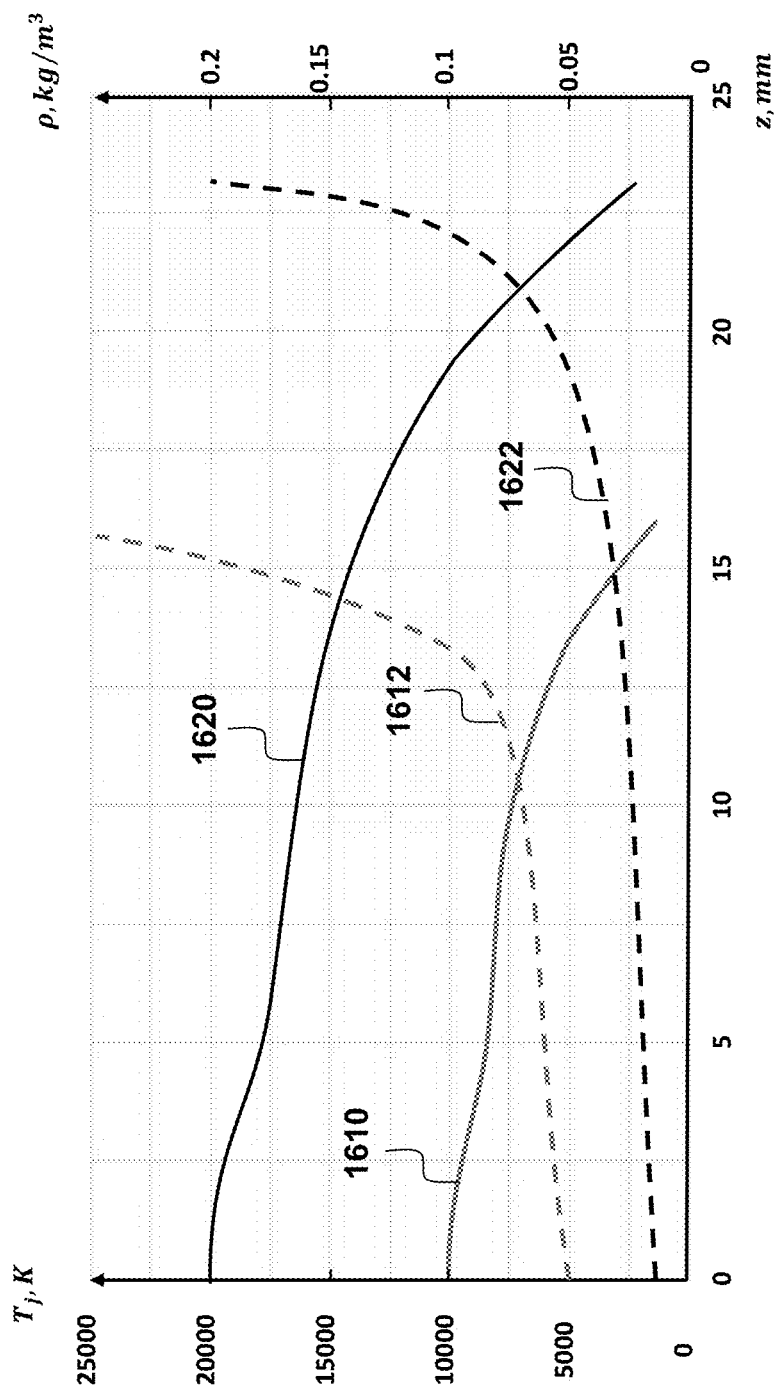
FIG. 16 is a plot of plasma temperature and density profiles along a flow axis for steady laminar flow with constant outlet temperature, according to an embodiment.

FIG. 16 is a plot of plasma temperature and density profiles along the flow axis for steady laminar flow with constant outlet temperature. In FIG. 16, the temperature-time profiles are represented as solid lines 1610 and 1612, and the density-time profiles are represented as dashed lines 1620 and 1622. Lines 1610 and 1620 are associated with plasma flow having a temperature at about 10,000 K, and lines 1612 and 1622 are associated with plasma flow having a temperature at about 20,000 K. Therefore, the temperature profile 1610 corresponds to a plasma flow having a temperature at about 10,000 K at the outlet that remains relatively constant between about 5 mm and about 10 mm where the density of the flow remains relatively low at around 0.05 kg/m$^3$ over the same distance for such a flow. After the initial drop, the temperature may decrease with a relatively low gradient. In some embodiments, the duration of stage I may be estimated as $\tau_L \approx \frac{1}{3}\tau_d$. Since the particle velocity is directly related to temperature, the velocities of flows may be considered constant for stage I (f>1/$\tau_L$).

Plasma Flow Lengths

In some embodiments, the relationship of respective flow lengths may affect the interaction zone between a pulse plasma flow and a base plasma flow. When unrestricted by time, the flow lengths may be based on temperature, speed, and diameter of plasma flow. In some embodiments, the flow lengths may be controlled by the duty and frequency of pulses to optimize radial expansion. In some embodiments, the flow lengths may be substantially equal to maximize the interaction zone of the base plasma flow and pulse plasma flow. For a predetermined base plasma flow temperature and pulse plasma flow temperature, the duty of pulses and velocity ratio of target and initiator plasma may be adjusted such that the base plasma flow length and pulse plasma flow length are substantially equal. More specifically, target plasma can be plasma having high density and low temperature, e.g., plasma with energy and power that is minimized. During plasma generation, initiator plasma can be generated within a plasma-generating device and used to generate a plasma jet. Accordingly, initiator and target plasma can be generated during sequential time periods (e.g., first, second) of a plasma flow development cycle to produce a radially expanded plasma flow. Target plasma can create volume for interacting with high speed and high energy/power plasma flow but can also correspond to axial plasma flow and narrow, low energy, plasma flow concentrated in relatively high heat flux. It is therefore desirable to reduce or minimize a duration of target flow to avoid such negative impacts of target flow.

Figure 17:
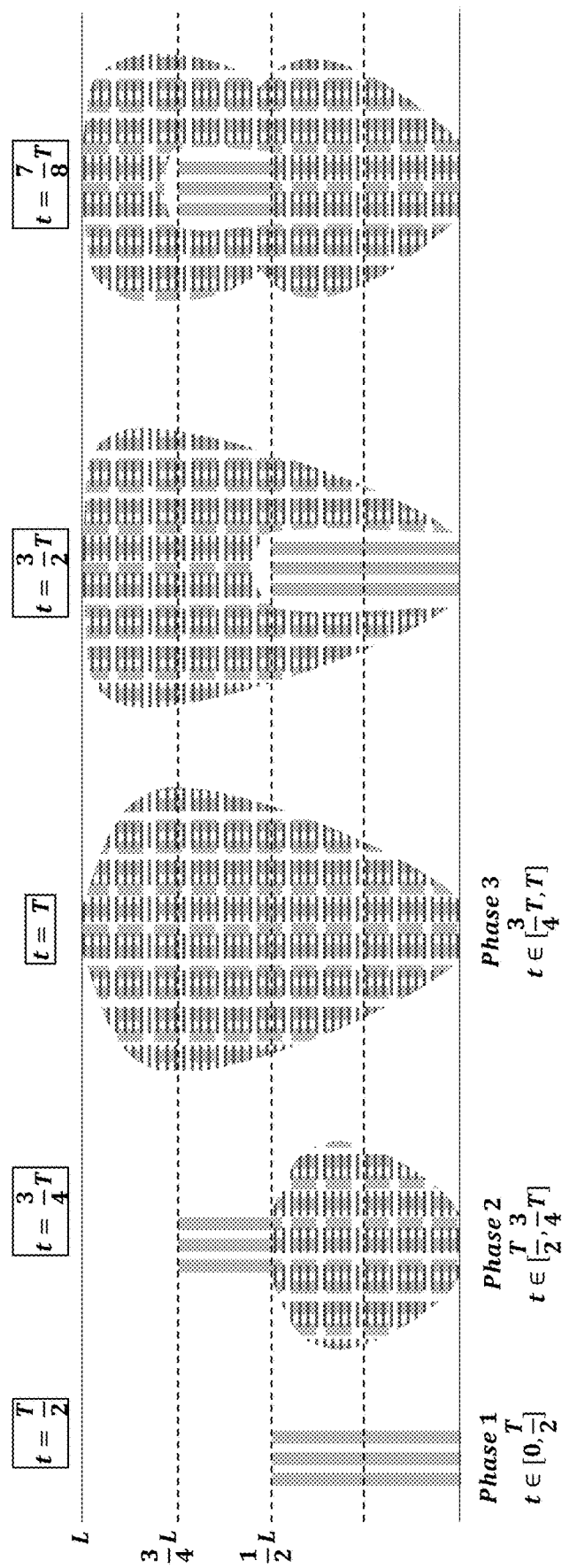
FIG. 17 is a schematic diagram of plasma flow with oscillating outlet temperature and equal length of target and initiator flows, according to an embodiment.

Kinematic criteria may be formulated in case of constant velocities, e.g., when base-pulse plasma flows interaction occurs at stage I. FIG. 17 illustrates three phases of plasma flow development during a single period. For example, a temperature pulse duty cycle D=0.5 and velocities ratio $U_{pulse}/U_{base}=2$, where $U_{pulse}$ and $U_{base}$ are the velocities of outlet temperature of pulse and base plasma flows, respectively. The base plasma flow and the pulse plasma flow can have the same maximum length (L=$U_{base}$ T=$U_{pulse}$ $t_{pulse}$, where $t_{pulse}$ is the temperature pulse duration and T is the period duration).

In a first phase, the base plasma flow may not be affected by the pulse plasma flow. The duration of this phase may be T/2. In a second phase, the pulse plasma flow may interact with some part of base plasma flow. At t=¾T, half of the length may be affected by the pulse plasma flow, but the next quarter of length may be occupied by the predominantly axial base plasma flow. In a third phase at t=T, all of the volume may be affected by the pulse plasma flow. As shown in FIG. 17, a degree of radial expansion may depend on a distance from the outlet.

Figure 18:
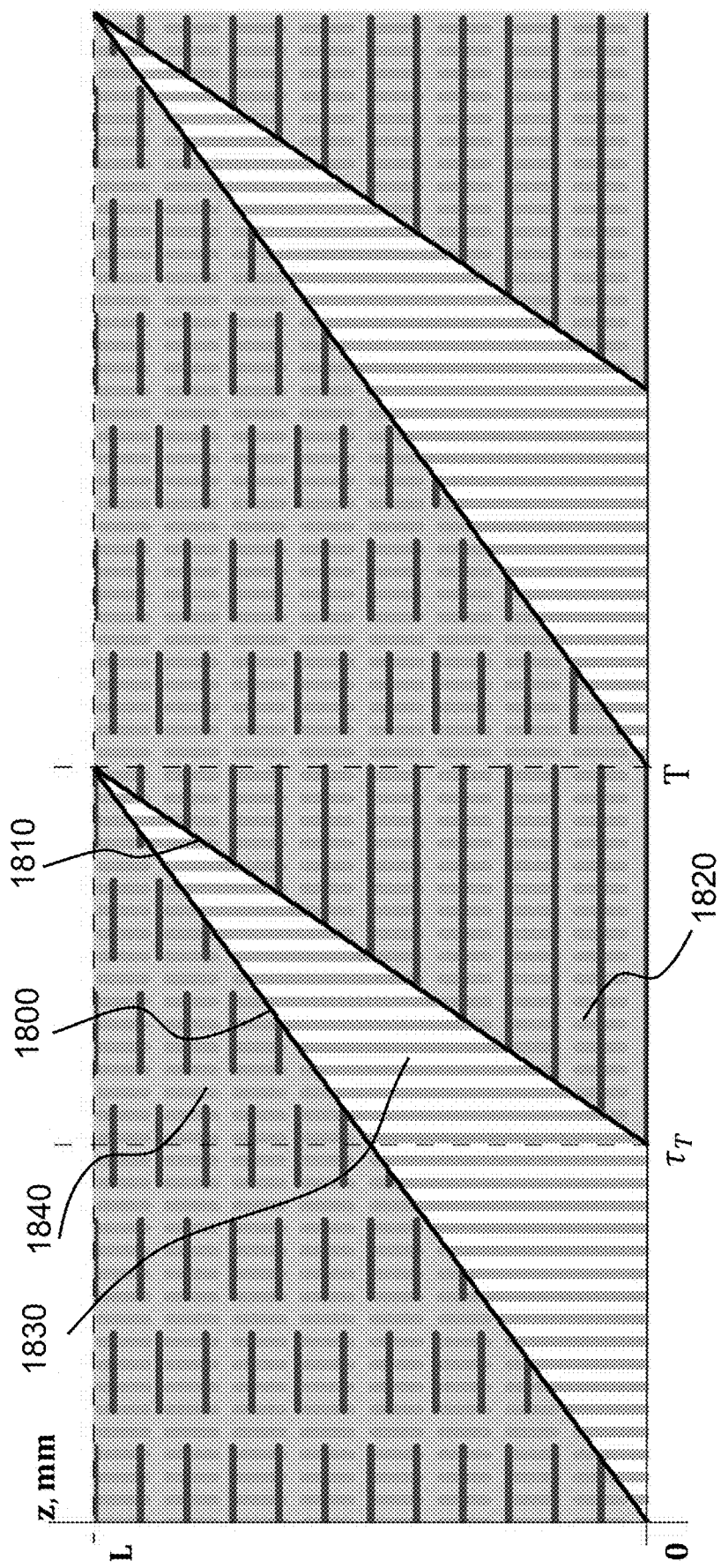
FIG. 18 is a plot of length and time of interactions of low and high temperature plasma flow with high frequency pulses, according to an embodiment.

The overlap between the base plasma flow and the pulse plasma flow may correspond to a first approximation for estimating a ratio of radially to axially propagated plasma. FIG. 18 is a graphical illustration of such an approximation. FIG. 18 is a plot of length and time of interactions of low and high temperature plasma flow. The vertical lines in FIG. 18 correspond to an axial gradient of a combined plasma flow. The horizontal lines correspond to a radially expanded gradient of the combined plasma flow. A spacing between the lines correspond to density, i.e., the larger the space between the lines, the lower is the density and the darkness of the lines corresponds to the velocity, with darker lines representing higher velocity. FIG. 18 shows an axial cross-section of an active zone and plasma type as a function of time (for two time periods). During one time period, there is an area of axial base plasma (e.g., thick sparse vertical light lines), and an area where the target and initiator plasma occupy the same volume. FIG. 18 further illustrates the axial and radial components at various times and distances from the outlet. The collision probability inside a predetermined area of the target-initiator intersection may depend on a set of parameters. However, for a first approximation, the radial to axial ratio may be estimated as an intersection area to axial area ratio.

FIG. 18 illustrates a front 1800 of the base plasma flow and front 1810 of the pulse plasma flow. In some embodiments, the probability of collision and consequent radial expansion close to the outlet may be high when the pulse plasma flow has started. As the pulse plasma flow propagates over a distance away from the outlet, the probability of collision may increase. For an arbitrary time τ during the first period shortly after the pulse plasma flow is initiated, the probability of collision and the degree of radial expansion is high at point 1820 close to the outlet. Since the pulse plasma has not "caught up" completely at point 1830, the active zone may be filled predominantly with the base plasma flow with a low chance of collision. However, even further from the outlet at the same time at point 1840, the active zone may be filled with predominantly radially expanded plasma from the previous interaction between the base plasma flow and pulse plasma flows from the previous period that has not yet dissipated into the surrounding environment or been "pushed" out by the base plasma flow. In FIG. 18, there is no distance where the base plasma flow operates by itself or where the pulse plasma flow operates by itself. In some embodiments, the respective temperatures, the period, and the duty may be optimized to prevent such occurrences.

Figure 19:
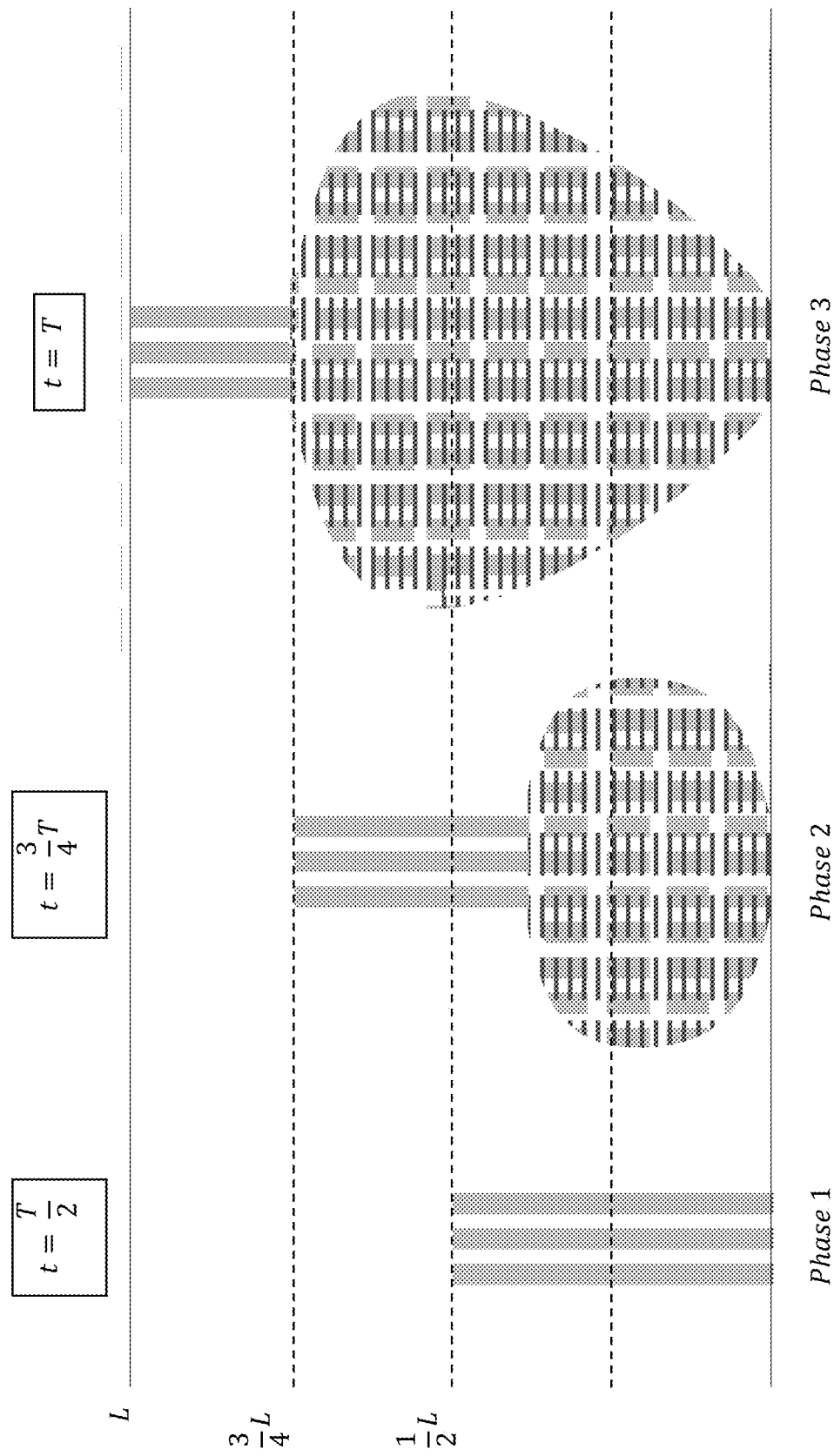
FIG. 19 is a schematic diagram of plasma flow with oscillating outlet temperature, according to an embodiment.
Figure 20:
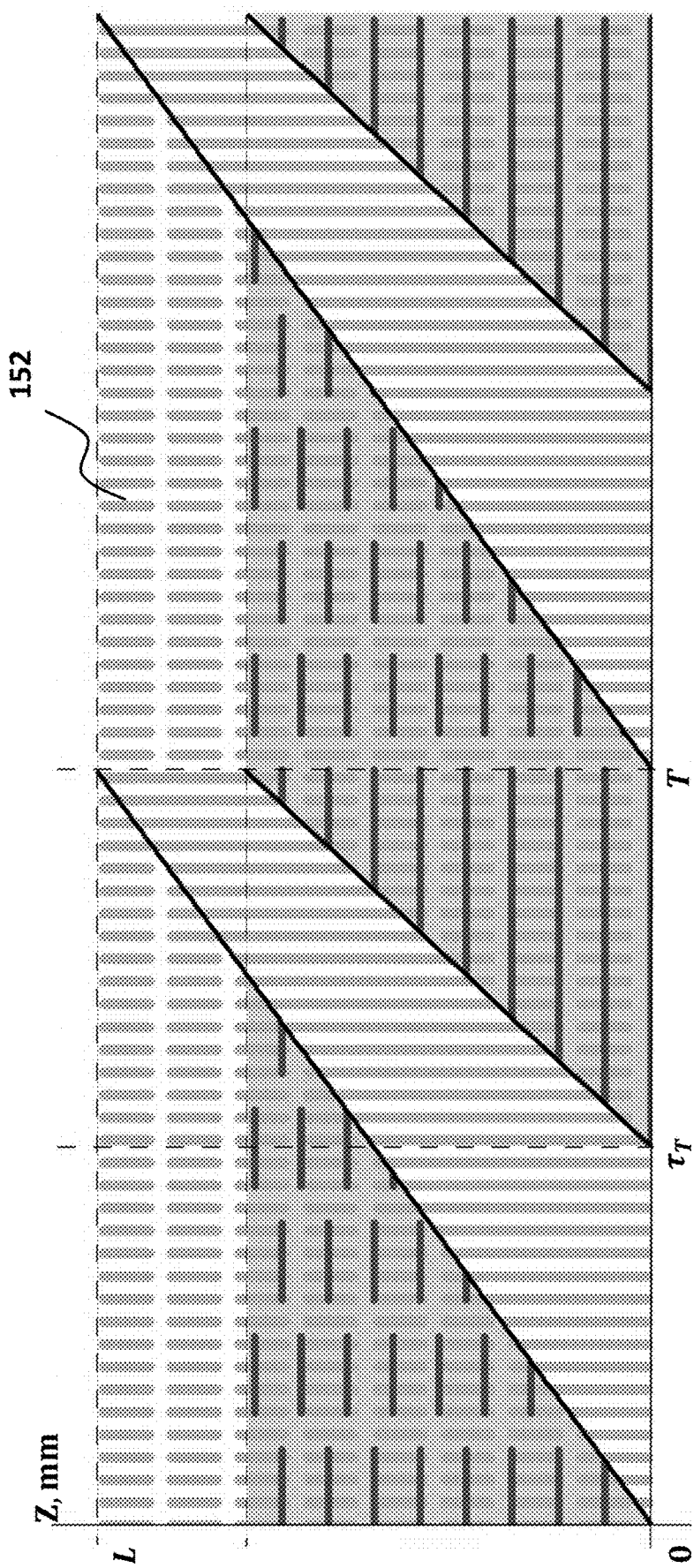
FIG. 20 is a plot of length and time of interactions of low and high temperature plasma flow with high frequency pulses, according to an embodiment.

For comparison, FIGS. 19 and 20 illustrate embodiments where a base plasma flow length is longer and the pulse plasma flow does not extend to the distal-most portions of the active zone (e.g., due to the sub-optimal selection of the low and high temperatures, period, and duty cycle). As a result, there may be a tail of base plasma flow. FIG. 19 is a schematic diagram of plasma flow with oscillating outlet temperature. The maximum length of the target may be greater than the maximum length of the initiator. FIG. 20 is a plot of length and time of interactions of relatively low and high temperature plasma flow.

Figure 21:
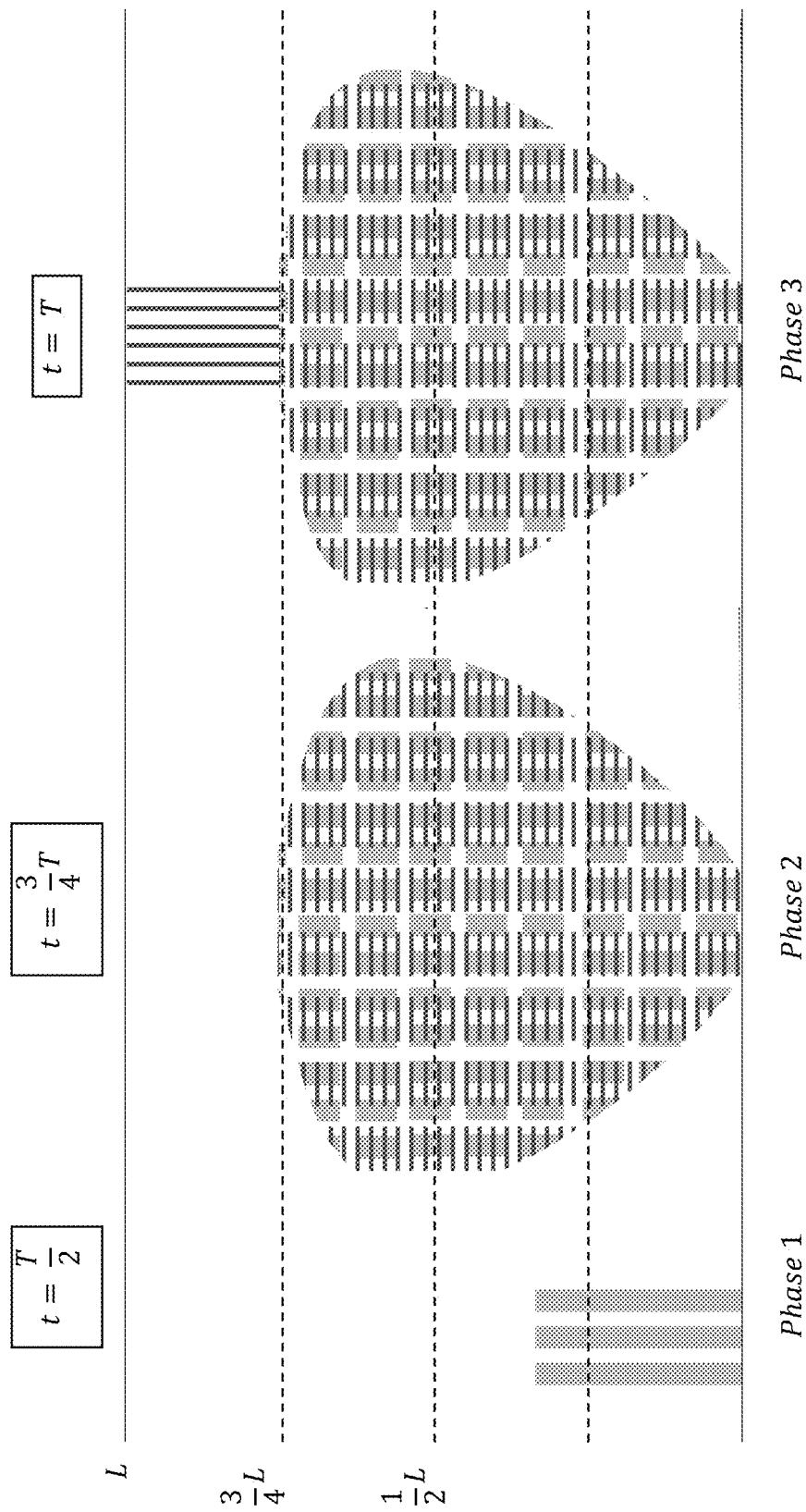
FIG. 21 is a schematic diagram of plasma flow with oscillating outlet temperature, according to an embodiment.
Figure 22:
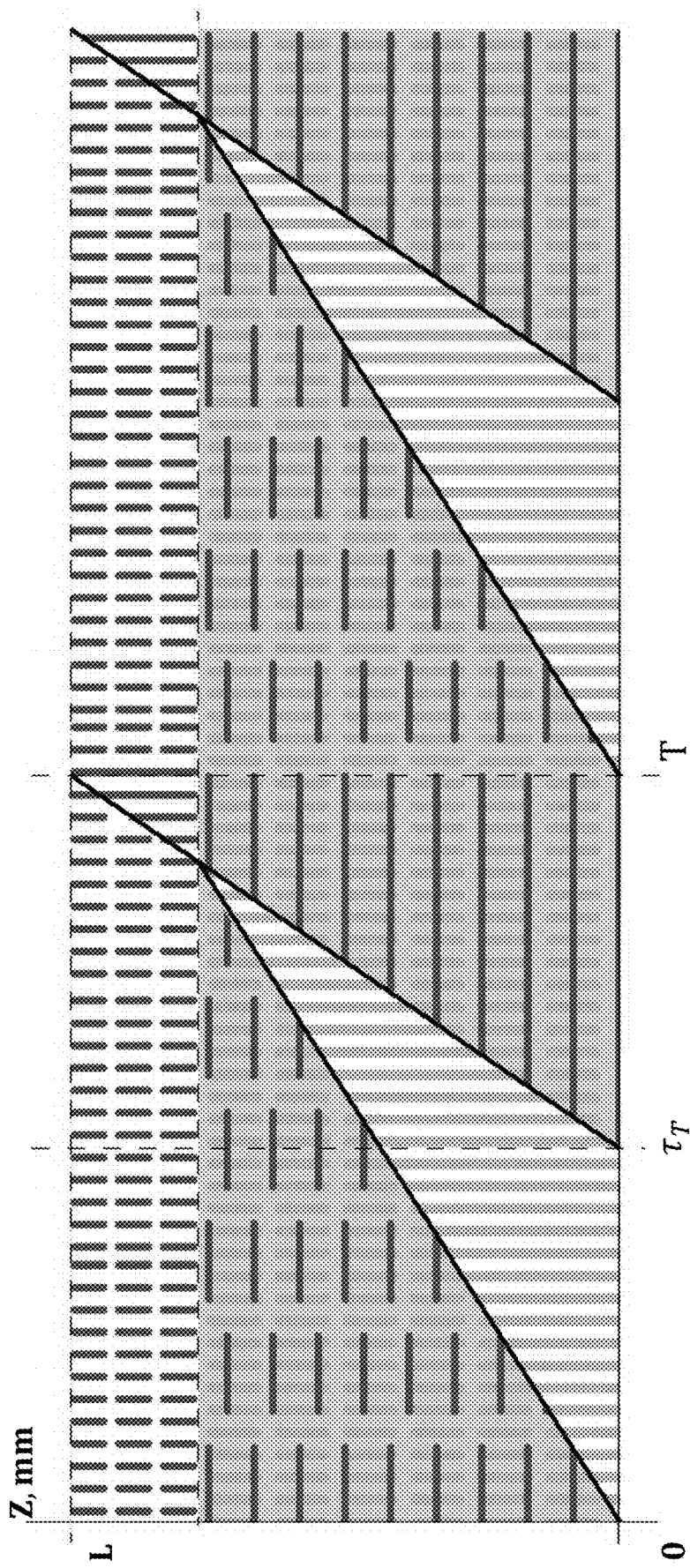
FIG. 22 is a plot of length and time of interactions of low and high temperature plasma flow with high frequency pulses, according to an embodiment.

For further comparison, FIGS. 21 and 22 illustrate an instance where the pulse plasma flow overshoots the base plasma flow leaving the axial pulse plasma operating at the distal end of the active zone (e.g., due to the sub-optimal selection of the low and high temperatures, period, and duty cycle). FIG. 21 is a schematic diagram of plasma flow with oscillating outlet temperature. FIG. 22 is a plot of length and time of interactions of relatively low and high temperature plasma flow with high frequency pulses. Comparing FIGS. 17 and 18 with FIGS. 19-22, the highest radial to axial ratio may correspond to the selection of parameters shown in FIGS. 17 and 18, where the length achieved by the base plasma flow during a base plus pulse period is equal to the length achieved by the pulse plasma flow during the pulse period. Therefore, the optimization of a set of parameters corresponds to increasing the radial expansion probability based on the lengths of the base plasma flow and pulse plasma flow being substantially equal under such conditions.

In some embodiments, equal length may be achieved based on a duty of pulses and velocity ratio. In particular, parameters can be selected such that a length of a base plasma flow during the period T is the same as the length of the pulse plasma flow during the temperature pulse period, as given by:

$$L = U_{base} T = U_{pulse} t_{pulse} \quad (19)$$

$$\frac{U_{base}}{U_{pulse}} = D \quad (20)$$

where U is the speed of the respective flows and D is the duty cycle.

For example, a suitable pulse plasma flow temperature can be selected based on a predetermined duty cycle and base plasma flow temperature, as calculated using the equations above. For example, the axial/radial component ratio may be estimated for various duty values as shown in FIG. 18. Further calculations may be based on FIGS. 23A-23C illustrating plots of radial oscillation ratio and length in an interactive volume of plasma flow.

Figure 23C:
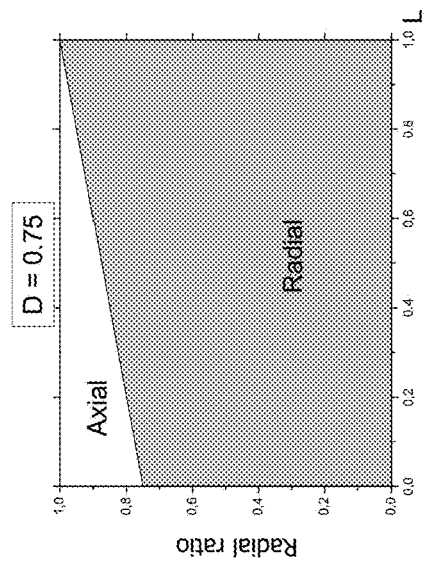
FIGS. 23A-23C are plots of radial oscillation ratio and length in an interactive volume of plasma flow, according to an embodiment.
Figure 23B:
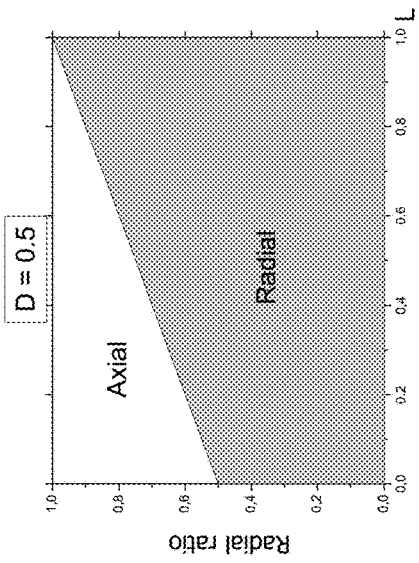
Figure 23A:
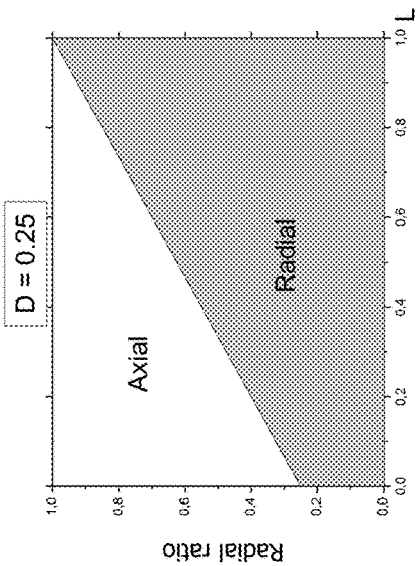

As depicted in FIGS. 23A-23C, a predominant radial oscillation may occur in the active zone when a duty cycle of the temperature pulses D>0.25. In some embodiments, a duty cycle of less than about 0.25 may not provide sufficient radial expansion for some medical applications. In some embodiments, a duty cycle of about 0.25 corresponds to an upper boundary condition on the temperature/speed ratio of a base plasma flow and pulse plasma flow. FIGS. 23A-23C illustrate that a higher ratio of base plasma flow and pulse plasma flow intersection may be achieved at relatively higher duty values. Additionally or alternatively, averaging the radial and axial components per one period of outlet temperature oscillation may provide a lowest radial ratio in proximity to the outlet and provide a highest radial ratio at a distal end of the active zone of the plasma flow. Such a distribution is consistent with a bottle-shaped plasma flow shown in FIG. 3. In such cases, the plasma flow diameter may be thinner at a proximity of the outlet due to the higher fraction of axially propagated plasma in this area.

Since velocity is a function of plasma temperatures, the criteria for equal length of plasma flows may be expressed as a function of temperatures, given by:

$$\frac{U_{base}(T_{base})}{U_{pulse}(T_{pulse})} = D \quad (20a)$$

When choking conditions are met, this ratio may be replaced by the sound speed ratio for a choked flow. Alternatively, when choking conditions are not met, this ratio can be calculated based on Rayleigh conditions. The Rayleigh conditions (e.g., propagation according to Rayleigh waves) provide a simplified model for calculating inlet and outlet parameters for gas flow heated in a channel.

Figure 24:
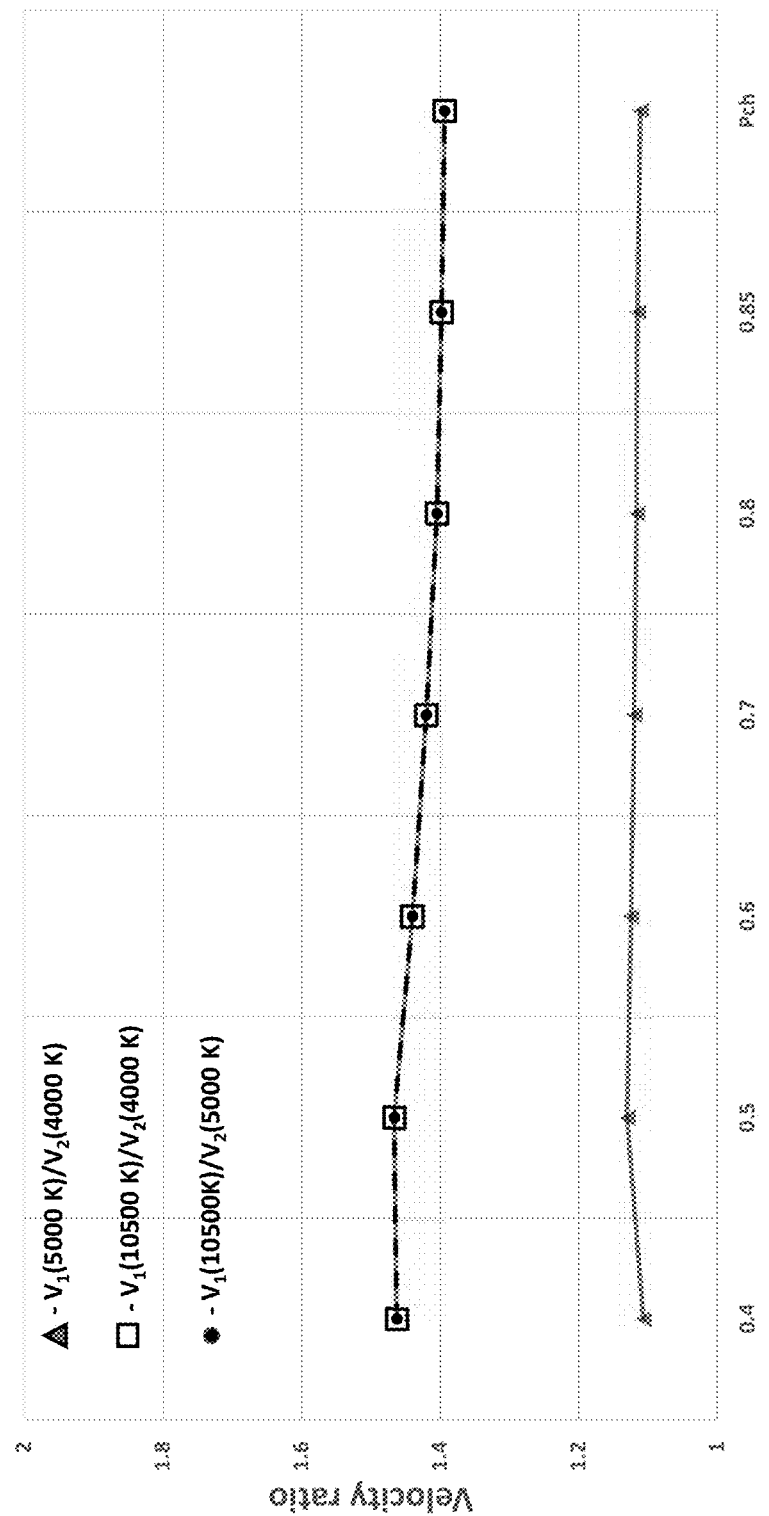
FIG. 24 is a plot of target-initiator velocity ratio and pressure for Rayleigh and choked flows, according to an embodiment.

FIG. 24 is a plot of target-initiator velocity ratio and pressure for Rayleigh flow and choked flows. FIG. 24 illustrates a velocity ratio as a function of inlet pressure $P_{inl}$, where $P_{ch}$ corresponds to a choked pressure. A velocity ratio may be calculated as a sound speed ratio for argon. Experimentally measured outlet velocities at various inlet pressures for argon at plasma flow temperatures of about 4,000 K, about 5,000 K, and about 10,500 K, and Rayleigh conditions may be used to calculate the presented velocity ratio for Rayleigh flow, as shown in FIG. 24. The plasma flow temperature may be measured using a calorimetry probe inserted in plasma flow. The velocity ratio for a wide range of base plasma and pulse plasma flow temperatures may be assumed constant for the following analysis as the ratio provides a close approximation for both the Rayleigh flow and choked flows. Therefore, the sound speed ratio may correspond to an equal length of the two flows, as given by:

$$\frac{a(T_{base})}{a(T_{pulse})} = D \quad (20b)$$

$$a = \sqrt{\frac{\gamma RT}{M}} \quad (21)$$

where a is the speed of sound as a function of temperature, γ is the adiabatic index, and M is a molar mass of the plasma generating gas.

As described herein, the duty cycle D of the pulse plasma flow temperature may correspond to a fraction of radial expansion. Equation (20b) may be used to evaluate fixed values of the duty cycle. The dashed lines shown in FIG. 25 correspond to duty contours (e.g., level curves) that meet equation (20b). The sound speed of the argon plasma is a well-known quantity. A thickness of the dashed lines may illustrate the duty cycle value (i.e., thicker lines correspond to higher values of duty cycle). To decrease a higher ratio of axial plasma flow, an upper limit for the pulse plasma flow temperature may be introduced. This limit may depend on a base plasma flow temperature. In some embodiments, a duty cycle D=0.25 may be used as reference value to estimate an upper limit of pulse temperature $T_{pulse}^{max}$ as a function of base plasma flow temperature $T_T$:

$$\frac{a(T_{base})}{a(T_{pulse}^{max})} = 0.25 \Rightarrow T_{pulse}^{max}(T_{base}) \quad (22)$$

In some embodiments, for a fixed base plasma flow temperature, the pulse plasma flow temperature may be lower in order to reach higher values of duty. However, if the temperature difference between relatively high and low intensive plasma flows is small, then the probability of collision inside the target-initiator intersection area may be low as well. For example, if the duty is about D≈1, then there is almost no difference between base plasma flow and pulse plasma flow. Instead of having the highest radial fraction, the flow may form an axial laminar jet. Therefore, the probability of collision needs to be considered to determine optimal conditions. In some embodiments, the collision probability may be based on a local concentration of target and initiator particles and velocity ratio.

As discussed above, FIG. 16 depicts an embodiment of plasma density profile along a flow axis. The density may be determined based on a temperature-distance profile and the relationship between the density and temperature (which may be found in literature). The density may increase as the plasma flow temperature decreases along the axis. A higher probability of collision may be achieved if the ratio of speed of the two plasma flows and the ratio of density of the two plasma flows are relatively high. In some embodiments, a plasma density ratio may be correspond to higher collision probability since both the velocity and density depend on temperature. Similarly, equation (20b) may be evaluated for various fixed values of density ratios. The solid lines in FIG. 25 may represent constant density ratios. The density ratios calculated for argon plasma are based on literature values. The thickness of the solid lines further indicate a density ratio where thicker lines correspond to a higher density ratio. In the same manner, a lower limit of the pulse plasma flow temperature may be introduced to avoid lower collision probability in the active zone. In some embodiments, a density ratio of about 2 may be a reference value used to estimate a lower limit of pulse temperature $T_{pulse}^{min}$, given by:

$$\frac{\rho(T_{base})}{\rho(T_{pulse}^{min})} = 2 \Rightarrow T_{pulse}^{min}(T_T) \quad (23)$$

For a predetermined base plasma flow temperature, the pulse plasma flow temperature may be at least as high so to have at least a density ratio of about two.

Figure 25:
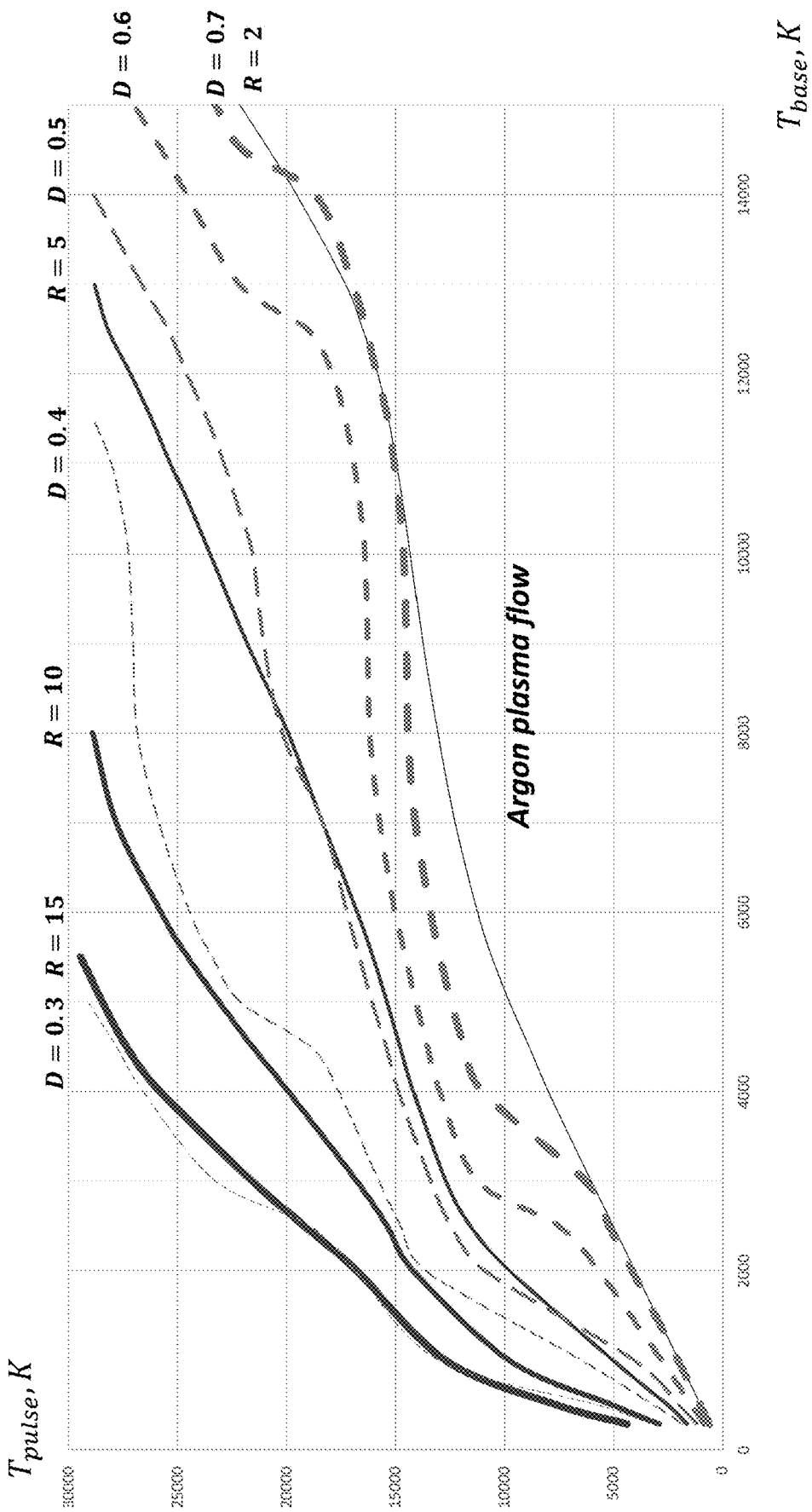
FIG. 25 is a plot of duty and density ratio relationships for radial expansion with argon as a plasma generating gas, according to an embodiment.

FIG. 25 is a plot of duty and density ratio relationships for radial expansion with argon as a plasma generating gas. As shown in FIG. 25, both criteria for a higher duty and a higher density ratio correspond to boundary conditions on the region where radial expansion is prevalent. At the same time, the criteria have opposite requirements. For example, the pulse plasma flow temperature can be maximized for a predetermined target temperature in order to increase collision probability. However, the pulse plasma flow temperature if minimized increases an interaction zone. Therefore, there can be an optimal area with a higher fraction of radial expansion. In other words, for a predetermined base plasma flow temperature, a range of pulse plasma flow temperatures may provide a set of predetermined (e.g., optimal) conditions.

Figure 26:
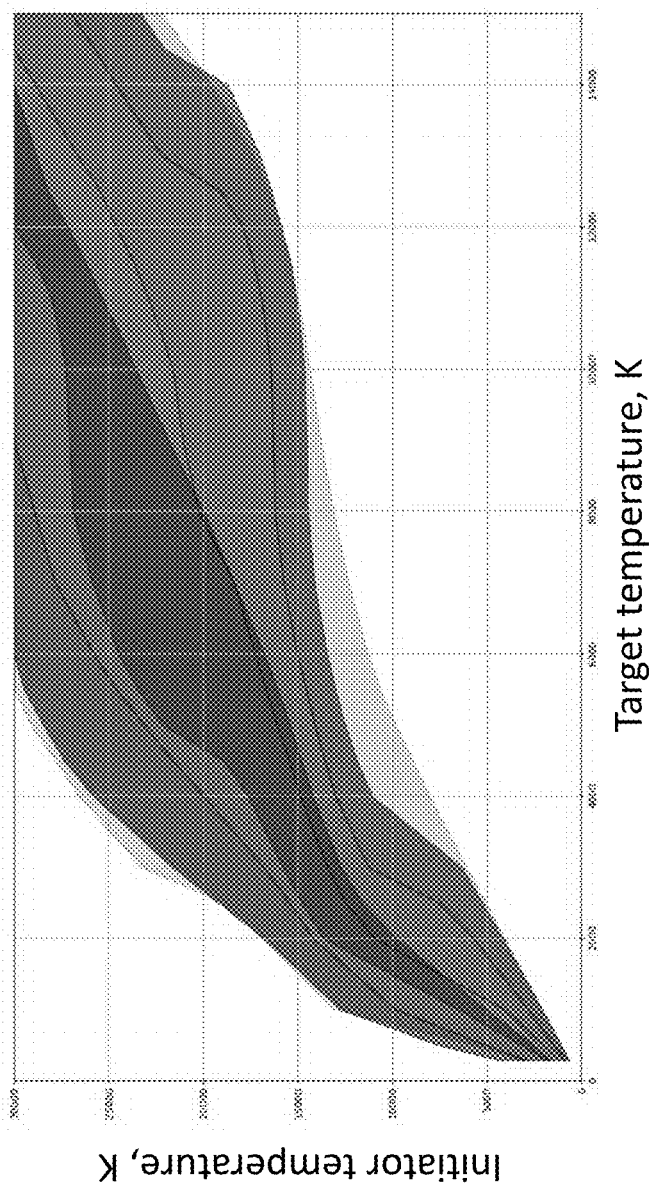
FIG. 26 is a plot of target temperature and initiator temperature for optimal radial expansion, according to an embodiment.

FIG. 26 is a plot of target temperature and initiator temperature for predominant radial expansion. FIG. 26 illustrates an arbitrary region for predominant radial expansion. For example, a base plasma flow temperature may be about 4,000 K. In some embodiments, a predetermined (e.g., sufficient) radial expansion may be generated with a pulse plasma flow temperature in a range between about 7,500 K and about 26,500 K. In some embodiments, the pulse plasma flow temperature may be in a range between about 11,000 K and about 26,000 K. In some embodiments, the range may be between about 12,500 K and about 20,000 K. In some embodiments, the range may be between about 14,000 K and about 17,500 K. A set of pulse plasma flow temperature ranges may be determined using FIG. 26 for a predetermined base plasma flow temperature. The intensity of shading in FIG. 26 corresponds to a fraction of radial expansion based on duty and density ratio criteria, with darker shading representing a higher (more desirable) fraction.

Figure 27:
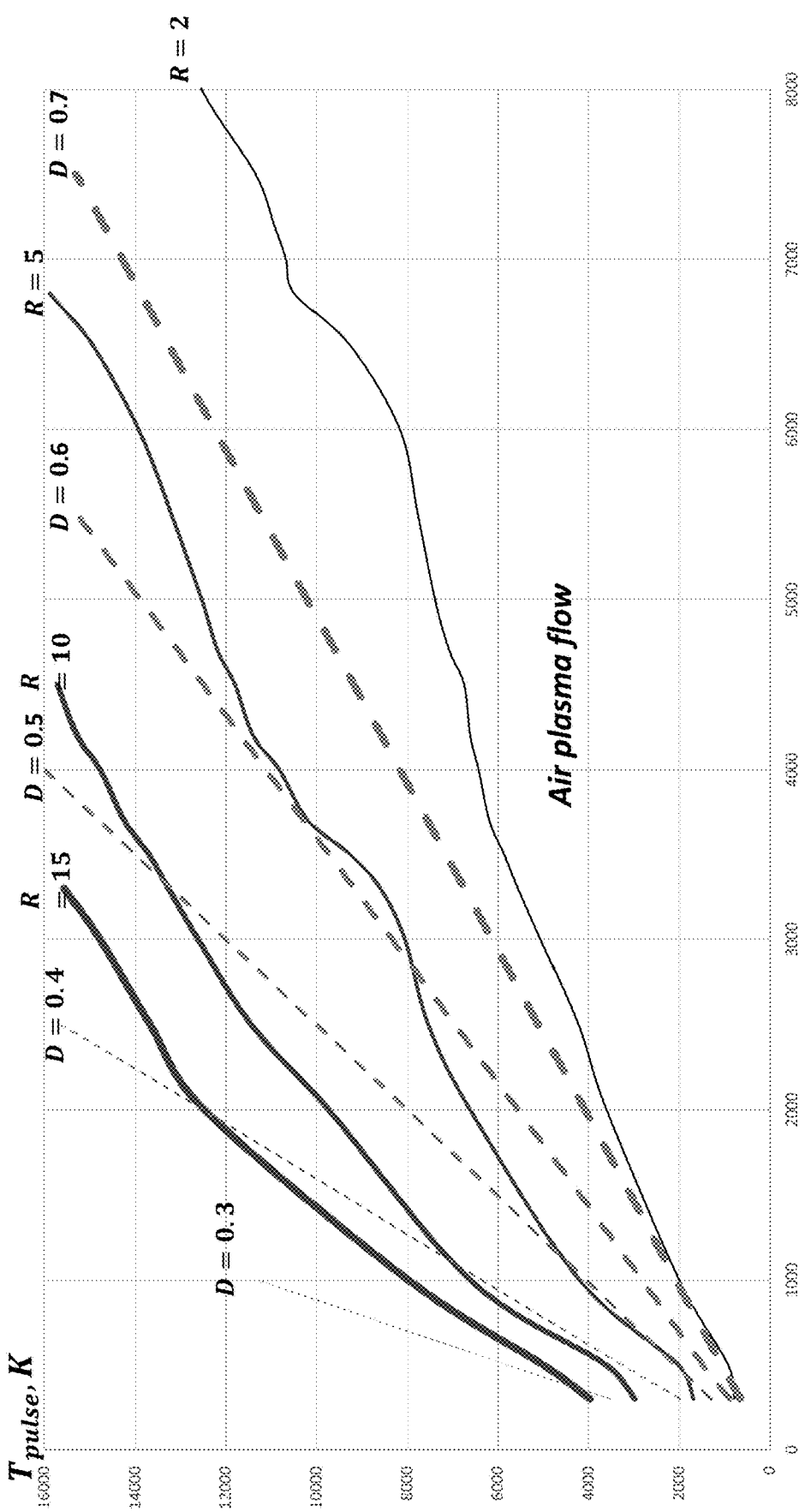
FIG. 27 is a plot of duty and density ratio relationships for radial expansion with air as a plasma generating gas, according to an embodiment.

FIG. 25 illustrated density and speed ratios calculated based on thermodynamic parameters of argon as plasma generating gas. Similar data may be obtained for other gases or their mixtures. For example, FIG. 27 illustrates density and speed ratios based on thermodynamic parameters of air as plasma generating gas. The dashed lines of FIG. 27 indicate duty contours (level curves) that meet the criteria of equation (20b), and the solid lines represent constant density ratios. The density ratios are based on air densities known from literature. For simplicity, the speed ratio was estimated assuming that adiabatic index is a weak function of temperature. Accordingly, the speed ratio is evaluated as a ratio of square roots of the corresponding temperatures. Similar conclusions about optimal region with prevalent radial expansion are valid for air or other gases or mixtures since various gases have the same temperature tendencies of thermodynamic parameters.

Figure 28:
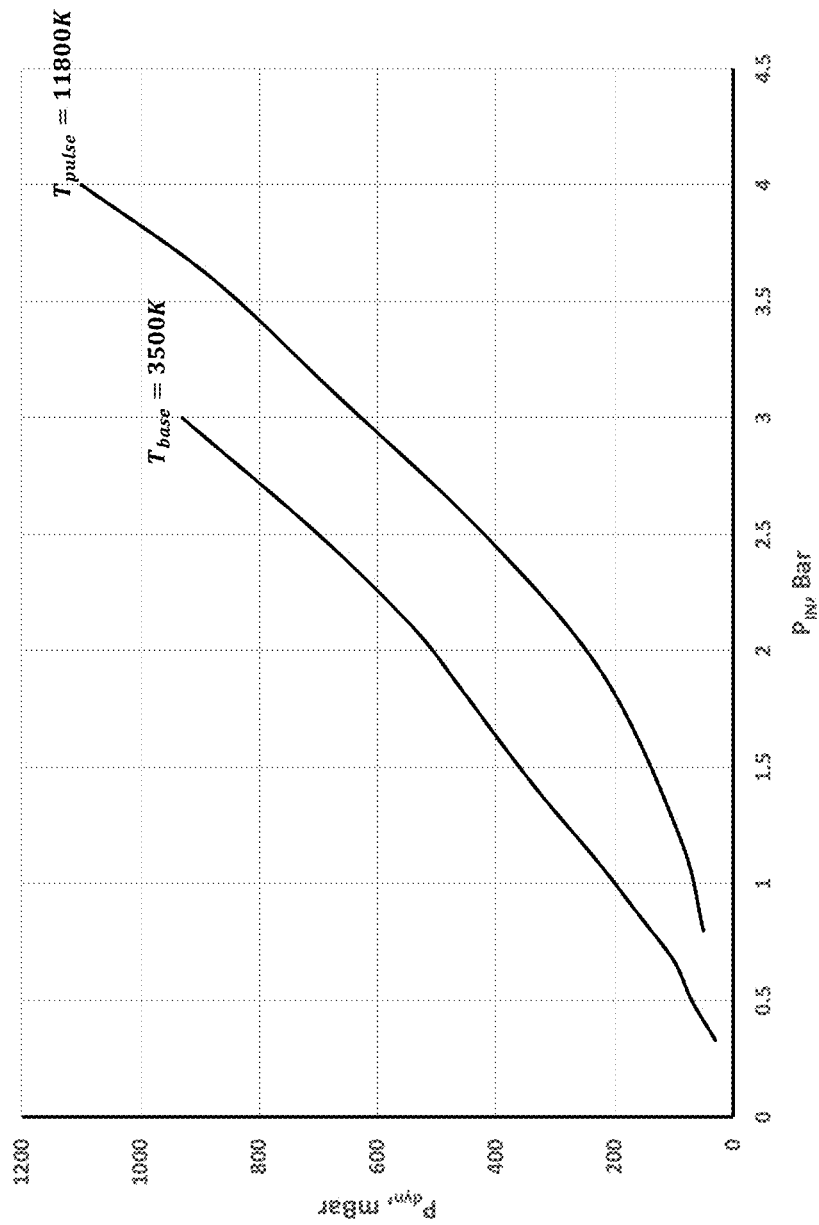
FIG. 28 is a plot of plasma flow pressure and inlet pressure, according to an embodiment.

FIG. 28 is a plot of plasma flow pressure and inlet pressure including experimental data of dynamic pressure of pulse plasma flow and base plasma flow. In some embodiments, the base temperature may be about 3,500 K and pulse temperature may be about 11,800 K. In some embodiments, the density ratio $\rho(T_{base})/\rho(T_{pulse})$ may be about 5 and a velocity ratio $U(T_{pulse})/U(T_{base})$ may be about 1.8. The dynamic pressure of base plasma flow may be higher than the dynamic pressure of pulse plasma flow. As a result, the base plasma flow may displace the residual plasma flow without mixing and filling the volume with base plasma flow. The higher dynamic pressure of base plasma flow may be positive since it may reset the conditions for each repetition of base and pulse plasma flows. Therefore, at the start of a new outlet temperature oscillation cycle, the outlet base plasma flow may not be affected by previous pulse plasma flow. Furthermore, the kinematic criteria may not depend on the number of base-pulse flow repetitions.

However, the kinematic model described herein may have limitations related to a relationship between input device parameters and a corresponding outlet temperature-time profile, as described in more detail herein. In the kinematic model, the velocity ratio of base to pulse plasma flow may be used to derive a criteria for radial expansion. The absolute value of velocity also implies certain restrictions. For example, if the input parameters such as inlet gas flow and outlet diameter result in a considerably low value of outlet velocity, then the plasma jet may not form or "fade away" within a predetermined (e.g., short) distance due to the cooling of the plasma flow. Therefore, a predetermined minimum velocity of plasma jet may be required to achieve predetermined plasma jet length. In some embodiments, a ratio of length to outlet diameter may be about 50 to about 100 for a laminar plasma jet. In some embodiments, a minimum plasma ratio $L/d_{out}$ of about 25 may be used to formulate limitations for relationships between input parameters.

In some embodiments, the cooling of a plasma jet with constant outlet temperature may be estimated based on the following equations for an outlet plasma jet in a laminar mode. For example, the plasma jet may have a cylindrical shape with uniform radial temperature distribution. An axial temperature of the jet may decrease due to diffusion of air flow inside the side walls of the plasma jet. The incoming air flow may be proportional to a surface area of the plasma jet walls. In some embodiments, the axial temperature gradient may be calculated as follows:

$$G_{IN} C_P \frac{dT}{dz} = -g_{air} \pi d_{OUT} h_{air} \quad (24)$$

where Cp is a heat capacity of plasma, hair is air enthalpy, and $g_{air}$ is air flux per unit area. The plasma jet length may be derived and may be given by:

$$L_j = \frac{G_{IN}}{\pi d_{OUT}} \frac{1}{g_{air}} \int_{T_a}^{T_{out}} \frac{C_p}{h_a} dT \quad (25)$$

where $T_{out}$ and $T_a$ are outlet temperature and threshold temperature, respectively, that define the plasma jet length.

In this demonstrated model, laminar plasma flow may correspond to a plasma jet length being proportional to an inlet gas flow length and inversely proportional to an outlet diameter. If the conditions for laminar flow are not met, then the jet length cannot be approximated using Equation 25.

Figure 29:
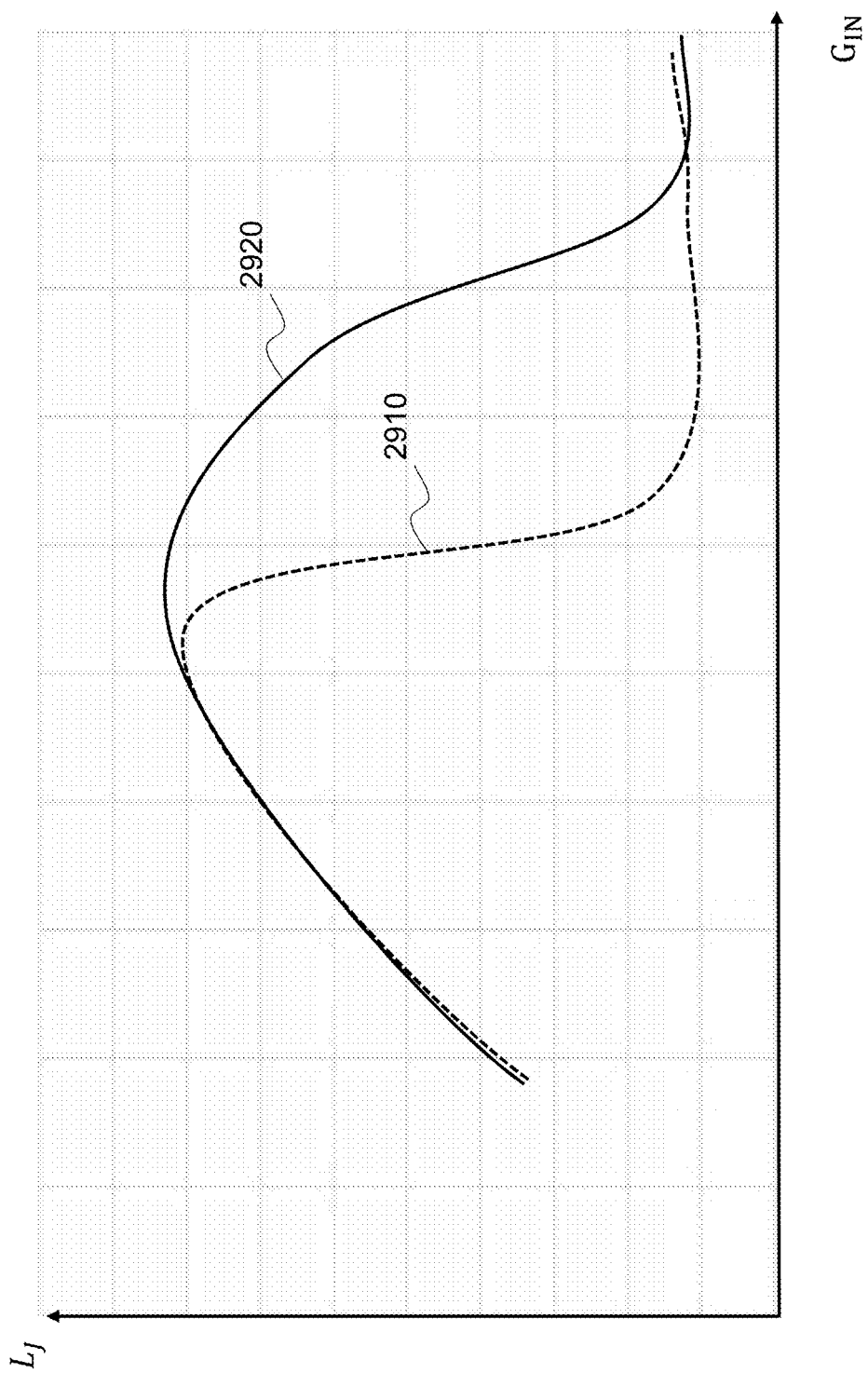
FIG. 29 is a plot of plasma jet length and inlet gas flow, according to an embodiment.

FIG. 29 is a plot of plasma jet length and inlet gas flow including experimental data of plasma jet length dependence on inlet gas flow. At relatively lower gas flow rates, the plasma flow may be in a laminar mode, and the plasma jet length be proportional to an increase of flow rate. At predetermined gas flow values, the plasma jet length may reach its maximum. Plasma flow may immediately shift to a turbulent mode (2910) with an abrupt drop of jet length or may have a transition region (2920) where the jet length slowly decreases, as shown in FIG. 29. Transitional region (2920) may include a relatively wide range of gas flow rates for predetermined parameters. For example, for an outlet diameter of about 0.5 mm and an outlet temperature of about 12,200 K, the maximum jet length may correspond to a gas flow of about 0.17 l/min and $L/d_{out}$ of about 90. In some embodiments, the ratio $L/d_{out}$ may decrease to about 60 when the flow rate increases about three times. A transitional region of plasma jet having a predetermined ratio $L/d_{out}$ may be used for radial expansion of the plasma jet since its behavior is not substantially different from laminar mode and the conditions of the described kinematic model may be met.

In some embodiments, for interpolation of experimental data for various outlet diameters, temperature and inlet gas flow, the following empirically derived equation is given:

$$L_j = \frac{A^*(T_{out})}{d_{OUT}^p} G_{IN} \quad (26)$$

where $A^*(T_{out})$ is a function of temperature that may be smoothly interpolated between measured values for a predetermined range of temperatures.

Equation 26 uses empirical index p for outlet diameter to address nonuniform radial distribution of temperature in the plasma jet. As discussed herein, a plasma jet ratio $L/d_{out}$ may be more than 25 in some embodiments. Thus, a maximum outlet diameter for the fixed value of inlet gas flow and outlet plasma temperature may be given by:

$$d_{OUT}^{max} = p + 1 \sqrt{\frac{G_{IN} A^*(T_{out})}{25}} \quad (27)$$

Figure 30:
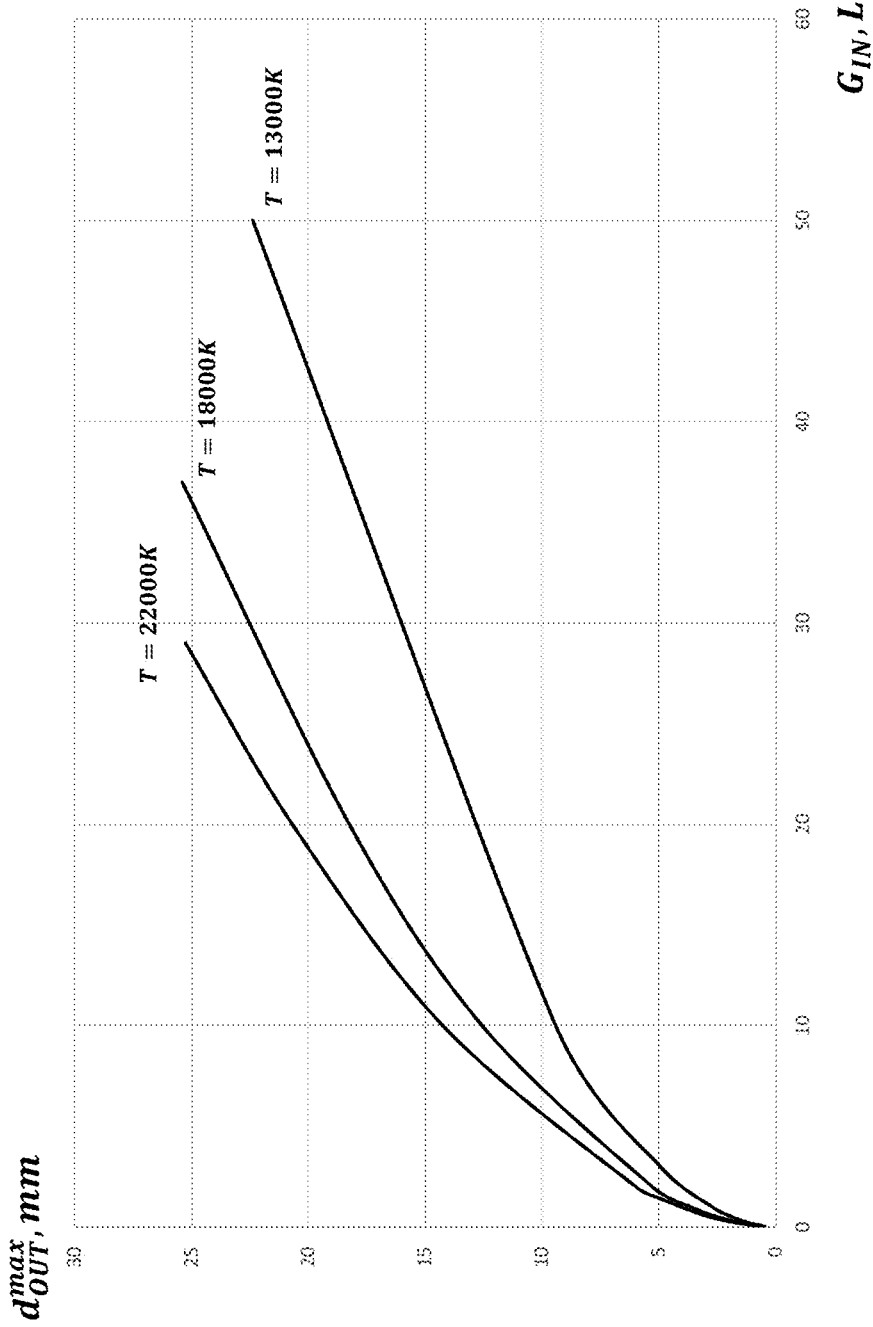
FIG. 30 is a plot of dependence of maximum outlet diameter on inlet gas flow for various outlet temperatures, according to an embodiment.

FIG. 30 shows dependence of maximum outlet diameter on inlet gas flow for various outlet temperatures. In some embodiments, the maximum diameter may be higher for a higher temperature. However, gas flow rates for pulse plasma and base plasma for oscillating outlet temperature may not be equal to the inlet gas flow rate $G_{IN}$, as shown in Equation 27. The actual gas flow rate for pulse plasma may be lower than for base plasma, as shown in Equations 12 and 13. The maximum outlet diameter may limit the minimal velocity of the plasma jet. In some embodiments, the average outlet velocity may be estimated based on the gas flow rate:

$$<U_{min}> = \frac{G_{IN}}{\rho \frac{\pi (d_{OUT}^{max})^2}{4}} \quad (28)$$

In some embodiments, the radial distribution of velocity for a small outlet diameter may be estimated as parabolic, and the axial velocity may be related to an average velocity by the expression $U_{axial}=1.5\ U_{average}$. A more accurate estimation of a relation between axial and average velocities may be based on a radial distribution of outlet temperature. In some embodiments, the relation between axial and average velocities may be calculated using Eq. 17:

$$\frac{U_{average}}{U_{axial}} = \frac{\frac{8}{d_{out}^2} \int_0^{d_{out}/2} a(T(r)) r dr}{a(T_{axial})} \quad (29)$$

In some embodiments, ranges for the period of outlet temperature-time profile may be determined based on minimal jet velocity conditions. As described herein, the period of temperature oscillation may be less than a development time of the plasma jet. In some embodiments, the maximum duration of a base plasma or pulse plasma may be limited by the time necessary to form the plasma jet having a maximum length. In some embodiments, the maximum plasma jet length with predominant radial expansion for the minimal velocity may be $L=25^* d_{OUT}$. Assuming that the average axial pulse plasma flow speed $U_{pulse}^a$ may be about one half of the pulse plasma speed at the outlet, then the pulse plasma flow length may be estimated as $L=D^*U_{pulse}^a{}^*T=0.5^*D^*U_{pulse}^*T$. Thus, the period restrictions may be given by:

$$T \leq \frac{25 * d_{OUT}}{D * 0.5 * U_{pulse}} \quad (30)$$

Combining with Eq. 28, the estimation of period may be rewritten as:

$$T \leq \frac{\pi \rho A^*(T_{out})}{d_{OUT}^p} \quad (31)$$

Figure 31:
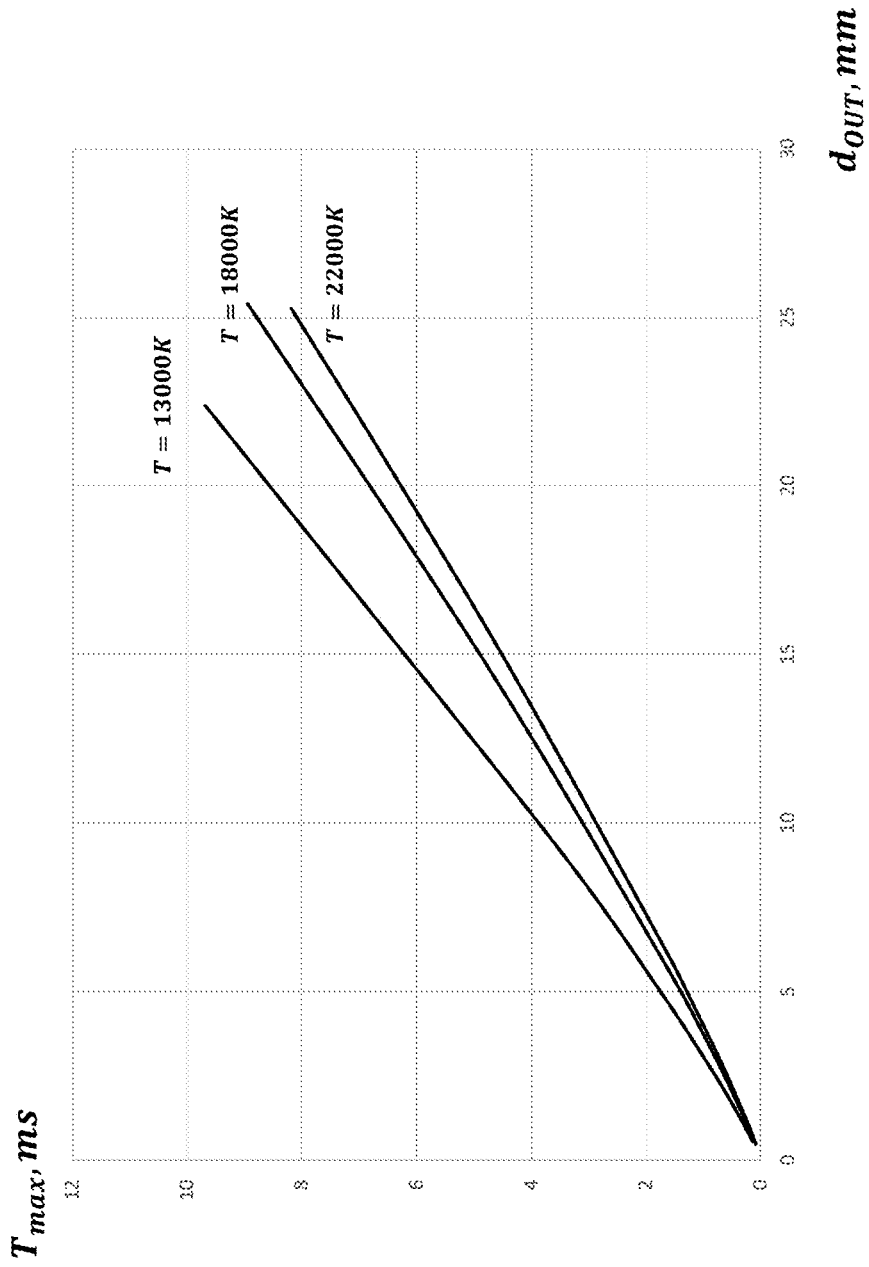
FIG. 31 is a plot of dependence of maximum period on outlet diameter for various outlet pulse temperatures, according to an embodiment.
Figure 32:
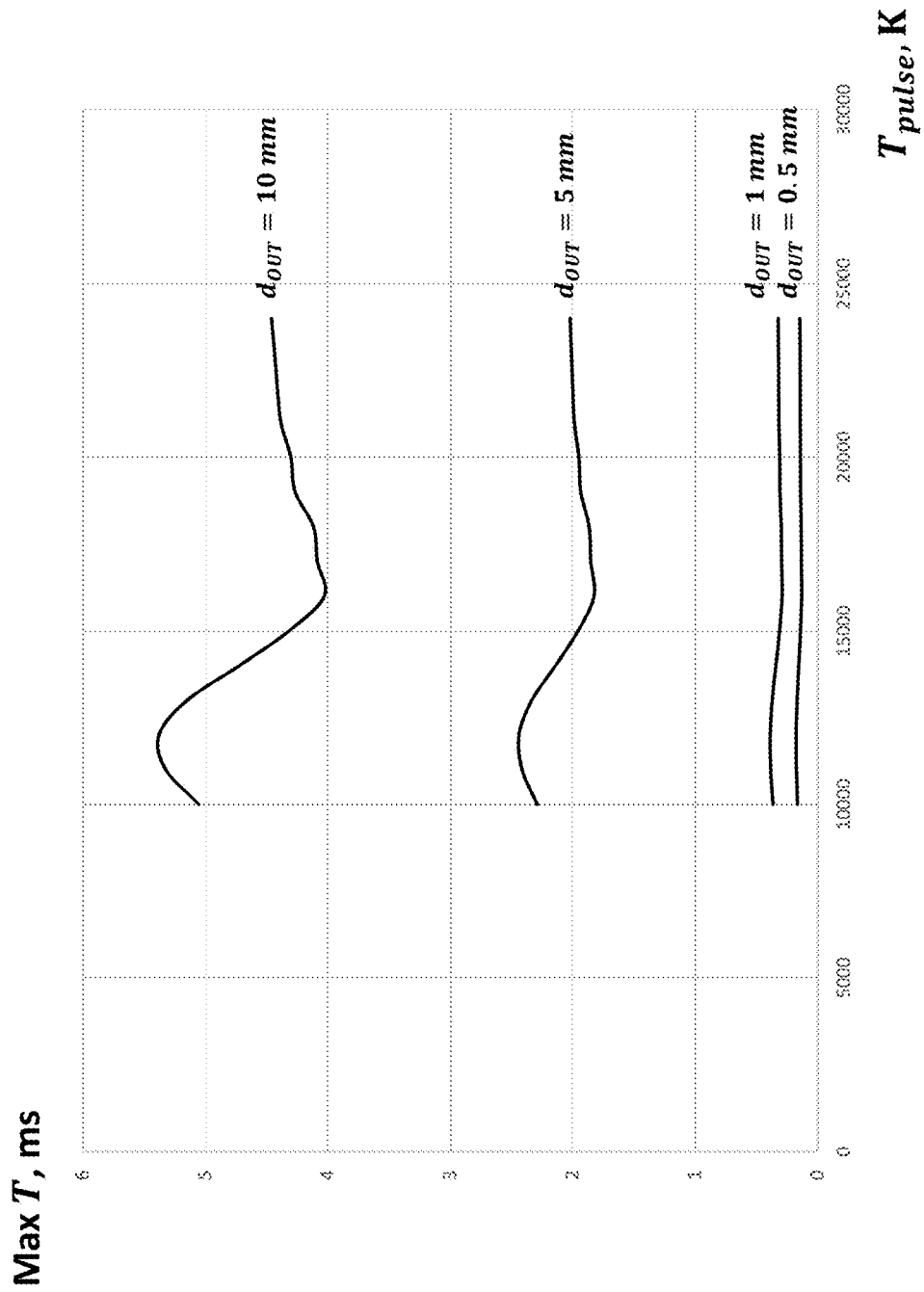
FIG. 32 is a plot of dependence of maximum period on outlet pulse temperature, according to an embodiment.
Figure 33:
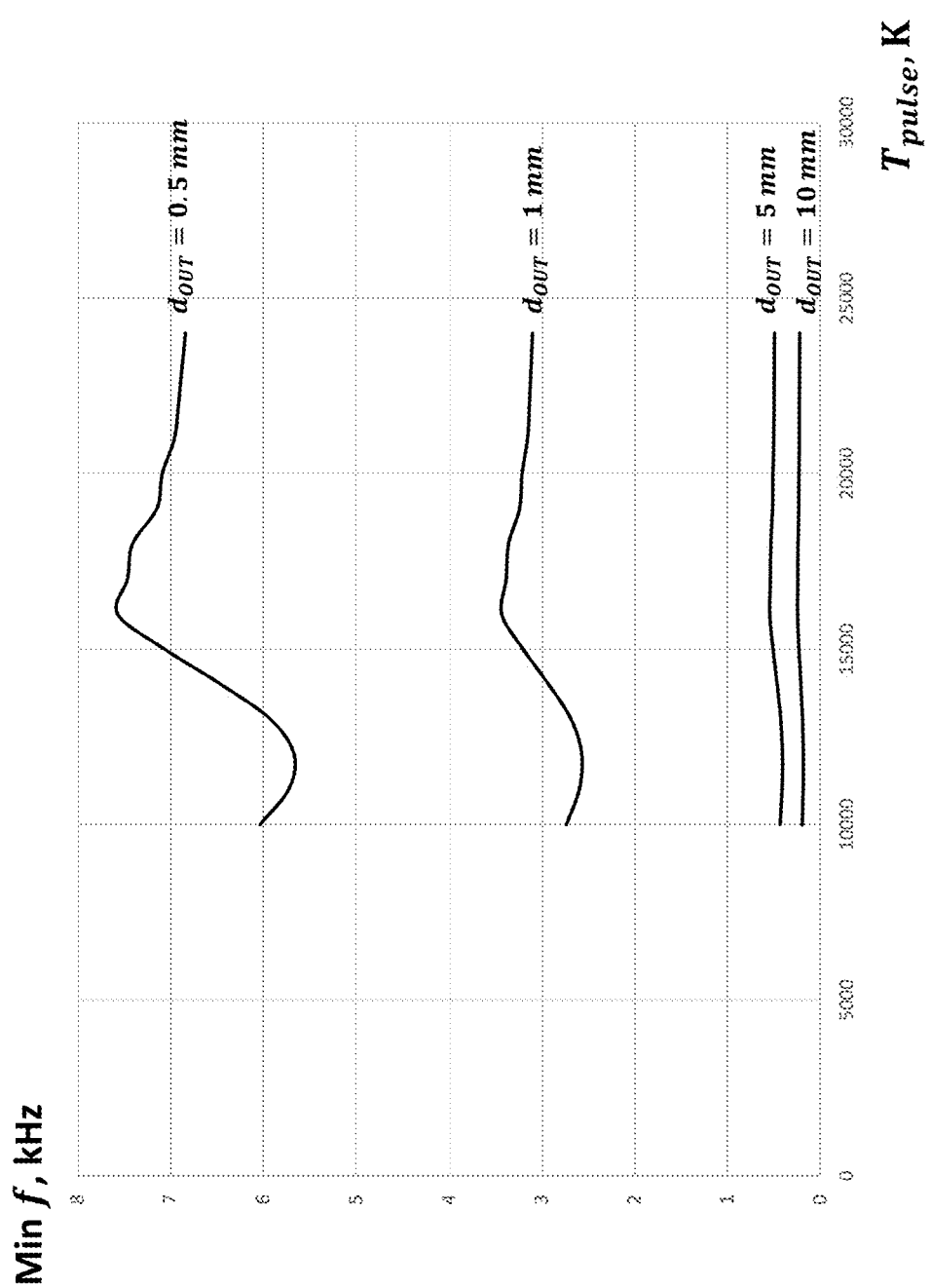
FIG. 33 is a plot of dependence of minimum frequency on outlet pulse temperature, according to an embodiment.

FIG. 31 is a plot of dependence of maximum period on outlet diameter for various outlet pulse temperatures. FIG. 32 is a plot of dependence of maximum period on outlet pulse temperature. FIG. 33 is a plot of dependence of minimum frequency on outlet pulse temperature. For a fixed outlet diameter and a range of pulse temperatures, FIG. 32 and FIG. 33 illustrate the maximum period and corresponding minimum frequency of outlet temperature oscillations to provide conditions for radial expansion of resulting plasma jet.

It should be noted that the obtained restrictions apply where the plasma flow is in a laminar mode (e.g., laminar) and in certain cases in a transition mode for a set of predetermined input parameters. Table 1 lists a set of period and frequency relationships for various temperatures.

TABLE 1

Maximum period and minimum frequency relationships.

| $T_{out}$, K $d_{OUT}$, mm | 13,000K $T_{max}$ | 18,000K $T_{max}$ | 22,000K $T_{max}$ | 13,000K $f_{min}$ | 18,000K $f_{min}$ | 22,000K $f_{min}$ |
|---|---|---|---|---|---|---|
| 0.5 | 170 μs | 135 μs | 140 μs | 5.9 kHz | 7.4 kHz | 6.9 kHz |
| 1 | 370 μs | 300 μs | 320 μs | 2.7 kHz | 3.4 kHz | 3.1 kHz |
| 5 | 2.3 ms | 1.9 ms | 2 ms | 430 Hz | 540 Hz | 500 Hz |
| 10 | 5.1 ms | 4.1 ms | 4.4 ms | 190 Hz | 240 Hz | 230 Hz |
| 25 | 14.6 ms | 11.7 ms | 12.6 ms | 70 Hz | 90 Hz | 80 Hz |

In some embodiments, conditions for a flow to remain laminar may be based on the Reynolds number. The Reynolds number, Re, corresponds to whether a flow tends to be laminar or turbulent. In some embodiments, the Reynolds number for output parameters of the plasma flowing from a plasma-generating device may be given by:

$$\text{Re} = \frac{g_{out} d_{OUT}}{\mu}, \quad (32)$$

where $g_{out}$ is outlet plasma mass flux, $\mu$ is the dynamic viscosity of plasma, and $d_{OUT}$ is the outlet diameter.

In some embodiments, for cylindrical flows, which may be preferable for certain applications, Re*=2000. In a real plasma-generating device, other factors may introduce fluctuations of generating parameters. As a result, reducing the Reynolds number may correspond to a turbulent flow transition. In some embodiments, a critical Reynolds number may be in range between about 200 and about 2000.

In some embodiments, the fixed outlet temperature and the Reynolds number may be proportional with a value of outlet diameter based on a comparison of equations 27 and 32. As a result, at a predetermined value of a maximum outlet diameter and corresponding inlet gas flow rate, a Reynolds number may exceed a threshold (e.g., critical value) for a laminar mode. Thus, for a predetermined outlet temperature, a maximum outlet diameter and relatively higher diameter values may results in turbulent flow. For example, for temperatures in a range between about 13,000 K and about 22,000 K, and a critical Reynolds number of 2,000, the maximum possible outlet diameter may be about 130 mm and about 30 mm.

Figure 34:
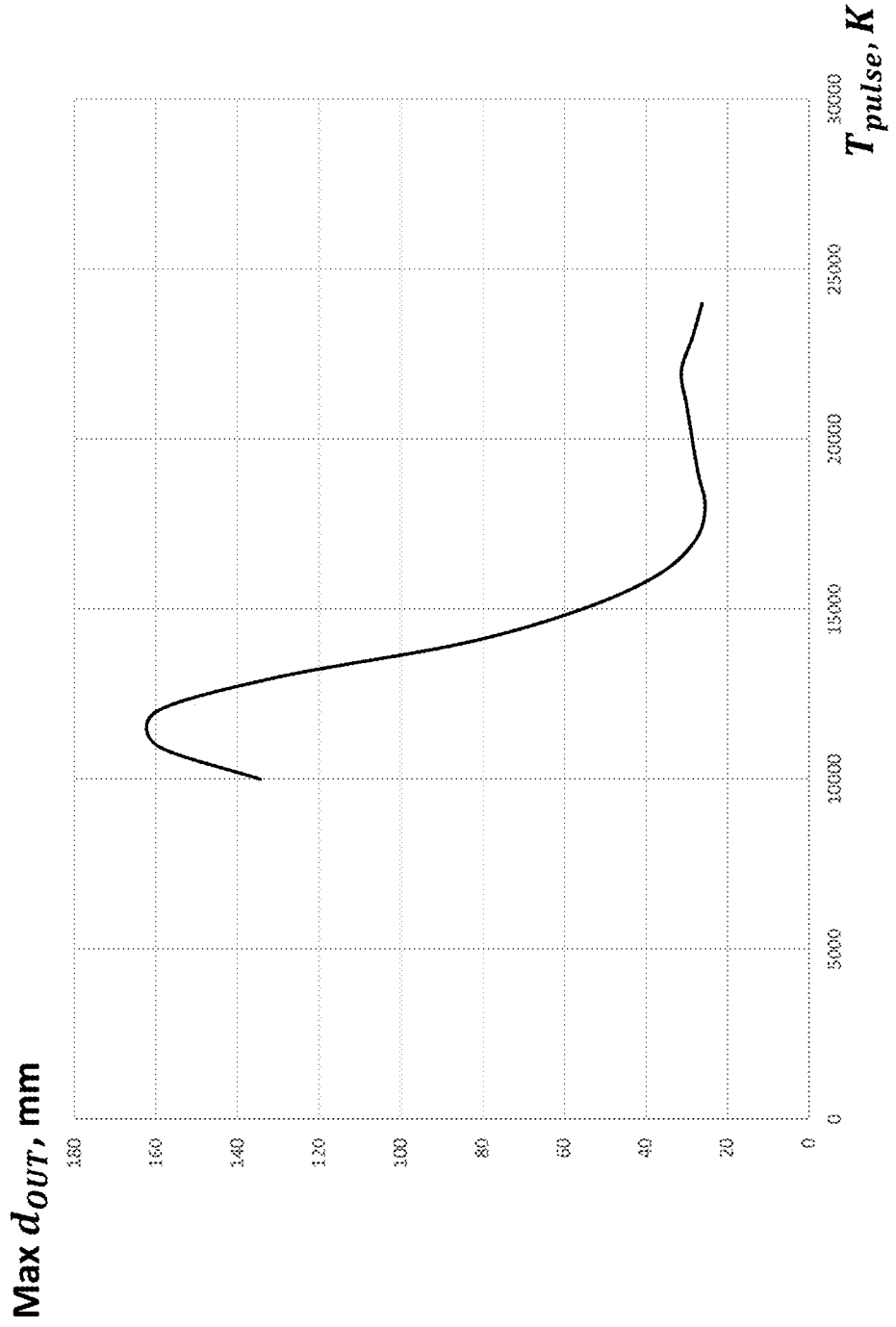
FIG. 34 is a plot of dependence of maximum outlet diameter on outlet pulse temperature, according to an embodiment.

FIG. 34 is a plot of dependence of maximum outlet diameter on outlet pulse temperature, according to an embodiment. For example, FIG. 34 illustrates a maximum outlet diameter based on Eq. 27 when a Reynolds number reaches a value of about 2,000. For higher values of outlet diameter, the resulting plasma flow is in an undesirable turbulent mode.

For a predetermined outlet diameter and outlet plasma temperature, a Reynolds number may limit the maximum mass flux for laminar flow. Alternatively, the mass flux may be based on gas flow rate and outlet diameter. Thus, Eq. 32 may be given by:

$$\text{Re} = \frac{G}{\frac{\pi d_{OUT}}{4} \cdot \mu} \quad (33)$$

where G is a gas flow rate which is equal to inlet gas flow rate $G_{IN}$ in case of constant outlet temperature.

In some embodiments, the actual gas flow rate may be separately calculated for pulse plasma and base plasma for cases involving oscillating outlet temperature, as shown in Equations 12 and 13. A dynamic viscosity μ may be defined by a plasma temperature. According to Eq. 33, there may be a maximum gas flow rate corresponding to the predetermined outlet diameter and plasma temperature.

Figure 35:
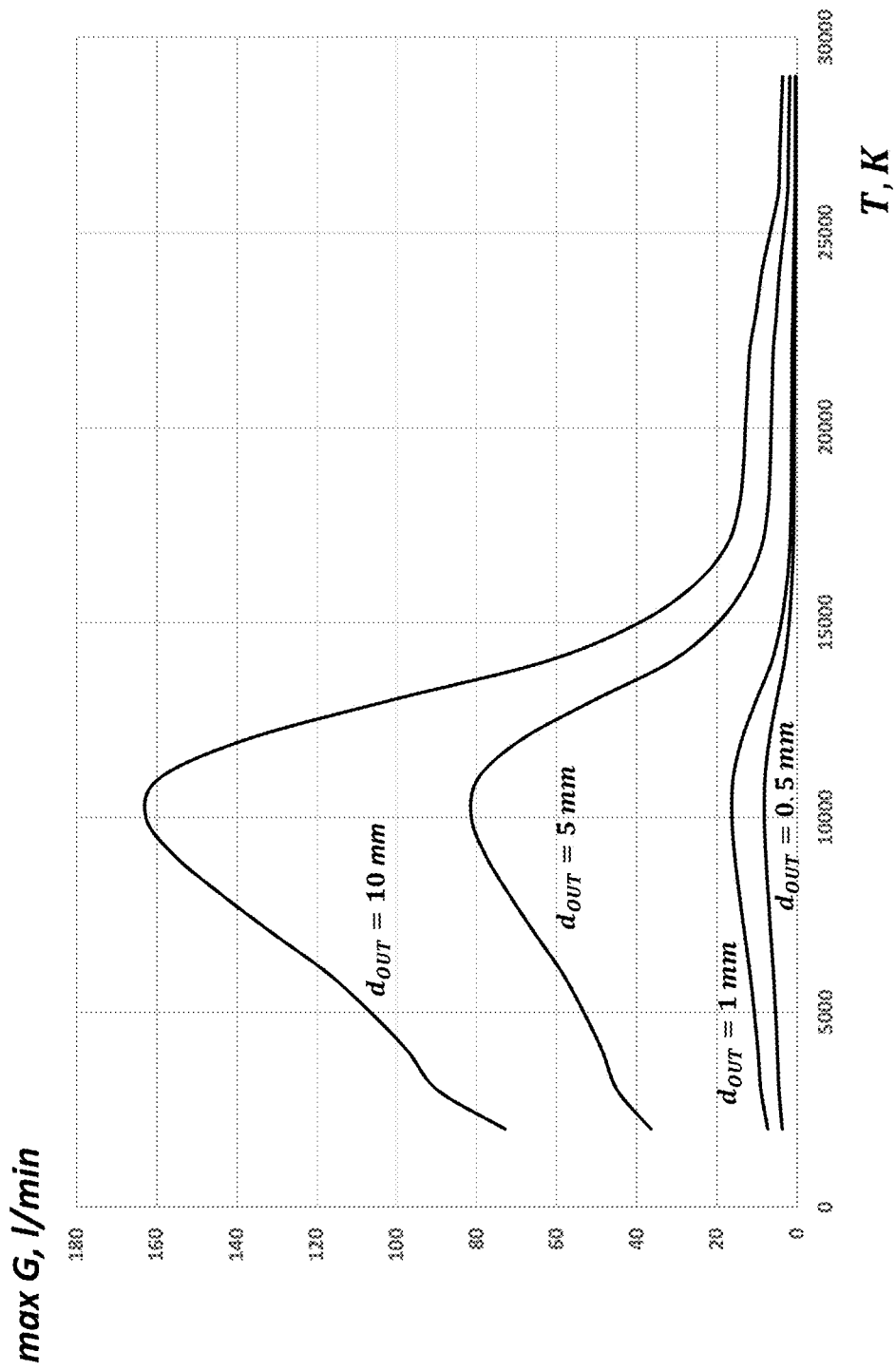
FIG. 35 is a plot corresponding to a critical gas flow rate for a Reynolds number of 2000, according to an embodiment.

FIG. 35 is a plot corresponding to a critical gas flow rate for Reynolds number of about 2000. In some embodiments, outlet gas flow may be less than a calculated critical gas flow rate to avoid turbulent mode of plasma flow. As illustrated in FIG. 35, a maximum gas flow rate may increase with higher outlet diameters. Combining Equations 12, 13, and 33, a maximum inlet gas flow rate may be limited to avoid turbulent mode based on the following equations:

$$G_{IN} < \text{Re}^* \cdot \frac{\pi d_{OUT}}{4} \cdot \mu(T_{base}) \cdot \left( D \sqrt{\frac{T_B}{T_P}} + (1-D) \right) \quad (34)$$

$$G_{IN} < \text{Re}^* \cdot \frac{\pi d_{OUT}}{4} \cdot \mu(T_{pulse}) \cdot \left( D + \sqrt{\frac{T_P}{T_B}} (1-D) \right) \quad (35)$$

In some embodiments, inlet gas flow may have a lower limit defined by a minimum working pressure for maintaining a plasma flow. Based on Eq. 10, the lower limit may be estimated based on a mass flux in the heating channel. Experimental data may suggest that a mass flux of at least about 10 kg/m²s is needed to generate laminar plasma flow. Thus, the minimum inlet gas flow rate may be given by:

$$G_{IN} \geq K \cdot \frac{\pi d_H^2}{4} \left( D + \sqrt{\frac{T_P}{T_B}} (1-D) \right) \quad (36)$$

where K is an empirically measured constant of about 10 kg/m²s, and $d_H$ is a diameter of a heating channel.

In some embodiments, the heating of base plasma by pulse plasma in the area of overlap may be a parameter of a base-pulse plasma flow interaction model. For example, the collision probability may rapidly drop when a difference in the flow speed is not substantial. This may be another reason why the collision probability drops when the base-target interaction occurs in stage III. An energy balance equation for the base plasma flow heated by the pulse plasma flow electrons may be given by:

$$\rho C_P \frac{dT}{dt} = \frac{3}{2} \delta \nu n_e k (T_i - T) \quad (37)$$

where ρ is the density of the base plasma, $C_p$ is heat capacity of the base plasma, δ is the average fraction of energy that an electron transfers to a colliding heavy particle of the base plasma flow, $n_e$ is the electron density of the pulse plasma flow, and k is the Boltzmann constant.

For a boundary condition:

$$t = 0; T(0) = T_{base}; \text{ and } a = \rho C_P; b = \frac{3}{2} k v n_e \delta, T(t)$$

may be given by:

$$T(t) = T_{pulse}\left[1 - \exp\left(-\frac{b}{a}t\right)\right] + T_{base}\exp\left(-\frac{b}{a}t\right) \tag{38}$$

A duration of time $t_F$ to increase the temperature of target flow to $2T_T$ may be given by:

$$t_F = -\frac{a}{b}\ln\left(\frac{T_{pulse} - 2T_{base}}{T_{pulse} - T_{base}}\right) \approx \frac{0.2 \times \rho \times C_P}{k \times \delta \times v_{ea} \times n_{epulse}} \tag{39}$$

In some embodiments, the time period $t_F$ may be a characteristic time to heat the base plasma flow, and may thereby significantly decrease the collision probability. In some embodiments, the minimum frequency to avoid heating of target plasma flow may be estimated based on the above equations. In some embodiments, the calculated minimum frequency may be a function of base plasma flow temperature as illustrated in FIG. 36.

Figure 36:
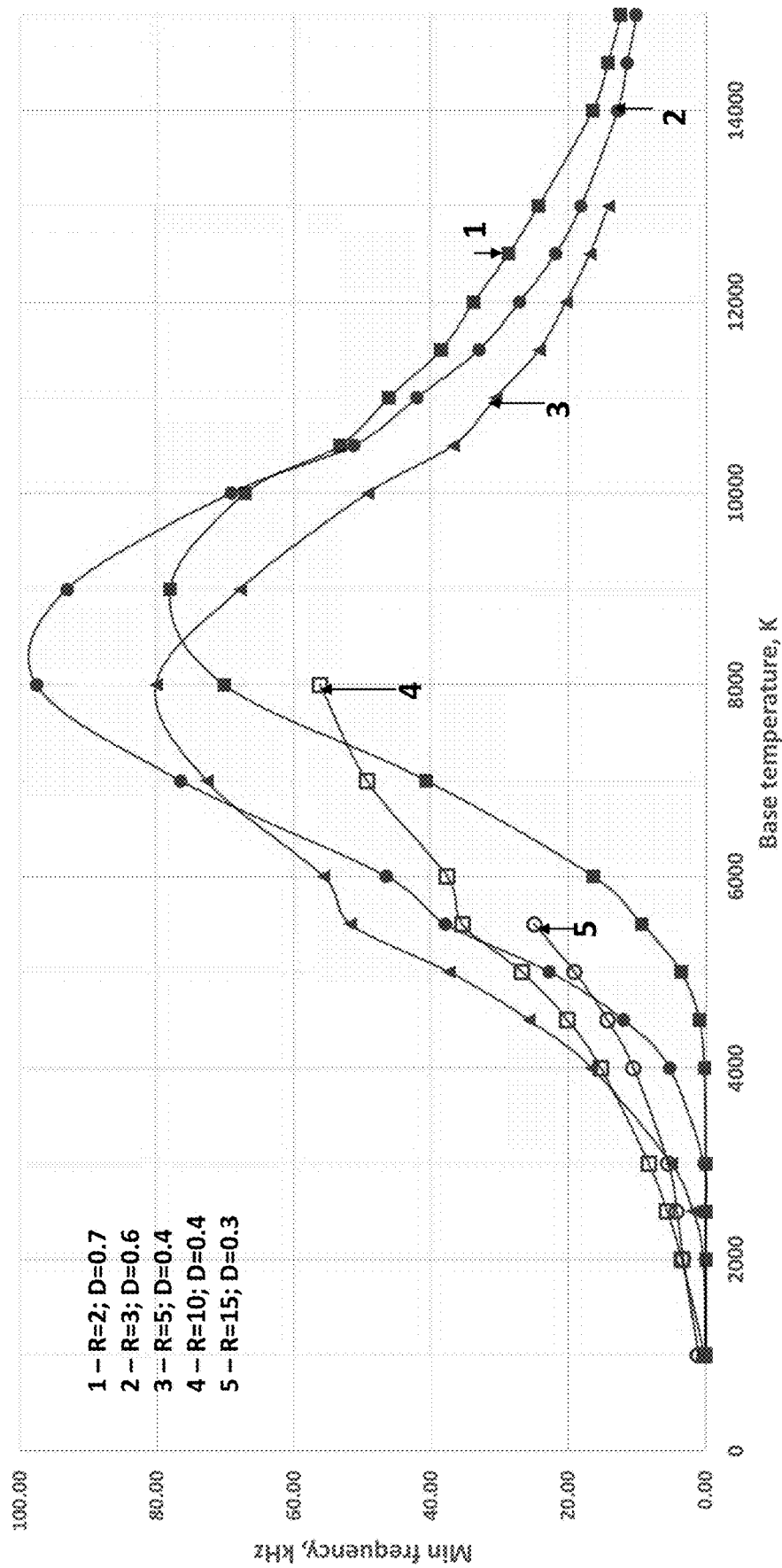
FIG. 36 is a plot corresponding to frequency relationships for avoiding significant heating of low intensity plasma, according to an embodiment.

FIG. 36 is a plot corresponding to frequency relationships to avoid significant heating of low intensity plasma. The curves shown in FIG. 36 are calculated for pulse plasma flow temperatures corresponding to a set of density ratios. In some embodiments, the heating of base plasma by pulse plasma occurs in the area of overlap. When radial expansion conditions are met, the affected base plasma particles may propagate radially to reduce interaction with pulse plasma. As a result, the actual characteristic time of when a difference between base plasma and pulse plasma becomes insufficient to provide the desired degree of radial expansion may be expected to be higher than the time obtained in Eq. 39. The experimental data for an outlet diameter between about 0.5 mm and about 1.5 mm shows radial expansion of a plasma jet for frequency of at least about 4 kHz.

The kinematic criteria described herein has two underlying assumptions of a rectangular temperature-time profile and the occurrence of base-pulse plasma flow interactions at stage I of front propagation ($f > 1/\tau_L$). These conditions may not be optimal for generating predominant radial expansion of the plasma flow. In some embodiments, maximizing the collision probability (characterized by the density ratio) and maximizing the interaction zone of the two flows (characterized by the pulse duty cycle of rectangular pulses) may increase the predominant radial expansion of the plasma flow. However, maximizing both features simultaneously may be difficult due to implied constraints. However, experimental results may improve parameter optimization.

In some embodiments, density profiles for laminar base plasma flow and pulse plasma flow may be compared, as shown in FIG. 16. The density ratio may increase substantially in a distal end of the active zone. As a result, the density ratio in this region may be increased while a pulse plasma flow outlet temperature is maintained, to thereby satisfy an equal length condition of the plasma flows. In some embodiments, the pulse plasma flow may collide with base plasma flow at stage II or III of the base plasma flow front propagation, i.e. at lower frequencies (see FIGS. 37B and 37C). Interaction at stage III may be ignored for predominant radial expansion because the base plasma flow has mixed with air at stage III. However, optimizing parameters in this manner may increase the probability of collision at stage II.

In some embodiments, a temperature-time profile may have a more complex waveform than a rectangular pulse in order to increase an interaction zone and maintain a relatively high density ratio of base plasma and pulse plasma flows. FIGS. 38A-38F illustrate several examples of illustrative temperature-time profiles configured to increase radial expansion while minimizing the time-volume of the axial component of the base plasma flow. In FIG. 38D, the pulse may include several decreasing temperature steps. Initially, the pulse has a relatively high temperature to ensure a relatively high density ratio. Then, the pulse temperature may decreases by several smaller steps. FIG. 38A depicts the corresponding axial plasma component in the active-zone/time coordinates. The pulse plasma flow front speed may decrease, thus efficiently prolonging the time when the pulse plasma flow reaches the length of the target plasma flow. Therefore, the volume of the base-pulse plasma flow overlap may increase while maintaining a relatively high density ratio.

In some embodiments, an ideal temperature pulse curvature may: (1) increase an effective value of duty $D_{eff} = \tau_p/T$ to reduce the zone of axially propagated base plasma flow; and (2) increase the collision probability of plasma particles at various distances from the outlet by keeping the relatively high density ratio at different distances from the outlet during pulse plasma flow front propagation. FIG. 38E illustrates another pulse of a substantially parabolic shape that gradually goes from a maximum value to a predetermined value between the base plasma flow temperature and the pulse plasma flow temperature, and then steps down to the base plasma flow temperature. The corresponding axial plasma component is shown in FIG. 38B. In another example, the pulse may have the shape shown in FIG. 38F. The base plasma flow may be formed by a series of smaller pulses. After the initial spike to the pulse plasma temperature, the temperature may undergo a number of pulses. Each subsequent pulse may have a lower peak value and a lower bias value. FIG. 38C illustrates a corresponding axial component of the base plasma flow in the active-zone/time space. In some embodiments, the pulses may increase the duty cycle and increase the collision probability. The pulses shown in FIG. 38A-38C are exemplary pulses. In some embodiments, the shape of the pulse affects the degree of radially propagated plasma at different distances from the outlet.

In some embodiments, for some applications, an axial component at a distal end of the plasma flow may include length of the base plasma flow being substantially equal to a length of the pulse plasma flow. For these applications, the parameters may be optimized to shape the plasma flow in a desired way. In some embodiments, a degree of radial expansion may be characterized by the resulting shape of plasma flow. In some embodiments, for a laminar plasma flow with a constant temperature, the ratio of the average jet diameter to outlet diameter $D_J/D_{OUT}$ may be in the range of between about 2 to about 4, where $D_J$ may be an average plasma flow diameter, with the boundary between the plasma flow and the surrounding medium considered to be an about 1,000 K isotherm contour. In some embodiments, an average flow diameter of a plasma flow with predominant radial expansion may correspond to a $D_J/D_{OUT}$ ratio of about 5 to about 10. In some embodiments, a scale of axial plasma flow expansion may be defined by a $L_J/D_{OUT}$ ratio, which may be about 50 and about 100 for laminar plasma flow, and about 15 and about 50 for predominantly radially expanded plasma flow (e.g., temperature threshold is about 1,000 K for $L_J$). In some embodiments, a plasma flow length may be shorter if the temperature at the outlet or the flow of the plasma-generating gas is lower. Thus, the plasma flow length may be expressed as $L_J=\lambda D_{OUT}$, where $\lambda$ is a coefficient that depends on the outlet temperature and flux $\lambda(T, g)$. In some embodiments, a characteristic time of the plasma flow $\tau_d$ may be given by:

$$\tau_d = \frac{L_J}{U_J} = \frac{\lambda D_{OUT}}{U_J} \qquad (40)$$

In some embodiments, the resulting plasma flow length may define a "working distance" for a plasma-generating device. The term "working distance" may refer to a range of distances from an outlet of the plasma-generating device that achieves a desired effect on the surface being treated. In some embodiments, the plasma flow length may depend on the plasma flow speed, which may depend on distance due to cooling of the plasma flow by surrounding media such as air, and heating by the pulse plasma flow.

Figures 39A, 39B, 39C:
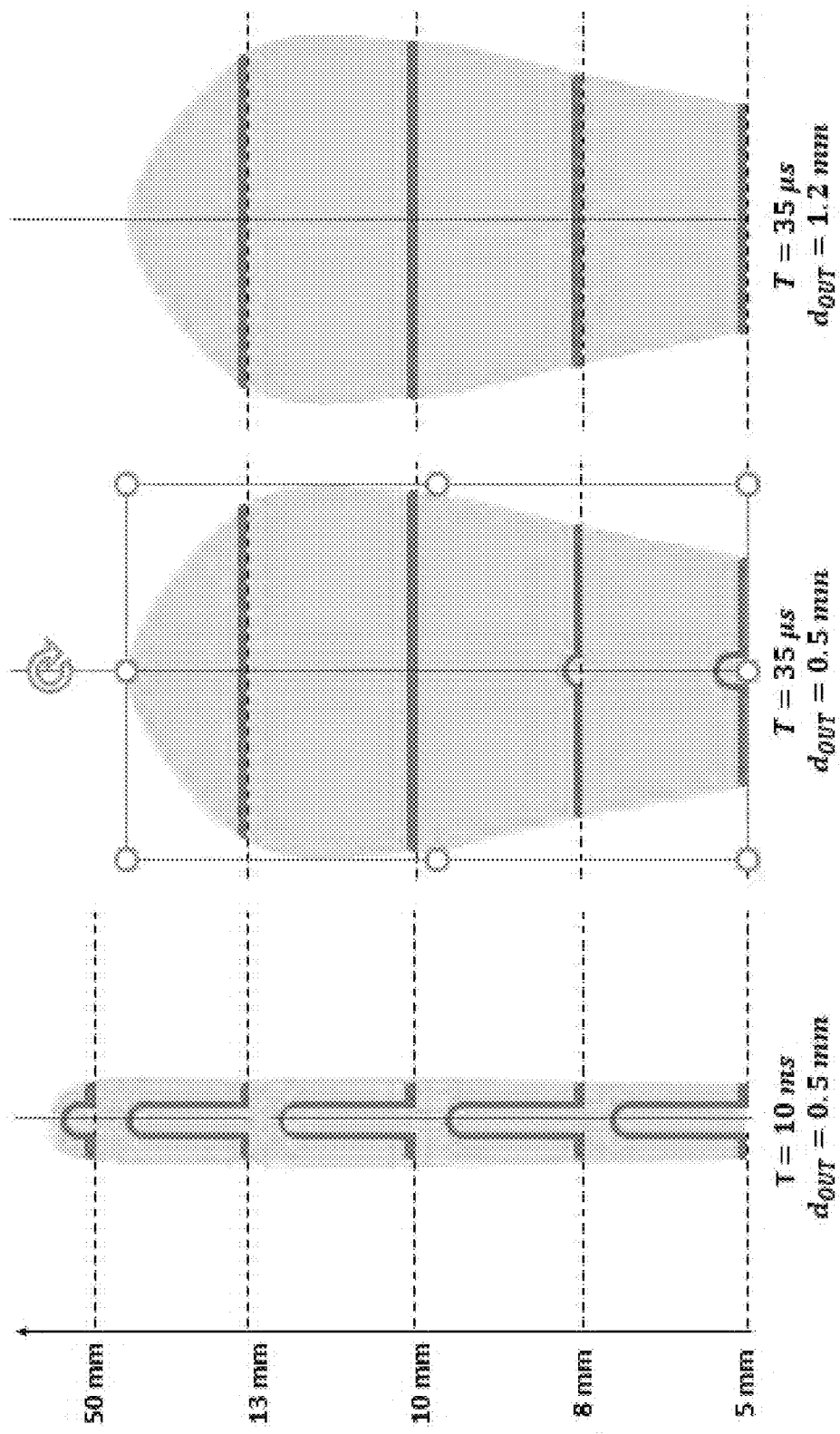
FIGS. 39A-39C are schematic diagrams of plasma flow and tissue, according to an embodiment.

FIGS. 39A-39C illustrates experimental validation of the effect of radial expansion of a plasma jet. In particular, FIGS. 39A-39C depict plasma flow generated with different conditions on tissue sample. After exposure of tissue sample to laminar plasma flow for a relatively short fixed period of time, as shown in FIG. 39A, two distinguishable regions may be visually detected. For example, an outlet diameter of the jet may be about 0.5 mm. A tissue crater may be formed at the intersection of a plasma jet axis and tissue surface. The depth of the crater may depend on the distance between the sample surface and nozzle of a plasma-generating device. In some embodiments, the crater may be formed due to tissue vaporization as a result of high temperature plasma flow. In some embodiments, a vaporization rate may be directly related to plasma temperature and mass flux. Since the plasma temperature may slowly decrease along the plasma jet axis, the depth of the crater may also decrease if the sample is exposed to the plasma flow for the same time interval. In some embodiments, plasma temperature may substantially decrease in a direction transverse to a plasma jet direction. As a result, areas of coagulated tissue surface may be observed next to the formed crater. For example, coagulation may be observed if local plasma flow temperature is higher than a predetermined value (e.g., about 70° C. for an exposure time of about 1 second to about 3 seconds). During this set of experiments, the tissue sample was located at different distances from the nozzle of the plasma-generating device. The geometric characteristics of the formed crater and coagulated tissue area were monitored. Tracking of these parameters enabled estimation of a plasma jet shape.

FIG. 39A illustrates a plasma flow with oscillating outlet temperature between about 6,000 K and about 14,000 K with an oscillation period of about 10 ms. As shown in FIG. 39A, a plasma jet length of about 50 mm and a diameter of coagulated area of 3 mm are observed. The crater observed in the middle indicates that the plasma flow temperature and mass flux are considerably high and correspond to a high vaporization rate of the tissue sample. This is an expected result for laminar plasma flow. FIG. 39B illustrates experimental data for plasma flow with the same conditions as for FIG. 39A but for an oscillation period of about 35 μs. According to the theoretical model described herein for generating a radially expanded plasma flow, the radial expansion of plasma jet may be observed for the corresponding frequency of outlet temperature oscillation (e.g., about 30 kHz). Indeed, as shown in FIG. 39B, the diameter of a coagulated area significantly increased up to about 20 mm, which is about 7 times larger than the observed diameter for laminar flow with the same temperature range of outlet plasma flow. Moreover, the plasma jet length decreased as expected in this example. The observed crater in FIG. 39B indicates that still there is a small fraction of axially propagated flow close to the nozzle. However, the depth of the crater may be substantially lower due to a lower fraction of axially propagated plasma flow.

FIG. 39C illustrates another example of plasma flow with predominantly radially expanded plasma flow. In this case, the outlet diameter may be about 1.2 mm and have a similar temperature range of outlet plasma flow with the same oscillation period of about 35 μs. The results reveal formation of coagulation area of about 20 mm without forming a crater for all distances in range from about 5 mm to about 15 mm. Therefore, a negligible or no fraction of axially propagated flow was observed for the tested distances. The results also show that a jet diameter in the radial expansion zone may be maintained with same temperature-time profile when an outlet diameter increased from about 0.5 mm to about 1.2 mm.

In some embodiments, an output thermodynamic parameter may include the temperature-time profile of the plasma flow temperature at the outlet. Specifically, a thermodynamic parameter may include a temperature relationship between the base and the pulse plasma and the frequency of oscillations between them. In some embodiments, a speed ratio may be directly related to the temperature. However, an absolute speed value for a predetermined plasma flow may depend on the ratio between ambient pressure and active chamber pressure, and whether the flow is choked or in a Rayleigh state. From a practical point of view, in some embodiments for predominantly radially expanded plasma flows, higher values of velocities may be more desirable. This desire may be attributed to the plasma length and the distance range of the plasma-generating device. In some embodiments, the plasma flow length may be estimated using $L=U_T T=U_T/f$ and the maximum value may be $L=\lambda(T, g)D_{OUT}$. In some embodiments, the maximum plasma flow length may be limited by the absolute value of outlet plasma speed and outlet diameter. The maximum possible speed that may be achieved may be the speed of sound at a predetermined temperature of the plasma-generating gas without an adaptive outlet nozzle. When working pressure is higher than critical pressure, the outlet speed may achieve M>1 with an adaptive outlet nozzle, where M is a Mach number. Moreover, in some embodiments, frequency relationships might also limit the working distance. Therefore, the outlet flow may be in a choked state to achieve the speed M>1. Thermodynamically, this means that the flux or working pressure may be higher.

In some embodiments, predetermined ranges of thermal energy (e.g., gas mass flow) may be delivered (for a specific application) to the surface being treated. In some of these embodiments, the working distance may not be increased by increasing pulse plasma temperature. If the required working distance is desired to be increased without changing the plasma-generating gas mass flow, the base plasma flow temperature may have low-frequency oscillation between two or more temperatures, with each level having a corresponding temperature-time profile. An example of such a temperature-time profile is shown in FIG. 40.

Figure 40:
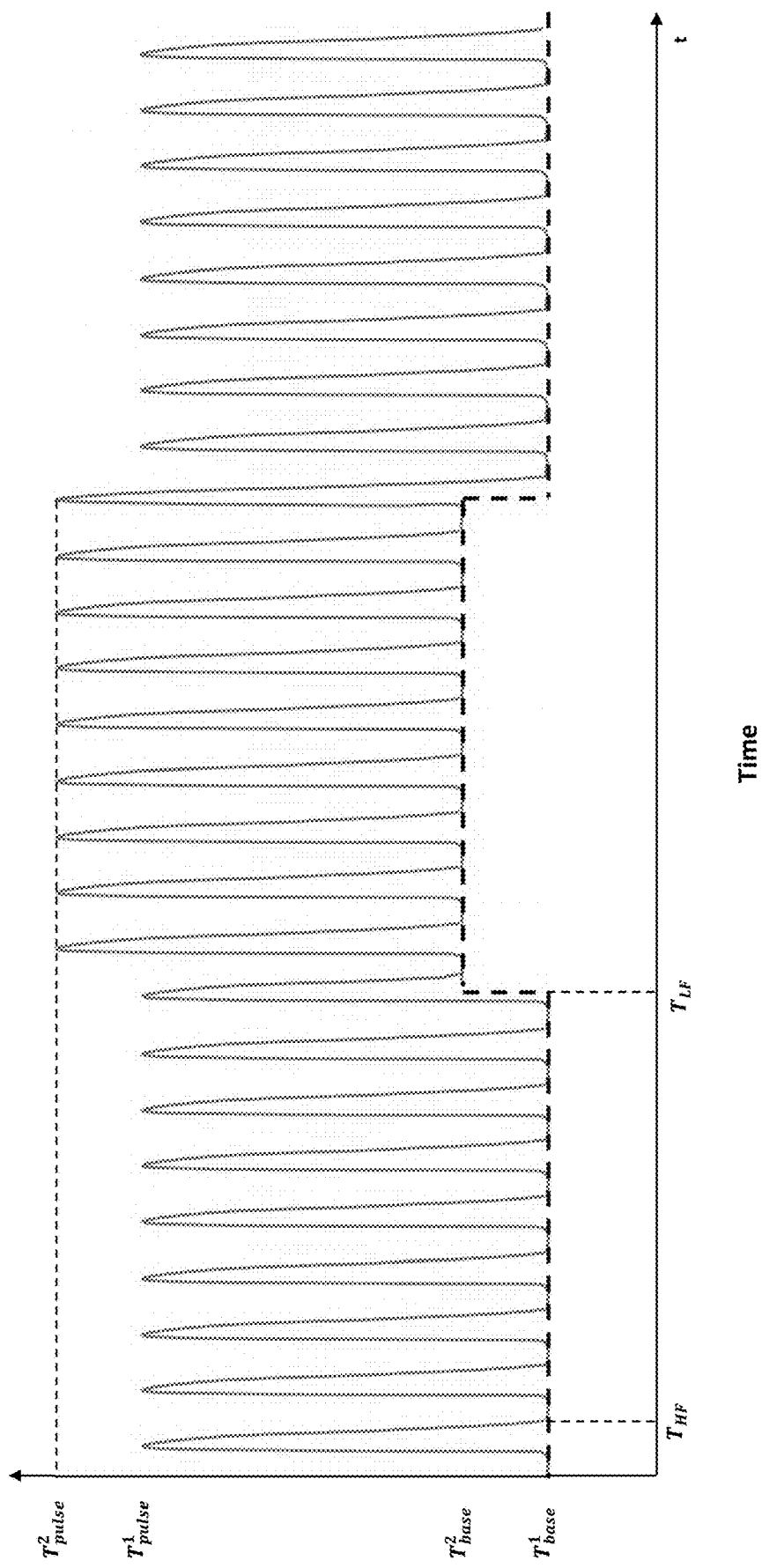
FIG. 40 is a plot of amplitude and time for oscillation outlet temperature, according to an embodiment.
Figure 41:
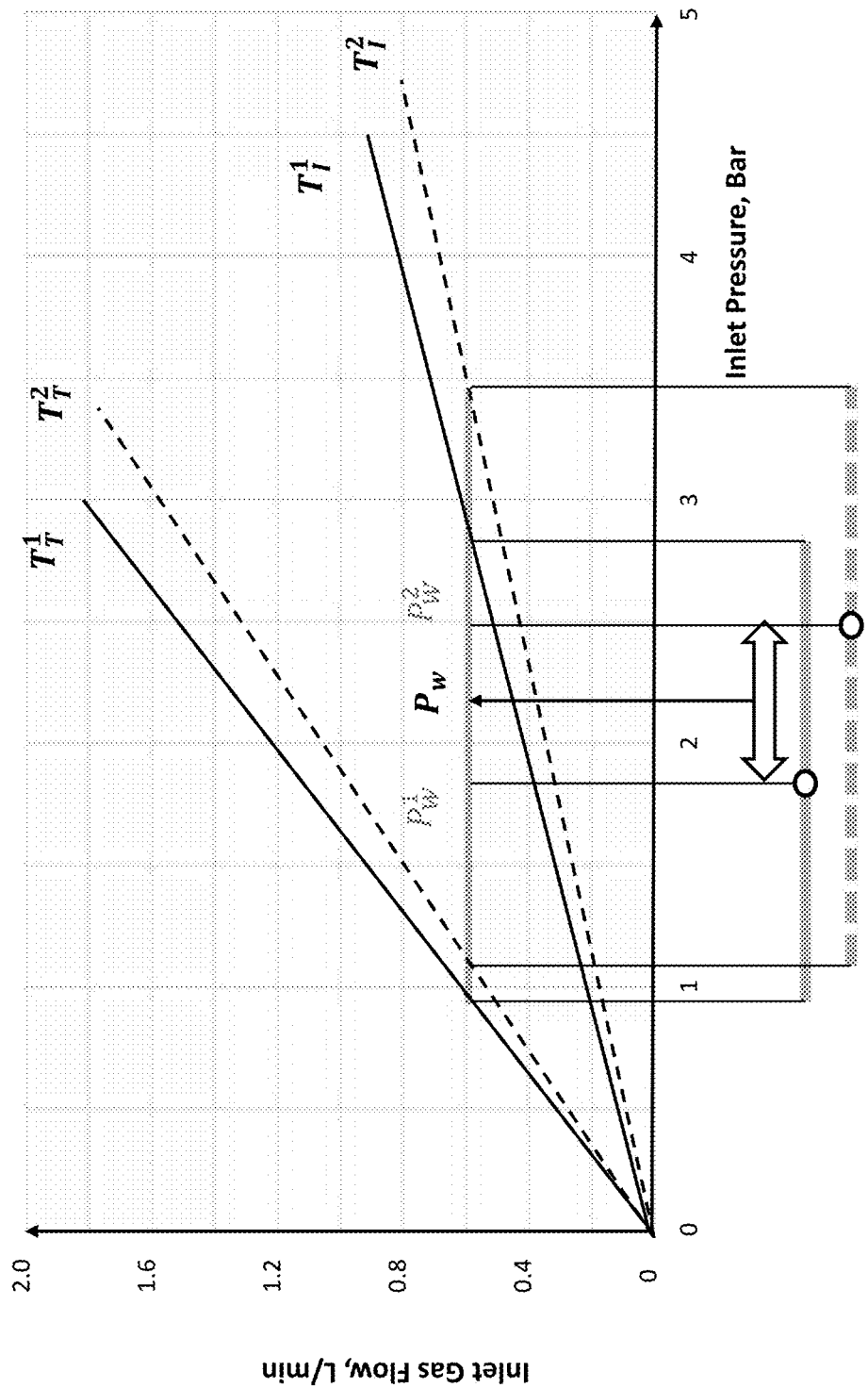
FIG. 41 is a plot of inlet gas flow and inlet pressure for boosting working pressure by oscillation of outlet temperature with two levels of amplitudes and frequencies, according to an embodiment.

In FIG. 40, the temperature oscillates between base plasma flow temperature $T_{base}$ and the pulse plasma flow temperature $T_{pulse}$ temperatures with high frequency $f_{HF}=1/T_{HF}$. The base plasma flow temperature oscillates between $T_{base}^1$ and $T_{base}^2$, and the pulse flow temperature oscillates between $T_{pulse}^1$ and $T_{pulse}^2$ with lower frequency $f_{LF}=1/T_{LF}$, respectively. The resulting composite temperature-time profile includes the first temperature-time profile that operates on $(T_{base}^1, T_{pulse}^1)$ oscillations and frequency $f_{HF}$ and a second temperature-time profile that operates on $(T_{base}^2, T_{pulse}^2)$ oscillation. The working pressure of the plasma flow generated as a result of this composite profile can be calculated as shown in FIG. 41. FIG. 41 is a plot of inlet gas flow and inlet pressure for boosting working pressure by oscillation of outlet temperature with two levels of amplitudes and frequencies. In some embodiments, if $P_w^1$ and $P_w^2$ are the working pressures for the first constituent temperature-time profile and the second constitute temperature-time profile, the resulting inlet pressure is between $P_w^1$ and $P_w^2$. In some embodiments, if a duty of low frequency pulses is $D_{LF}$, then the inlet pressure may be obtained using the equation:

$$P_w = P_w^1 + D_{LF}(P_w^2 - P_w^1) \qquad (41)$$

Equation (41) may be derived from equation (5). As a result of such low frequency pulses, the working pressure $P_w$ may be higher than if it would be for the first temperature-time profile. Similar considerations are true for the region $(T_{base}^2, T_{pulse}^2)$, but the working pressure $P_w$ may be lower than if it would be for the second temperature-time profile. In some embodiments, the inlet pressure may affect the flow length. For a first interval 154, the plasma flow length may be higher than it would have been had the first temperature-time profile been used by itself. The resulting composite profile may result in the plasma flow that "superimposes" the elongated flow that would result if the first temperature-time profile is used by itself and possibly shortened flow that would result if the second temperature-time profile is used by itself. Moreover, since plasma flow speed may be generated as a result of the composite, the temperature-time profile may have different speeds of base and pulse plasma flows compared to the plasma flows generated by the application of the first temperature-time profile or second temperature-time profile individually.

In some embodiments, the distribution of radial expansion along the flow axis may be changed. Therefore, the active zone may also change compared to the plasma flow, as compared to the flows generated as a result of the first and second time-temperature profiles applied individually. Overall, modulating the outlet plasma flow temperature with several characteristic frequencies and amplitude levels as described herein may be used to adjust the working pressure to a predetermined value to configure the shape of the plasma flow to achieve a predetermined effect for a predetermined application.

EXAMPLES

The following examples illustrate how the shape of a plasma jet may depend on a set of parameters. Unless specified otherwise, the temperature-time profile in these examples may have a rectangular shape of pulses, for example, as shown in FIG. 9.

Example 1

Figure 42A:

Example 1 includes a gas inlet flow of about 0.5 L/min, a diameter of a heating portion of about 0.4 mm, an outlet diameter of about 0.5 mm, a base or target temperature of about 3,000 K, and a period of outlet temperature-time oscillation of about 25 µs. The duty may be set to about 0.5 as a compromise for reasonable density and velocity ratio of target and initiator flows, as shown in FIG. 25. The initiator temperature may be equal to about 13,400 K for the same volume of target and initiator plasma flow. The resulting plasma jet shape is schematically illustrated in FIG. 42A.

Example 2: Frequency or Period of Outlet Temperature-Time Oscillation

Figure 42B:
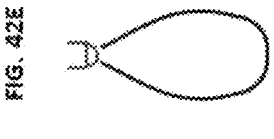

For the same conditions as in Example 1, but with a period of outlet temperature-time oscillation T of about 50 µs, the resulting plasma jet shape is schematically illustrated in FIG. 42B. The increase of period leads to elongation of radially expanded plasma flow, since the plasma jet length may be estimated as $L=U_T T$, according to Eq. 19. If the period is substantially longer than the relationships presented in Eq. 30, then laminar plasma flow may be generated.

Example 3: Volumes of Target and Initiator Plasma Flows

Figure 42C:
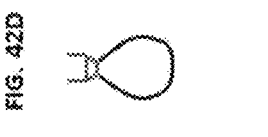

For the same conditions as in Example 1, but with the initiator temperature of about 16,000 K, the resulting plasma flow may take the form illustrated in FIG. 42C. In this case, the volume of initiator flow and specific length of the initiator flow may be higher than for the target flow. As a result, a partial laminar flow may be formed at the end of a radially expanded part of the plasma jet as shown in FIG. 42C.

Example 4: Heating Channel Diameter

Figure 42D:
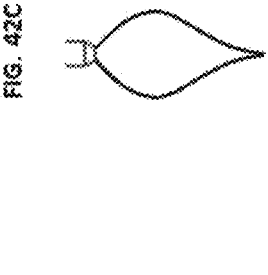

For the same conditions as in Example 1, but with a diameter of the heating channel of about 0.6 mm, the resulting plasma flow may take the form illustrated in FIG. 42D. The length of a resulting plasma jet may decrease because the increase of a heating channel diameter may correspond to a working pressure drop, which in turn may result in lower velocities that the outlet plasma flow may reach.

Example 5: Gas Inlet Flow

Figure 42E:
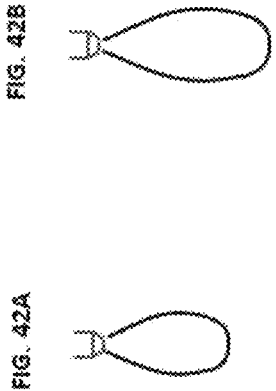

For the same conditions as in Example 1, but with a gas flow inlet of about 0.7 L/min, the resulting plasma flow may take the form illustrated in FIG. 42E. An increase of gas flow inlet may be equivalent to an increase of working pressure, as shown in Eq. 10. The higher working pressure may boost the outlet plasma velocity that may be reached. Thus, the plasma jet shape may enlarge with the higher values of inlet gas flow.

Example 6: Outlet Diameter

For the same conditions as in Example 1, but with outlet diameter of about 0.6 mm, the resulting plasma flow may take the form illustrated in FIG. 42F. In this example, higher expansion of an adaptive nozzle may further increase the outlet plasma flow velocity. In some embodiments, the increase of outlet flow velocity may be achieved if the working pressure is considerably high such that the pressure difference between working and ambient pressure may be actually realized by adaptive nozzle to increase the outlet velocity. For some applications, the working pressure may be intentionally increased to use higher expansion of adaptive nozzle to increase the diameter of jet while keeping low outlet mass flux. Such an approach may be used to achieve a high cross-sectional area of plasma flow with low power density. This may be useful for controlling heating of a comparatively large surface area.

Example 7: Duty of the Outlet Temperature Pulses

For the same conditions as in Example 1, with a duty of about 0.4, the initiator temperature may be about 16,000 K to meet conditions of the same target and initiator volume of plasma flow. In this example, a higher degree of radial expansion may be achieved and a higher fraction of target axial flow may be obtained in the first part of plasma flow as schematically shown in FIG. 42G. In case of a duty D of about 0.6 with an initiator temperature of about 11,200 K to maintain the same volume of target and initiator plasma flow, the opposite situation is realized: the lower degree of radial expansion may be achieved, and a lower fraction of target axial flow may be obtained, as illustrated in FIG. 42H.

Example 8: Target Temperature

For the same conditions as in Example 1 with a target temperature of about 10,000 K, the initiator temperature may be about 21,500 K to meet conditions of the same target and initiator volume of the plasma flow. In this example, a target velocity may be higher compared to Example 1. As a result, the length and diameter of resulting plasma may be increased, as illustrated in FIG. 42I.

Example 9: Optimization of Outlet Temperature-Time Profile

For Example 9, the inlet gas flow, diameter of heating channel, and outlet diameter may be the same as in Example 1. The outlet temperature-time oscillation may have a profile given by the dash line in FIG. 2, with a target temperature of about 3,000 K, maximum initiator temperature of about 16,000 K, and effective duty of about 0.6. In comparison to Example 1, the resulting plasma jet may have a higher degree of radial expansion, and the impact of axial target flow may have a lower fraction, as illustrated in FIG. 42J.

Parameters for Therapeutic Application

As discussed above, the duty between the pulse-initiator and base-target plasma flow may be in a range between about 0.4 and about 0.6 to generate predominantly radially expanded plasma flow and to achieve the same volume of pulse and base plasma flows. Variation of pulse and base temperatures and duty may affect the plasma flow shape as discussed in the examples herein and shown in FIGS. 42A-42J. Control of the shape and energy of plasma flow may be used to broaden an area of possible applications for the methods described herein. Some applications might require a predetermined ratio between radially expanded and laminar fraction of plasma flow. For example, in a therapeutic application, a plasma-generating device may generate nitric oxide for patient treatment. In some embodiments, a high temperature of plasma flow may be used to generate a high concentration of nitric oxide. To avoid damage due to the high temperature, the plasma flow may be rapidly cooled down to a lower temperature (between about 30° C. and about 60° C.) that both protects from overheating and allows delivery of the nitric oxide before it decomposes in the atmosphere. In some embodiments, a method for therapeutic application may include a high temperature (>10,000° C.) pulse-initiator plasma and low temperature base plasma flow with low duty that may be configured for rapid cooling of the plasma flow. For instance, a duration of pulses may be between about 10 μs and about 25 μs. The period T may be in a range of between about 50 μs and about 50 ms. Thus, the duty may be substantially lower than a predetermined "optimal" range, thereby decreasing the fraction of radially expanded plasma flow. Nonetheless, the remaining small fraction of radially expanded plasma flow may produce a high concentration of nitric oxide. Due to a low duty of the pulses, the resulting plasma flow may be effectively cooled down to desired temperature for subsequent use. Moreover, the radial propagation the temperature gradient of plasma flow may be more uniform compared to turbulent or laminar flow, thus enabling a stable condition for uniform generation of nitric oxide.

General Conditions for Generating Predominantly Radially Expanded Flow

Figure 43:
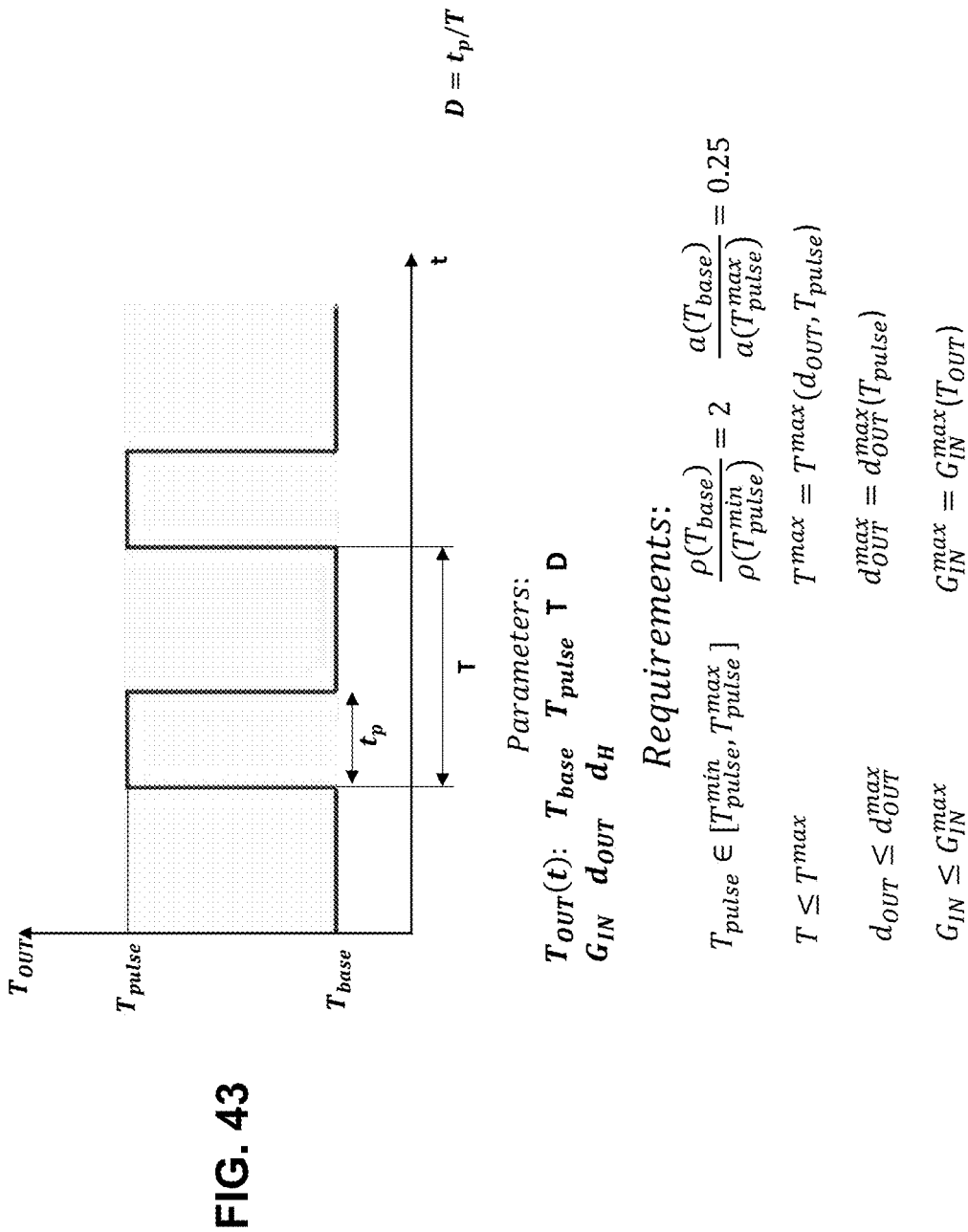
FIG. 43 is a plot of amplitude and time for temperature-time profile and input parameters, according to an embodiment.

With reference to FIG. 43, a set of parameters for a temperature-time profile of outlet plasma temperature and parameters of the plasma-generating device may include a base and pulse temperature $T_{base}$ and $T_{pulse}$, period T and duty D. Input plasma-generating device parameters may include inlet gas flow $G_{IN}$, outlet diameter $d_{OUT}$, and heating channel diameter $d_H$.

First, for a predetermined base temperature $T_{base}$, the pulse temperature may be in a range between about $T_{pulse}^{min}$ and about $T_{pulse}^{max}$. A lower boundary may be defined by a threshold for minimal density ratio of about 2. An upper boundary may be defined by a threshold for minimum speed of sound ratio of about 0.25:

$$\frac{\rho(T_{base})}{\rho(T_{pulse}^{min})} = 2 \Rightarrow T_{pulse}^{min}(T_T)$$

$$\frac{a(T_{base})}{a(T_{pulse}^{max})} = 0.25 \Rightarrow T_{pulse}^{max}(T_{base})$$

Figure 44:
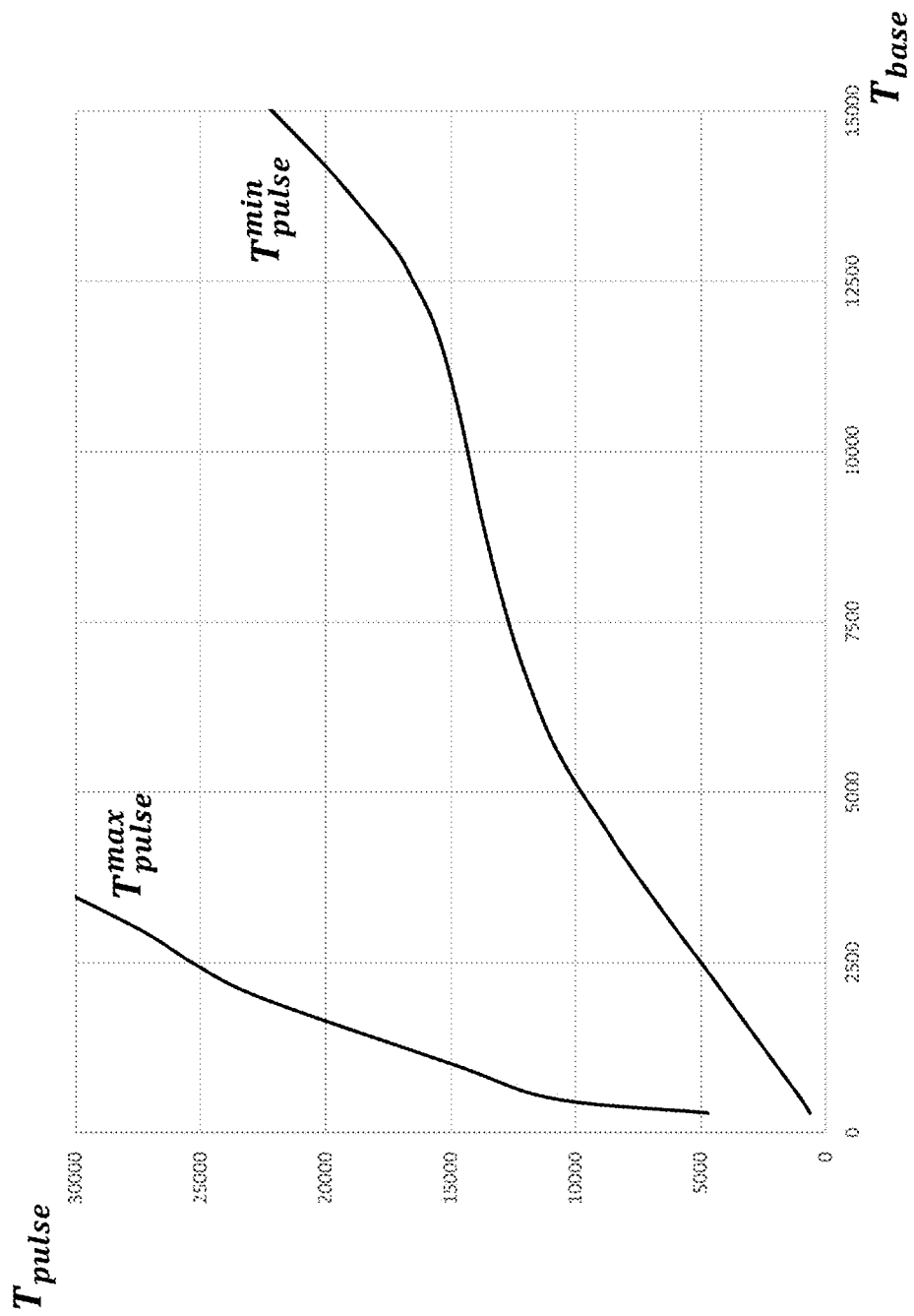
FIG. 44 is a plot of lower and upper boundaries for pulse temperature for argon plasma, according to an embodiment.
Figure 45:
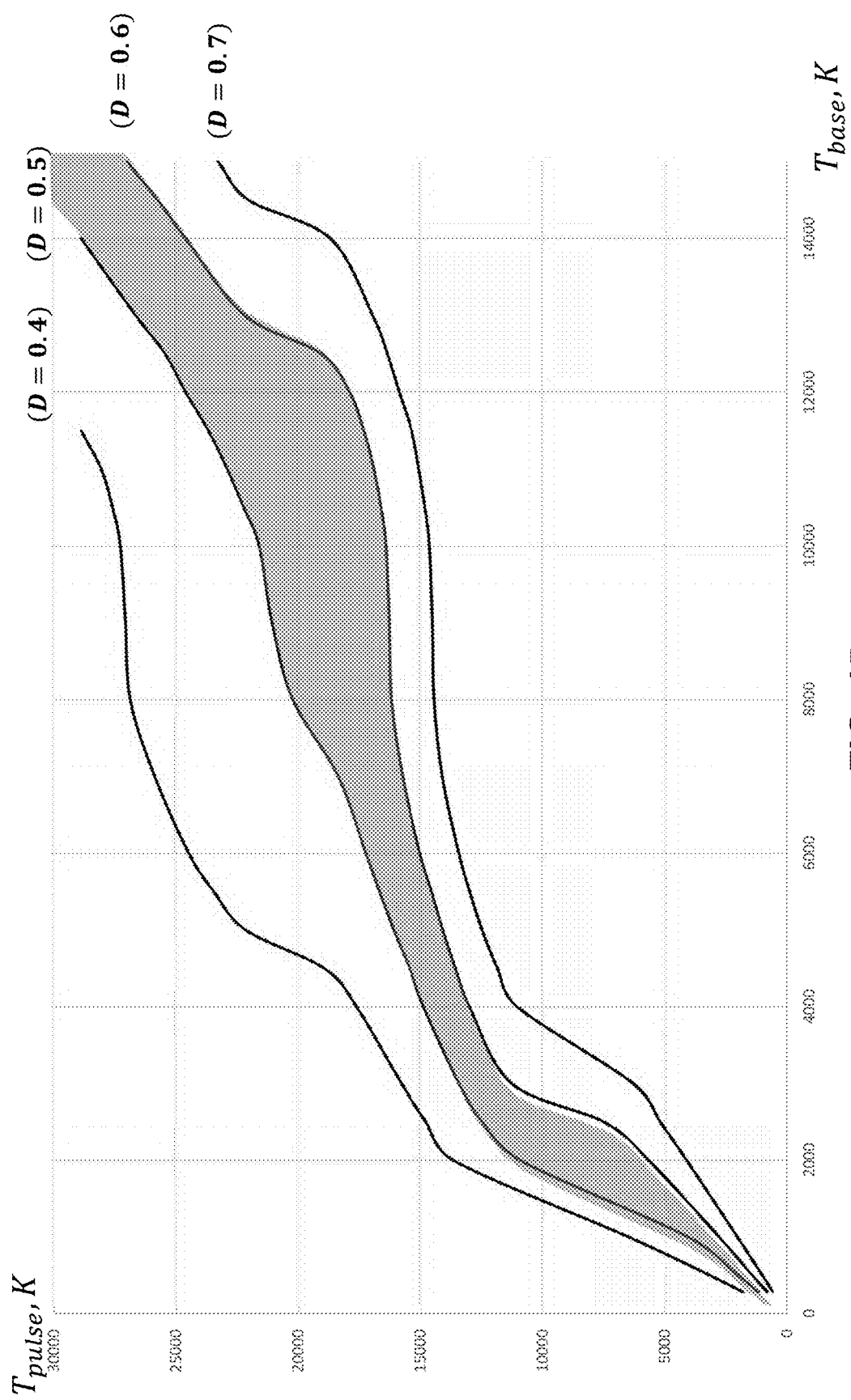
FIG. 45 is a plot of lower and upper boundaries for pulse temperature for argon plasma, according to an embodiment.
Figure 46:
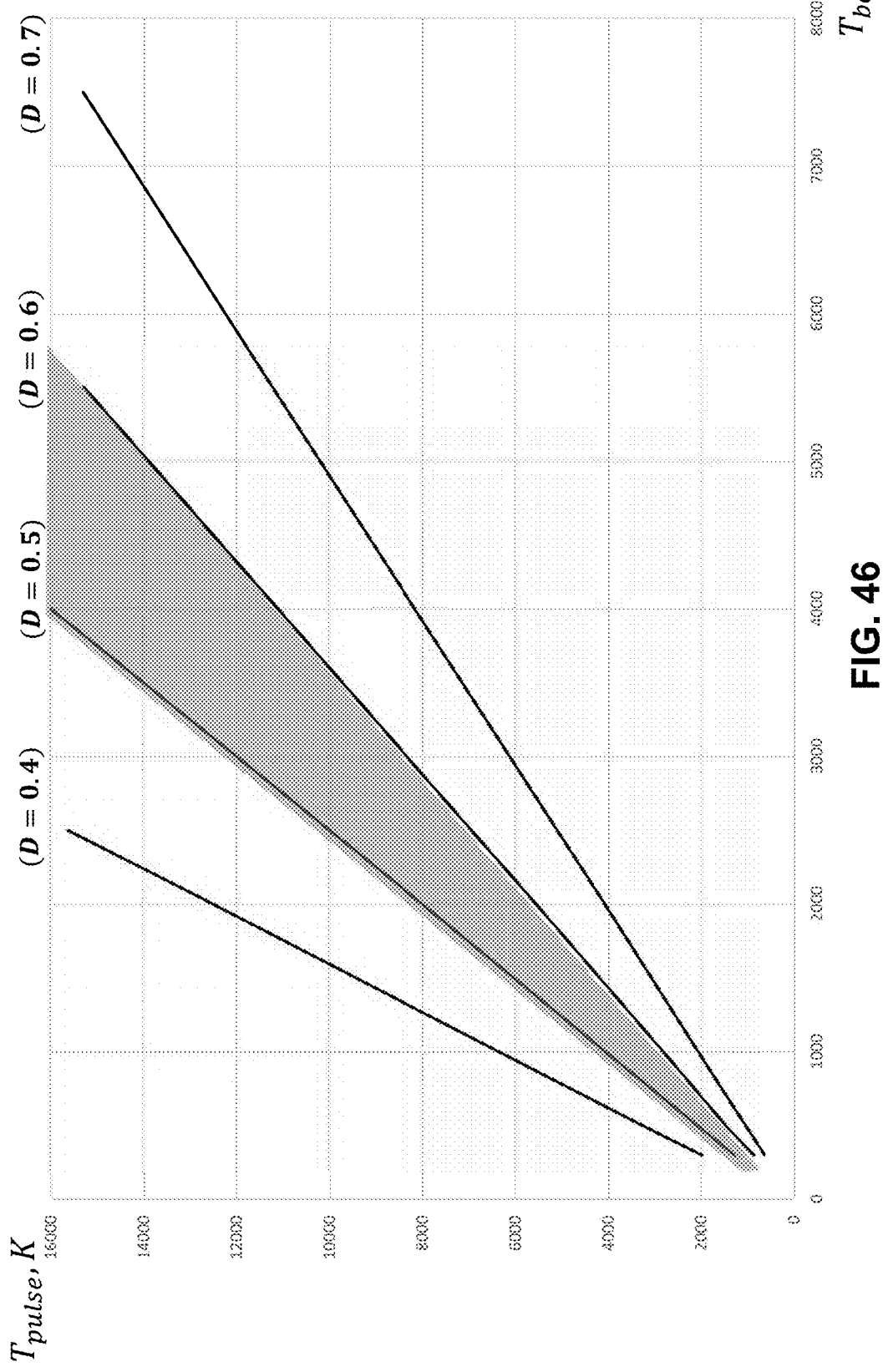
FIG. 46 is a plot of lower and upper boundaries for pulse temperature for air plasma, according to an embodiment.

FIG. 44 illustrates bottom and top boundaries of pulse temperature for predetermined base temperatures up to about 15,000 K where argon is the plasma generating gas. An optimal pulse temperature range for argon plasma is shown in FIG. 45. Similarly, an optimal pulse temperature range for air plasma is shown in FIG. 46.

Figure 47:
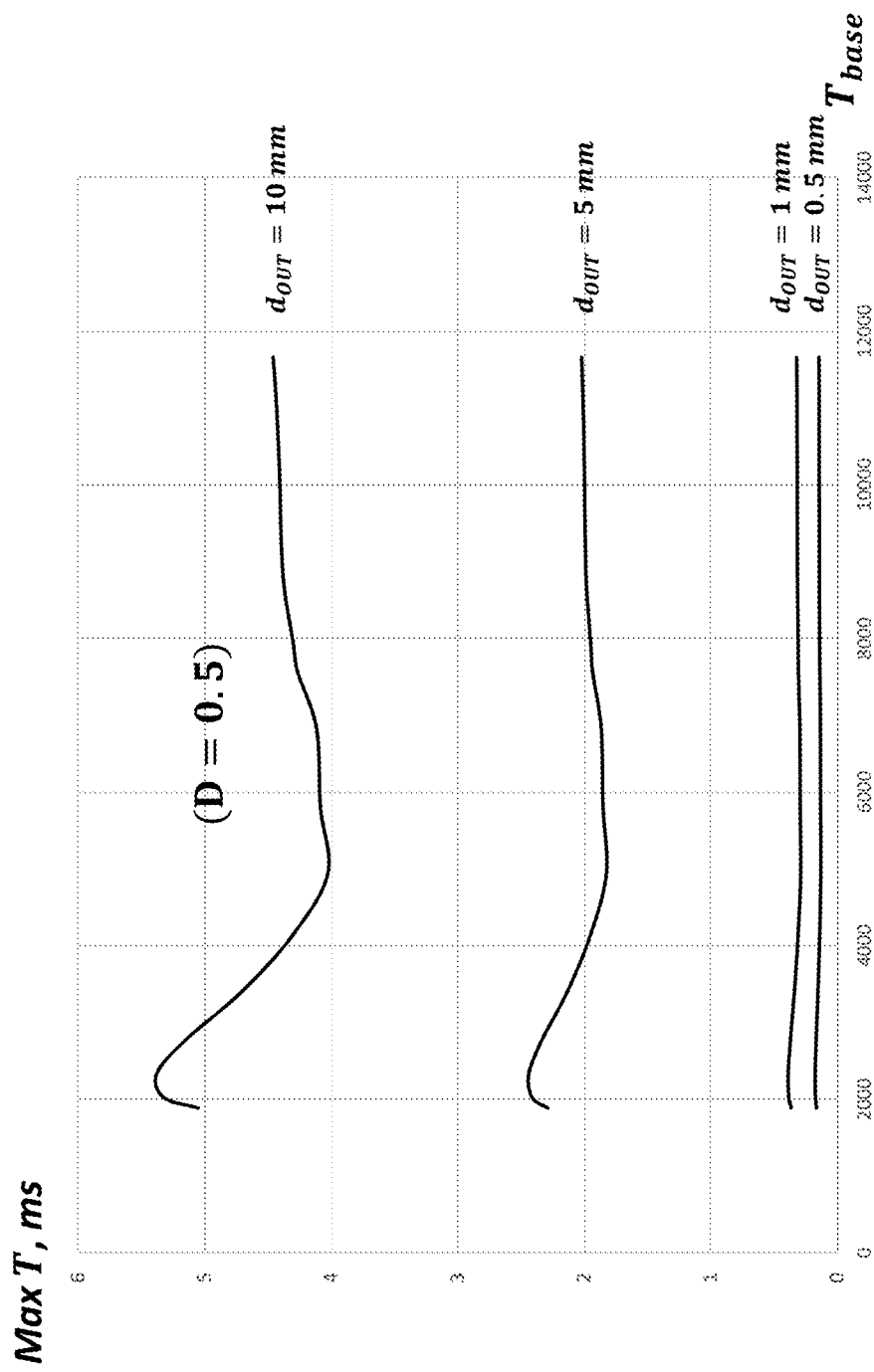
FIG. 47 is a plot of dependence of maximum period on outlet base temperature, according to an embodiment.
Figure 48:
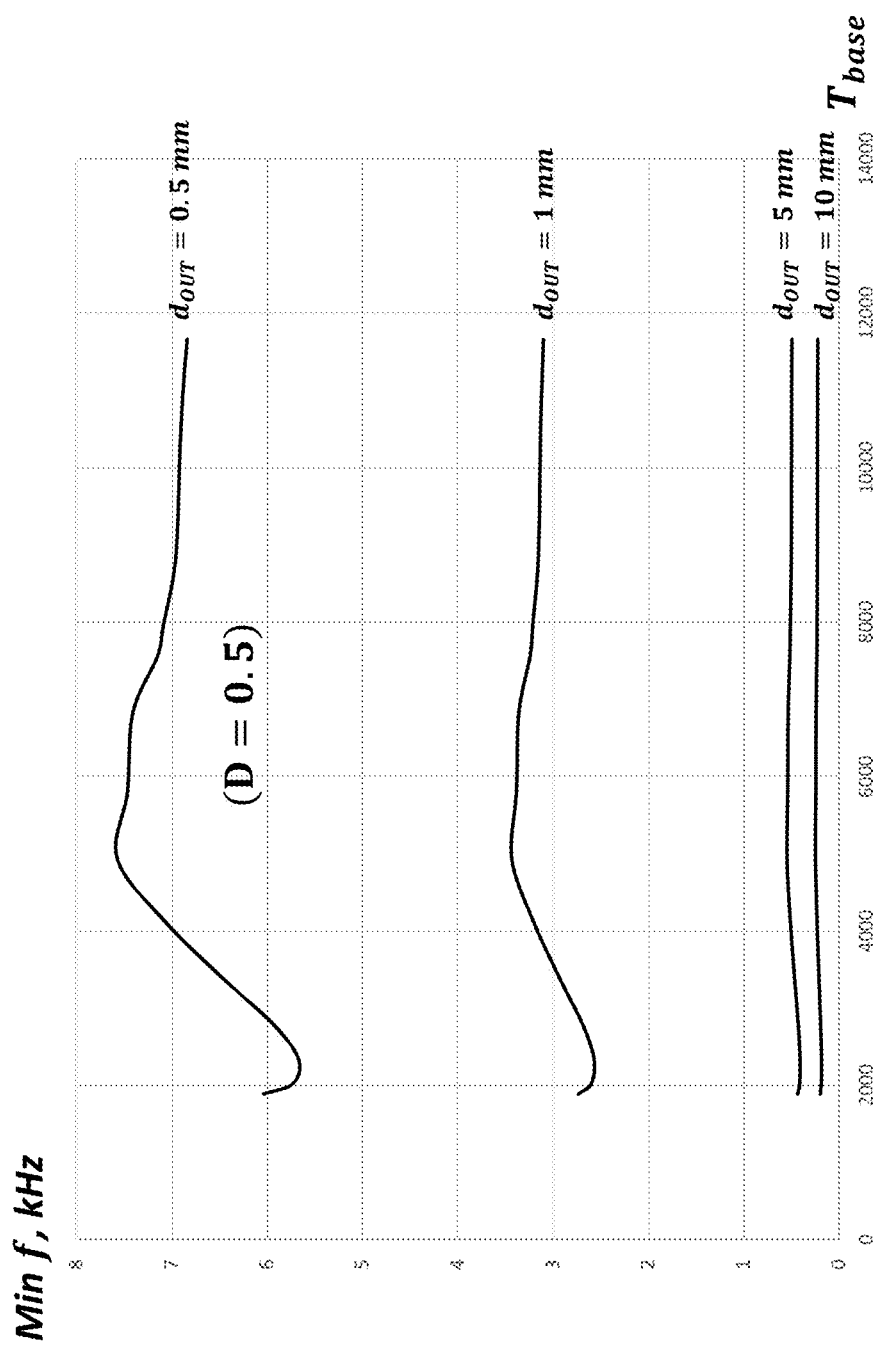
FIG. 48 is a plot of dependence of minimum frequency on outlet base temperature, according to an embodiment.
Figure 49:
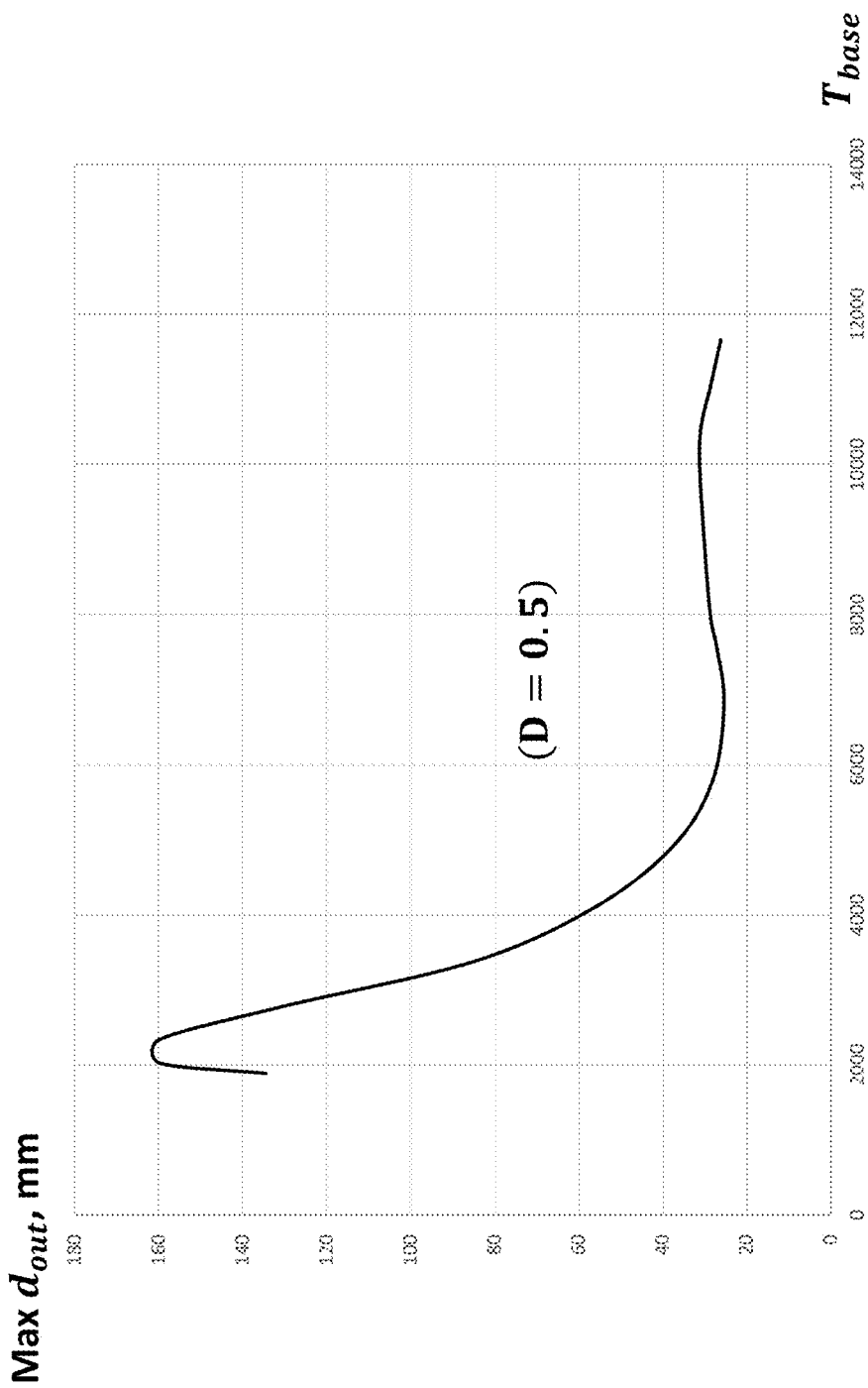
FIG. 49 is a plot of dependence of maximum outlet diameter on outlet base temperature, according to an embodiment.

Second, in some embodiments, a period of oscillation may be less than a predetermined value $T^{max}$, that may be defined by outlet diameter and pulse temperature. FIG. 32 and Table 1 illustrate the dependence of $T^{max}$ on pulse temperature for a set of outlet diameters. FIG. 33 illustrates a plot for a corresponding minimum frequency of outlet temperature oscillation $f^{min}$. In some embodiments, the pulse temperature may be in an optimal range. The $T^{max}$ and $f^{min}$ graphs may be represented using the corresponding base temperature as shown in FIG. 47 and FIG. 48, respectively.

Third, in some embodiments, an outlet diameter may be less than predetermined value $d_{OUT}^{max}$, that may be defined by outlet pulse temperature. FIG. 34 illustrates a dependence of $d_{OUT}^{max}$ on pulse temperature. This relationship may be based on critical Reynolds number for minimal outlet velocities.

Figure 50:
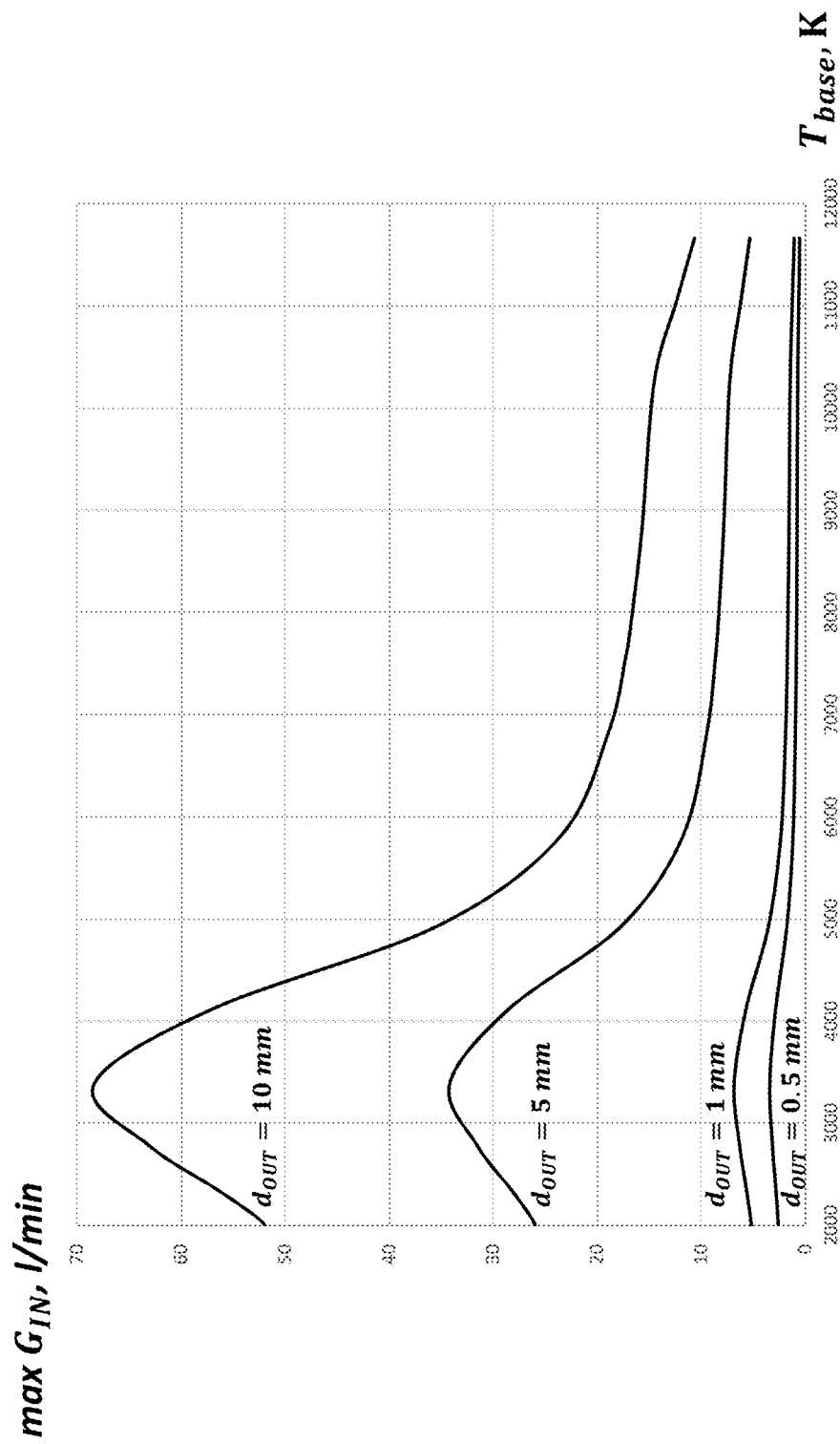
FIG. 50 is a plot of dependence of maximum inlet gas flow on base temperature for pulse-base ratio, according to an embodiment.
Figure 51:
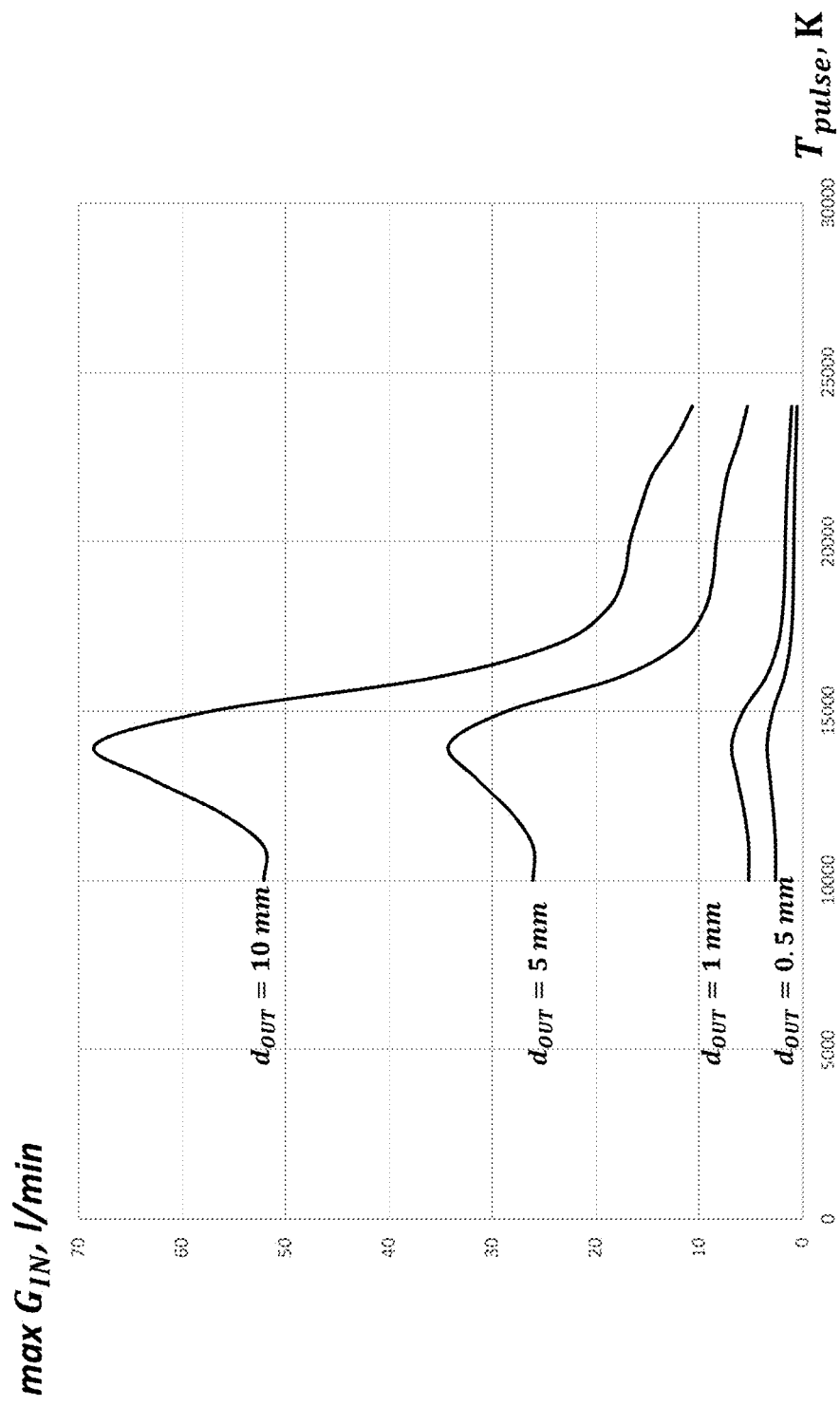
FIG. 51 is a plot of dependence of maximum inlet gas flow on pulse temperature for pulse-base ratio, according to an embodiment.

Fourth, in some embodiments, to avoid turbulent mode, the inlet gas flow rate may be less than critical inlet gas flow for pulse and base plasma flows with a Reynolds number of about 2,000, as shown in Eq. 34 and 35. In some embodiments, the maximum inlet gas flow rate may be linearly proportional to an outlet diameter. Considering the pulse temperature may be in an optimal range, an example of a maximum inlet gas flow rate is shown in FIG. 50 for base temperature and FIG. 51 for pulse temperature.

Fifth, in some embodiments, mass flux in a heating channel may be sufficient to provide minimal working pressure to maintain plasma flow.

$$G_{IN} > K \cdot \frac{\pi d_H^2}{4}\left(D + \sqrt{\frac{T_P}{T_B}}(1-D)\right)$$

Figure 52:
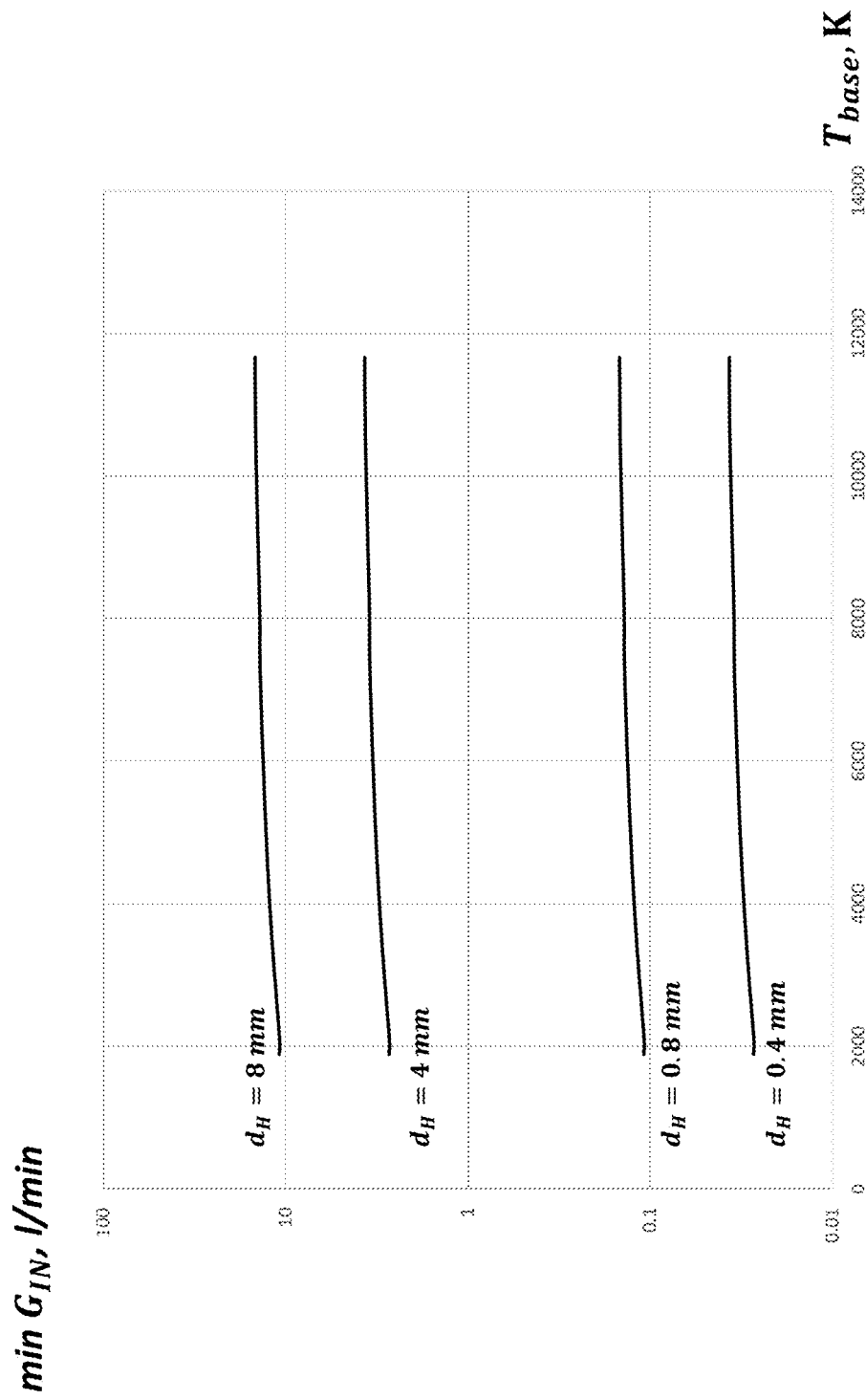
FIG. 52 is a plot of dependence of minimum inlet gas flow on base temperature for pulse-base ratio, according to an embodiment.
Figure 53:
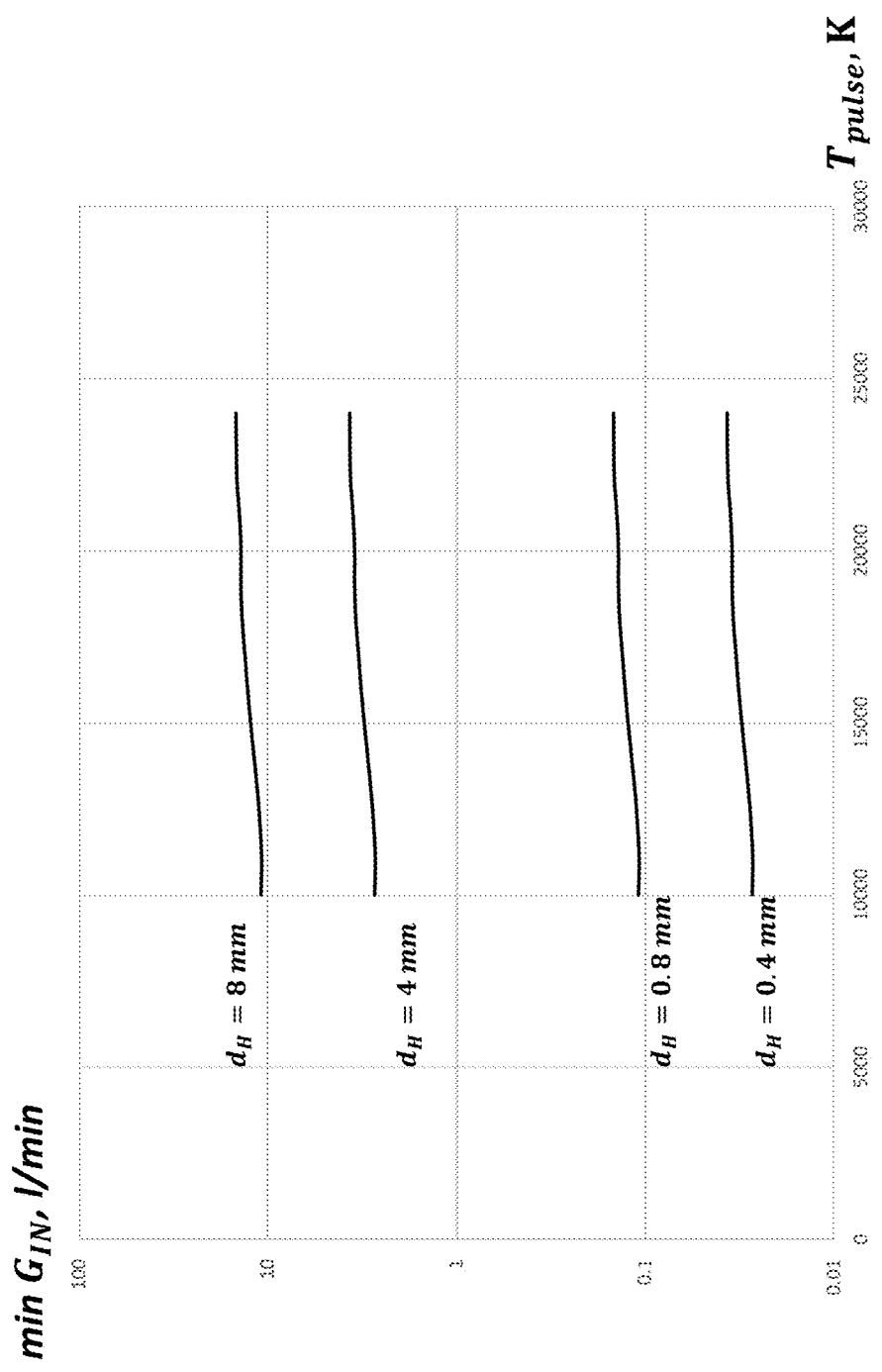
FIG. 53 is a plot of dependence of minimum inlet gas flow on pulse temperature for pulse-base ratio, according to an embodiment.

When the pulse temperature is in an optimal range, an example of a minimum inlet gas flow rate is shown in FIG. 52 for base temperature and FIG. 53 for pulse temperature and various diameter of heating channel.

Figure 54:
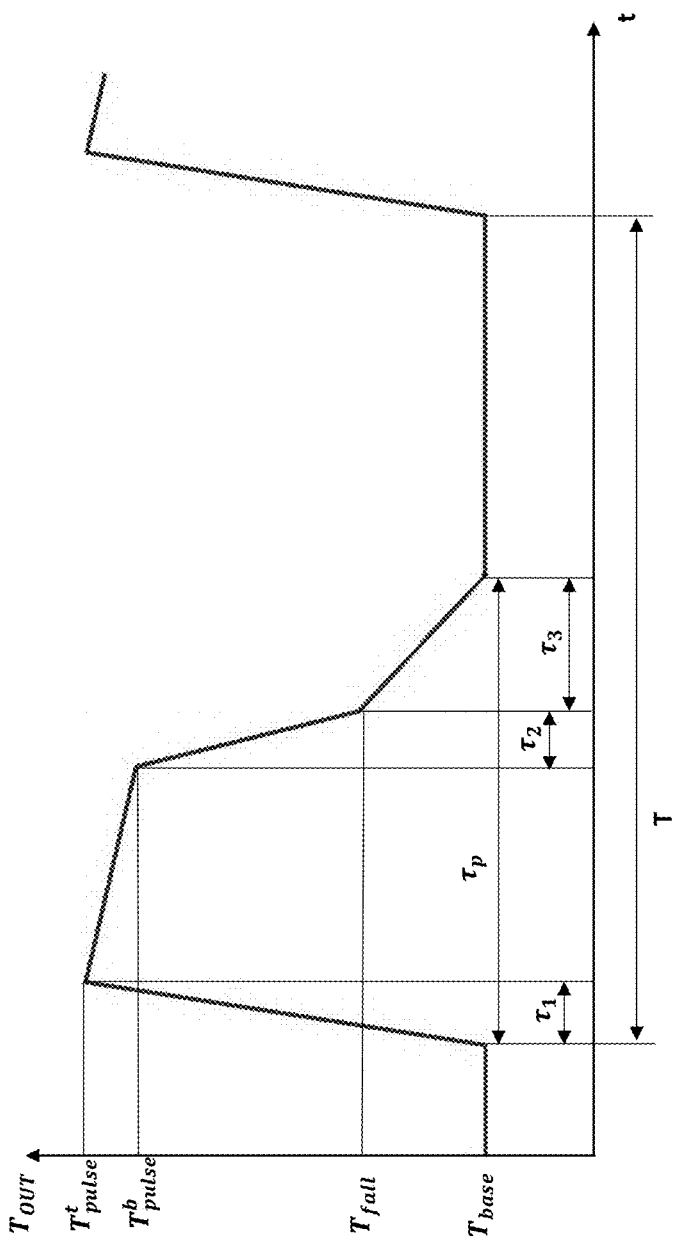
FIG. 54 is a plot of a temperature-time profile, according to an embodiment.

General High Frequency (HF) Pulses for Generating Predominant Radial Expansion Plasma Flow FIG. 54 illustrates a general outlet temperature-time profile for base-target and pulse-initiator plasma having a set of parameters including base temperature level, period of pulse repetition, temperature pulse rise and fall times, temperature pulse delay fall time, and pulse temperature. For example, base temperature level $T_{BASE}$ may be defined for a predetermined type of action. For example, $T_{BASE}$ may be set to a relatively low level, such as about 2,000 K and about 4,000 K, for controlled heating of an object without vaporization and sublimation of the treated surface boundary. $T_{BASE}$ may be set to relatively higher level (e.g. about 9,000 K and about 11,000 K) for controlled speed of vaporization of the treated surface boundary. A period of pulses repetition T may be between about 10 µs and about 50 µs. Temperature pulse rise and fall times $\tau_1$ and $\tau_2$ may be between about 0.01·T and about 0.1·T. Temperature pulse delay fall time $\tau_3$ may be between about 0.2~T and about 0.4·T. Pulse temperature $T_{PULSE}^t$=top optimal boundary of $T_{PULSE}$ for the predetermined $T_{BASE}$:

$$\frac{a(T_{base})}{a(T_{pulse})} = 0.5$$

In some embodiments, pulse temperature $T_{PULSE}^b$=bottom optimal boundary of $T_{PULSE}$ for the predetermined $T_{BASE}$:

$$\frac{a(T_{base})}{a(T_{pulse})} = 0.6$$

In some embodiments, pulse temperature $T_{FALL}$=(0.2-0.4) ($T_{PULSE}^b - T_{BASE}$). In some embodiments, pulse temperature duration $\tau_p$ may define the effective duty $$D = \frac{\tau_p}{T},$$

which may be in a range of between about 0.4 and about 0.6. In some embodiments, a base level of temperature in the temperature-time profile may slowly oscillate with considerably lower frequency, as shown in FIG. 40. As discussed herein, such low frequency oscillation may be used to build up the working pressure and tune the shape and the energy level of a plasma jet. In some embodiments, low frequency oscillation may be in range of between about 100 Hz and about 1 kHz.

3. Plasma-Generating System

Overview

Plasma-generating devices that do not modulate required oscillations of outlet thermodynamic parameters may be poorly configured to generate predominantly radially expanded plasma flows. Moreover, degradation and erosion processes associated with certain plasma-generating device may prevent such devices from stable robust operation.

As used herein, a plasma-generating device may refer to a handpiece configured to generate and discharge plasma. The plasma-generating device may refer collectively to the handpiece, a console unit, and connecting wires and hoses for the transmission of energy, such as electric current, plasma-generating gas, coolant, and other substances and/or signals between the console unit and the handpiece. In some embodiments, the console unit may include a current control power supply. The handpiece and current control power supply are described in more detail herein.

Figure 55:
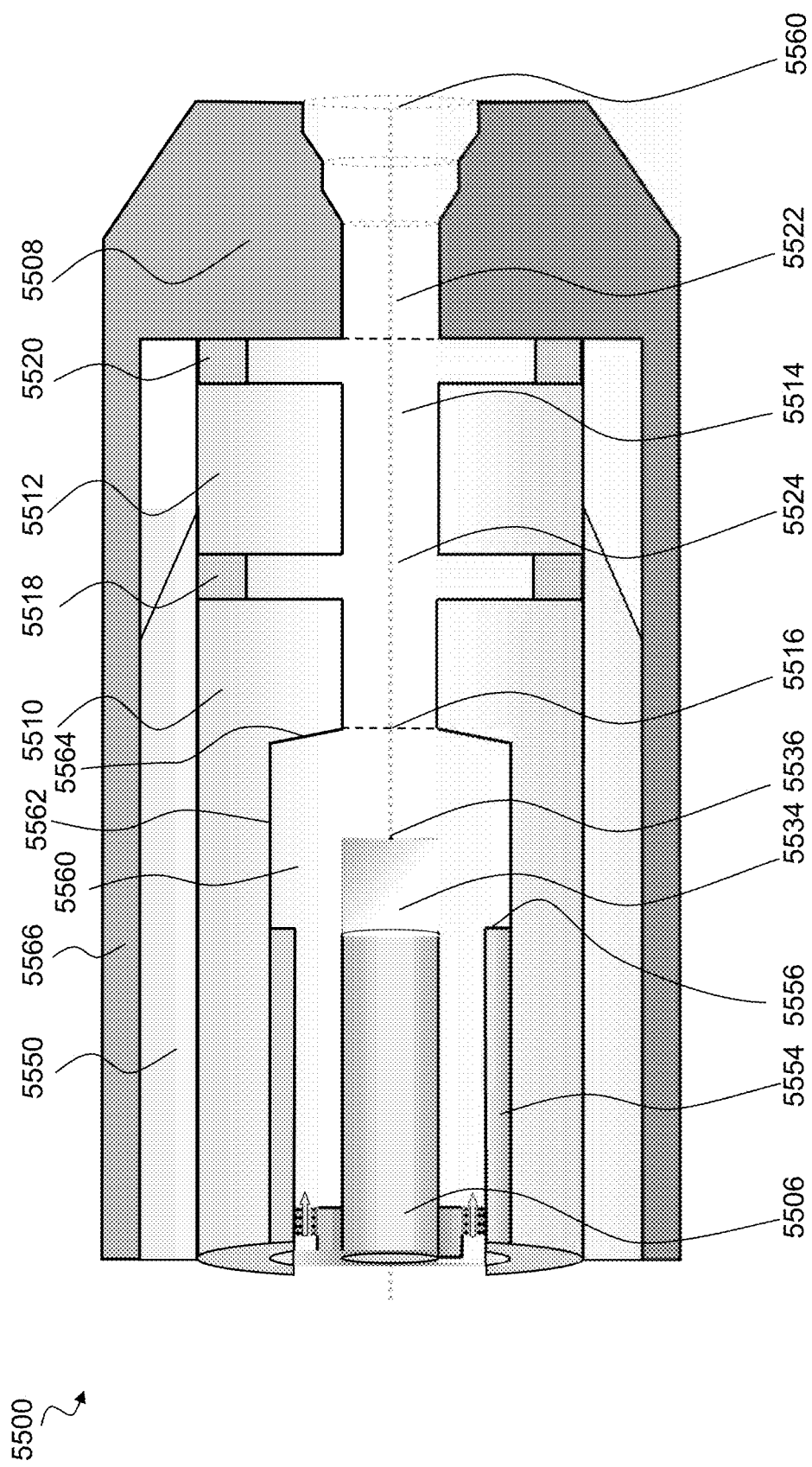
FIG. 55 is a cross-sectional side schematic view of a plasma-generating device, according to an embodiment.

FIG. 55 shows a longitudinal cross-section of one embodiment of a plasma-generating device 5500. Plasma-generating device 5500 can include components that are structurally and/or functionally similar to those of other plasma-generating devices described herein (e.g., plasma-generating device 100, 5700, etc.). The cross-section depicted in FIG. 55 is along a longitudinal axis of the plasma-generating device 5500. In operation, plasma flows from a proximal end of the generator (left side of FIG. 55) and may be discharged from outlet 5560 (right side of FIG. 55). The flow of plasma gives meaning to the terms "upstream" and "downstream." The discharge end of generator 5500 may be referred to as the distal end. In general, the term "distal" refers to facing the discharge end of the generator; the term "proximal" refers to facing the opposite direction of distal. The terms "distal" and "proximal" may be used to describe the ends of generator 5500 as well as its elements.

The plasma-generating device 5500, as shown in FIG. 55 may comprise a cathode 5506, anode 5508, and two (or more) intermediate electrodes 5510 and 5512, arranged upstream of anode 5508. In some embodiments, the intermediate electrodes 5510 and 5512 and anode 5508 may be annular and form a plasma channel 5514, which extends from a position downstream of cathode 5506 and through anode 5508. Anode 5508 may form outlet 5560, from which plasma may be discharged. Inlet 5516 of plasma channel 5514 may be at its proximal end. In plasma channel 5514, plasma may be heated and discharged through outlet 5560. Intermediate electrodes 5510 and 5512 may be insulated and separated from direct contact with each other and anode 5508 by respective annular insulator washers 5518 and 5520. In some embodiments, plasma channel 5514 may include a heating portion 5524 partially formed by intermediate electrodes 5510 and 5512 and anode portion 5522 formed by anode 5508.

In the embodiment shown in FIG. 55, cathode 5506 may be formed as an elongate cylindrical element. In some embodiments, cathode 5506 may be made of tungsten, optionally with additives, such as lanthanum. Such additives may be used, for example, to lower the temperature that the distal end of cathode 5506 reaches.

In some embodiments, the distal portion of cathode 5506 may have a tapering end portion 5534 (e.g., tapered portion). In some embodiments, tapering portion 5534 may have a conical shape that forms a tip point 5536 (e.g., distal tip) at the distal-most end of cathode 5506, as shown in FIG. 55. In some embodiments, cathode 5534 may be a truncated cone. In other embodiments, cathode tip 5534 may have other shapes (e.g., tapering toward anode 5508). In some embodiments, plasma-generating device 5500 may further comprise a plastic water divider 5550 that together with outside surfaces of intermediate electrodes 5510 and 5512, anode 5508, and outside surfaces of insulators 5518 and 5520, and an inside surface of the outer sleeve 5566 connected to anode 5508 form a cooling channel. Even though outer sleeve 5566 may be integrally connected to the anode, the portion of the integral structure to which positive electrical charge may be applied and concentrated may be considered to be anode 5508. The remaining outer portion may not carry electric charge and may be considered a passive outer sleeve 5566.

In some embodiments, a first intermediate electrode 5510 may define a plasma chamber 5560 that connects to an inlet 5516 of plasma channel 5514. In some embodiments, plasma chamber 5560 may have a cylindrical portion 5562 and, in some embodiments, may optionally have a transitional portion 5564 that connects the cylindrical portion 5562 to a plasma channel inlet 5516. In some embodiments, a cross-sectional area of cylindrical portion 5562 may be greater than a cross-sectional area of plasma channel inlet 5516.

FIG. 55 also depicts an insulator sleeve 5554 extending along and around a portion of cathode 5534. In some embodiments, cathode 5506 may be arranged substantially in the center of the through hole of insulator sleeve 5554. In some embodiments, an inner diameter of insulator sleeve 5554 may be greater than the outer diameter of cathode 5506. The difference in these diameters may result in a gap formed by the outer surface of cathode 5506 and the inner surface of insulator sleeve 5554. In some embodiments, insulator sleeve 5554 may be made of a temperature-resistant material, such as ceramic, temperature-resistant plastic, combinations thereof, and the like. In some embodiments, insulator sleeve 5554 may be configured to protect constituent elements of plasma-generating device 5500 from heat generated by cathode 5506, and in particular by cathode tip 5534 during operation. In some embodiments, insulator sleeve 5554 and cathode 5506 may be arranged relative to each other so that the distal end of cathode 5506 projects beyond the distal end 5556 of insulator sleeve 5554.

In some embodiments, cathode chamber 5560, as shown in FIG. 55, may have a circular cross-section. In some embodiments, cathode chamber 5560 and plasma channel 5514 may be arranged substantially concentrically to each other. In some embodiments, cathode 5506 may be arranged substantially concentrically with plasma chamber 5560. In some embodiments, cathode 5506 may extend into plasma chamber 5560.

In some embodiments, the proximal end of cathode 5506 may be connected to an electrical conductor connected to a power supply. In some embodiments, anode 5508 may be connected to the power supply. In some embodiments, a gas flow controller (not shown in FIG. 55) may be connected to the plasma-generating device. During operation, the plasma-generating gas may flow from a gas controller (e.g., controller 102 depicted in FIG. 1) through an expansion chamber (e.g., expansion chamber 104 depicted in FIG. 1) and into the gap formed by the outside surface of cathode 5506 and the inside surface of insulator sleeve 5554. In some embodiments, the plasma-generating gas may flow along cathode 5506 inside insulator sleeve 5554 toward anode 5508. (As mentioned above, this direction of the plasma flow gives meaning to the terms "upstream" and "downstream" as used herein.) As the plasma-generating gas passes distal end 5556 of insulator sleeve 5554, the gas may enter into cathode chamber 5560. The plasma generating gas may be heated by the electric arc formed between cathode 5506 and anode 5508. This heating of the passing plasma-generating gas may result in the formation of a plasma flow discharged from outlet 5560. By controlling the current applied between cathode 5506 and anode 5508 and the plasma-generating gas flow rate, the desired temperature-time profile may be created at outlet 5560 of generator 5500.

Figure 57:
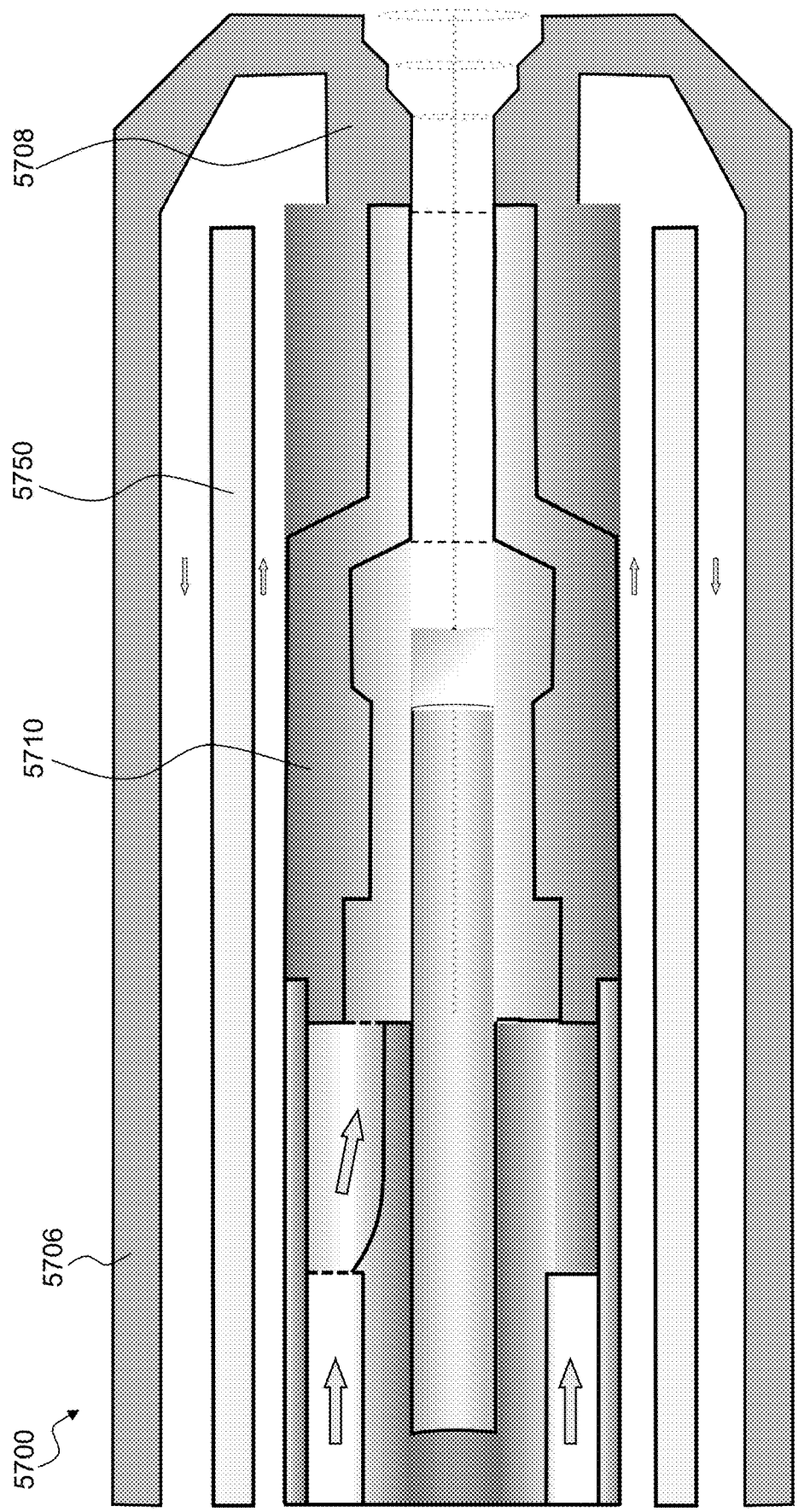
FIG. 57 is a cross-sectional side schematic view of another plasma-generating device, according to an embodiment.

FIG. 57 depicts an alternative embodiment of a plasma-generating device 5700. Plasma-generating device 5700 can include components that are structurally and/or functionally similar to those of other plasma-generating devices described herein (e.g., plasma-generating device 100, 5500). In some embodiments, plasma-generating device 5700 may include an isolator 5710 having a complex shape as shown in FIG. 57. In some embodiments, the isolator 5710 may have a shape similar to the inner walls of insulator sleeve 5554, cathode chamber or plasma chamber 5560, and plasma channel 5514. In some embodiments, the isolator 5710 may be made of high temperature resistant material with high heat conductivity. In some embodiments, the isolator 5710 may be made of aluminum nitride ceramics that may have a thermal conductivity of about 280 W/(m·K). For comparison, a thermal conductivity of copper alloys used for intermediate electrodes in some embodiments may be in range of between about 350 W/(m·K) and about 400 W/(m·K). In some embodiments, the isolator 5710 may take the place of the insulator sleeve 5554, first intermediate electrode 5510, other intermediate electrodes 5512, and separators 5518 and 5520. In some embodiments, the heat conductivity of isolator 5710 may need to be relatively high to avoid overheating. Similar to device 5500, a water divider 5750 together with outside surfaces of isolator 5710 and inside surface of an outer sleeve 5706 connected to anode 5708 may form a cooling channel, in some embodiments.

In some embodiments, a plasma-generating device may include a cathode including a tapered distal portion, and an anode disposed downstream from the cathode and being electrically insulated from the cathode. In some embodiments, the anode may define an opening therethrough. In some embodiments, a plurality of intermediate electrodes may be disposed between the cathode and the anode. The plurality of intermediate electrodes may be electrically insulated from each other and from the anode and the cathode. In some embodiments, each intermediate electrode from the plurality of intermediate electrodes may define an opening therethrough such that the openings in the plurality of intermediate electrodes and the anode collectively define a plasma channel for discharging a plasma flow. In some embodiments, the plasma channel may include a first portion having a first cross-sectional diameter, and a second portion having a second cross-sectional diameter. In some embodiments, the first cross-sectional diameter may be at least four times the second cross-sectional diameter. In some embodiments, an insulator sleeve may extend along a surrounding a portion of the cathode.

In some embodiments, a distance from a distal end of the cathode to the second portion of the plasma channel may be at least 1.5 times the second cross-sectional diameter. In some embodiments, the opening in the anode has a cross-sectional diameter at a proximal end of the anode that may be less than a cross-sectional diameter at a distal end of the anode. In some embodiments, an outer sleeve may be coupled to the anode, and a divider may be disposed between the outer sleeve and the plurality of intermediate electrodes, the divider with outside surfaces of the plurality of intermediate electrode, an outside surface of the anode, and an inside surface of the outer sleeve collectively defining a cooling channel for cooling the plasma channel.

In some embodiments, the cathode may be disposed in a cathode chamber having a diameter $d_{CC}$. In some embodiments, the diameter $d_{CC}$ may be at least four times the second cross-sectional diameter. In some embodiments, a distance between a distal end of the insulator sleeve and a distal end of the cathode is at least a diameter of the cathode and less than 1.6 times the diameter of the cathode. In some embodiments, a length of the anode may be between two times to eight times a diameter of the anode.

Heating Channel and Anode Channel

In some embodiments, the plasma-generating device as shown in FIG. 55 may comprise a cathode assembly which may include a cathode holder, ceramic insulator and tungsten cathode affixed in a cathode holder, an anode, and two or more intermediate electrodes. The anode and the intermediate electrodes may form a plasma channel. The first intermediate electrode that may be closest to the cathode may also form a cathode chamber around the cathode ends. The plasma channel may comprise three channels including a cathode chamber, a heating channel 5524, and an expansion portion of an anode channel. The diameter of the expansion portion may increase toward the anode end.

In some embodiments, heating portion 5524 may be formed by two or more intermediate electrodes. In some embodiments, heating portion 5524 may be formed by a single intermediate electrode or by six or more intermediate electrodes.

In some embodiments, heating channel 5524 may be configured to heat the plasma-generating gas to a predetermined (e.g., relatively high) temperature to provide a predetermined temperature profile of outlet plasma. For the fixed current going between cathode and anode, the smaller diameter of heating channel 5525, $d_H$, may correspond to a relatively higher arc temperature and hence a relatively higher temperature of outlet plasma. Therefore, a predetermined relationship between current and diameter of heating channel may be maintained to generate plasma.

In some embodiments, oscillating outlet plasma temperature may be configured to generate predominantly radially expanded and volumetrically oscillating plasma flows. In terms of plasma-generating device 5500, the current may be configured to oscillate to provide predetermined outlet plasma conditions. In some embodiments, the applied oscillating current may be characterized by RMS current. The term RMS current may refer to alternating current calculated as a root mean square.

In some embodiments, if plasma-generating device 5500 is subject to size constraints, such as for key hole surgeries, a max RMS current may be limited to between about 12 A and about 15 A. This relationship arises from a cross-section restriction for current conductive elements of the generator and heat dissipation from a plasma channel to cooling water. In some embodiments, operation of a plasma-generating device with a small cross-sectional area at higher RMS current may not be practical due to high current density that correspond to high amount of generated heat that cannot be efficiently dissipated by a cooling system having a small diameter. The total RMS current may affect heat losses to an anode channel. For example, for argon plasma anode losses, $Q_A$ may be $Q_A=10*I_{RMS}$ (W), where $I_{RMS}$ is RMS current.

For the sake of simplicity, the following heating channel relationships may be based on a surgical application embodiment, which may imply a predetermined size of a plasma-generating device and RMS current restriction. In some embodiments, a predetermined temperature range and profile of outlet plasma flow may be defined by both RMS current and a diameter of a heating channel. This means that for plasma-generating devices having a larger cross-sectional area, an appropriate scaling of the parameters may be applied to meet the same relationship.

In some embodiments, to generate volumetrically oscillated plasma flow with controlled axial and predominant radial expansion, the structure of RMS current $I_{RMS}$ may include a predetermined range of relatively low frequency current with amplitudes of between about 2 A and about 30 A with a period of oscillation $T_{LF}$ between about 5 ms and about 50 ms, and a duty D of between about 0.05 and about 0.6, and a relatively high frequency current with amplitudes of between about 5 A and about 30 A with a period of oscillation $T_{HF}$ of between about 10 µs and about 50 µs and a duty D of between about 0.25 and about 0.75. In some embodiments, a max RMS current may not directly limit the maximum current rather than relationship between relatively high and low current duration. For example, the structure of current may include a small fraction of high current with an amplitude of about 30 A while an RMS current may still be lower than about 12 A.

In some embodiments, a diameter of a heating channel may be determined based on a predetermined temperature range of outlet plasma. In some embodiments, a plasma-generating system may be configured to generate outlet plasma with various extent of radial and axial components. Therefore, the diameter and length of a heating channel may be adjusted to provide plasma with temperature in range of between about 2,000 K and about 25,000 K. In some embodiments, heating of the inlet room temperature gas may occur due to energy transfer from arc electrons to heavy particles of the plasma-generating gas. In some embodiments, the heat may radially dissipate towards the heating channel walls that may be cooled by water. The corresponding energy balance for propagated plasma-generating gas may be given by:

$$\rho v c_p \frac{dT}{dz} + \frac{1}{r}\frac{d}{dr}\left(\lambda r \frac{dT}{dr}\right) = \frac{3}{2}\delta v n_e k(T_e - T) \qquad (42)$$

where T is gas temperature, z and r are axial and radial variables, $\rho$ is gas density, $\upsilon$ is gas flow velocity, $c_p$ is specific heat capacity, $\lambda$ is gas thermal conductivity, $T_e$ and $n_e$ are electron temperature and concentration, $\nu$ is collision frequency, and k is the Boltzmann constant.

In some embodiments, an arc electron temperature may be defined by heating with conducted power density P=jE and cooling by gas and walls of a heating channel. The relationship between electron temperature, arc current, and diameter of a heating channel may be comparatively complex and in many cases may be estimated based on empirical dependencies. In some embodiments, an average electron temperature $T_e$ may be proportional to the ratio of arc current to the diameter of heating channel $I/d_h$. More precise dependencies may use a combination of ratio $I/d_h$ and heating channel diameter $I/d_h^2$ for a predetermined range of diameters $d_h$ and currents.

It should be noted that in Eq. 42 and other estimations, energy losses due to radiation are not considered. However, their contribution might shift the resulting temperature plateau values or slightly affect the heating rate. The comparison of calculated values with experimental data, involving measurements for heating channel of various diameters in a range of between about 0.4 mm and about 1.2 mm shows a reasonable approximation for the purposes described herein.

Figure 59:
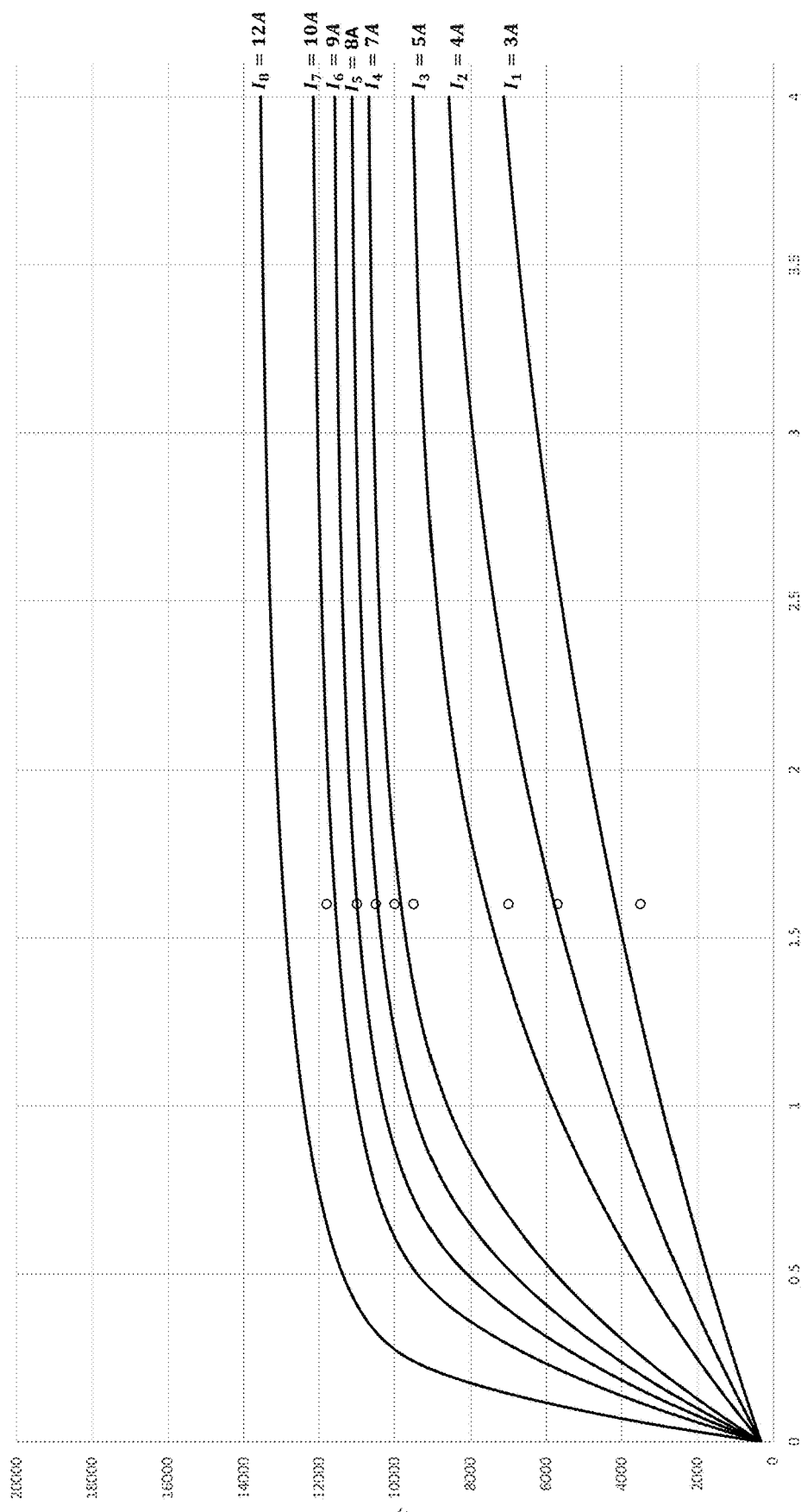
FIG. 59 is a plot of average temperature distribution along a heating channel, according to an embodiment.

FIG. 59 demonstrates the experimental (shown in FIG. 59 as points) and theoretical (shown in FIG. 59 as lines) distribution of average plasma temperature along an axis of a heating channel for the fixed mass flow and diameter of the heating channel and constant current in the range of between about 3 A and about 12 A. As shown, the gas may be gradually heated until it reaches a plateau where the generated heat due to the collisions with electrons may proportionally dissipate by radiation and radial heat diffusion to cool the walls of the heating channel. In some embodiments, the relatively higher current may correspond to a relatively higher temperature of electric arc and hence to higher temperature of electrons $T_e$. In some embodiments, electron temperature may define the initial heating rate and the temperature of the plateau. For relatively low values of current, an initial heating rate may be considerably lower and the temperature may not reach the plateau within the first 4 mm. These results show that at a relatively higher current, the gas may be heated to a maximum temperature within a short distance while longer distances may be required for relatively lower current. This effect may be beneficial since a sufficiently short heating channel may be used to obtain a predetermined (e.g., high, low) plasma outlet temperature.

Figure 60:
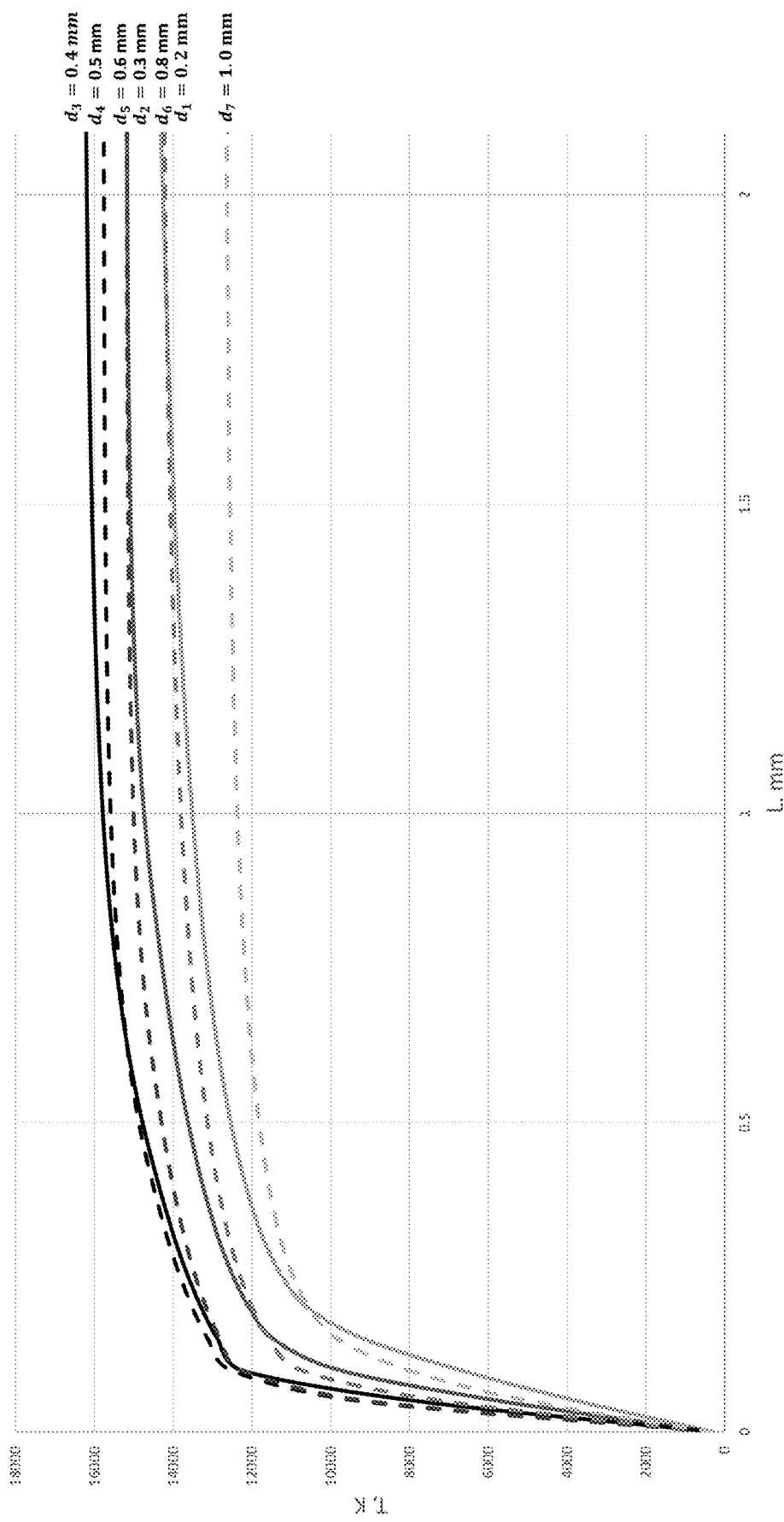
FIG. 60 is a plot of average temperature distribution along a heating channel for relatively high current, according to an embodiment.
Figure 61:
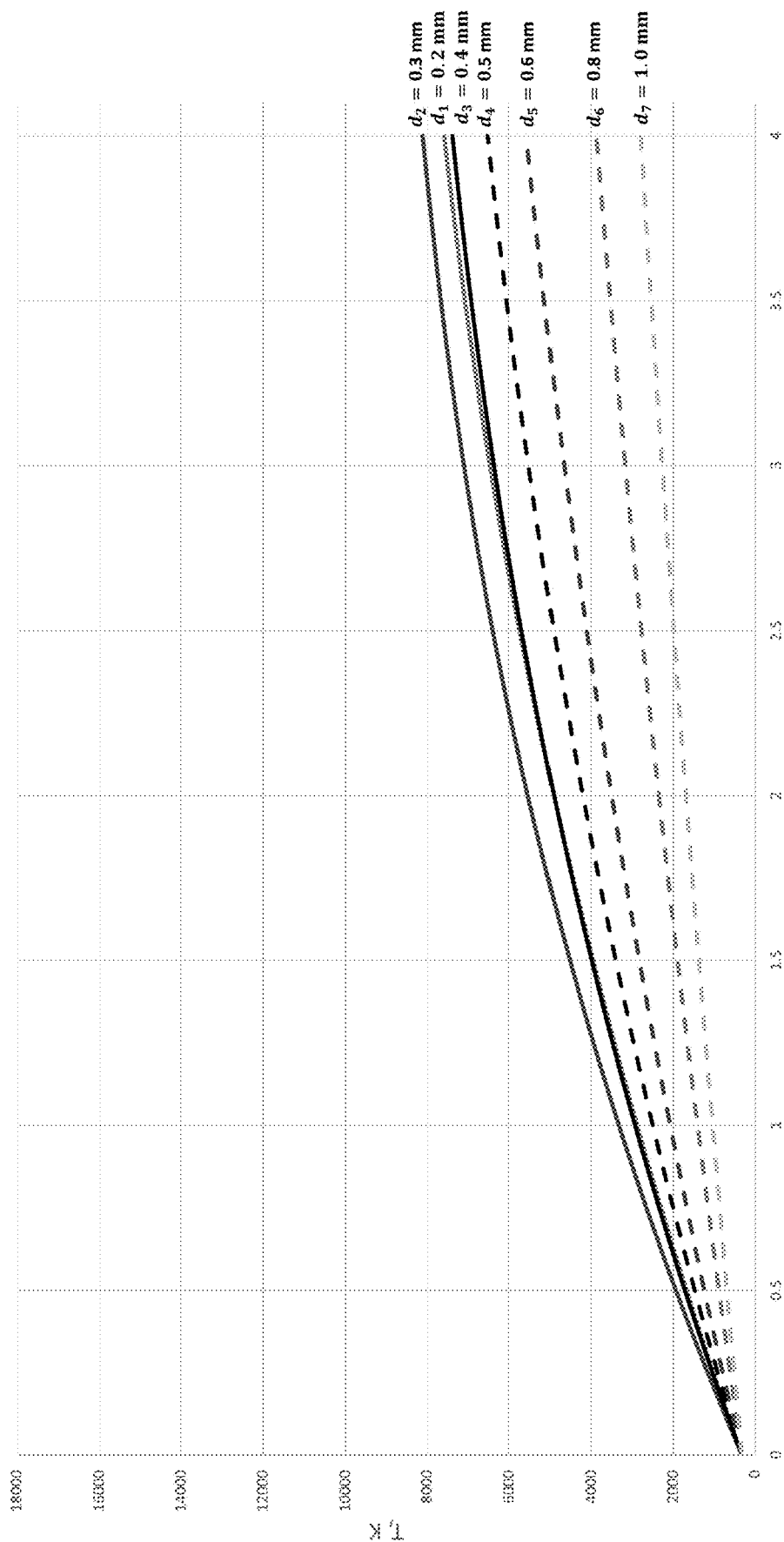
FIG. 61 is a plot of average temperature distribution along a heating channel for relatively low current, according to an embodiment.

FIGS. 60 and 61 illustrate a calculated average temperature distribution for various diameters of a heating channel in a range of between about 0.2 mm and about 1 mm, with a constant current of between about 20 A and about 4 A, respectively. In some embodiments, diameters of heating channels $d_1$-$d_7$ corresponds to about 0.2 mm, about 0.3 mm, about 0.4 mm, about 0.5 mm, about 0.6 mm, about 0.8 mm, and about 1.0 mm, respectively. In some embodiments, the effect of diameter at relatively high current shows that the highest temperature plateau may be reached for a diameter of about 0.4 mm. The larger diameter may result in a relatively low maximum outlet plasma flow temperature due to relatively low electron temperature $T_e$. The smaller diameter, however, may result in a decreased maximum outlet plasma flow temperature. This may be due to higher heat losses to a cooling system that may be affected by high radial temperature gradient for small diameters of heating channel. As shown in FIG. 61, at a relatively low current, the plasma temperature may gradually increase along the axis and a smaller diameter may generally correspond to higher temperatures. At a relatively low current, it takes a higher distance to reach the plateau. Moreover, for a heating channel of between about 0.2 mm and about 0.3 mm, the maximum temperature may be higher than for a heating channel diameter of about 0.4 mm in contrast to the observed dependence for relatively high current. In comparison to relatively high current, the observed difference for relatively low current may be mainly due to lower electron temperature at the low current, and hence a lower temperature gradient that may result in lower heat losses at a smaller diameter of a heating channel. For relatively high currents, the observed diameter that corresponds to the maximum temperature of the plateau might slightly shift due to a higher temperature gradient. However, for a predetermined range of temperature, this effect may not be substantial.

In some embodiments, a plasma-generating device may be configured to generate predominantly radially expanded and volumetrically oscillating plasma flows for surgical application utilizing pulse currents of various levels, such as at about 15 A, about 20 A, and about 30 A to achieve various degree of radial expansion for adjusting the applied energy to the tissue. Experiments show that a diameter of heating channel may be about 0.4 mm. This relationship was found to be optimal for some embodiments to achieve a high range of outlet plasma temperature and show competitive performance for various regimes of outlet temperature oscillation.

The demonstrated calculation of average plasma temperature (FIGS. 59, 60, 61) along the axis of heating channel may correspond to gas flows for surgical application, which may be between about 0.2 l/min and about 0.6 l/min. In some embodiments, the range may be related to energy that may be required to achieve various effects on tissue during the treatment with the plasma-generating device. In some embodiments, the length of the entire heating channel may depend on the flow rate of the plasma generating gas. In some embodiments, a longer heating channel may be required to heat plasma generating gas with a greater flow rate. In some embodiments, for a predetermined range of gas flow, a length of the heating channel may be about 1 mm.

In some embodiments, the length of each intermediate electrode forming heating channel 84, $l_{ie}$, may depend on a diameter of heating channel $d_h$ and may be in the range of between about one time to two times a diameter of $d_h$. In some embodiments, a flow rate of plasma generating gas may have a heating channel formed by at least two intermediate electrodes. In some embodiments, the length of the entire heating channel $l_h$ may be approximated by multiplying the number of intermediate electrodes that form the heating channel by the length of such an intermediate electrode $l_{ie}$.

In some embodiments, electrons of an electric arc may be transferred to an anode surface while generated plasma propagates towards an anode outlet. In some embodiments, an anode channel design may be configured to level the static pressure of outlet plasma flow to about the ambient pressure. This may be achieved using, for example, adaptive nozzle design, where the diameter of an anode nozzle may be configured to expand towards the outlet such that the plasma flow may uniformly expand to the new diameter. In some embodiments, leveling the static pressure of outlet plasma with ambient pressure may be useful for surgical applications where excess static pressure may increase the risk of gas embolism or blood vessel blockage caused by gas penetration in the blood vessels.

As previously discussed, the plasma flow may be generally choked at the expansion section of the channel where plasma flow propagates. In some embodiments, the choked condition may occur in the anode channel where the gas flow expands. Anode channel expansion may occur in various ways based on an application of the plasma-generating device. In some embodiments, a relationship for the anode channel may be that the ratio of outlet cross-sectional area to an inner cross-sectional area of a heating channel may be adjusted to reduce the static pressure of outlet plasma at least relative to ambient pressure. For example, an adaptive nozzle design may be used.

In some embodiments, an outlet diameter $d_{OUT}$ of the anode may be calculated using Eq. 16. For example, for a heating channel of about 0.4 mm, a working pressure of about 5 bars and an outlet temperature of about 5,000 K and an outlet diameter of about 0.45 mm may be used to avoid excessive static pressure of plasma flow and increase the velocity about 1.6 times. In some embodiments, higher value of outlet diameters, such as about 0.5 mm, may be used in some applications, such as surgical procedures, to protect against excessive static pressure. It should be noted that adaptive nozzle design may involve a predetermined hydrodynamical shape (e.g., de Laval nozzle) of the channel to facilitate the uniform expansion of plasma flow and avoid excessive friction at the anode surface. In some embodiments, excessive friction may induce small perturbation in plasma flow that may result in a shorter length of a plasma jet.

For a therapeutic application such as an antimicrobial treatment of tissue due to release of nitric oxide during operation of plasma-generating device, a larger diameter of a plasma jet may be beneficial since it expands the area of treatment, thereby making the treatment easier for an operator and taking less time to perform. In some embodiments, an expansion of plasma flow may be achieved in the anode channel. In some embodiments, a gas flow rate may be comparatively higher to increase the working pressure in the cathode chamber and allow higher expansion of plasma flow in the anode channel by adaptive nozzle design with a larger outlet diameter. Moreover, the higher expansion of the anode channel may increase the plasma flow velocity. This may be useful to achieve better conditions for radial expansion of plasma flow.

Figure 62:
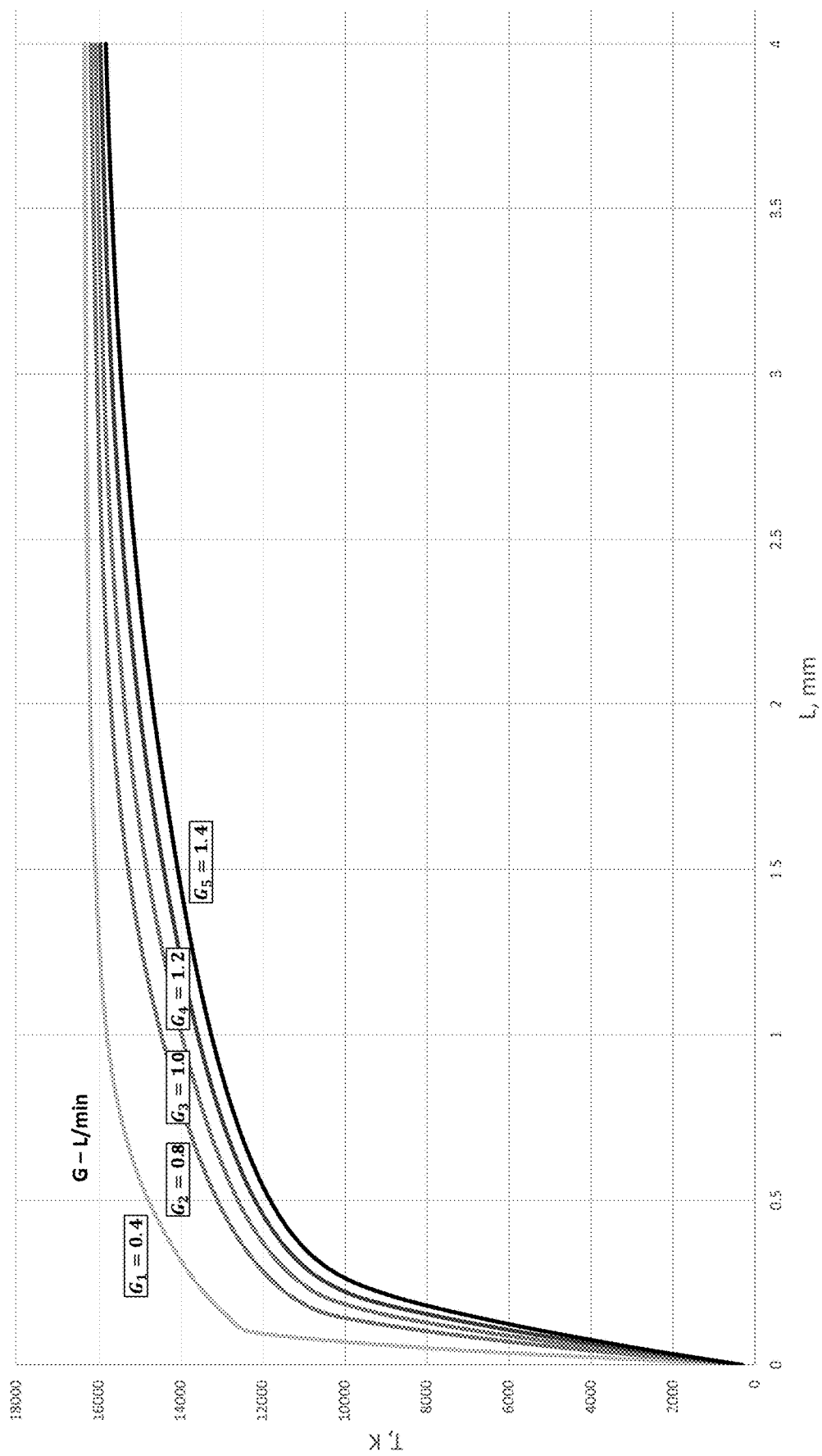
FIG. 62 is a plot of an average temperature distribution along a heating channel for relatively high current, according to an embodiment.

For an application that requires relatively high gas flow, the optimal length of a heating channel may be longer than for previously discussed surgical applications. FIG. 62 shows the calculated average temperature distribution for various gas flows in a range of between about 0.4 l/min and about 1.4 l/min at constant current of about 20 A. In some embodiments, gas flows $G_1$-$G_5$ corresponds to about 0.4 l/min, about 0.8 l/min, about 1.0 l/min, about 1.2 l/min, and about 1.4 l/min, respectively. As shown in FIG. 62, the length of a heating channel may be adjusted for relatively higher gas flows. For example, a suitable length of the heating channel may be between about 3 mm and about 4 mm for a gas flow of about 1.4 l/min.

In some embodiments, heating channel relationships may be based on a size constraint and energy demands of a predetermined application (e.g., medical procedure). For other applications, a geometric relationship may be scaled to maintain the ratio of applied RMS current to a diameter of heating channel of a plasma-generating device. Maintaining this ratio may generate similar electron temperatures in the electric arc and a similar range of plasma temperatures. In some embodiments, the gas flow rate may define the applied energy range to the treated object. For example, to meet the relationships for the length of heating channel, the mass flux in the heating portion may be maintained.

Cathode Chamber

In some embodiments, plasma-generating devices that operate with oscillating current that generate predominantly radially expanded and/or volumetrically oscillating plasma flows may have more stringent requirements compared to other continuous plasma-generating devices. Oscillating current involves additional dynamic processes in a cathode-anode system related to erosion and stable plasma generation. Accordingly, certain plasma-generating devices may fail (e.g., degrade) if they operate with oscillating current and the high frequency described herein.

Cathode-anode failure in the presence of current oscillation with high or low frequencies has been experimentally analyzed to establish parameter ranges for the plasma-generating devices described herein. The experimental setup focused on minimizing degradation and prolonging the lifetime of the plasma-generating device for a wide range of operating conditions including the shapes of current-time profiles and characteristic frequencies of oscillation. Geometric relationships of various component dimensions were obtained. In some embodiments, these relationships may be satisfied for a sufficiently stable and robust operation.

Figure 63:
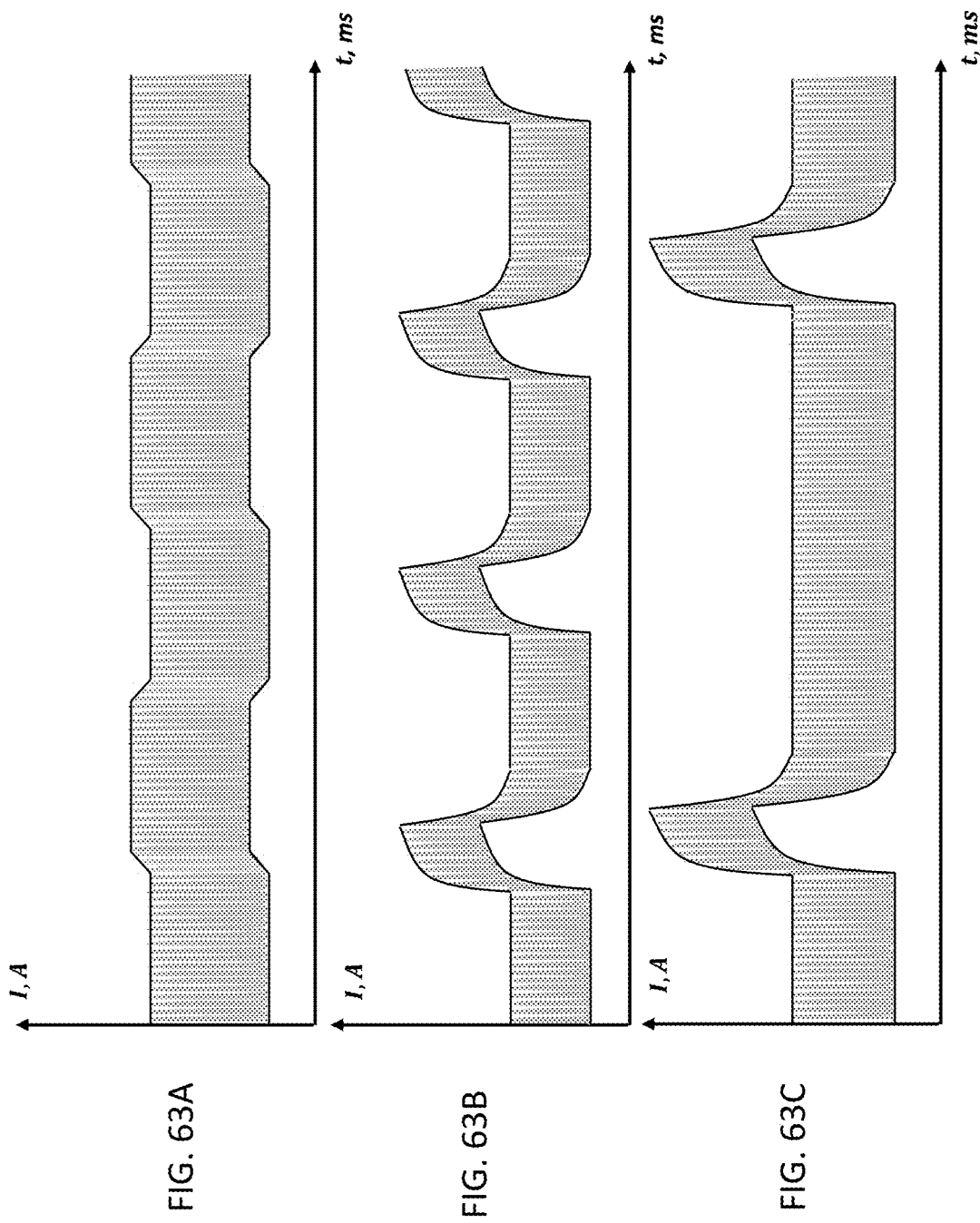
FIGS. 63A-63C are plots of current oscillation for performance tests, according to an embodiment.

In some embodiments, a performance test may include 3 regimes (lasting for about 20 minutes each) of arc current oscillation with low frequency (LF) and high frequency (HF) pulses. FIG. 63A illustrates LF pulses with RMS current of $0.3 \cdot I_{RMS}^{max}$ and HF pulses with RMS current of $0.7 \cdot I_{RMS}^{max}$. FIG. 63B illustrates LF pulses with RMS current of $0.4 \cdot I_{RMS}^{max}$ and HF pulses with RMS current of $0.6 \cdot I_{RMS}^{max}$. FIG. 63C illustrates LF pulses with RMS current of $0.5 \cdot I_{RMS}^{max}$ and HF pulses with RMS current of $0.5 \cdot I_{RMS}^{max}$. $I_{RMS}^{max}$ is a maximum RMS current for the plasma-generating device. Such experimental setup may be chosen to ensure stable and reliable generation of plasma within various conditions.

Figure 58:
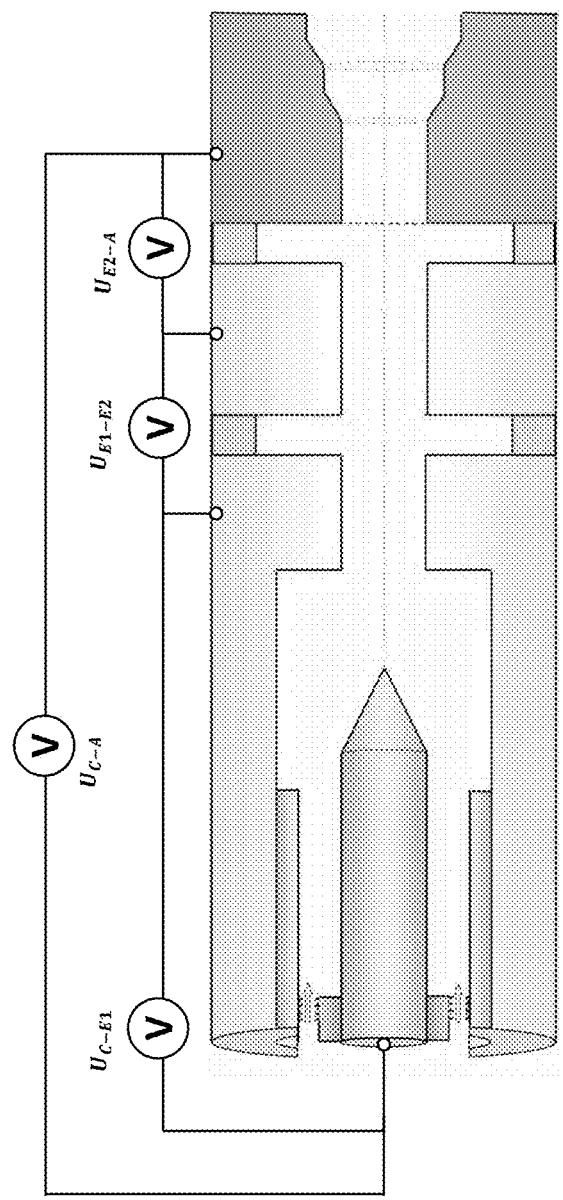
FIG. 58 is a cross-sectional side schematic view of measurement points of a plasma-generating device, according to an embodiment.

Voltage and current between various parts of a plasma-generating device (e.g., plasma-generating device 100, 5500, 5700) were measured to investigate possible negative factors. FIG. 58 schematically illustrates the connection locations and corresponding designation for voltages, namely $U_{C\text{-}E1}$ for cathode chamber, $U_{E1\text{-}E2}$ for heating channel, and $U_{E2\text{-}A}$ for anode channel. For some experiments, a total voltage between cathode and anode $U_{C\text{-}A}$, or a voltage between a first electrode (e.g., first electrode 5510) and anode $U_{E1\text{-}A}$ was monitored.

Figure 56:
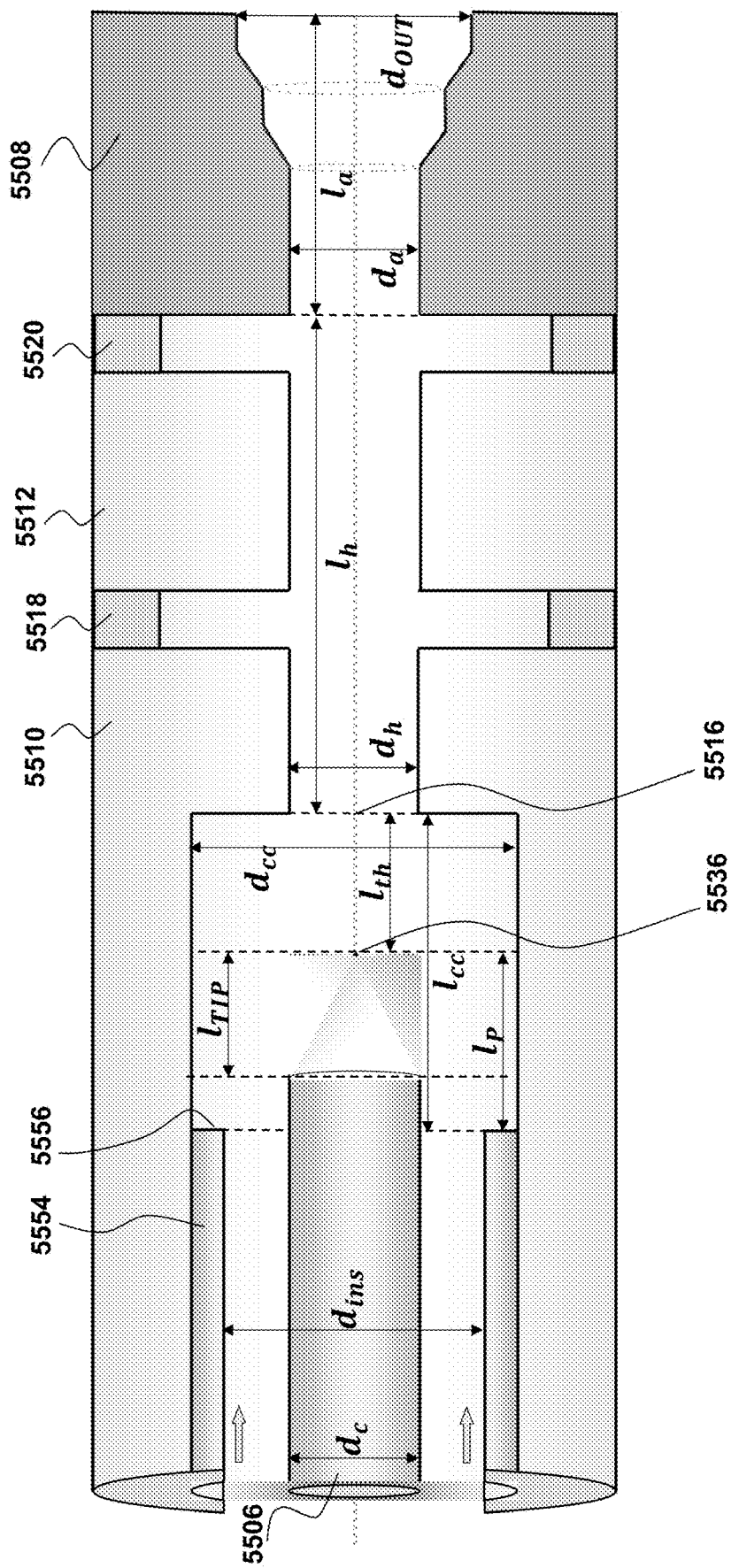
FIG. 56 is a cross-sectional side schematic view the plasma-generating device depicted in FIG. 55, according to an embodiment.
Figure 64:
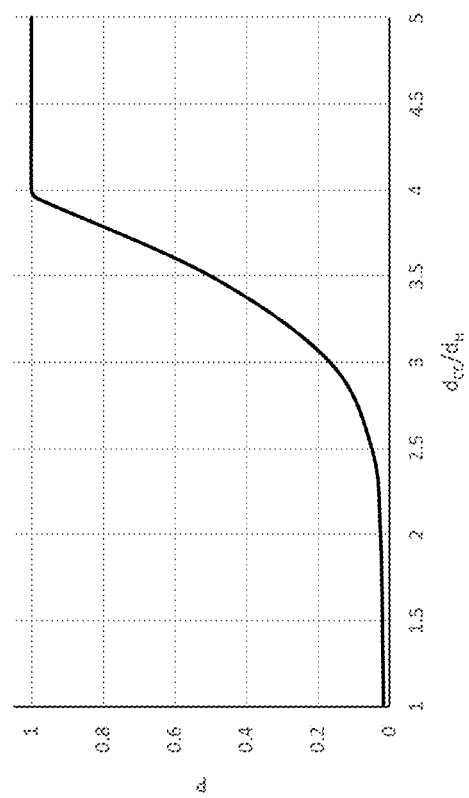
FIG. 64 is a plot of lifespan acceptance criteria and cathode chamber diameter, according to an embodiment.

With reference to FIG. 56, the geometric relationships between the components of the plasma-generating device 5500 were varied, and for each combination of parameters, performance tests were carried out. The strongest effect on degradation of plasma-generating device was found when the diameter of cathode chamber 5560 and specifically its cylindrical portion 5562 (e.g., $d_{cc}$), was varied in relation to the diameter of heating channel 124 (e.g., $d_h$). FIG. 64 shows lifespan acceptance criteria P may depend on a ratio $d_{cc}/d_h$. This acceptance criteria was calculated as a ratio of operation time that the plasma-generating device worked before it failed to the total time of the performance test, which may be about 60 minutes in some embodiments. If P=1, than the generator could operate for at least 60 minutes.

In some embodiments, the variation of other parameters of plasma-generating device 100 were shown (based on the performance tests) to be less critical than the variation of a diameter of cylindrical portion 5562 of cathode chamber 5560.

In some embodiments, the distance between a cathode tip end point 5536 and the heating channel inlet 5516 (e.g., $l_{TH}$, tip to heat channel distance), may be at least about 1.5 times larger than the diameter of heating channel 5524 (e.g., $d_h$). In other words, the cathode tip end point position may be at a predetermined distance from a proximal end of the heating channel to avoid the influence of the heating channel. If the heating channel is too close to a cathode tip, it may effectively "reduce" the diameter of cathode chamber 5560. As discussed above, in some embodiments, a small diameter of the cathode chamber may have a negative effect on device lifespan. For the same reason, the cathode tip end point 5536 may not be inside the insulator sleeve 5554 in some embodiments, and the protruding distance between distal edge 5556 of insulator sleeve and cathode tip end point 5536 (e.g., $l_p$) may be at least equal to the cathode diameter (i.e., diameter of the cylindrical part of cathode 5506) (e.g., $d_c$).

In some embodiments, a sufficiently short protruding distance $l_p$ may be configured to efficiently cool the cathode by incoming gas. In some embodiments, the ratio of protruding distance to cathode diameter de may be at most about 1.6. Furthermore, to ensure reliable cooling of the cathode 5506, a ratio of the inside diameter of insulator sleeve 5554 (e.g., $d_{INS}$), and cathode diameter $d_c$ may be in the range of between about 0.7 and about 0.85.

Table 2 summarize the results of performance testing and indicates suitable ranges and optimal parameters of a plasma-generating device.

TABLE 2

Tested and acceptable range and parameters of plasma-generating devices

| Parameter | Parameter designation | Tested range | Acceptable operation range | Suitable operation values |
|---|---|---|---|---|
| Heating channel diameter, mm | $d_H$ | (0.2-1.0) mm | (0.4-1.0) mm | 0.4 mm |
| Heating channel length, mm | $l_H$ | (1.5-6.0) · $d_H$ | (2-5) · $d_H$ | 3 · $d_H$ |
| Cathode diameter, mm | $d_C$ | (0.5-1.0) mm | (0.5-1.0) mm | 0.5 mm |
| Cathode tip length, mm | $l_{tip}$ | (1.0-2.5) · $d_C$ | (1.5-2.0) · $d_C$ | 1.9 $d_C$ |
| Cathode chamber diameter, mm | $d_{CC}$ | (1.0-5.0) · $d_H$ | ≥4.0 · $d_H$ | 1.8 mm |
| Tip-to-heating channel distance, mm | $l_{TH}$ | (0.5-3.0) · $d_H$ | ≥1.25 · $d_H$ | 0.7 mm |
| Cathode tip protrusion, mm | $l_P$ | (0-20) · $d_C$ | (1.0-1.6) · $d_C$ | 1.4 mm |
| Cathode chamber length, mm | $l_{CC}$ | $l_{TH}$ + $l_P$ | $l_{TH}$ + $l_P$ | 2.1 mm |
| Inner insulator diameter, mm | $d_{INS}$ | (1.1-2.5) · $d_C$ | (1.1-1.4) · $d_C$ | 1.2 mm |
| Anode diameter, mm | $d_A$ | (0.4-2.0) mm | (0.4-2.0) mm | 0.5 mm |
| Anode length, mm | $l_A$ | (2.0-8.0) · $d_A$ | (2.0-4.0) · $d_A$ | 2 mm |

The performance tests described herein facilitate the design of plasma-generating devices configured to operate with oscillating arc current that avoid rapid degradation of the cathode-anode system. The following discussion includes analysis of dynamic processes in the cathode-anode system and erosion mechanisms in plasma-generating devices that reduce detrimental effects.

In some embodiments, the generation of thermal plasma may begin with a cold cathode and include operating phases such as spark, glow, and arc discharge. In a first phase (e.g., spark), an electric spark may be generated between a cathode and an anode using a relatively high electric field and voltage. Then, the accelerated electrons of the spark may interact with plasma-generating gas in a glow phase (e.g., second phase) to form positively charged ions, which in turn may bombard the cathode. The glow phase may be maintained by relatively high voltage and relatively low currents. As the current increases, a part of the cathode may be sufficiently heated by bombardment of returning ions to induce thermal emission of electrons from cathode. Next, in an arc discharge phase (e.g., third phase), the emitted electrons may reach a predetermined number large enough such that the arc current between the cathode and the anode may be maintained by a relatively low voltage. The current density in the third phase may be substantially larger compared to a first and second phase. In some embodiments, the high current may be necessary to heat the gas to a high temperature.

In some embodiments, when a plasma-generating device uses a constant current, a stationary cathode potential may be established. A total electric arc current through the cathode may include negatively charged emitted electrons, positively charged bombarding ions, and returned back-diffused electron currents.

$$I(t) = I_{ee} + I_i - I_{bde} \qquad (43)$$

where $I_{ee}$, $I_i$, and $I_{bde}$ are total or integrated current of emitted electrons, bombarding ions, and returned electrons over cathode surface, respectively.

In some embodiments, these currents may be directly related to energy balance of the cathode surface. In some embodiments, the heating mechanism of the cathode and the incoming heat flux to the cathode surface may include bombarding the returning ions $Q_i$, and back-diffusing plasma electrons $Q_{bde}$. In some embodiments, the cooling mechanism and outgoing heat flux may include thermal emission of cathode electrons $Q_{ee}$ and dissipated energy Q by conduction through the cathode body and by vaporization of the cathode material at high temperatures.

$$Q_i + Q_{bde} = Q_{ee} + Q \qquad (44)$$

For steady-state operation, when the cathode and plasma temperatures do not change, the energy balance of the cathode surface may be given as follows:

$$Q = I_i\left(\frac{5}{2}\frac{kT_h}{e} + U_c + A_i - A_f\right) + I_{bde}\left(\frac{5}{2}\frac{kT_e}{e} + A_f\right) - I_{ee}\left(2\frac{kT_s}{e} + A_f\right) \qquad (45)$$

where $T_h$, $T_e$ are respectively ion and electron temperature in proximity of cathode surface, and $T_s$ is cathode surface temperature. $U_c$ may be cathode potential drop in the sheath, $A_i$, $A_f$ are respectively gas ionization energy and work function of cathode material.

In some embodiments, characteristic times of the processes involved in the energy balance may vary. For example, a characteristic time for heat diffusion through plasma with a characteristic length of 1 mm may be in a range of between about 10 ms and about 50 ms. For plasma-generating devices operating with relatively high frequency, an arc current rate-of-rise and rate-of-fall may be in a range of between about 5 A/μs and about 10 A/μs for a leading edge of a current pulse and between about 10 A/μs and about 30 A/μs for a trailing edge of a current pulse. For these conditions, the characteristic time of arc current development may be in a range of between about 0.5 μs and about 1 μs.

In some embodiments, characteristic times that relate to the processes of plasma state establishment may include the parameters of current and energy balance. In some embodiments, the terms "plasma development time" and "plasma recombination time" may be used to estimate time to establish ion concentration and plasma temperature radial distribution corresponding to steady-state operation with constant current. In some embodiments, a plasma development time may refer to when arc current demand increases and ion concentration and plasma temperature are temporally lower than corresponding values in steady-state operation. In some embodiments, a plasma recombination time may refer to when arc current is decreased and excess ion concentration and plasma heat dissipates until it reaches values that correspond to a new steady-state operation with lower arc current. In some embodiments, plasma development and recombination time may refer to a plasma state in the cathode-anode channels and are different from a development/recombination time of plasma jet that refers to outlet plasma jet characteristics.

In some embodiments, plasma recombination time may be defined by a heat diffusion mechanism and, as described above, may be significantly lower than a characteristic time of arc current change. In some embodiments, for cylindrical channels, the faster diffusion rate may be achieved for smaller diameter of channel and lower wall temperature.

In some embodiments, the described characteristic times may define how fast the corresponding parameters such as arc current and ion current may be changed. In some embodiments, the ion current and corresponding heat flux due to returned ions may depend on ion concentration in the proximity of a cathode surface. Accordingly, heating fraction by ion bombardment may be defined by plasma state and may not immediately respond to the arc current change due to the difference in characteristic times.

The equations (43) and (45) describe equilibrium of established currents and energy balance for steady-state operation at constant arc current. In some embodiments, when equilibrium is reached, the difference in characteristic times may not affect the plasma-generating device. However, in case of non-steady-state operation, a difference in characteristic times may shift the current and energy balance. The shift in current balance may result in a higher fraction of ion current that, in turn, may increase the energy fraction that needs to be dissipated by cathode body. In some embodiments, rapid changes of arc current may correspond to an even higher shift in balance. In case of operation with oscillating current, the energy balance may be significantly shifted, and accumulated excess of heat energy may result in overheating of the cathode. The following experiments were carried out to analyze the influence of this effect for oscillating arc current.

Figure 65A:
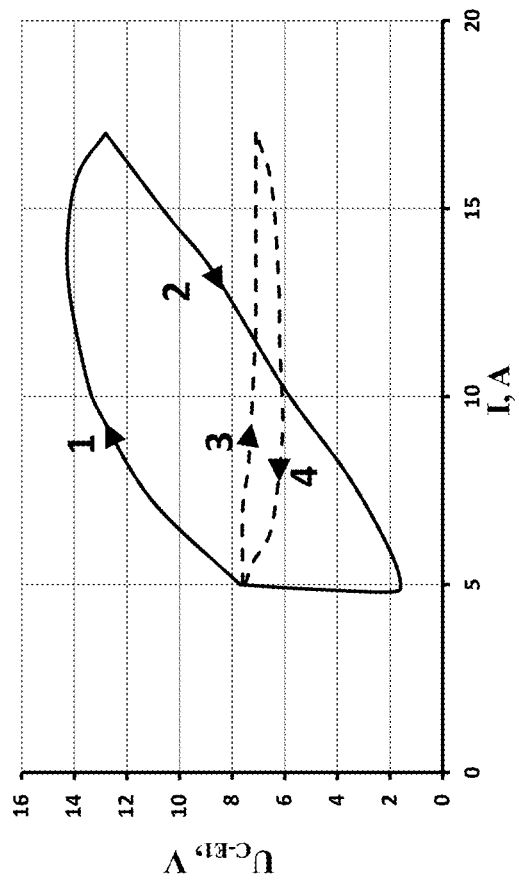
FIGS. 65A-65B are plots of volt-ampere characteristics for $U_{C-E1}$ and $U_{E1-A}$, according to an embodiment.
Figure 65B:
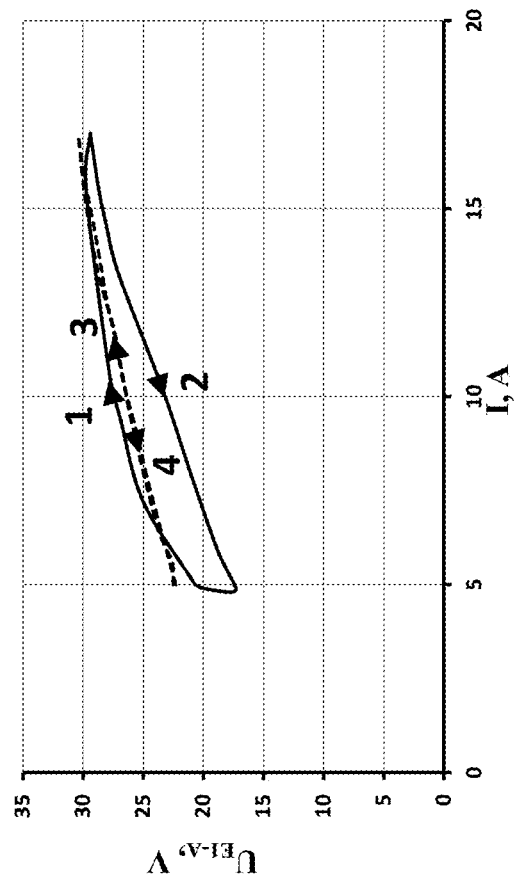

In some embodiments, a rapid degradation of an cathode-anode system was observed for operation with oscillating current at high frequencies. In some embodiments, the term "cathode chamber potential drop" may refer to the voltage measured between cathode 5506 and first intermediate electrode 5510. In some embodiments, the term "heating channel potential drop" may refer to the voltage measured between first intermediate electrode 5510 and anode 5508. FIGS. 65A and 65B show volt-ampere characteristics for oscillating arc current with relatively high (solid lines) and relatively low frequency (dash lines). The measured voltage in FIG. 65A corresponds to cathode chamber potential drop $U_{C-E1}$, and in FIG. 65B corresponds to heating and anode channel potential drop $U_{E1-A}$. The relatively high frequency results in distortion of the characteristics in comparison to low frequency. To investigate the factors corresponding to the observed voltage, distortion voltage was measured for cathode chamber $U_{C-E1}$, heating channel $U_{E1-E2}$, and anode channel $U_{E2-A}$, as shown in FIG. 58. The observed voltage distortion mainly occurs for cathode chamber potential drop $U_{C-E1}$. No significant difference between high and low frequency may be found for heating channel or anode channel as may be seen in FIG. 65B. Thus, the major contributor to this effect may be near-cathode processes. The observed distortion in volt-ampere characteristics indicates that at high frequencies, the difference in characteristic times of cathode processes play a role in current and energy balance.

FIG. 66B shows a schematic of a typical time scan of cathode chamber potential drop $U_{C-E1}$ for oscillating current with relatively low frequency 160 and relatively high frequency 162. The corresponding current oscillates between $I_1$ and $I_2$ (FIG. 66A). The actual period of oscillation T may be substantially longer for low frequency 160 than for high frequency 162. The current change rate $(I_2-I_1)/\Delta\tau_I$ may be much higher for high frequency 162. In case of a slowly changed current and low frequency 160, the voltage may be oscillating between $U_1$ and $U_2$, which relates to stationary values for constant current $I_1$ and $I_2$, respectively. In some embodiments, if the frequency of oscillation is increased, the current change rate may be increased to maintain the shape of a current profile. In some embodiments, if the frequency is sufficiently high, the resulting shape of a voltage time scan may correspond to high frequency 162.

In some embodiments, when the current is rapidly raised from $I_1$ to $I_2$, at the point 166 (FIG. 66B) the voltage may go higher than stationary value $U_2$, which refers to established voltage at constant current $I_2$. In some embodiments, the higher voltage may be necessary to develop conditions for new energy and current balance, corresponding to current $I_2$. In some embodiments, an accelerated increase of emitted electrons may occur, and hence an increase of ion concentration near the cathode and an increase of cathode temperature due to higher number of returned ions and finally cathode heat balance. In FIG. 66B, the voltage reaches its peak at the point 166, and then it decreases towards stationary value $U_2$, but before reaching $U_2$ at the point 168, the current demand may rapidly decrease. In some embodiments, at the point 170, the ion concentration in the surrounding plasma may be substantially larger than the corresponding concentration for steady-state operation at current $I_1$. In some embodiments, before oversaturated plasma recombines to level of current $I_1$, the fraction of ion current may be much higher compared to stationary one. As a result, the cathode chamber potential drop may reach very low values close to zero, and then recover towards a stationary value $U_1$.

Experiments have been conducted to verify the influence of plasma state on current and energy balance. FIGS. 67A-67B demonstrate time scans of arc current and cathode chamber potential drop $U_{C-E1}$ for oscillating current with fixed shape of current pulses but different interval $\tau_i$ between pulses. With reference to FIGS. 67A-67B, at the end of a current pulse at the point 172, the cathode chamber potential drop may reach almost the same value. At this moment, the ion concentration in the proximity of cathode surface may be considered the same for $\tau_i$ of 10 and 30 μs (FIGS. 67A-67B). In some embodiments, when the arc current is reduced to a base value, the cathode chamber potential drop $U_{C-E1}$ may reach a minimum value at point 174, and then may rise until point 176 when a new pulse may be started. As discussed herein, the observed minimum may be explained by a higher fraction of ion current in the current balance. As the excess of ion concentration recombines, the cathode chamber potential drop $U_{C-E1}$ may increase and for a sufficiently long interval duration $\tau_i$ to reach value $U_1$ 180. In some embodiments, if the interval duration $\tau_i$ is shorter than the time of plasma recombination, then the cathode chamber potential drop $U_{C-E1}$ may not reach value $U_1$ at point 176 (FIG. 67A). In some embodiments, when the arc current is increased to a pulse value, the cathode chamber potential drop $U_{C-E1}$ may reach a peak 178. In some embodiments, a relatively higher value of voltage may increase the ion concentration to the level corresponding to pulse arc current. In some embodiments, if the interval duration $\tau_i$ is shorter than the time of plasma recombination, then a low voltage peak may be observed since the ion concentration at the start of the pulse is higher. As shown in FIG. 67, for shorter interval duration the peak of the cathode chamber potential drop $U_{C-E1}$ may be indeed lower.

Figure 68:
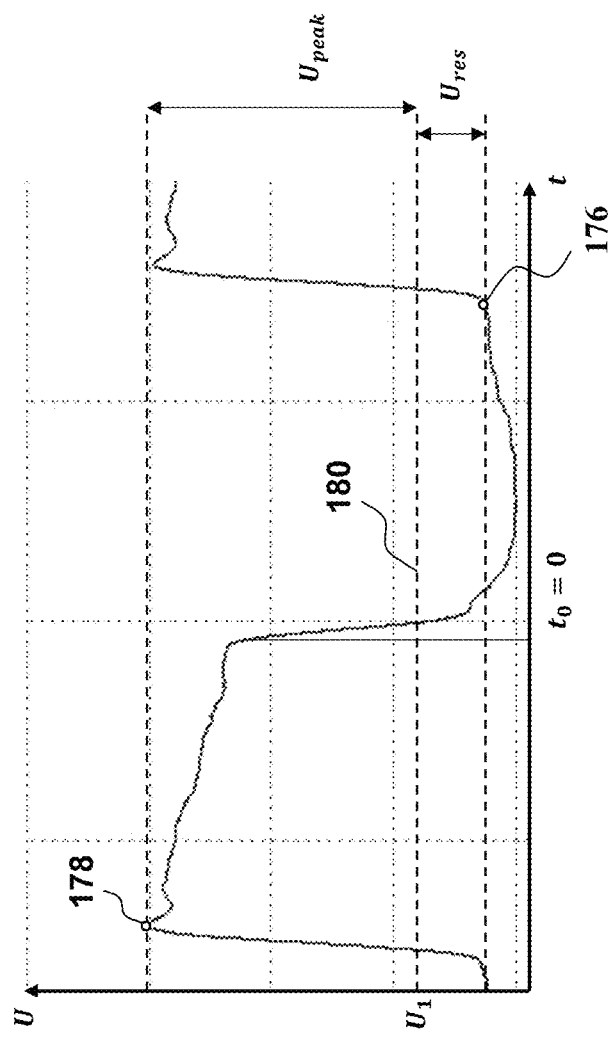
FIG. 68 is a plot of a time scan of $U_{C-E1}$, according to an embodiment.

With reference to FIG. 68 and the discussion above, base voltage $U_1$ refers to the cathode chamber potential drop $U_{C-E1}$ at point 176 when the interval duration $\tau_i$ may be substantially longer than plasma recombination time. Residual voltage $U_{res}$, calculated as a difference between base voltage $U_1$ and the voltage value at the point 176, may be used to estimate the plasma recombination time. Peak-to-base voltage $U_{p-b}$, calculated as difference between peak voltage and base value $U_1$, may characterize the difference between required ion concentration for the pulse arc current and ion concentration at the start of the arc current pulse.

Figure 69:
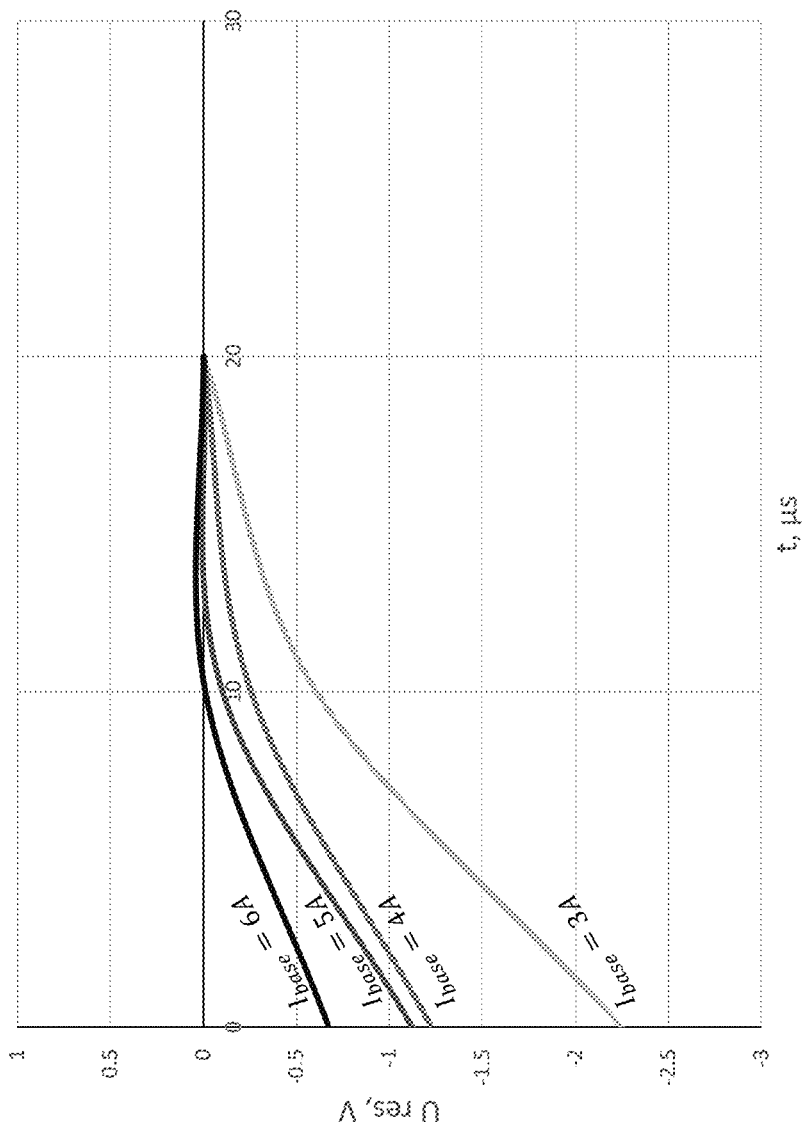
FIG. 69 is a plot of residual voltage $U_{res}$ and time, according to an embodiment.
Figure 70:
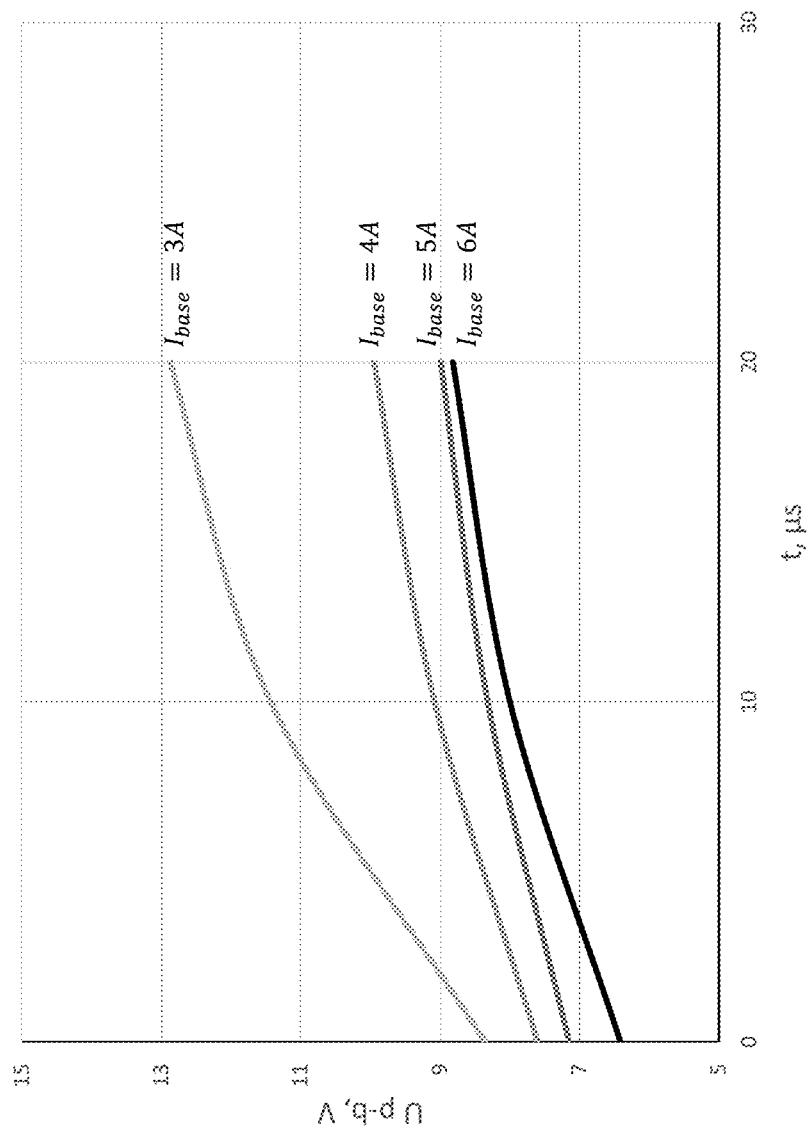
FIG. 70 is a plot of peak-to-base voltage $U_{p-b}$ and time, according to an embodiment.

FIGS. 69 and 70 demonstrate measured residual voltage $U_{res}$ and peak-to-base voltage $U_{p-b}$ depending on interval duration $\tau_i$ for the fixed pulse shape and amplitude and base arc current in range of between about 3 A to about 6 A. As shown in FIG. 69, the residual voltage $U_{res}$ may decrease for longer interval duration $\tau_i$ and characteristic time of plasma recombination may be estimated as between about 20 µs and about 40 µs in some embodiments. It may be noted that plasma recombination time may be related to dissipation of excess of plasma heat. Thus, it may depend on cathode chamber diameter and an efficiency of cooling. The fixed shape and amplitude of current pulses may result in the same ion concentration at the end of the current pulse. For lower values of base arc current, the fixed ion concentration at the end of current pulse may result in higher fraction of ion current when arc current drops to base level. As consequence, the residual voltage $U_{res}$ may reach higher values for lower values of base arc current. Similarly, FIG. 70 demonstrates that for short interval duration $\tau_i$, peak-to-base voltage $U_{p-b}$ may be comparatively low, thus indicating that plasma did not recombine during this period. The observed high values of peak-to-base voltage $U_{p-b}$ for lower base arc current may be a direct result of a greater difference between ion concentration at the start of the arc current pulse and ion concentration corresponding to pulse value of arc current.

In some embodiments, the minimum of the cathode chamber potential drop $U_{C-E1}$ at point 174 may be due to a higher fraction of ion current observed and a comparatively slow current decrease rate of 6 A/ms. This may indicate that the detrimental process of "additional" cathode heating due to shift of energy balance occurs when arc current is decreased. The detrimental process may not be completely avoided since the surrounding plasma cannot be immediately removed or recombined at the end of the current pulse. Therefore, for practical applications, the intensity of this detrimental effect may be decreased, and efficient cooling of the cathode may be realized. For example, the intensity of this detrimental effect may be reduced by decreasing ion concentration or temperature in the vicinity of the cathode surface.

Figure 71:
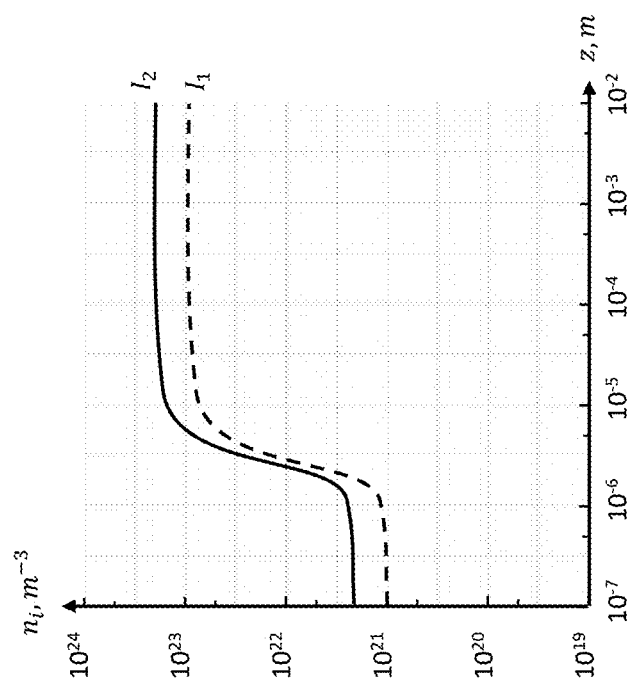
FIG. 71 is a plot of ion concentration in the proximity of a cathode surface in case of steady-state operation at constant current, according to an embodiment.

FIG. 71 illustrates a schematic of ion concentration distribution for stationary $I_1$ and $I_2$ currents. Due to recombination of ions at the cathode surface, the ion concentration may be lower in the thin near-cathode layer or cathode sheath. In some embodiments, the ions may diffuse to the cathode sheath from the adjacent layer. For simplicity of explanation, the surrounding concentration may be considered constant. In some embodiments, at near-cathode area thermodynamic characteristics, which includes ion concentration, may be different from plasma. The near-cathode area, also known as the non-equilibrium layer, is different from plasma that may be in a local thermodynamic equilibrium. In some embodiments, the non-equilibrium layer may be divided into several sublayers that includes: (1) a cathode sheath where emitted electrons may be accelerated and ions recombine on a cathode surface; and, (2) an ionization zone where emitted electrons ionize the plasma-generating gas.

In some embodiments, as shown in FIG. 71, the arc current may heat the surrounding plasma and relatively higher current may correspond to a relatively higher degree of ionization of plasma, thus increasing the ion concentration. When the current is rapidly changed from $I_2$ to $I_1$, the ion concentration may not drop immediately in contrast to current, and may contribute to a higher fraction of ion current to a cathode surface. This may result in higher heat flux to the cathode. Increasing ion current may provide redaction of emission electron from a cathode surface and reduction of cooling. Over many cycles of current oscillation, a small imbalance in heat flux may correspond to overheating of the cathode and failure. In some embodiments, higher ion concentration may bring higher ion current to the cathode and a higher temperature. Therefore, each ion may bring more thermal energy to the cathode.

Figure 72:
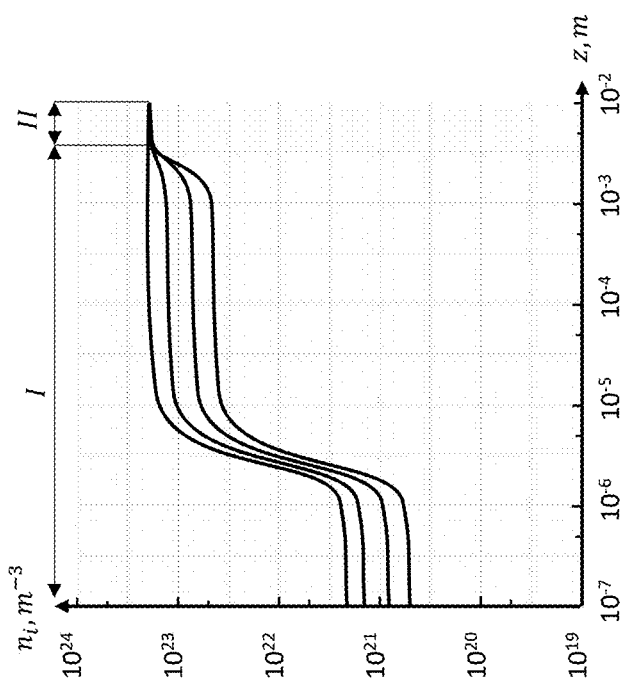
FIG. 72 is a plot of ion concentration in the proximity of a cathode surface depending on a ratio $d_{cc}/d_h$, according to an embodiment.

In some embodiments, a cathode chamber may be configured to avoid cathode overheating when predominantly radially expanded and volumetrically oscillating plasma is generated. This may require cooling of the cathode including efficient cooling of a cathode body and minimizing input heat flux to the cathode. Input heat flux may be reduced by decreasing an ion concentration in the proximity of cathode active area. In some embodiments, with reference to FIG. 56, a diameter of cathode chamber 5560 and specifically its cylindrical portion 5562 (e.g., $d_{cc}$) may be increased relative to a diameter of heating channel 5524 (e.g., $d_h$). Therefore, the plasma temperature and hence the ion concentration in the proximity of a cathode active area may be lower compared to the heating channel. FIG. 72 illustrates ion concentration distribution depending on various ratios of $d_{cc}/d_h$. Region I in FIG. 72 may refer to an ion concentration in a cathode chamber. Region II corresponds to ion concentration in the heating channel. This concentration may be defined by an average value of plasma temperature in the heating channel and may correspond to about 16,000 K in FIG. 72. The displayed lines correspond to $d_{cc}/d_h$ ratios of 1, 2, 3 and 4. In some embodiments, the ion concentration drops about one order of magnitude when a $d_{cc}/d_h$ ratio is increased from 1 to 4.

Figure 73:
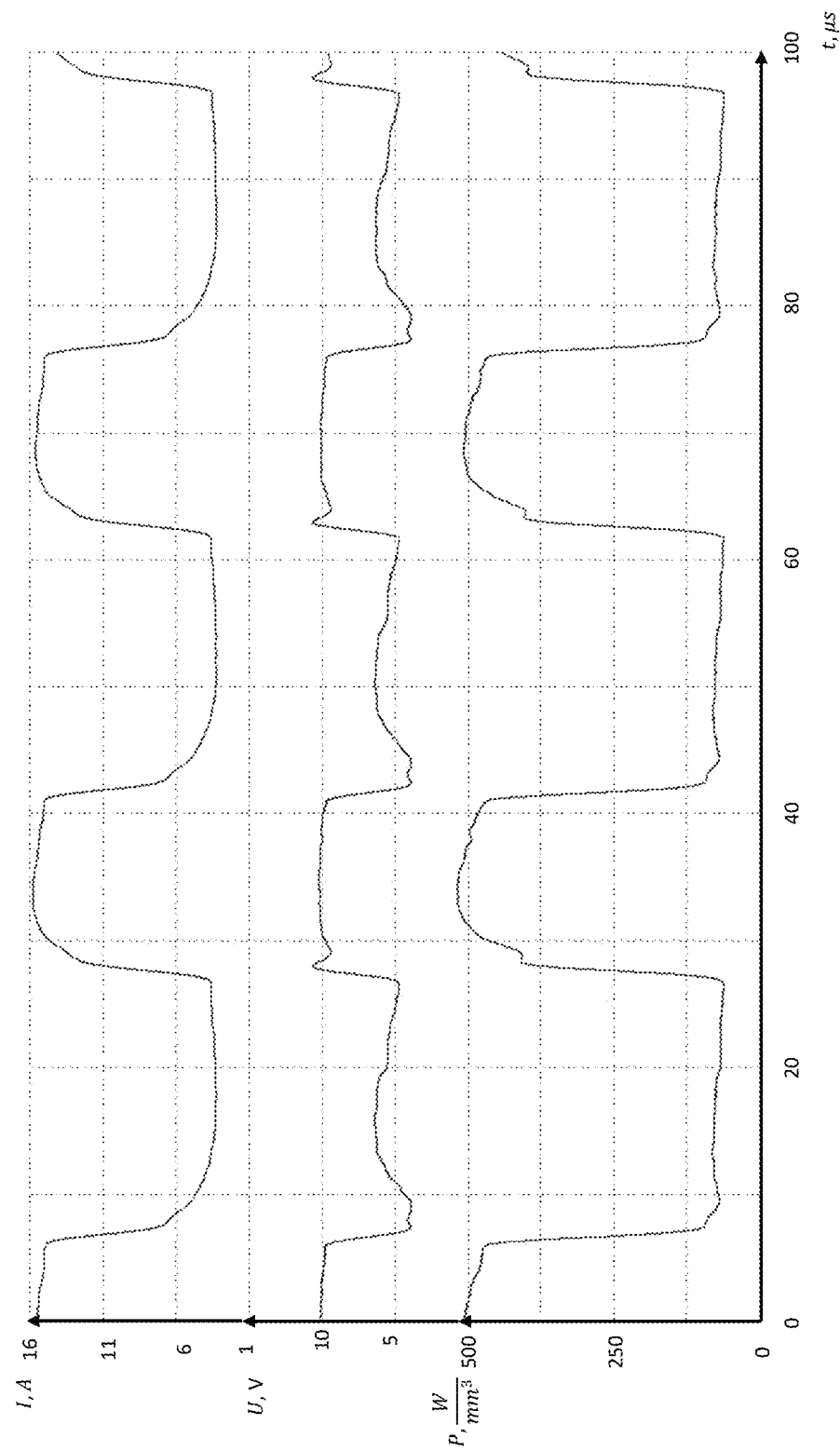
FIG. 73 is a plot of a time scan of arc current $U_{C-E1}$ and power density for $d_{cc}/d_h=2$, according to an embodiment.
Figure 74:
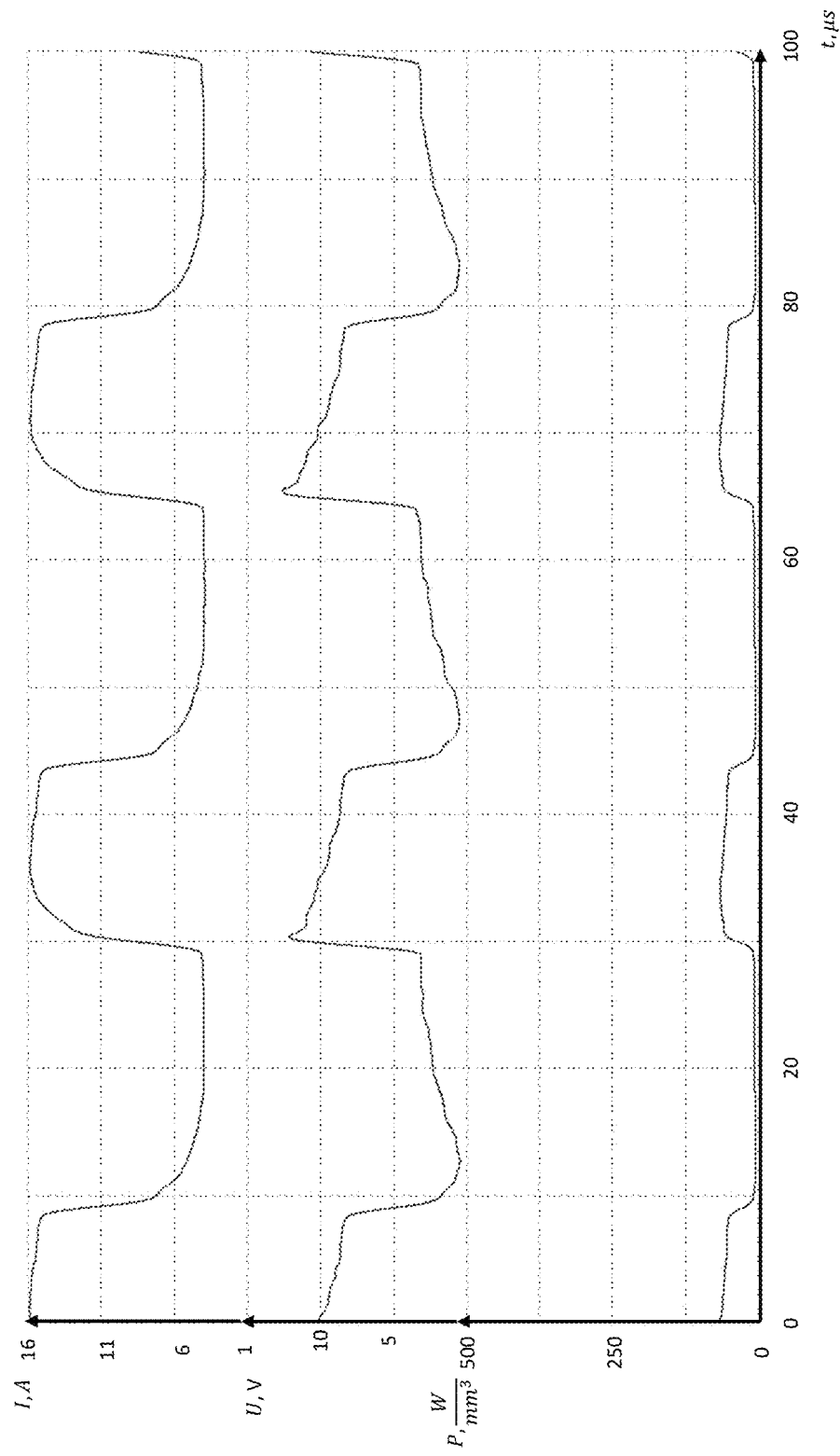
FIG. 74 is a plot of a time scan of arc current $U_{C-E1}$ and power density for $d_{cc}/d_h=4$, according to an embodiment.

FIGS. 73 and 74 correspond to oscillograms for respective embodiments with cathode chambers of different diameters ($d_{cc}/d_h$ ratio may be 2 and 4 for FIG. 73 and FIG. 74, respectively). The oscillograms display a voltage A, current B, and power density C measured for relatively high frequency current pulses. The voltage was measured between cathode 5506 and first intermediate electrode 5510 to estimate the potential change in proximity of cathode active area. In some embodiments, the plasma-generating device with a $d_{cc}/d_h$ ratio of about 2 fails to generate plasma within first several minutes of operation while the generator with a $d_{cc}/d_h$ ratio of about 4 may smoothly operate for hours. In both cases, the voltage behavior may be similar to voltage oscillation 162, as described with reference to FIG. 66B. However, the power density for the exemplary embodiment of FIG. 74) may be one order of magnitude lower than average. It should be noted that the displayed power density may correspond to a total energy density that includes heating of a cathode, plasma in cathode chamber and a small portion of a heating channel. In some embodiments, significant electrode degradation may correspond to oscillating current in contrast to constant current operation. At a constant current, relatively high heat energy delivered to the cathode by ion bombardment may be proportionally balanced by a higher number of emitted electrons. As mentioned above, in case of oscillating current, the rapid decrease in current may correspond to a higher fraction of ion current that brings more heat to the cathode for a duration of time corresponding to plasma recombination to a degree of ionization related to a lower arc current value.

Figure 75:
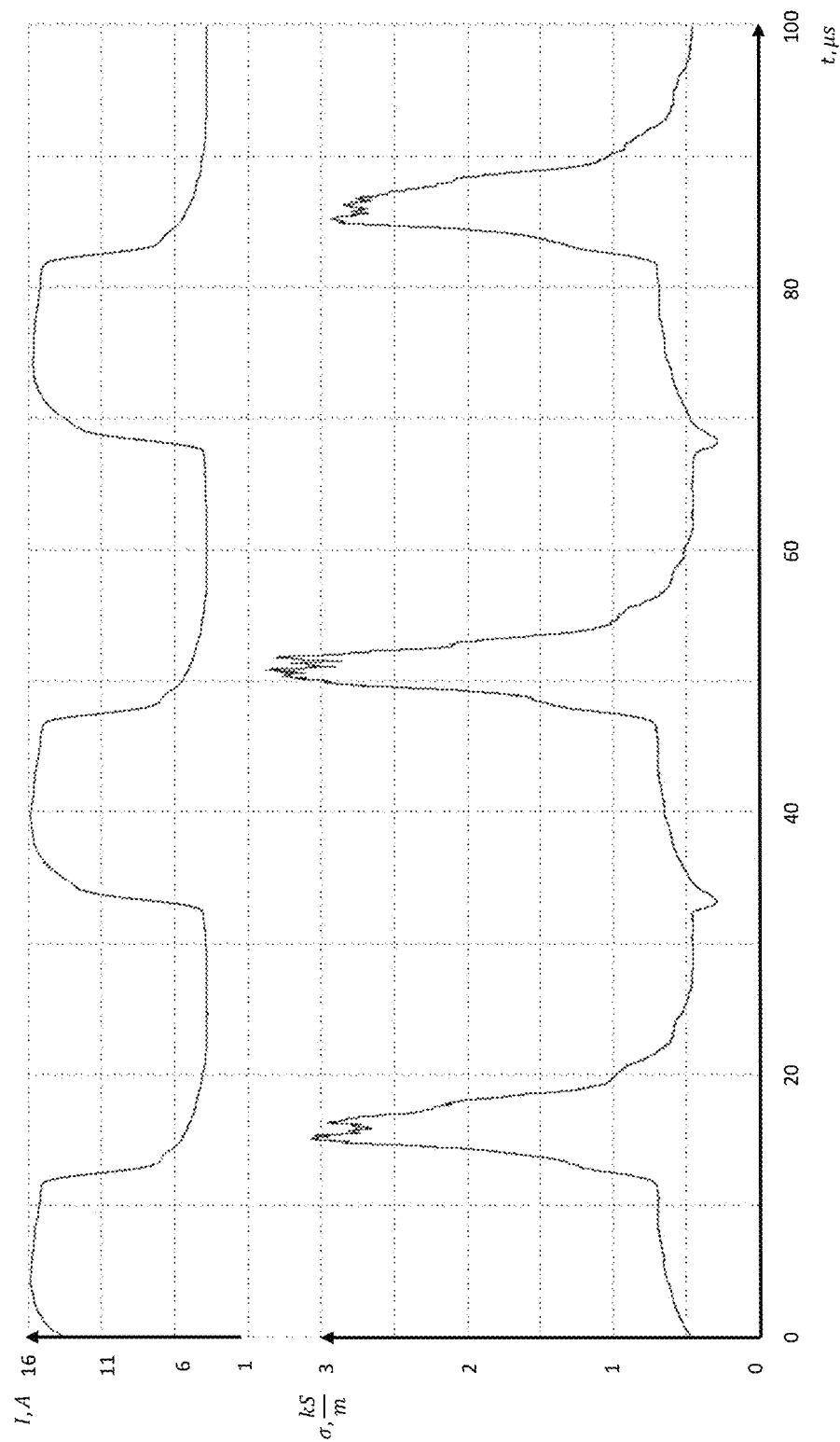
FIG. 75 is a plot of a time scan of arc current and conductivity for an oscillating arc current, according to an embodiment.

FIG. 75 show a conductivity B oscillogram for relatively high frequency current pulses. In some embodiments, the conductivity may be estimated as an average value based on cathode chamber geometry. The graph depicted in FIG. 75 is a qualitative estimation of conductivity. The real (e.g., actual or measured) conductivity may depend on arc shape and may vary across the axis of a plasma-generating device (e.g., 100, 5500, 5700). The observed peak in conductivity right after a current drop may indicate an increased ion current fraction to the cathode surface. During this interval of time, the heat delivered to the cathode surface may be significantly larger for a $d_{cc}/d_h$ ratio of about 2 in comparison to a $d_{cc}/d_h$ ratio of about 4.

In some embodiments, the additional heating of cathode 5506 may occur when arc current demand is decreased. In some embodiments, an increase in cathode chamber diameter may reduce the ion concentration and ion temperature in a vicinity of a cathode surface, thus reducing the detrimental effect of cathode overheating. In some embodiments, a relatively larger cathode chamber diameter may result in longer plasma recombination time in the cathode chamber since excess plasma heat may dissipate mainly through the cathode chamber wall. In some embodiments, despite an increase of plasma recombination time, a larger diameter of a cathode chamber may improve a lifespan of the plasma-generating devices as shown in Table 2.

Figure 76:
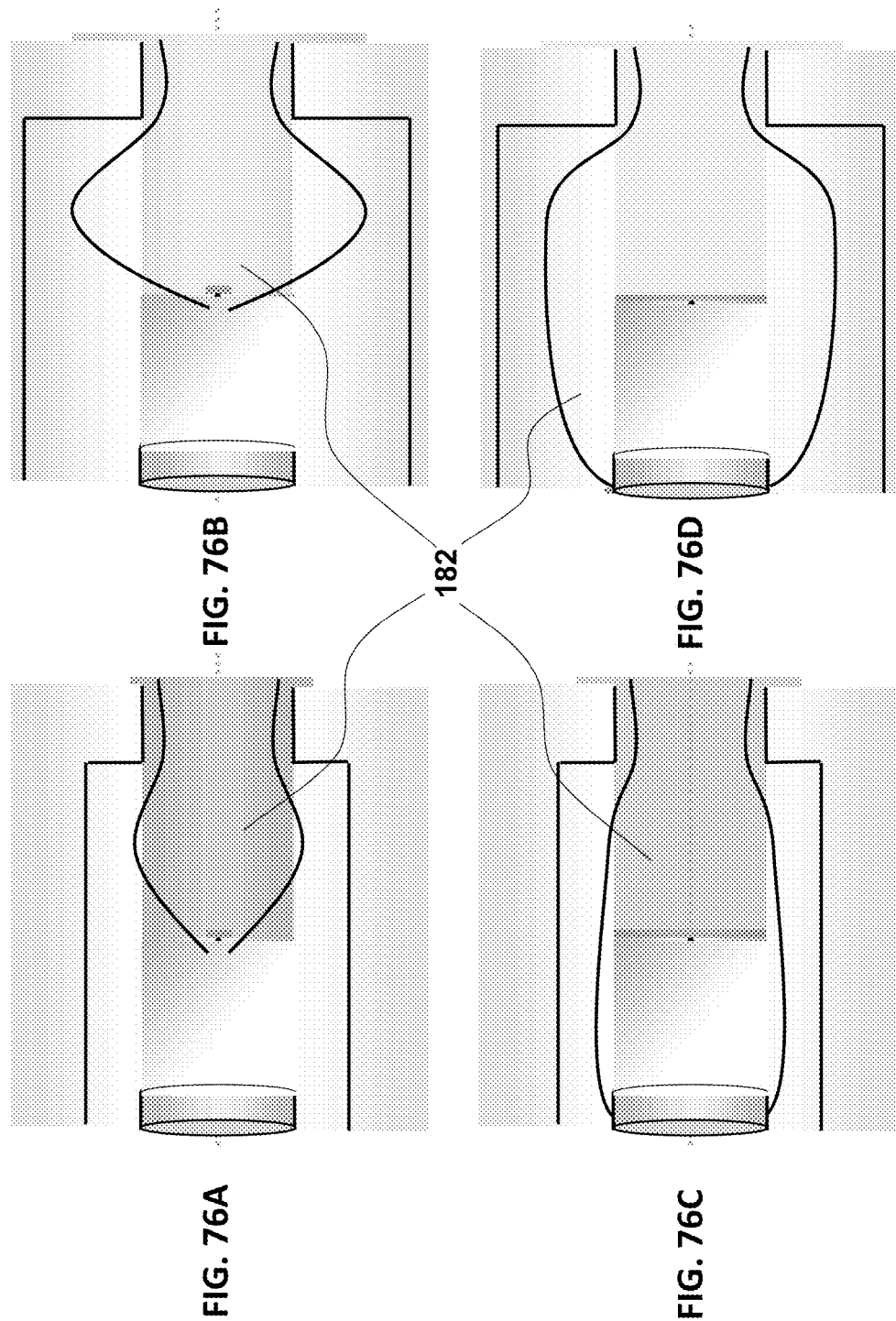
FIGS. 76A-76D are cross-sectional side schematic views of a spot and diffuse mode of arc attachment, according to an embodiment.

In some embodiments, an electric arc attachment may correspond to a degradation mechanism of a cathode. The arc attachment may be generally relatively narrower than the arc column 182, or more specifically transverse geometrical dimensions of the arc. Current transfer from thermionic cathodes to an arc plasma may occur in various ways. In some embodiments, there may be two distinguished modes: the spot attachment where near cathode current may be localized in one of more relatively small areas as shown in FIGS. 76A and 76B, and a diffuse mode where near cathode current is distributed over a larger area of cathode surface as shown in FIGS. 76C and 76D. For a spot attachment, the cathode temperature on the spot surface may be considerably higher compared to the cathode body. In the diffuse mode, an amount of the attachment surface increases relative to the spot attachment and plasma can penetrate inside a ceramic insulator and increase a current density of arc in a cathode region. In some embodiments, higher current density can increase temperature and a plasma concentration around the cathode surface during a pulse duration. Accordingly, in some embodiments, a cathode may receive a more intensive ion current when the pulse current drops to a low base value and reduces electron emission current to cool the cathode.

When the cathode is cold, the area of attachment may be relatively small. After several high frequency current pulses, the temperature of the cathode may increase so that during the period of a rapid current increase, the area of the attachment may expand over the entire surface area of the cathode and even to the cathode surface inside ceramic insulator 154 as shown in FIG. 76E. Under these circumstances, the power density and ion concentration in the vicinity of cathode surface that is inside the insulator sleeve 5554 (see FIGS. 55-56) may bring additional heat by ion and returned electrons current from plasma. After a predetermined period of time, intensive cathode erosion may begin. Therefore, to maintain the proper functionality of the cathode, it may be necessary to control the exact location and the size of the area of the electric arc attachment to the cathode surface during the periods of rapid current increase and fall in each high frequency pulse of plasma.

In some embodiments, a plasma-generating device (e.g., 100, 5500, 5700) configured to operate with oscillating arc current may be characterized based on performance experiments and a discussion of possible detrimental effect of cathode overheating due to shift of energy balance.

First, with reference to FIGS. 55 and 56, the ratio of the diameter of cathode chamber 5560 and specifically a cylindrical portion 5562 (e.g., $d_{cc}$), and the diameter of heating channel 5524 (e.g., $d_h$) may be at least about 4.

$$\frac{d_{cc}}{d_h} \geq 4$$

This relationship may reduce plasma temperature and ion concentration in the vicinity of a cathode surface, thus reducing (e.g., suppressing) the detrimental effect of ion bombardment. Additionally, the cathode tip may be at a sufficient distance from a heating channel to avoid influence of the heating channel on plasma temperature and ion concentration near a cathode active area. This relationship may correspond to another relationship.

Second, the ratio of the distance between cathode tip end point 5536 and the heating channel inlet 5516 (e.g., $l_{TH}$) (tip to heat channel distance), and the diameter of heating channel 5524 (e.g., $d_h$), may be at least about 1.5.

$$\frac{l_{TH}}{d_h} \geq 1.5$$

In some embodiments, the insulator sleeve 5554 may be configured to cool the cathode body by an inlet gas. The geometric relationships for the insulator sleeve may be correspond to an arc attachment to the cathode surface.

In some embodiments, the electric arc may have a spot attachment mode and the spot may be located at cathode tip end point 5536 on a surface of cathode 5506. In some embodiments, a diffuse mode attachment may be not desirable since arc attachment and plasma may enter inside insulator sleeve 5554 and even deteriorate a cathode holder. In some embodiments, switching to a diffuse mode may occur when a large area of the cathode has reached a predetermined high temperature to emit a considerable number of electrons from larger area. In some embodiments, to avoid switching to a diffuse mode, the non-tip portion and some of the tip portion of cathode may be cooled.

In some embodiments, the efficiency of cathode cooling by an inlet gas may depend on an inner diameter of insulator sleeve 5554. In some embodiments, a smaller diameter may be preferable in some applications because a gas speed inside the insulator sleeve may be higher, thus reducing the time of heat exchange between gas and cathode. As a result, a cooler gas may reach the end of cathode tip. Moreover, a relatively larger diameter may result in a larger difference between gas temperature in a direction transverse to an axis of the plasma-generating device 5500. As a result, for a larger diameter, the heated gas may propagate along the cathode surface while a cooler gas may propagate along the surface of insulator sleeve 5554. In some embodiments, the lowest limit of an insulator sleeve inner diameter may be governed by a hydrodynamic drag of inlet gas that substantially increases with a decreasing gap between cathode 5506 and insulator sleeve 5554.

In some embodiments, a position of insulator sleeve 5554 may have role in cathode cooling. If the end of insulator sleeve may be located close to cathode tip end point 5536, it may be equivalent to reducing the cathode chamber diameter in proximity of arc attachment spot. As discussed above, this undesirable situation may correspond to cathode overheating. In contrast, if the end of insulator sleeve may be located far away from cathode tip end point 5536, the efficiency of cathode cooling may be decreased. The optimal conditions for the positioning of insulator sleeve was found experimentally based on performance tests as discussed above. Based on the described factors, efficient cooling of cathode body may be accomplished by the following conditions.

First, the ratio of the length of the portion of cathode tip protruding beyond the distal edge 5556 of insulator sleeve 5554 $l_p$, to the cathode 5506 diameter (cylindrical part of cathode) de may be in the range of between about 0.0 and about 1.6.

$$1.0 \le \frac{l_p}{d_c} \le 1.6$$

Second, the ratio of the cathode tip 5534 length ($l_T$) to cathode 5506 diameter (cylindrical part of cathode) $d_c$, may be in the range of between about 1.5 and about 2.0.

$$1.5 \le \frac{l_T}{d_c} \le 2.0$$

In some embodiments, for a predetermined range of plasma flow temperature required for medical applications, the following requirements related to the heating portion of the plasma-generating device may be met:

First, the diameter of the heating portion, $d_h$ may be in the range of between about 0.4 mm and about 1.0 mm. Second, the ratio of the length of the anode portion of the plasma channel length, $l_{anode}$ to the diameter of the anode portion of the plasma channel, $d_{anode}$, may be in the range of between about 2 and about 4.

$$2 \le \frac{l_{anode}}{d_{anode}} \le 4$$

Third, for surgical applications, the diameter of the anode portion of the plasma channel may be the same as the diameter of the outlet in the above discussion, $d_{out}$, that is in the range of between about 0.3 mm and about 0.6 mm.

Turning back to the dimensions of the cathode chamber, it may be desirable in some embodiments to maximize the diameter of cathode chamber 5560. If the plasma-generating device has an outer diameter of about 5 mm (a size suitable for laparoscopic surgery), the maximum diameter of the cathode chamber may be about 1.8 mm. Larger diameters may modify the structural integrity of other elements.

It is noted that the dimensions described herein merely constitute exemplary embodiments of the plasma-generating device and may be varied according to the field of application and the desired plasma properties.

Current Control Power Supply

According to the methods of generating predominantly radially expanded plasma flows described herein, the shape of resulting plasma flow may be modified by varying the radial expansion degree along the axis of plasma jet. The conditions of radial expansion may be modified within short time intervals for dynamic control of a shape of a plasma jet. In some embodiments, thermal energy of individual plasma particles may be adjusted to a predetermined range of energies by regulating the base plasma or target temperature of plasma.

In some embodiments, dynamic control of a plasma jet shape, temperature, and heat flux may improve thermal plasma-based technology. For example, dynamically controlled plasma flow may solve certain disadvantages of plasma jets and enable complex material treatment procedures. Some plasma jets may have poor precision and non-uniform impact on treated material for turbulent flows and high radial temperature gradient for laminar plasma jets. Dynamic control of a plasma jet shape, temperature, and heat flux may independently and simultaneously solve certain problems related to material treatment or processing such as well-controlled heat transfer to the surface, vaporization, pyrolysis, cleaning, modification, etc.

Some embodiments of plasma-generating device may operate on a wide range and various conditions of oscillating current to generate plasma jet with controlled shape and energy range of individual particles. In some embodiments, a current control signal having a high time resolution of a current change rate may be configured to control plasma shape generation. Some embodiments of a current control generator for a plasma-generating device may use one or more current patterns configured to provide efficient and dynamic control of a plasma jet shape and energy level. As discussed herein, applied current to the plasma-generating device may depend on geometric factors of a plasma-generating device and more specifically the diameter of a heating channel. In some embodiments, instead of using absolute value of current, the relationships for the current control generator may be based on a ratio of current to diameter of a heating channel $d_H$.

Figure 77:
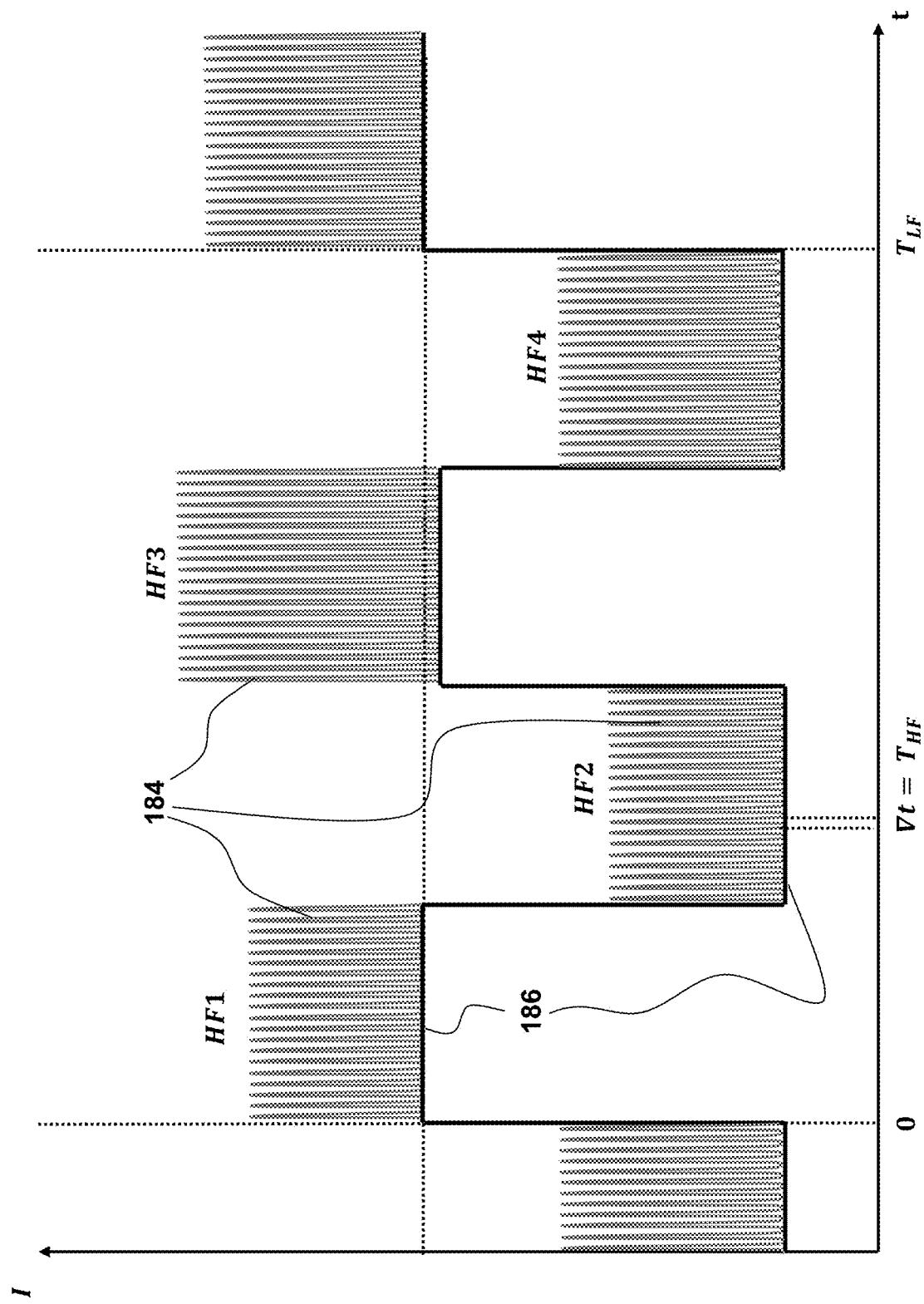
FIG. 77 is a plot of current and time for frequency oscillation, according to an embodiment.

With reference to FIG. 77, relatively high frequency oscillation $f_{HF}$ 184 may refer to the frequency of current pulses that regulate plasma flow expansion or plasma jet shape. As described herein, radial expansion may be controlled based at least in part on the shape and amplitude of high frequency oscillation. In some embodiments, a base current level 186 of relatively high frequency oscillations may define the energy range of individual plasma particles. The energy range of individual particles is not the same as an energy range of heat flux transferred to the treated surface. In some embodiments, the energy of individual particles may be defined by the plasma temperature, while the total energy that may be applied to treated object may be defined by both plasma temperature and plasma mass flux, i.e. the total energy may include the sum of energies transferred by all the plasma particles. In some embodiments, relatively low frequency oscillation $f_{LF}$ may refer to the frequency of repetition of the complete pattern of the base current level. The corresponding period of relatively low and high frequency oscillation may be defined as $1/f_{LF}$ and $1/f_{HF}$, respectively. As shown in FIG. 77, the frequency, shape, and amplitude of high frequency oscillation may vary for different parts of low frequency oscillation.

4. Medical Applications

In some embodiments, a plasma-generating device such that those described herein (e.g. plasma generating device 100, 5500, etc.) may be used in medical or surgical applications. In some embodiments, a plasma-generating device may be configured to apply predetermined current patterns suitable for different medical applications. In some embodiments directed to medical applications, a predominantly radially expanded plasma flow may be used in combination with: (1) other predominantly radially expanded plasma flows; (2) radially expanded plasma flows having axial expansion; or (3) substantially continuous plasma flows.

In the following sections, several examples of medical applications are described, with respective illustrations of plasma flow and/or current patterns suitable for generating such plasma flow. Many of these procedures and treated tissue applications can require individual instruments, and some treatment may require synchronized and precise control of vaporization and heat diffusion processes.

Table 3 includes a list of different types of procedures and treated tissue, along with associated tissue properties and suitable power ranges for each. In some embodiments, the power range for a procedure, measured in W, may correspond to a predetermined plasma jet power level and temperature profile to achieve a particular type of action for a respective procedure.

TABLE 3

Tissue properties and suitable power range for certain surgical procedures.

| Procedure description/ treated tissue | Tissue properties | | | Suggested power range for a procedure, W |
|---|---|---|---|---|
| | Intensity of blood flow on surface | Tissue density | Tissue perfusion | |
| Spot Coagulation | low | all types | med | 50-60 |
| Lympho-sealing | no | all types | all types | 30-50 |
| lung | med | very low | med | 50-65 |
| spleen | high | low | high | 50-65 |
| pancreas | med | low | med | 40-55 |
| muscle | high | med | med | 60-75 |
| liver | high | med | high | 80-100 |
| kidney | high | high | high | 80-100 |
| Dissection pure | high | low | high | 25-65 |
| Dissection blend | high | low | high | 40-75 |
| Vaporization pure | med | low | med | 40-65 |
| Vaporization blend | med | low | med | 45-75 |
| Cut pure | high | med | med | 45-85 |
| Cut blend | high | med | med | 50-90 |

Tables 4 and 5 summarize a set of suitable protocols (e.g., parameter settings or ranges) of a plasma-generating device for various applications. In each example, two types of plasma flows may be generated: the relatively low intensity plasma flow with relatively low temperature TL base of the temperature-time profile, and the relatively high intensity plasma flow with the relatively high temperature TH base. In some embodiments, the low intensity plasma flow may be a predominantly radially expanded plasma flow that may not destruct tissue. In some embodiments, the high intensity plasma flow may be a predominantly radially expanded plasma flow, a radially and axially expanded plasma flow, as well as a continuous plasma flow.

For Table 4, where current includes two base levels (e.g., low base level BL, high base level BH), a set of parameters may be understood as described below. $I_{BL}/d$, A/mm may correspond to a ratio of low base current level A to heating channel diameter mm. $I_{BH}/I_{BL}$ may correspond to a ratio of a high level of base current to a low level of base current. $I_{PL}/I_{BL}$ may correspond to a ratio LF pulse current to a low level base current. $I_{PL}$ may be associated with a LF pulse level for low level base current. $T_{LF}$, ms may correspond with a period of a low frequency current. $D_{LF}$ may correspond to duty of low frequency current oscillation. $T_{HFL}$, µs may correspond to a period of a high frequency pulse current for a low level of base current. $D_{HFL}$ may correspond to a duty of high frequency current pulses for a low level of base current. $T_{HFH}$, µs may correspond to a period of a high frequency pulse current for a high level of base current. $D_{HFH}$ may correspond to a duty of high frequency current pulses for a high level of base current. $T_{HFH}$, µs may correspond to a period of a high frequency pulse current for a high level of base current. $D_{HFH}$ may correspond to a duty of high frequency current pulses for a high level of base current.

For Table 5, where current has a single base level, a set of parameters may be understood as described below. $I_B/d$, A/mm may correspond to a ratio of base current level A to heating channel diameter mm. $I_{LF}/I_B$ may correspond to a ratio of LF pulse current to base current. $I_{HF}/I_B$ may correspond to a ratio of HF pulse current to a base current. $T_{LF}$, ms may correspond to a period of low frequency current. $T_{HF}$, µs may correspond to a period of high frequency pulse current. $D_{LF}$ may correspond to a duty of low frequency current oscillation. $D_{HF}$ may correspond to a duty of high frequency current pulses.

TABLE 4

Parameters for certain surgical procedures using current having two base levels, i.e., low base level (BL) and high base level (BH)

| Procedure description/ tissue | Gas Flow, L/min | $I_{BL}/d$, A/mm | $I_{BH}/I_{BL}$ | $I_{PL}/I_{BL}$ | $T_{LF}$, ms | $D_{LF}$ | $T_{HFL}$, µs | $D_{HFL}$ | $T_{HFH}$, µs | $D_{HFH}$ |
|---|---|---|---|---|---|---|---|---|---|---|
| Spot Coagulation | 0.4-0.55 | 7.5-10 | 0.1-0.7 | 2.5-5 | 5-20 | 0.4-0.6 | 20-50 | 0.3-0.6 | 20-50 | 0.3-0.6 |
| Lympho-sealing | 0.3-0.5 | 7.5-10 | 1.5-4 | 2.5-5 | 30-40 | 0.1-0.2 | 20-50 | 0.3-0.6 | 20-50 | 0.3-0.6 |
| lung | 0.2-0.3 | 7.5-10 | 2.5-5 | 2.5-5 | 30-40 | 0.1-0.2 | 20-50 | 0.3-0.6 | 20-50 | 0.3-0.6 |
| spleen | 0.2-0.3 | 7.5-10 | 1.7-3 | 2.5-5 | 25-35 | 0.1-0.15 | 20-50 | 0.3-0.6 | 20-50 | 0.3-0.6 |

TABLE 4-continued

Parameters for certain surgical procedures using current having
two base levels, i.e., low base level (BL) and high base level (BH)

| Procedure description/ tissue | Gas Flow, L/min | $I_{BL}/d$, A/mm | $I_{BH}/I_{BL}$ | $I_{PL}/I_{BL}$ | $T_{LF}$, ms | $D_{LF}$ | $T_{HFL}$, μs | $D_{HFL}$ | $T_{HFH}$, μs | $D_{HFH}$ |
|---|---|---|---|---|---|---|---|---|---|---|
| pancreas | 0.2-0.3 | 7.5-10 | 1-2 | 2.5-5 | 25-35 | 0.1-0.15 | 20-50 | 0.3-0.6 | 20-50 | 0.3-0.6 |
| muscle | 0.35-0.45 | 7.5-10 | 1.2-2.3 | 2.5-5 | 30-35 | 0.05-0.1 | 20-40 | 0.3-0.6 | 20-40 | 0.3-0.6 |
| liver | 0.4-0.5 | 7.5-10 | 2.5-4 | 2.5-5 | 30-40 | 0.1-0.15 | 20-50 | 0.3-0.6 | 20-50 | 0.3-0.6 |
| kidney | 0.45-0.55 | 7.5-10 | 2.5-5.3 | 2.5-5 | 20-25 | 0.05-0.1 | 20-50 | 0.3-0.6 | 20-50 | 0.3-0.6 |
| Dissection pure | 0.15-0.3 | 10-12.5 | 1.2-3 | 1-2 | 5-10 | 0.1-0.2 | 20-50 | 0.3-0.6 | 20-50 | 0.3-0.6 |
| Dissection blend | 0.15-0.3 | 10-12.5 | 1.4-3.2 | 1.4-2.5 | 5-10 | 0.1-0.2 | 20-45 | 0.4-0.6 | 20-45 | 0.4-0.6 |
| Vaporization pure | 0.2-0.3 | 12.5-15 | 1.7-3 | 1.0-1.4 | 5-15 | 0.1-0.15 | 30-50 | 0.3-0.6 | 30-50 | 0.3-0.6 |
| Vaporization blend | 0.2-0.3 | 12.5-15 | 1.7-3 | 1-1.6 | 5-15 | 0.1-0.15 | 20-40 | 0.4-0.6 | 20-40 | 0.4-0.6 |
| Cut pure | 0.2-0.35 | 12.5-16.2 | 0.7-1.4 | 1.0-1.6 | 5-10 | 0.15-0.25 | 30-45 | 0.3-0.6 | 30-45 | 0.3-0.6 |
| Cut blend | 0.2-0.35 | 12.5-16.2 | 0.7-1.4 | 1.2-2 | 5-10 | 0.15-0.25 | 20-40 | 0.4-0.6 | 20-40 | 0.4-0.6 |

TABLE 5

Parameters for certain surgical procedures using current with single base level

| Procedure description/ tissue | Gas Flow, L/min | $I_B/d$, A/mm | $I_{LF}/I_B$ | $I_{HF}/I_B$ | $T_{LF}$, ms | $T_{HF}$, μs | $D_{LF}$ | $D_{HF}$ |
|---|---|---|---|---|---|---|---|---|
| Spot Coagulation | 0.4-0.55 | 7.5-10 | 0.13-0.67 | 2.5-5 | 5-20 | 20-50 | 0.4-0.6 | 0.3-0.6 |
| Lympho-sealing | 0.3-0.5 | 7.5-10 | 1.5-4 | 2.5-5 | 30-40 | 20-50 | 0.1-0.2 | 0.3-0.6 |
| lung | 0.2-0.3 | 7.5-10 | 2.5-5 | 2.5-5 | 30-40 | 20-50 | 0.1-0.2 | 0.3-0.6 |
| spleen | 0.2-0.3 | 7.5-10 | 1.75-3 | 2.5-5 | 25-35 | 20-50 | 0.1-0.15 | 0.3-0.6 |
| pancreas | 0.2-0.3 | 7.5-10 | 1-2 | 2.5-5 | 25-35 | 20-50 | 0.1-0.15 | 0.3-0.6 |
| muscle | 0.35-0.45 | 7.5-10 | 1.25-2.33 | 2.5-5 | 30-35 | 20-40 | 0.05-0.1 | 0.3-0.6 |
| liver | 0.4-0.5 | 7.5-10 | 2.5-4 | 2.5-5 | 30-40 | 20-50 | 0.1-0.15 | 0.3-0.6 |
| kidney | 0.45-0.55 | 7.5-10 | 2.5-5.33 | 2.5-5 | 20-25 | 20-50 | 0.05-0.1 | 0.3-0.6 |
| Dissection pure | 0.15-0.3 | 10-12.5 | 1.2-3 | 1-2 | 5-10 | 20-50 | 0.1-0.2 | 0.3-0.6 |
| Dissection blend | 0.15-0.3 | 10-12.5 | 1.4-3.25 | 1.4-2.5 | 5-10 | 20-45 | 0.1-0.2 | 0.4-0.6 |
| Vaporization pure | 0.2-0.3 | 12.5-15 | 1.67-3 | 1.0-1.4 | 5-15 | 30-50 | 0.1-0.15 | 0.3-0.6 |
| Vaporization blend | 0.2-0.3 | 12.5-15 | 1.67-3 | 1-1.6 | 5-15 | 20-40 | 0.1-0.15 | 0.4-0.6 |
| Cut pure | 0.2-0.35 | 12.5-16.2 | 0.77-1.4 | 1.0-1.6 | 5-10 | 30-45 | 0.15-0.25 | 0.3-0.6 |
| Cut blend | 0.2-0.35 | 12.5-16.2 | 0.77-1.4 | 1.2-2 | 5-10 | 20-40 | 0.15-0.25 | 0.4-0.6 |

Figure 87:
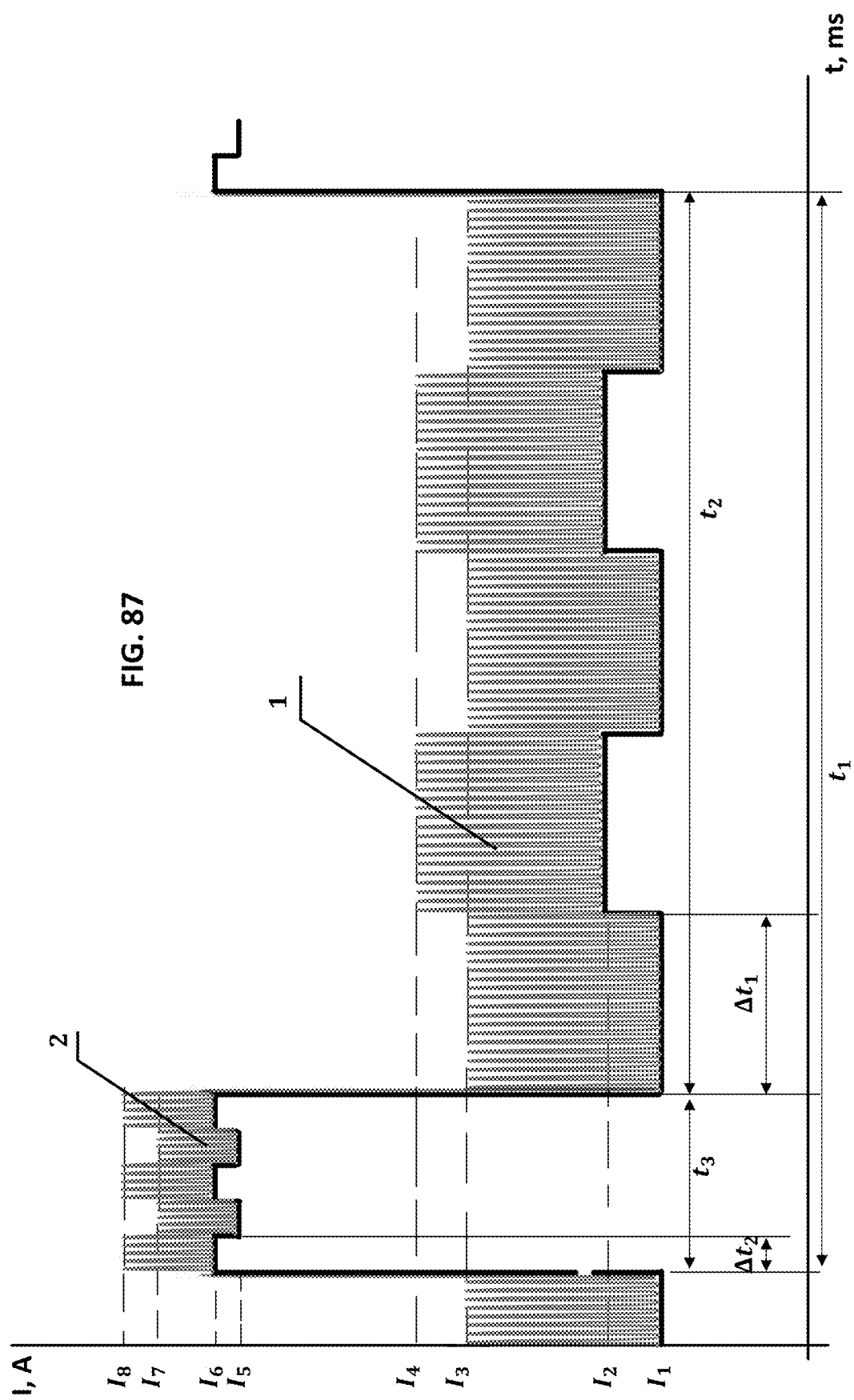
FIG. 87 is a plot of current and time applied within a plasma-generating device, according to an embodiment.
Figure 88:
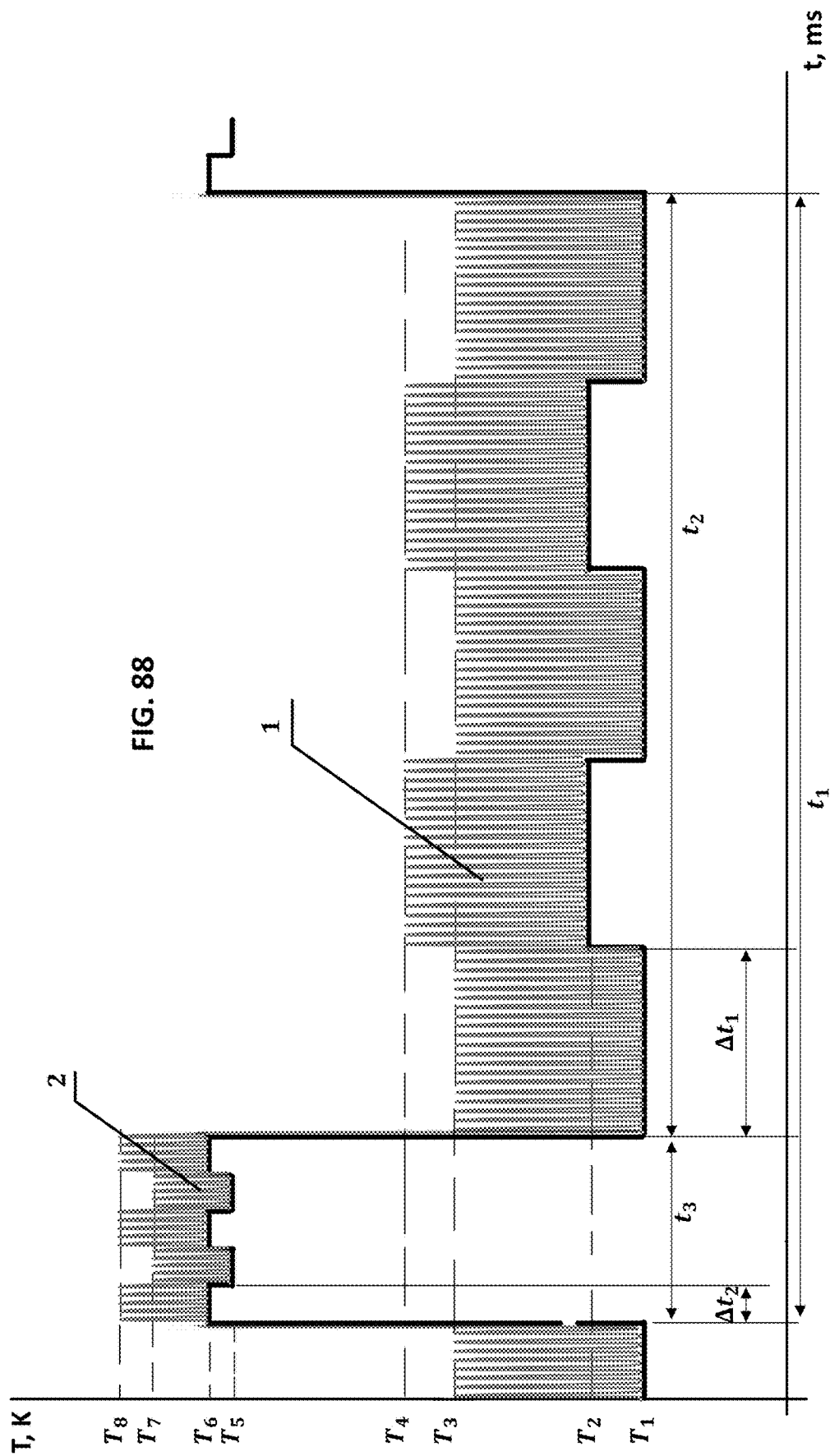
FIG. 88 is a plot of temperature and time of an outlet plasma flow, according to an embodiment.

FIG. 88 shows a generalized temperature-time profile that may be used for a variety of medical applications. The temperature-time profile shown in FIG. 88 largely tracks the diameter current-time profile shown in FIG. 87. Referring to the discussion above, this temperature-time profile shows various base plasma flow temperatures at the outlet. It may be understood that each of the base temperatures may have corresponding high-frequency high-temperature pulses "on top" of base temperature plasma flows.

Experiments show that the delay between changing the current in the power supply and changes in temperature may be in the order of nanoseconds, and for the purposes of this discussion the changes in the temperature of the plasma at the generator outlet may be considered instantaneous. Generally, tracking the current pattern, the base temperature oscillates between low temperature TL and high temperature TH. Low temperature TL may be in the range of between about 2,000 K and about 15,000 K and high temperature TH may be in the range of between about 4,000 K and about 30,000 K, but the low temperature TL may be always lower than the corresponding high temperature TH. In other words, if the low temperature may be set to, for example, about 7,000 K, then the high temperature TH may be set to a temperature higher than about 7,000 K, or for example, about 20,000 K.

In some embodiments, as shown in FIG. 88, the low and high temperatures may not be uniform and may exhibit predetermined variations. For low temperatures, these variations may occur at about 5 ms intervals, although different intervals in the range of between about 1 ms and about 10 ms may be contemplated. In some embodiments, the low temperature may correspond to up to about 10 variations, but in some embodiments, such as the one tracking the current pattern shown in FIG. 79C, no low temperature variations occur. In some embodiments, the magnitude of low temperature variations may be in the range of between about 500 K and about 1,000 K, but may depart from this range. For high temperatures, these variations may occur at about 1 ms intervals, or in the range of between about 0.2 ms and about 2 ms. In some embodiments, the high temperature may correspond to up to about 5 variations. In some embodiments, such as the one tracking the current pattern shown in FIG. 83A, no high temperature variations occur. In some embodiments, the magnitude of high temperature variations may be in the range of between about 1,000 K and about 2,000 K.

In some embodiments, and as shown in FIG. 88, the time-temperature profile may be periodic with the period, for example, in the range of between about 6 ms and about 65 ms. To distinguish the terminology associated with changes and oscillations of the base plasma flow temperature among different values with temperature oscillations between the base temperature and the pulse temperature, the following terminology may be used. From the viewpoint of the plasma medicine, a medical procedure may be considered as causing a predetermined effect on the tissue by the plasma flow. Continuous plasma flows may accomplish a primary effect on the tissue, with other desirable outcomes being merely side effects of the primary purpose for which the plasma flow characteristics have been chosen. For example, if a continuous plasma flow has been chosen for cutting tissue, any coagulation or blood vaporization effects that this continuous plasma flow may produce may be coincidental side effects.

In some embodiments, the use of temperature profiles such as in FIG. 88 allows for the development of two or more plasma flows that may have different intended effects on the tissue. Additionally or alternatively, in situations where the periodic effect of one type of plasma may be desired, the second plasma flow may be generated for maintaining a plasma flow in in the handpiece while minimizing its effect on the tissue surface being treated by minimizing the plasma flow length by increasing the frequency of high-frequency oscillations.

In some embodiments, a method may include discharging, from an outlet of a plasma-generating device, a plasma flow having a directional axis, the plasma flow alternating between a first configuration including plasma having a first temperature higher than about 1,000 K between first and second points along the directional axis, the first point being closer to the outlet than the second point, and a second configuration including plasma having a second temperature higher than about 1,000 K between third and fourth points along the directional axis, the third point being closer to the outlet than the fourth point and the fourth point being closer to the outlet than the second point. The plasma flow may be directed at a treatment surface disposed between the second point and the fourth point.

In some embodiments, discharging the plasma flow alternating between the first and second configurations includes discharging the plasma flow in the first configuration for a first duration and discharging the plasma flow in the second configuration for a second duration. In some embodiments, the first duration can be greater than the second duration, while in other embodiments, the second duration can be greater than the first duration.

In some embodiments, discharging the plasma flow in the first configuration for the first duration may cause evaporation of liquid from the treatment surface and may not cause substantial damage to the treatment surface. In some embodiments, the first duration may be about five times the second duration. In some embodiments, the first temperature may alternate between first and second values, the first value being lower than the second value, and the second temperature may alternate between third and fourth values, the third value being lower than the fourth value and higher than the second value.

Vaporization, Sublimation, and Controlled Heating

The plasma-generating device described herein can be configured for thermal processing of the materials including, but not limited to, vaporization/sublimation of the object surface without heat transfer inside the object (V/S), controlled heating of the material avoiding potential damage of the object due to local overheating (CH), and combined simultaneous V/S and CH treatment with precise control of both procedure (combined V/S & CH).

Generally, vaporization is a conversion of an object layer to gaseous form via evaporation, sublimation and pyrolysis. Vaporization of the object surface without heat transfer inside the object may be useful for applications such as cleaning, drying, and etching, since it allows removal of the layer of the treated object without damaging the rest of the material. Moreover, if the rest of the object is not heated during the procedure, it may not undergo thermal expansion such that no additional mechanical tension is formed, thereby preserving the initial structure of the object except for the vaporized layer.

In some embodiments, analysis of heat transfer of a treated surface may help understand the parameters of the three procedures (V/S, CH and combined V/S and CH). In some embodiments, the heat flow transferred to the object surface may depend on plasma jet temperature and mass flux at the surface. In some embodiments, the heat flux may be calculated based on the formula:

$$q = h(g_{js})(T_j - T_o) \tag{46}$$

where $h(g_{js})$ is a heat transfer coefficient that may be directly related with plasma mass flux $g_{js}$ at the object surface. $T_j$ may be a plasma jet temperature at the surface.

In some embodiments, plasma mass flux $g_{js}$ at the object surface may be estimated based on an outlet mass flux and ratio of plasma jet cross-sectional area at the nozzle outlet and object surface.

$$g_{js} \approx \frac{A_o}{A_s} g_{jo}$$

where $A_o$, $A_s$ is a cross section area transverse to the plasma jet axis at the nozzle outlet and at the object surface, respectively. $g_{jo}$ is a mass flux at the nozzle outlet.

In some embodiments, the heat transfer coefficient $h(g_{js})$ may be a complex function of mass flux. For the sake of simplicity, the heat transfer coefficient may be considered to be proportional to mass flux. In this case, the heat flux may be estimated based on the following expression:

$$q = H^* \frac{g_{jo}}{A_s}(T_j - T_o) \tag{47}$$

In some embodiments, the heat flux to the object surface may both vaporize the surface layer and diffuse inside the object. In some embodiments, the heat equation may be given by:

$$q = H^* \frac{g_{jo}}{A_s}(T_j - T_o) = \rho E_v U_v - \lambda \frac{\partial T}{\partial z}(z = 0) \tag{48}$$

where $\rho$, $\lambda$ is density and thermal conductivity of the object, $E_v$ is specific energy of vaporization and $U_v$ is a vaporization rate that may defines how fast the object surface location moves due to vaporization of the material. ∂T/∂x (z=0) is a temperature gradient at the surface.

Figure 78:
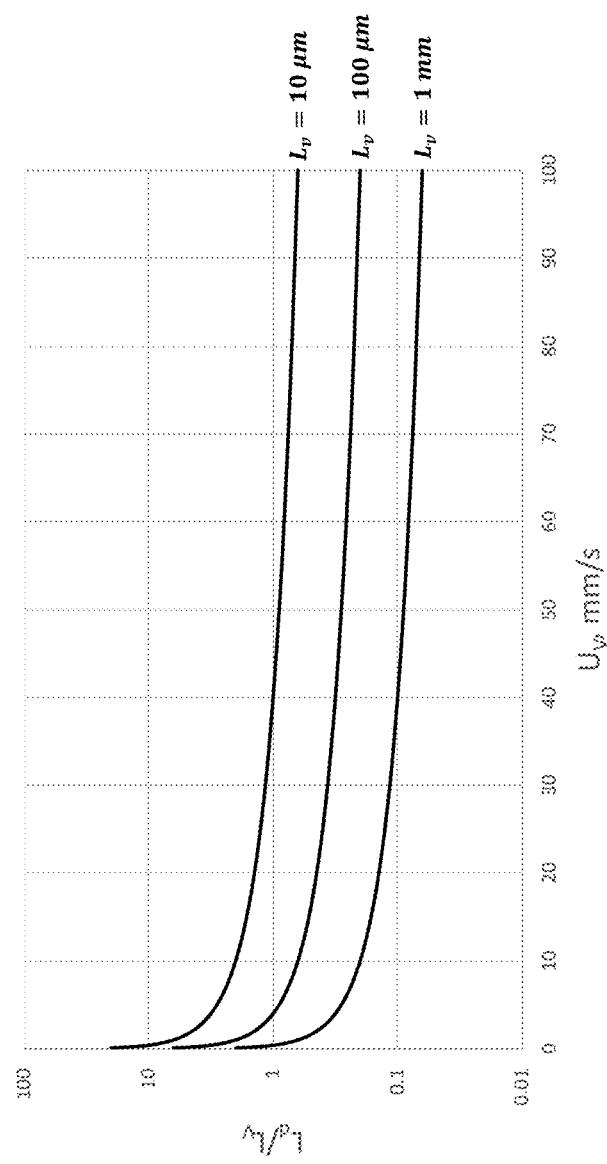
FIG. 78 is a plot of ratio estimation of vaporized layer thickness to heat penetration length, according to an embodiment.

In some embodiments, since the diffusion rate may be defined by temperature distribution in the vicinity of the surface, vaporization may be dominant. In some embodiments, if a vaporization rate is comparable with diffusion heat transfer, then vaporization of the treated object without heating the rest of the object may be achieved. In some embodiments, the thickness of the removed layer during time interval $\Delta T$ may be calculated as $L_v = U_v \cdot \Delta \tau$. For the same time interval, a penetration length of heat into the treated object may be estimated as $L_d = \sqrt{4 \cdot k \cdot \Delta \tau}$, where k is thermal diffusivity of the treated object. Based on these estimations, FIG. 78 depicts that a ratio of vaporized layer thickness to heat penetration length may substantially decrease with higher values of vaporization rate. As a result, vaporization of an object surface without heat transfer inside the object may require a high vaporization rate (e.g., about 100 mm/s) that may be achieved by a high heat flux to the surface. A plasma jet generated at a constant current having a vaporization rate of about 100 mm/s may not be practical for many applications. For example, some surgical applications may require an average vaporization rate in range of between about 0.01 mm/s and about 2 mm/s.

In some embodiments, an average vaporization rate may be reduced by applying short pulses of high temperature plasma as shown in FIG. 79A. In some embodiments, the average vaporization rate may be adjusted by the duty of the pulses, which may be a ratio of pulse duration to period of pulse repetition. In some embodiments, the vaporization depth resolution may be defined by the minimum possible duration of the pulses. However, such an approach may have drawbacks. First, for relatively low vaporization rates, the pulse duration may be considerably shorter. For a vaporization depth of about 0.5 mm, the pulse duration may be no more than about 5 ms, and may be shorter if better vaporization depth resolution is desired. In some embodiments, ignition of plasma with subsequent heating to high temperature and pulse duration less than about 5 ms may have technical difficulties. Second, a predetermined mass flow for pulses may be generated to achieve high heat flux to the surface. According to Eq. 5 and Eq. 10, the inlet gas flow may be considerably higher to provide the required gas flow for the pulses with low duty to correspond to substantial consumption of gas between pulses that might be not desirable. For example, high mass flux may build excessive pressure for a small nozzle diameter. Alternatively, the working pressure may be pumped up during a pulse duration, but it may significantly complicate the system. Third, this approach targets a vaporization procedure of the material treatment. However, implementing additional procedures of treatment that involve controlled heat diffusion may require additional modifications.

Figure 79:
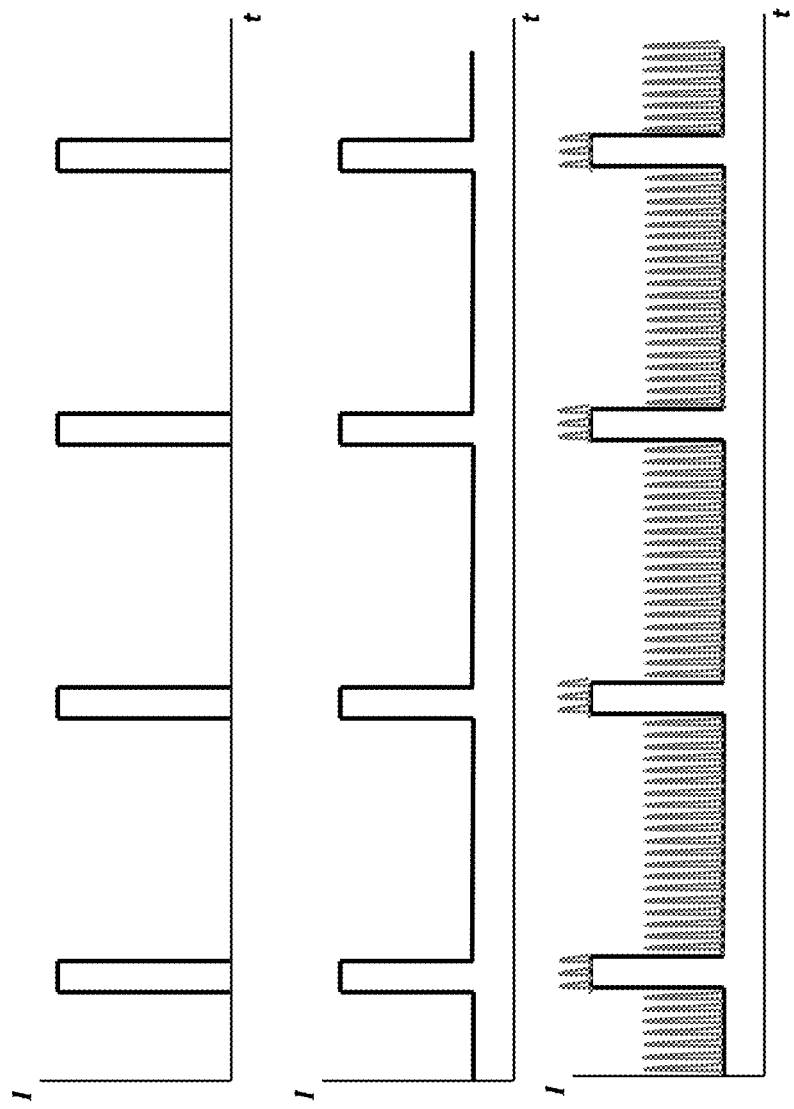
FIGS. 79A-79C are plots of current patterns to reduce the effective vaporization rate, according to an embodiment.
Figure 80:
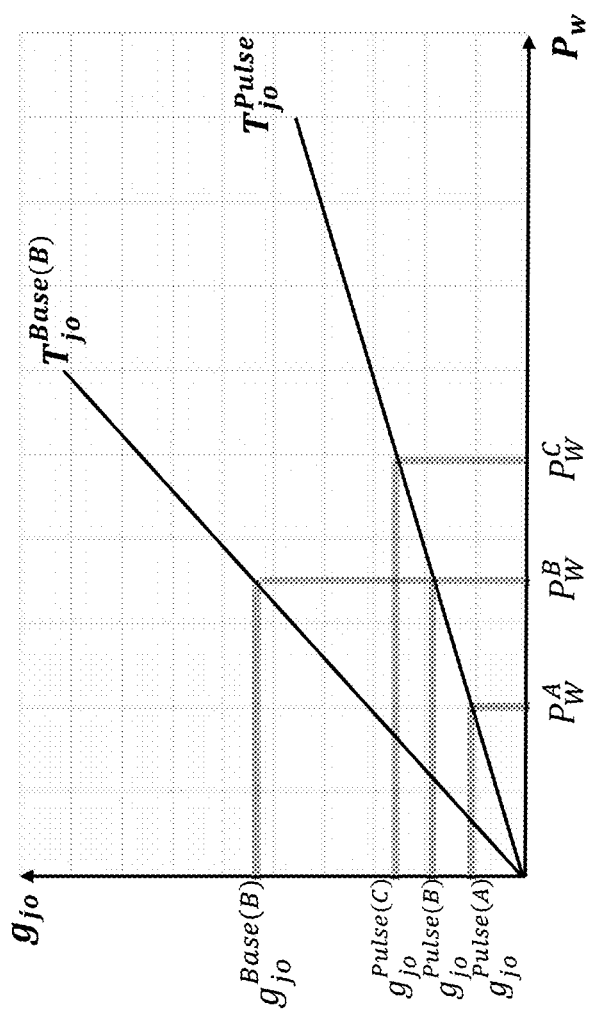
FIG. 80 is a plot of increasing pulse outlet mass flux with higher working pressure in a plasma-generating device, according to an embodiment.

FIG. 79B depicts a base current level between pulses configured to maintain the electric arc in the plasma-generating device and which addresses issues related to plasma ignition. In some embodiments, if the electric arc is maintained, the pulse duration may be substantially lower, thus improving vaporization depth resolution. In some embodiments, the base current level between pulses may also help build up working pressure. FIG. 80 shows that when the current pattern is changed from A to B (FIG. 79), the working pressure may increase from $P_W^A$ to $P_W^B$ and the pulse outlet mass flux may increase from $g_{jo}^{Pulse(A)}$ to $g_{jo}^{Pulse(B)}$. In some embodiments, the increase of pulse outlet mass flux may also be beneficial since a higher vaporization rate and hence better conditions for a vaporization procedure (V/S) may be achieved, as may be seen from Eq. 48. However, the relatively low current level between pulses may also generate a plasma jet of relatively lower temperature that may generate undesirable heat diffusion inside the treated object.

Figures 81A, 81B:
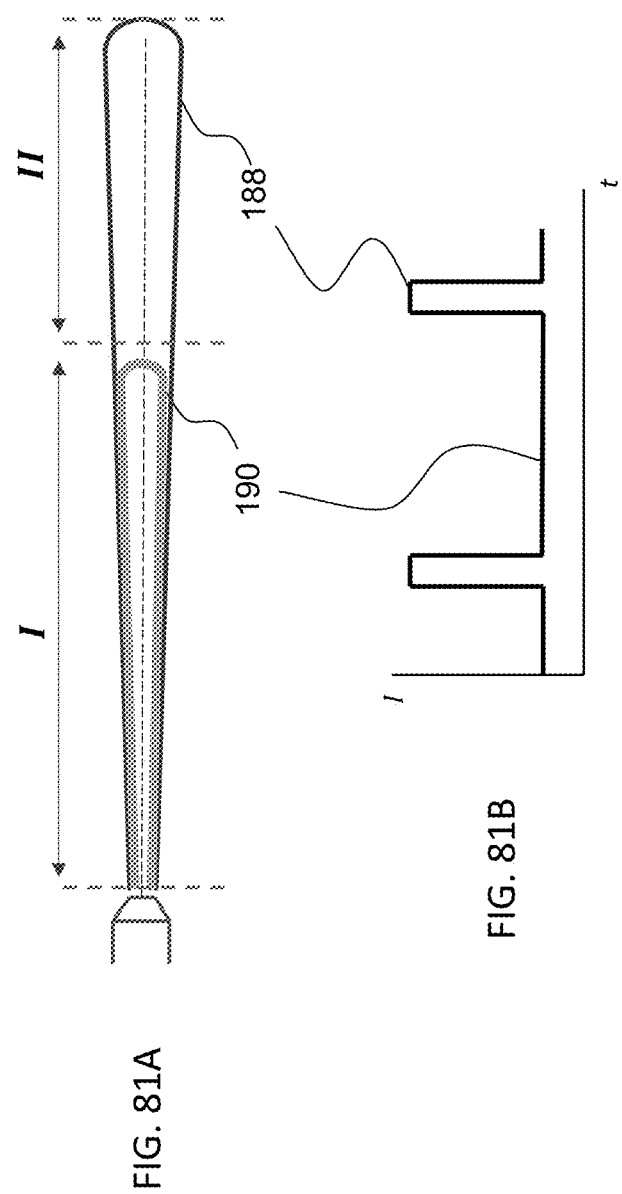
FIG. 81A is a schematic diagram of plasma flow for current pulses and a relatively low base current level between pulses, according to an embodiment.
FIG. 81B is a plot of current and time corresponding to FIG. 81A, according to an embodiment.

With reference to FIG. 81A, the term "high intensive plasma jet" refers to a plasma jet, that may be formed during current pulses and depicted by curve 188. The term "low intensive plasma jet" may refer to plasma jet, that may be formed between current pulses and depicted by curve 190. Because of high temperature of plasma particles, the high intensive plasma jet may have a longer longitudinal size and may be used for vaporization procedure without heat transfer inside the object. At the same time, low intensive plasma may have a shorter longitudinal size, thereby bringing undesirable heat transfer inside the object. In some embodiments, the zone II depicted in FIG. 81A may be used for a vaporization procedure. It should be noted that since the plasma jet shape may be defined by a temperature threshold, there may be heat flux outside of the depicted plasma jet. As a result, low intensive plasma may bring undesirable vaporization heat flux in zone II. Moreover, the impact of low intensive plasma on zone II may worsen based on a high mass flux $g_{jo}^{Base(B)}$ between the pulses (see FIG. 80).

In some embodiments, vaporization of the object surface without heat transfer inside the object may include avoiding the impact of low intensive plasma 190. In some embodiments, this may be achieved by reducing heat flux to the surface by low intensive plasma. According to Eq. 47, the heat flux may depend on one or more of jet temperature $T_j$, outlet heat flux $g_{jo}$, and a plasma jet shape, or more specifically the cross-sectional area transverse to the plasma jet axis at the object surface $A_s$. In some embodiments, outlet heat flux and jet temperature of low intensive plasma may have a complex relationship with high intensive plasma where optimization may correspond to lower values of base current limited by minimal arc current and degradation processes of a plasma-generating device. In some embodiments, an increase in a transverse cross-sectional area of a low intensive plasma jet may substantially reduce the undesirable heat transfer inside the object. However, the plasma jet shape may not be independently changed for high and low intensive plasma in case of laminar or turbulent flow.

Figures 82A, 82B:
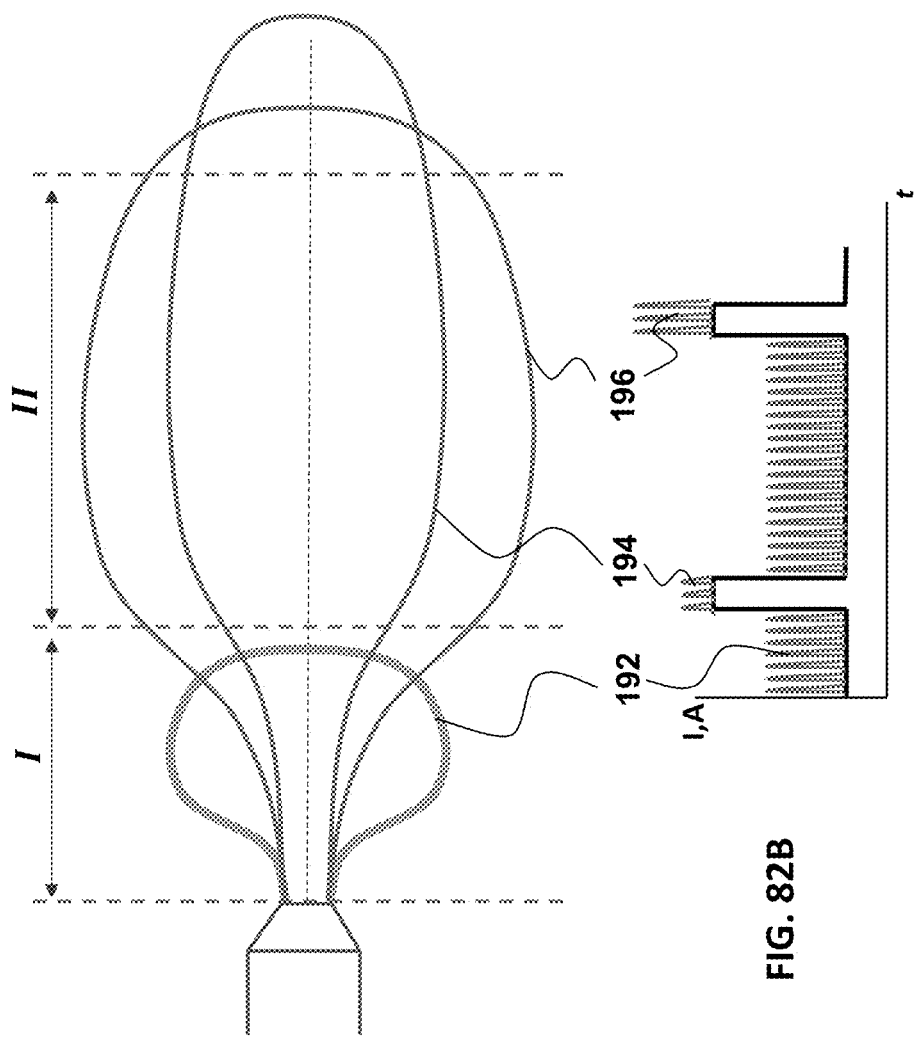
FIG. 82A is a schematic diagram of plasma flow depending on current base level and degree of radial expansion, according to an embodiment.
FIG. 82B is a plot of current and time corresponding to FIG. 82A, according to an embodiment.

In some embodiments, plasma jet shape control may reduce the negative effect of low intensive plasma for vaporization procedures. A predetermined plasma jet shape may be obtained by adding the high frequency oscillation of current on top of the current pattern as shown in FIG. 79C. The radial expansion of the low intensive plasma may be sufficiently high to suppress the heat flux of low intensive plasma towards zone II. As shown in FIG. 82A, the resulting low intensive plasma jet 192 has a high degree of radial expansion. Thus, vaporization procedure without heat transfer inside the object requires considerably lower radial expansion of low intensive plasma and treated object may be located in the zone II as shown in FIG. 82A.

The jet shape of high intensive plasma may be also controlled by adding smaller degree of radial expansion. As previously mentioned, the radial degree may be adjusted by the shape of high frequency oscillation of current. For example, jet shapes 194 and 196 demonstrate two possible plasma jet shapes of high intensive plasma based on corresponding high frequency current oscillation.

In case of additional high frequency oscillation, the terms high and low intensive plasma may be clarified. The term "low intensive plasma jet" may refer to shapes of plasma jet formed with relatively low base current 192. The term "high intensive plasma jet" may refer t all shapes of plasma jet that may be formed with relatively high base current 194, 196.

In some embodiments, a system may include a current generator configured to generate a current having a controlled pattern. The controlled pattern may include a first set of oscillations between a first base level and a first pulse level, the first pulse level being higher than the first base level, and a second set of oscillations between a second base level and a second pulse level, the second pulse level being higher than the second base level. A plasma-generating device may be configured to heat, in response to the current being applied to a heating portion of the plasma-generating device, a plasma-generating gas to generate a plasma flow within the plasma-generating device. The plasma flow alternating between a first configuration having a first degree of radial expansion and a second configuration having a second degree of radial expansion may be discharged from an outlet of the plasma-generating device, according to the controlled pattern of the current.

In some embodiments, the second base level may be greater than the first base level, and the second pulse level may be greater than the first pulse level. In some embodiments, the heating portion may include a heating channel, and a diameter of the heating channel may be no more than about 0.4 mm. In some embodiments, a diameter of the outlet may be greater than a diameter of the heating channel. In some embodiments, the first degree of radial expansion may be greater than the second degree of radial expansion. In some embodiments, the plasma flow may include an active zone defined by plasma having a temperature above about 1,000 K, the active zone having a diameter that may be at least ten times greater than a diameter of the outlet.

Figures 83A, 83B:
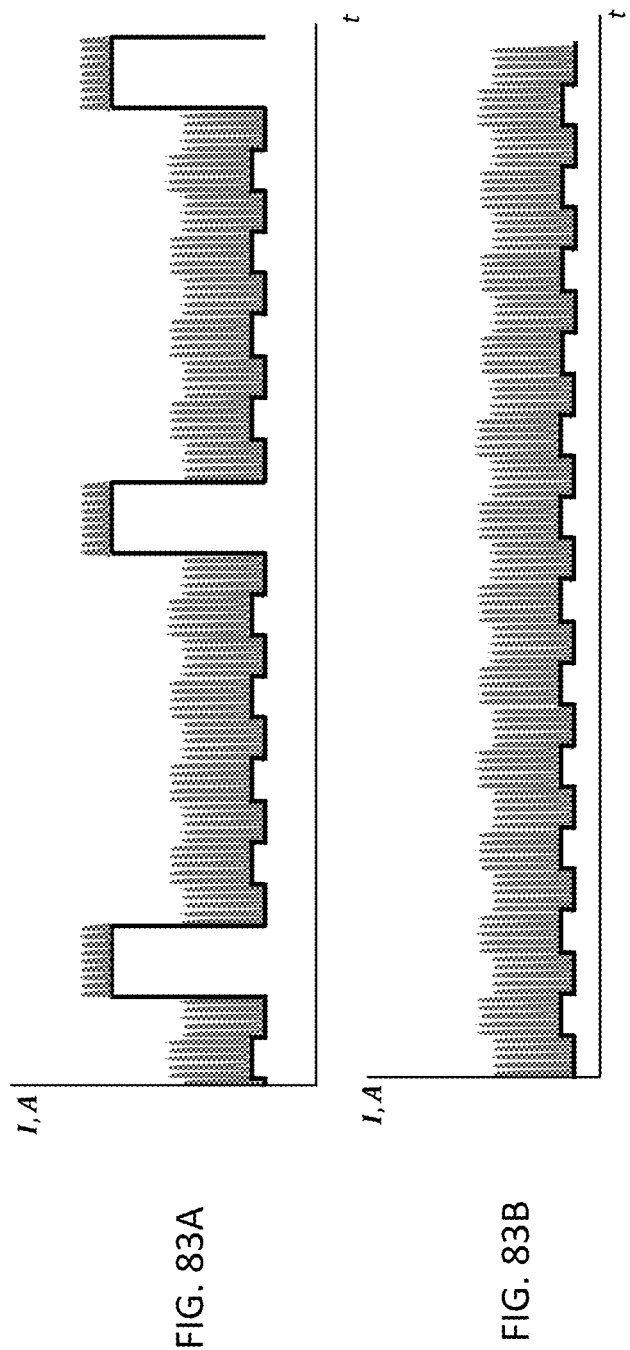
FIG. 83A is a plot of current and time for vaporization, according to an embodiment.
FIG. 83B is a plot of current and time for controlled heating, according to an embodiment.

In some embodiments, a current pattern may be improved for vaporization procedure by adding light oscillation of base current level for low intensive plasma as demonstrated in FIG. 83A. With reference to the methods, this additional oscillation of base current level may have several beneficial functions. First, working pressure may increase which may in turn increase heat flux for high intensive plasma to thereby enhance the evaporation rate. Second, radial expansion conditions of low intensive plasma may be improved. Third, the detrimental effect of cathode overheating may be lowered due to efficient increase of base current level.

In some embodiments, a procedure may include treating a sample with heat resulting in minimal or no damage to the treated sample due to local overheating. In some embodiments, a current pattern may include low intensive plasma jet with considerably high radial expansion is shown in FIG. 83B. Such a current pattern may be necessary to shift balance in the Eq. 48 towards predominant diffusion of heat flux inside a treated object. In some embodiments, a low level of base current may be used to reduce total heat flux and suppress vaporization process. In some embodiments, a diffusion rate may be adjusted by the inlet gas flow. As described herein, low frequency oscillation of base current level may play a positive role by improving conditions for radial expansion and decreasing negative effect of cathode overheating.

In some embodiments, vaporization and controlled heating treatment may be applied in procedures for homogenous objects. In some embodiments, a treated object may be heterogenous and controlled vaporization and heating may be used to achieve a desired effect. In some embodiments, a sequence of vaporization and controlled heating may be performed with various degrees for each treatment step. For surgical applications, a procedure might include simultaneous controlled vaporization and heating that targets one or more of drying of incoming flows of physiological liquids such as blood and lymph, tissue coagulation, vascular occlusion and coagulation (that might require penetration of plasma flow inside the open blood vessel), and tissue cutting.

Figure 84A:
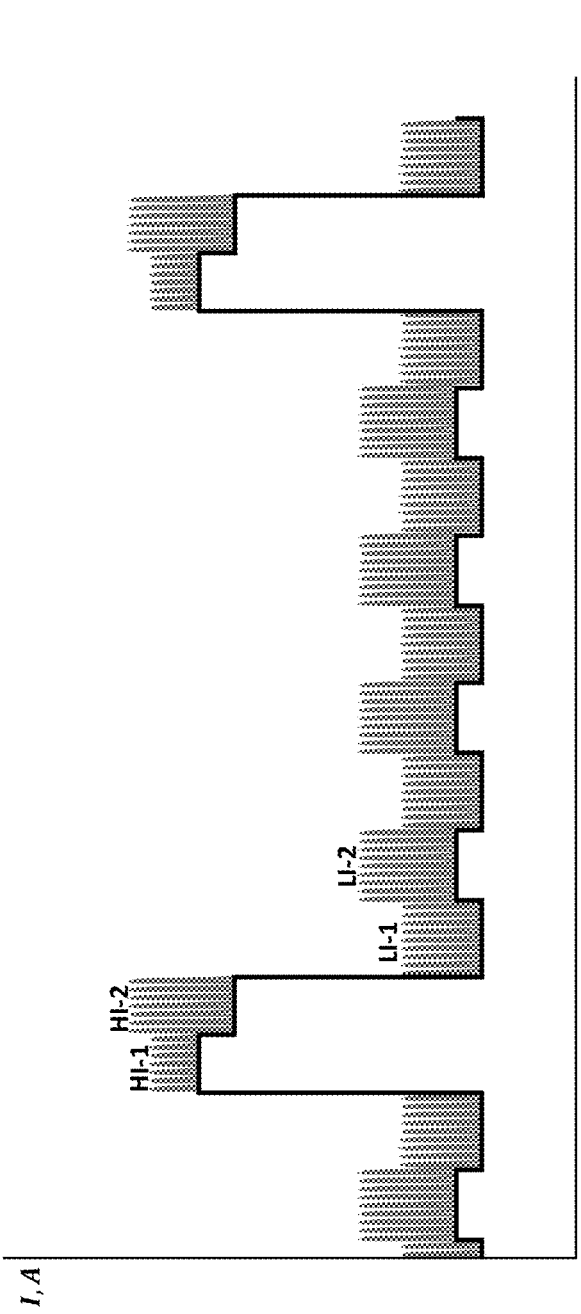
FIG. 84A is a plot of current and time for vaporization and heating, according to an embodiment.
Figure 84B:
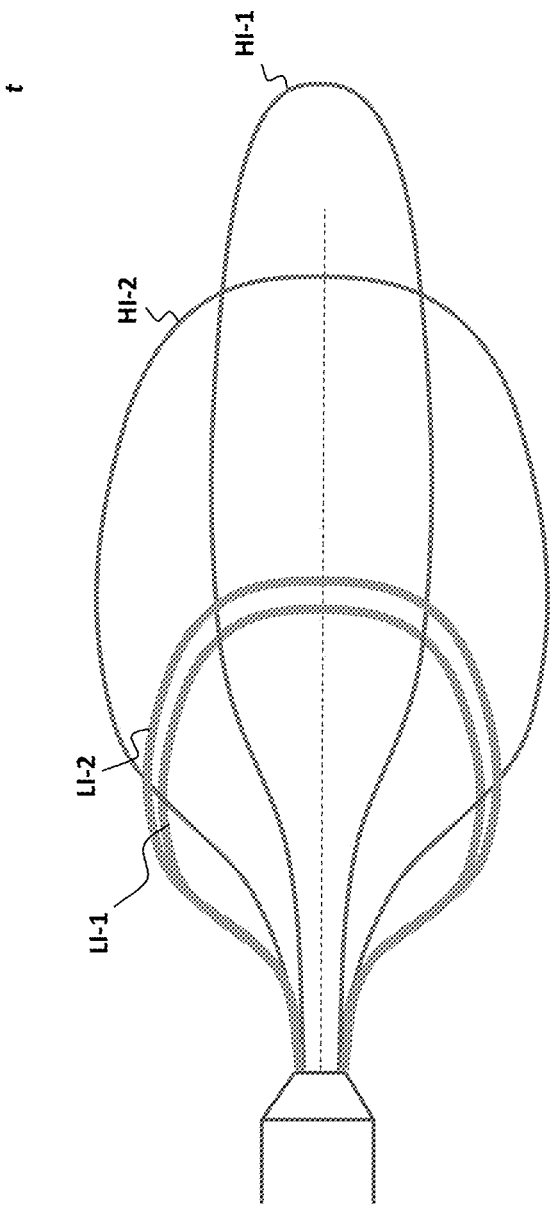
FIG. 84B is a schematic diagram of plasma flow corresponding to FIG. 84A, according to an embodiment.

In some embodiments, a predetermined current pattern may be applied to a plasma-generating device. The current pattern structure may include a low frequency oscillation of base current level and high frequency oscillation on top of base current level configured to adjust radial expansion of a plasma jet. In some embodiments, a base current level may be schematically divided into low and high base current levels for corresponding low and high intensive plasma jets. High intensive plasma jets may be responsible for moderate and predominant vaporization while low intensive plasma jets may be applied for moderate or predominant heat diffusion inside a treated object. As shown in FIG. 84, both high and low base current levels may include one or more parts with different base current and high frequency shape. In FIG. 84, HI-1 and HI-2 refer to parts of a current pattern that may result in corresponding high intensive plasma jets. Similarly, LI-1 and LI-2 refer to current patterns and corresponding low intensive plasma jets.

In some embodiments, the number of various parts of a current pattern, the duration of each of these parts and corresponding plasma jets may be adjusted to target specific application or procedure. For example, the depicted current pattern structure in FIG. 84 may be useful for some surgical procedures having tissue coagulation with various sizes of open blood vessels. High intensive plasma jet HI-2 with moderate radial expansion may result in blood drying, low intensive jets LI-1 and LI-2 may need to coagulate the dried tissue, and high intensive jet HI-1 with low radial expansion may penetrate deeper in the open blood vessel and result in occlusion and coagulation.

Figure 85:
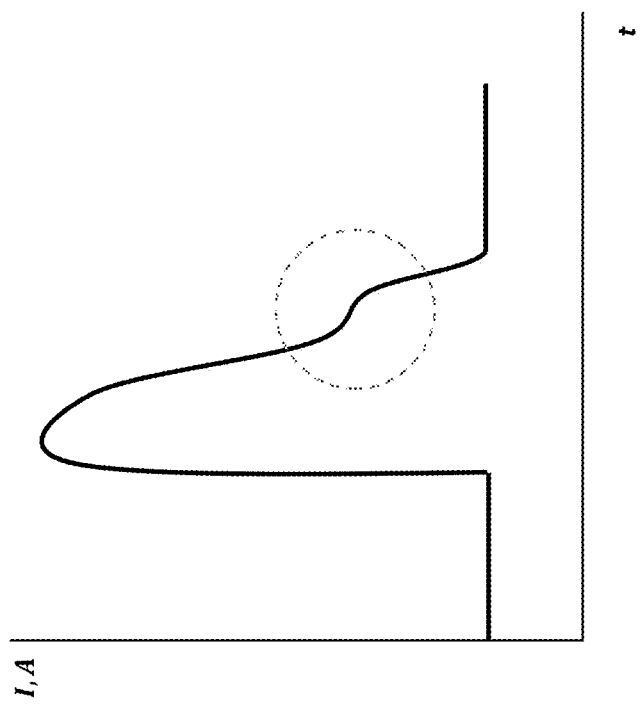
FIG. 85 is a plot of current drop overtime, according to an embodiment.

In some embodiments, one or more parts of a current pattern may be responsible for generating a plasma jet shape that may target a specific aspect of object treatment. In some embodiments, a current pattern may include two beneficial features. First, as previously discussed, light oscillation of low base current level may build up working pressure and decrease the detrimental effects of cathode overheating. This type of oscillation of base current level may be shown as LI-1 and LI-2 in FIG. 84. Second, for high and low frequency oscillation, a current drop rate may slow down towards the end of the current pulse as schematically demonstrated in FIG. 85. This shape of current may reduce a negative effect of cathode overheating due to slower rate of current decrease. Slowing down the drop rate at the end of current pulse may also result in a gradual reduction of plasma temperature and flow velocity. As discussed with respect to predominantly radially expanded plasma flows, the initiator plasma flow may slowly reduce its flow velocity, thus leading to efficient increase of pulse duty and better condition for optimal radial expansion.

In some embodiments, control of a current pattern structure may cover a set of object treatment procedures including controlled vaporization and controlled heat diffusion based on combinations of various plasma jet shapes with tunable radial expansion. In some embodiments, a current control generator for a plasma-generating device may have one or more processors that may meet the current output relationships including, but not limited to, providing low frequency current oscillation with current pulse resolution in a range of between about 0.1 ms and about 0.2 ms, providing high frequency current oscillation with current pulse resolution in a range of between about 0.1 μs and about 1 μs, and providing synchronization of the high and low frequency current oscillation.

In some embodiments, dynamic control of plasma jet shape and temperature may cover many types of complex procedures. Table 6 lists several examples with a variety of low and high intensive plasma jet shapes (FIG. 86) and typical vaporization and control heating procedures, that may be used with these shape combinations. In Table 6, "V/S" stands for vaporization procedure, "precision V/S" may refer to a smaller area of vaporization comparable with a nozzle diameter, while a spot corresponds to a larger area of the treated object. Base characteristics describe base current level of current pattern structure such as low base current level $I_{BL}$; high base current level $I_{BH}$; duty $D_{LF}$ and period $T_{LF}$ of low frequency pulses. Low and high intensive jet characteristics may describe parameters of high frequency oscillation for low and high intensive plasma jets, namely for low and high intensive jets, respectively, the pulse currents of high frequency oscillation may be designated as $I_{PL}$ and $I_{PH}$, duty is $D_{HFL}$ and $D_{HFH}$, period of oscillation $T_{HFL}$ and $T_{HFH}$.

As for controlled heating procedures ("CH-3"-"CH-6"), the high intensive plasma jet may be considered as a low intensive plasma jet with a slightly higher value of base current or more specifically, base currents $I_{BH}$ and $I_{BL}$ may be both low intensive plasma jets with a slightly different base current level that help boost up working pressure. In some embodiments, for controlled heating, it may be beneficial to not have high temperature plasma jet that would result in partial vaporization. In this case, the term "high intensive plasma jet" may be used for consistency of comparison to vaporization procedure, and also may be useful in terms of generalized current pattern structure for any type of procedures. To avoid local overheating, the radial expansion may be comparatively high for both low and high intensive plasma jet.

In some embodiments, more complex procedures may be achieved by tuning the shapes, temperature range, and duration for both high and low intensive plasma jets. The plasma jet shape adjustment may involve the radial expansion degree along the jet axis. For example, the radial expansion may be high in the middle and low at the distal end of plasma jet.

TABLE 6

Set of example plasma jet shapes, corresponding procedures and predetermined current pattern parameter range.

| | | Vaporization procedures | | | | Controlled heating | | | |
|---|---|---|---|---|---|---|---|---|---|
| | | Precision V/S w/o heat diffusion | Precision V/S with low heat impact | Large spot V/S w/o heat diffusion | Large spot V/S with low heat | Spot heating w/o V/S soft material | Spot heating w/o V/S dense material | Spot heating with V/S soft material | Spot heating with V/S dense material |
| Base | $I_{BL}$/d, A/mm | 5-10 | 10-15 | 5-10 | 10-15 | 10-20 | 10-20 | 10-20 | 10-20 |
| | $I_{BH}/I_{BL}$ | 5-20 | 5-20 | 5-10 | 5-10 | 1-2 | 1.5-3 | 2-5 | 3-10 |
| | $D_{LF}$ | 0.05-0.15 | 0.05-0.15 | 0.05-0.15 | 0.05-0.15 | 0.02-0.1 | 0.02-0.2 | 0.02-0.1 | 0.05-0.2 |
| | $T_{LF}$, μs | 0.5-10 | 0.5-10 | 0.5-10 | 0.5-10 | 10-35 | 10-35 | 10-35 | 10-35 |
| Low intensive jet | $T_{HFL}$, μs | 25-50 | 35-50 | 25-50 | 35-50 | 35-50 | 35-50 | 35-50 | 35-50 |
| | $D_{HFL}$ | 0.1-0.3 | 0.1-0.3 | 0.1-0.3 | 0.1-0.3 | 0.1-0.3 | 0.1-0.3 | 0.1-0.3 | 0.1-0.3 |
| | $I_{PL}/I_{BL}$ | 5-20 | 3-10 | 5-20 | 3-10 | 3-10 | 3-10 | 3-10 | 3-10 |
| High intensive jet | $T_{HFH}$, μs | not required | not required | 40-50 | 40-50 | 35-50 | 35-50 | 35-50 | 35-50 |
| | $D_{HFH}$ | not required | not required | 0.1-0.3 | 0.1-0.3 | 0.1-0.3 | 0.1-0.3 | 0.1-0.3 | 0.1-0.3 |
| | $I_{PH}/I_{BH}$ | not require | not require | 2-5 | 2-5 | 3-10 | 3-10 | 2-5 | 2-5 |
| Plasma jet shape (FIG. 86) | | V-1 | V-2 | V-3 | V-4 | CH-3 | CH-4 | CH-5 | CH-6 |

Figure 86:
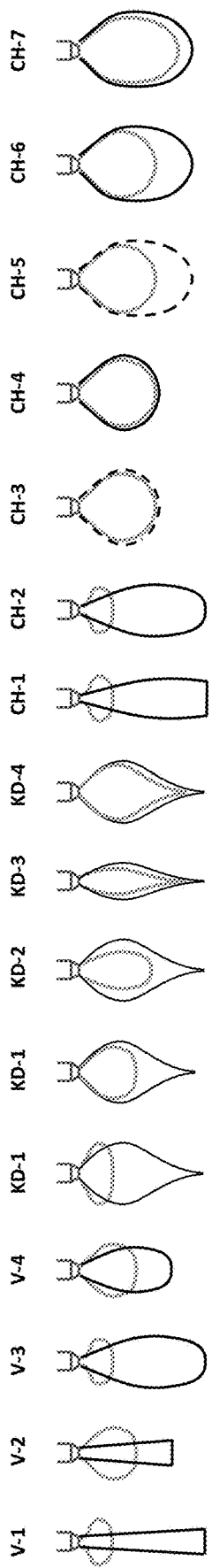
FIG. 86 is a set of schematic diagrams of different combinations of relatively high and relatively low plasma flows, according to an embodiment.

In FIG. 86, the high intensive plasma jet may be depicted by black lines and low intensive plasma jet may be depicted by gray lines. As shown in FIG. 86, for vaporization procedures ("V-1"-"V-4") the high intensive jet (black lines) may be longer and may be with different degrees of radial expansion, that may be as low as for laminar flow. At the same time, low intensive plasma jets (gray lines) may be considerably shorter to reduce or avoid the heat diffusion inside the treated object. In some embodiments, vaporization procedures may have substantially higher radial expansion and shorter distances for low intensive plasma jet compared to a high intensive jet. As previously discussed, the higher frequency may result in a shorter jet length. Therefore, for vaporization procedures, it may be desirable to have a higher frequency of oscillation for high intensive jet, i.e. $f_{HFL} > f_{HFH}$ ($T_{HFL} < T_{HFH}$). Also, for a higher radial expansion degree, the high frequency oscillation amplitude may be higher for low intensive plasma ($I_{PL} < I_{PH}$). In some embodiments, the low frequency pulse amplitude $I_{BH}$ may be considerably higher than low frequency base amplitude $I_{BL}$.

Lympho-Sealing

Systems, devices, and methods described herein can be used in a lympho-sealing procedure. In some embodiments, a lympho-sealing procedure may allow lymphatic drainage to be avoided during operation. In particular, lympho-sealing is a procedure in which the discharge of lymph may be stopped from a particular spot with minimal or no damage to the surrounding anatomic structures. Image CH-1 and CH-2 of FIG. 86 illustrate the resulting low and high intensive plasma jet shape for precision or spot lympho-sealing procedure. The high intensive plasma (black lines) jet may generate the evaporation of lymph from the surface being treated. Exposing tissue to high intensive plasma jet for a long period of time may evaporate the lymph from the tissue surface but may generate substantial damage. During the remaining 75% to 95% of a low frequency period, low intensity plasma jet (i.e., gray lines in FIG. 86 "CH-1") may be discharged. This low intensity plasma may have minimal or no effect on the tissue being treated. Accordingly, low intensity plasma flow length may be minimized by increasing the frequency of high-frequency pulses.

In some embodiments, a coagulation procedure may refer to controlled heating of the tissue to generate coagulation in a thin layer of tissue during operation to prevent blood or lymph flow to the tissue surface. Coagulation may be a natural process during wound healing. With coagulation procedures, a similar effect may be achieved by controlled heating of the tissue. For coagulation, the previously discussed controlled heating procedures may adjusted to obtain the required effect.

As previously mentioned, the absolute value of current may be not significant because the same current produces substantially different effects when applied to different handpieces. Rather, the ratio of current to the diameter of heating portion 124 (e.g., $d_{heat}$) may have a greater significance. The base current-to-heating-portion-diameter ratio may be referred to as I or "diameter current." The power supply used for such flows may be able to generate (and transmit to the handpiece) a generalized diameter current-time profile as shown in FIG. 87 that may be used for a variety of medical applications. Referring to the discussion above, this diameter current-time profile shows various base diameter currents. It should be understood that each of the base currents may have corresponding pulses.

In some embodiments, the diameter current may oscillate between low diameter current $I_L$ and high diameter current $I_H$. In some embodiments, low diameter current $I_L$ may be in the range of between about 5 A/mm and about 20 A/mm, and diameter current $I_H$ may be in the range of between about 25 A/mm and about 80 A/mm.

In some embodiments, as shown in FIG. 87, the relatively low and high diameter currents may not be uniform and may exhibit predetermined variations. For a low diameter current, these variations may occur at about 5 ms intervals although different intervals in the range of between about 1 ms and about 10 ms are contemplated. In some embodiments, the low diameter current may correspond to up to 10 variations per low frequency period, but in some embodiments, such as the one shown in FIG. 24, no low diameter current variations occur. In some embodiments, the magnitude of low diameter current variations may be in the range of between about 2 A/mm and about 5 A/mm, but departures from this range are also contemplated. In some embodiments, for high diameter current, these variations occur at about 1 ms intervals, although different intervals in the range of between about 0.2 ms and about 2 ms may be also contemplated. In some embodiments, the high diameter current may include up to about 5 variations per low frequency period, but in some embodiments, such as the one shown in FIG. 24, no high diameter current variations occur. The magnitude of high diameter current variations may be in the range of between about 5 A/mm and about 10 A/mm.

In some embodiments, and as shown in FIG. 87, the current-time profile may be periodic with the period ($t_1$) in the range of between about 6 ms and about 65 ms, although departures from this period may be also contemplated.

FIG. 88 shows a temperature-time profile that is associated with the current-time profile depicted in FIG. 87, with I1 corresponding to T1, I2 corresponding to T2, and so forth. The temperature-time profile depicted in FIG. 88 can produce plasma flows CH-1 and CH-2 depicted in FIG. 86. Specifically, in FIG. 88, the high intensity plasma flow may be produced by varying the high intensity base temperature according to a rectangular pulse train. In this example, the high intensity base temperature may have two levels at T5 and T6 and follows the patterns shown in FIG. 88 (T6-T5-T6-T5-T6). In some embodiments, the high intensity base temperature lasts for time t2 and each period of constant base temperature lasts for time Δt2. In some embodiments, high frequency pulses that have temperature T6 as the base may reach temperature T8 and high frequency pulses that have temperature T5 as a base may reach temperature T7. In some embodiments, high-intensity high-frequency pulses may have a frequency f2 and the duty cycle D2. In some embodiments, the low intensity plasma flow may be produced by varying the low intensity base temperature according to a rectangular pulse train. In this example, the low intensity base temperature may have two levels at T1 and I2 and follows the patterns (T1-T2-T1-T2-T1). In some embodiments, the low intensity base temperature may have a duration of time t3 and each period of constant base temperature may have a duration of time Δt1. In some embodiments, high frequency pulses having temperature T1 as the base may reach temperature T3 and high frequency pulses that have temperature T2 as the base may reach temperature T4. The high frequency pulses have a frequency f1 and duty cycle D1. In some embodiments, the low frequency period for this temperature-time profile may be t1. Table 7 sets forth example values for the above parameters. In some embodiments, variations from these example values may also be used to produce lymphosealing.

TABLE 7

| Lymphosealing | |
|---|---|
| T1, K | 3,000 |
| T2, K | 4,000 |
| T3, K | 12,000 |
| T4, K | 13,000 |
| T5, K | 14,000 |
| T6, K | 15,000 |
| T7, K | 16,000 |
| T8, K | 17,000 |
| t1, ms | 30 |
| t2, ms | 5 |
| t3, ms | 25 |
| Δt1, ms | 5 |
| Δt2, ms | 1 |
| f1, kHZ | 40-50 |
| D1 | 0.5 |
| f2, kHZ | 25-30 |
| D1 | 0.3-0.4 |

Adipose Tissue Dissection

Energy devices configured for adipose tissue dissection typically generate large quantities of smoke. For example, electrosurgical, laser, and ultrasonic devices may deliver concentrated thermal energy to vaporize adipose (e.g., fat) tissue, which generates smoke. The devices, systems, and methods described herein may be configured to dissect adipose fat without generating smoke, for example, by precisely melting adipose tissue into liquid, which can be removed, e.g., by mechanical force, before there is any vaporization. In some embodiments, a low intensity plasma jet having a duration of between of about 5 ms and about 10 ms may deliver energy sufficient to melt a surface of adipose tissue without melting underlying tissue. This can be followed by delivery of a high intensity plasma jet with a high dynamic pressure but low thermal energy for a duration of between about 0.5 ms and about 1 ms to remove the melted adipose tissue.

Generally, adipose or fat tissue can melt at a temperature between about 30° C. and about 50° C. In some embodiments, a melting heat may be between about 140 kJ/kg and about 200 kJ/kg. In some embodiments, a vaporization temperature can be between about 200° C. and about 300° C. In some embodiments, the heat of vaporization can be between about 250 kJ/kg and about 400 kJ/kg. Since these thermodynamic properties can be close to each other, it can be important to precisely control energy delivery such that fat tissue is melted without vaporization (or with reduced vaporization).

In some embodiments, a target plasma temperature between about 2,000 K and about 3,000 K, and an initiator plasma temperature between about 8,000 K and about 10,000 K may allow control of thermal energy for a low intensity plasma jet. In some embodiments, a pulse repetition period may be between about 40 μs and about 50 μs with a duty D between about 0.3 and about 0.4. In some embodiments, a radially oscillated plasma jet may include a jet volume having a homogenous temperature distribution and a length of active jet. In some embodiments, a relatively short duration low intensity plasma jet may be configured to heat an adipose tissue surface below its vaporization point.

In some embodiments, a high intensity jet may include a target plasma temperature between about 8,000 K and about 10,000 K, and an initiator plasma temperature between about 14,000 K and about 16,000 K. A pulse repetition period may be between about 40 μs and about 50 μs and a duty D may be between about 0.3 and about 0.4. These parameters ranges may allow kinetic energy and a dynamic pressure jet to remove melted adipose tissue but prevent vaporization by having a short duration. The period and duty for high frequency current pulses may be similar to the volumes of low and high intensity jets. A low frequency pulse duty D may be between about 5% and about 10% (e.g., about 0.05 and about 0.1) to avoid surface heating and allow kinetic energy to remove melted adipose tissue. In some embodiments, a jet outlet diameter of about 0.5 mm with the thermodynamic properties provided above may use an argon gas flow between about 0.15 L/min and about 0.2 L/min.

5. Embodiments for Generating Radially Expanded Plasma Flows

It will be appreciated that the present disclosure may include any one and up to all of the following embodiments.

Embodiment 1—HF Pulses to Generate Predominate Radially Expanded Plasma Flow HF pulses to generate predominant radial expansion plasma flow may comprise one or more of:

1. Base temperature level $T_{BASE}$ being set by requirements of the type of action. For example, base temperature level $T_{BASE}$ may be set to relatively low level such as about 2,000 K to about 4,000 K for controlled heating of an object without vaporization and sublimation of surface boundary and to a relatively higher level of about 9,000K to about 11,000 K for controlled speed of vaporization of surface boundary
2. Period of pulses repetition T being between about 10 μs and about 50 μs
3. Temperature pulse rise and fall times $\tau_1$ and $\tau_2$ being (0.01-0.1)·T. Temperature can vary (e.g., rise and fall) during a pulse-interval oscillation.
4. Temperature pulse delay fall time $\tau_3$ being (0.2-0.4)·T
5. Pulse temperature $T_{PULSE}^t$ (top optimal boundary of $T_{PULSE}$ for the given $T_{BASE}$) being:

$$\frac{a(T_{base})}{a(T_{pulse})} = 0.5$$

6. Pulse temperature $T_{PULSE}^t$ (bottom optimal boundary of $T_{PULSE}$ for the given $T_{BASE}$) being:

$$\frac{a(T_{base})}{a(T_{pulse})} = 0.6$$

7. Pulse temperature $T_{FALL}=(0.2-0.4)\cdot(T_{PULSE}^b - T_{BASE})$.

Figure 89:
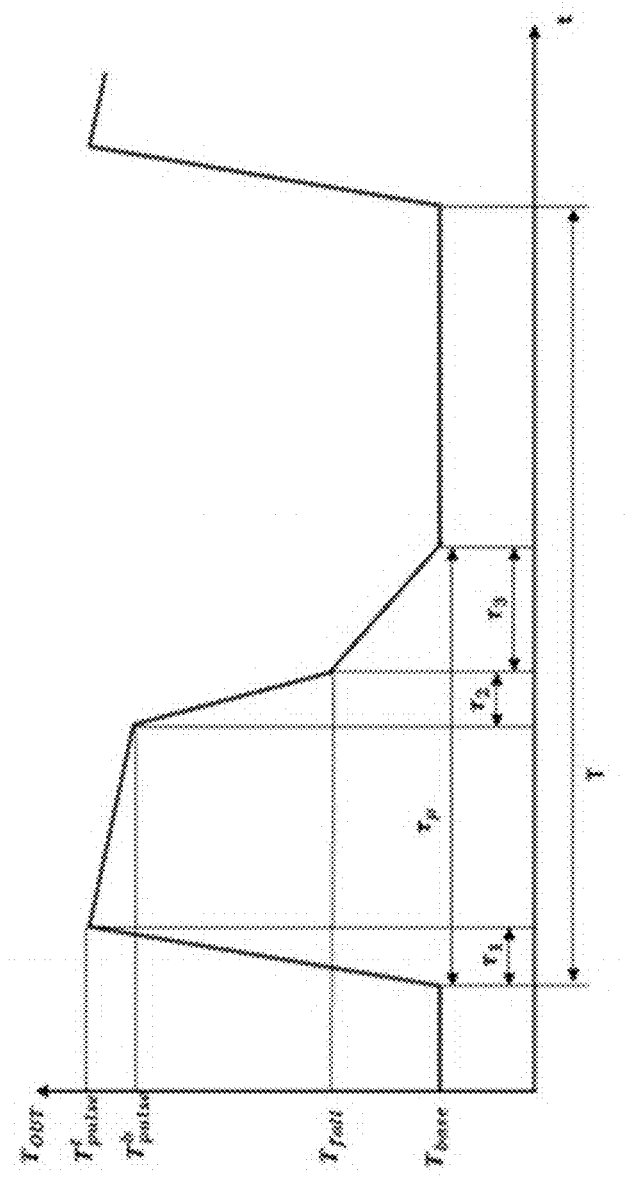
FIG. 89 is a plot of an example high frequency pulse, according to an embodiment.

FIG. 89 depicts an example HF pulse with the associated temperature parameters.

Embodiment 2—Method for Generating Predominantly Radially Expanded Plasma Flow A method to generate plasma flow with predominantly radially expanded plasma flow can involve one or more of the following considerations.

The outlet plasma flow with controlled degree of radial expansion is defined by the following input parameters: the outlet temperature-time profile of plasma flow, where the structure of temperature-time profile may define the shape of the plasma flow and average plasma particle energy; the inlet gas flow, where the inlet gas flow affects the working pressure in the active chamber of plasma-generating device and defines the range of outlet energy flow; the outlet diameter of plasma-generating device, where adaptive expansion nozzle increases the plasma flow velocity; the diameter or design of heating channel, which may affect the working pressure of plasma generating gas inside the active chamber of plasma-generating device.

The controlled radial expansion of plasma flow may be obtained with plasma-generating device if the following criteria are met: the energy applied to plasma-generating device may result in specific pattern of outlet temperature-time profile. The temperature-time profile may include repeated changes/switches between base and pulse temperature values, that correspond to base and pulse plasma flows, a density ratio of base to pulse plasma flow may be at least 2, a speed of sound of the pulse plasma flow at the pulse temperature may be at most 4 times the speed of sound of the base plasma flow at the base temperature, and the frequency of repetition may be higher than 1 kHz.

The relationship between the outlet temperature-time profile of plasma flow, the inlet gas flow, the outlet diameter of plasma-generating device, and diameter of heating channel meet the following requirements to form the steady plasma flow and avoid turbulent mode: Outlet diameter may be less than certain value $d_{OUT}^{max}$, that is defined by outlet pulse temperature. $d_{OUT}^{max}$ may be about 140 mm for pulse temperature of 10,000 K; $d_{OUT}^{max}$ may be about 160 mm for pulse temperature of 12,000 K; $d_{OUT}^{max}$ may be about 85 mm for pulse temperature of 14,000 K; $d_{OUT}^{max}$ may be about 40 mm for pulse temperature of 16,000 K; or $d_{OUT}^{max}$ may be about 30 mm for pulse temperature of 24,000 K.

To avoid turbulent mode, the inlet gas flow rate may be less than critical inlet gas flow for pulse and base plasma flows with a Reynolds number of about 2,000. The maximum inlet gas flow rate $G_{IN}$ may be linearly proportional to outlet diameter and defined by outlet pulse or base temperature. The maximum inlet gas flow $G_{IN}$ may be in a range of between about 0.5 l/min to about 4 l/min for an outlet diameter $d_{OUT}$=0.5 mm; the maximum inlet gas flow $G_{IN}$ may be in a range of between about 5 l/min to about 40 l/min for an outlet diameter $d_{OUT}$=5 mm; or the maximum inlet gas flow $G_{IN}$ may be in a range of between about 10 l/min to about 80 l/min for an outlet diameter $d_{OUT}$=10 mm.

Mass flux in a heating channel may be sufficient to provide minimal working pressure to maintain plasma flow. The minimum inlet gas flow rate $G_{IN}$ may be linearly proportional to the square of a heating channel diameter and defined by outlet pulse and base temperature.

$$\left(G_{IN} > K \cdot \frac{\pi d_H^2}{4}\left(D + \sqrt{\frac{T_P}{T_B}}(1-D)\right)\right).$$

In some embodiments, a minimum inlet gas flow $G_{IN}$ may be about 0.03 l/min to about 0.04 l/min for a heating channel diameter $d_H$=0.4 mm; a minimum inlet gas flow $G_{IN}$ may be about 0.12 l/min to about 0.15 l/min for a heating channel diameter $d_H$=0.8 mm; and/or a minimum inlet gas flow $G_{IN}$ may be about 12 l/min to about 15 l/min for a heating channel diameter $d_H$=8 mm.

An outlet temperature-time profile for predominantly radially expanded plasma flow may comprise repeating five regions with the total duration of T of about 10 μs to about 50 μs. In a first region, the temperature may be maintained at the base temperature. Base temperature level $T_{BASE}$ may be based on a type of action. For example, $T_{BASE}$ can be set to relatively low level (e.g., about 2,000 K to about 4,000 K) for controlled heating of an object without vaporization and sublimation of treated surface boundary and to relatively higher level (e.g., about 9,000 K to about 11,000 K) for controlled speed of vaporization of surface boundary. In a second region, the temperature may rapidly rise to a top pulse temperature during a time interval (0.01-0.1)·T. In a third region, the temperature may be slightly reduced to a bottom pulse temperature. In a fourth region, the temperature may be rapidly reduced to an intermediate value $T_{FALL}$ during a time interval (0.01-0.1)·T. In fifth region, the temperature may be reduced to an initial base temperature during a time interval (0.2-0.4)·T. A ratio of sound speed of the base plasma flow at the base temperature to sound speed of pulse plasma flow at atop pulse temperature may be equal to about 0.5.

$$\left(\frac{a(T_{base})}{a(T_{t\_pulse})} = 0.5\right).$$

A ratio of sound speed of the base plasma flow at the base temperature to sound speed of pulse plasma flow at a bottom pulse temperature may be equal to about 0.6.

$$\left(\frac{a(T_{base})}{a(T_{b\_pulse})} = 0.6\right).$$

An intermediate temperature may be given by $T_{FALL}$=(0.2-0.4)·($T_{PULSE}^b$−$T_{BASE}$).

An outlet temperature-time profile for predominantly radially expanded plasma flow may demonstrate optimal parameters for maximal radial expansion of plasma flow. However, some applications might require a fine adjustment of the degree of radial expansion and the shape of plasma jet. The following examples demonstrates how the plasma jet shape can be adjusted by varying the parameters: an increase of the total duration T from about 25 μs to about 50 μs may result in elongation of plasma jet shape; varying the optimal pulse temperature may result in non-equal volumes of base and pulse plasma flows and correspond to radially expanded plasma jet shape with small portion of laminar flow at the end; increasing the duration ratio of pulse to base plasma flow may result in smaller degree of radial expansion; varying the temperature-time profile shape may result in a different distribution of degree of radial expansion along the plasma jet axis; varying the inlet gas flow, the diameter of heating channel, the outlet diameter may affect the size of plasma flow and correspond to different volume energy distribution of the plasma flow.

In some embodiments, there can be deviations from the outlet temperature-time profile described above. For example, some therapeutic applications may use high temperature (e.g., greater than about 10,000° C.) pulse plasma flow and low temperature base plasma flow with low duty to provide rapid cooling of the plasma flow. For instance, a duration of pulses may be about 10 μs to about 25 μs, and the period T may be in a range of between about 50 μs to about 50 ms. Thus, the duty cycle may be substantially lower than the optimum range. The remaining small fraction of radially expanded plasma flow may produce high concentration of nitric oxide and due to low duty cycle of the pulses the resulting plasma flow may be effectively cooled down to desired temperature for subsequent use.

The working pressure in the active chamber may play an important role to control the outlet radially expanded plasma flow. Higher working pressure may allow an adaptive nozzle design that leads to the increase of the absolute velocity of outlet plasma particles, thus increasing the size of radially expanded plasma jet. The increase of plasma jet size without changing the temperature-time profile may spread the energy flow to higher area of treated surface that may be desirable for some procedures. The working pressure may remain steady while the outlet temperature is oscillating between base and pulse value for the wide range of frequencies. The established value of working pressure may be defined by an outlet temperature-time profile, the inlet gas flow and the diameter/design of heating channel. For some applications, excessive outlet static pressure may be avoided and adaptive nozzle diameter may be chosen to reduce the static pressure to ambient conditions.

Methods described herein can allow for dynamic control of a plasma jet shape. The dynamic control may be based on slow modulation to temperature-time profile such that the level of base and pulse plasma temperature changes with time leads to a change of plasma jet shape and average particle energy. The outlet temperature-time profile may include high-frequency (e.g., greater than about 1 kHz) and low-frequency (e.g., less than about 1 kHz) modulation of temperature. High-frequency modulation may define the temporal plasma jet shape and may meet the above written criteria to generate plasma jet with radial expansion. Low-frequency modulation may define the set of desired plasma jet shapes and duration of each of the shape. The modulation frequency may be lower than 1 kHz to avoid affecting the conditions for each plasma jet shape.

The low-frequency modulation may typically format least two plasma jet shapes with two corresponding base temperatures. For example, plasma flow with a lower base temperature may control the heating transfer inside the treated specimen, and plasma flow with relatively high base temperature may control the evaporation rate of the treated specimen. The structure of temperature-time profile with low and high frequency modulations may be expressed in following way: the temperature changes between base and pulse level with frequency more than about 1 kHz; the base level switches between at least two levels, such as low and high base temperature; the frequency of these switches may be lower than about 1 KHz; the pulse level switches between low and high pulse temperature and these switches may happen simultaneously and synchronized with base level switches; for each pair of base and pulse temperature levels the conditions for radial expansion of plasma jet may be met; the duration of each base level switch may be defined by the requirement of a particular application; for some applications, the temperature-time profile may also include the region with laminar plasma flow. In this case, the temperature may stay at a base level for a fixed duration The working pressure in the active chamber may remain steady even with additional low-frequency modulation at least for the frequencies more than about 10 Hz. This phenomenon may introduce additional ways to affect the plasma jet shape. Low-frequency modulation of temperature-time profile may be adjusted to tune the working pressure to the desired level. For example, the increase of working pressure may be beneficial to achieve bigger size of plasma flow shape with high base temperature. The increase of the working pressure may be achieved by increasing duration of plasma flow with high base temperature compared to plasma flow with low base temperature. However, this may result in higher energy impact of plasma shape with high base temperature that may not be desirable. Alternatively, the working pressure may be increased by applying a small oscillation of the low base temperature, while maintaining the plasma flow with high base temperature with the same duration.

The method allows for independent control of the shape of plasma jet, the average temperature of plasma particles, and total energy flux applied to the treated specimen. The various shapes of plasma jet may be obtained by tuning the degree of radial expansion, that is defined by outlet temperature-time profile. The average temperature of plasma particles may be controlled by shifting both base and pulse temperatures to the desired level while the ratio between the base and pulse temperatures may be adjusted to maintain the plasma jet shape. The energy flux may be adjusted by inlet gas flow and outlet diameter of plasma-generating device.

In some embodiments, the method includes generation of radially expanded plasma flow with dynamic control over the plasma flow shape, and the possibility of independent control of energy flux and average energy of plasma particles for tuning the treatment procedure to achieve unique effects by thermal interaction with the specimen. For example, the following procedures may be achieved with this method: vaporization/sublimation of the object surface without heat transfer inside the object; controlled heating of the material avoiding potential damage of the object due to local overheating; combined simultaneous vaporization/sublimation and controlled heating treatment with precise control of vaporization rate and heat diffusion rate.

Embodiment 3—Arc Discharge Device for Generating Predominantly Radially Expanded Plasma Flows An arc discharge plasma generating device can include an anode at a distal end of the device, the anode having a hole therethrough, a plurality of intermediate electrodes electrically insulated from each other and from the anode, each of the intermediate electrodes having a hole therethrough, wherein the holes in the intermediate electrodes and the hole in the anode form a hollow space having a first portion, which over a substantial length of this portion has a uniform first cross-sectional diameter, and a second portion, which over a substantial length of this portion has a uniform second cross-sectional diameter, the second portion being closer to the anode than the first portion; a cathode having a tapered distal portion narrowing toward a distal end of the cathode, a proximal end of the tapered portion being a base of the tapered portion, the tapered portion having a length being a distance from the base of the tapered portion to the distal end of the cathode; and an insulator sleeve extending along and surrounding only a portion of the cathode and having a distal end.

The following geometrical relationship between various parts of the plasma-generating device may be met: the ratio of the diameter of cathode chamber (first cross-sectional diameter) and the diameter of heating channel (second cross-sectional diameter) may be at least 4; a distance from the distal end of the cathode to the second portion of the hollow space (the heating channel inlet) may be at least 1.25 times the diameter of heating channel (second cross-sectional diameter); the gap between cathode and inner walls of insulator sleeve may be sufficient to deliver the required inlet gas flow without significant resistance in the gap; the ratio of the length of the portion of cathode tip protruding beyond the distal edge of insulator sleeve to the cathode diameter may be in the range of between about 1.0 to about 1.6; the protruding portion may be selected to avoid the attachment of arc inside the insulator sleeve; the ratio of the cathode tip length to cathode diameter may be in the range of between about 1.5 to about 2.0; the diameter of the heating portion may be in the range of between about 0.4 to about 1.0 mm; the proposed diameter allows to achieve high outlet plasma temperature of about 15,000 K to about 20,000 K; the bigger diameter may be used in alternative embodiment if the high outlet plasma temperature may not be required; the cathode diameter may be in range of between about 0.5 mm to about 2 mm; the ratio of the length of the anode portion to the diameter of the anode portion of the plasma channel may be in the range of between about 2 to about 4. The proposed ratio may be optimized to reduce heat losses to cooling system and provide proper operation for generating plasma flow. For surgical applications, the outlet diameter of the anode portion may be in the range of between about 0.3 mm to about 0.6 mm. For surgical applications, the outlet diameter of the anode portion may be in the range of between about 0.3 to about 0.6 mm.

For surgical applications, the geometrical values of various parts of the plasma-generating device can include: heating channel diameter may be about 0.4 mm; heating channel length may be about 1.2 mm; cathode diameter may be about 0.5 mm; cathode tip length may be about 1.0 mm; cathode chamber diameter may be about 1.8 mm; distance from the distal end of the cathode to the second portion of the hollow space (the heating channel inlet) may be about 0.7 mm; the length of the portion of cathode tip protruding beyond the distal edge of insulator sleeve may be about 1.4 mm; cathode chamber length may be about 2.1 mm; inside diameter of insulator sleeve may be about 1.2 mm; anode diameter may be about 0.5 mm; anode length may be about 2 mm.

For therapeutic applications, the device can include: an anode having adaptive nozzle with outlet anode diameter more than about 0.5 mm; a length of a heating channel may be about 3 mm to about 4 mm for gas flow of about 1.4 l/min. It is noted that the dimensions stated above merely constitute examples of the plasma-generating device and can be varied according to the field of application and the desired plasma properties.

An alternative example of plasma-generating device may comprise an isolator of complex shape that replaces the insulator sleeve, and a plurality of electrodes and separators between them. The shape of the isolator may copy the inner walls of insulator sleeve, cathode chamber, and heating portion described herein.

The arc discharge plasma generating device may be configured to suppress the overheating of the cathode during operation with predominantly radially expanded plasma flow. The expanded cathode chamber diameter may suppress the overheating effects of the cathode during the operation. The smaller diameter of heating channel may allow high plasma temperatures for operation with radially expanded plasma flow. The length of the heating channel and anode channel may be balanced to sufficiently heat the plasma-generating gas and avoid the high heat losses to the cooling system. An anode may have an adaptive nozzle shape that allows a boost to the absolute velocity of the outlet plasma flow that may be beneficial to achieve higher size of plasma jet.

Embodiment 4—Generator for Plasma Generating Device to Generate Predominantly Radially Expanded Plasma Flows A current control generator may be configured to supply current to a plasma-generating device to generate radially expanded plasma flow with dynamic control of a plasma jet shape may include of one or more processors that can meet the following current output requirements: provide low frequency current oscillation with current pulse resolution in a range of between about 0.1 ms to about 0.2 ms; provide high frequency current oscillation with current pulse resolution in a range of between about 0.1 μs to about 1 μs; provide synchronization of the high and low frequency current oscillation; the current control generator may be configured to provide RMS current to cover a whole range of desired plasma temperatures; the plasma temperature may be estimated as proportional to ratio of current to the diameter of heating channel; for a plasma-generating device with size constraints, such as for keyhole surgeries, the max RMS current may be limited to about 12 A to about 15 A to provide efficient cooling of the device during operation.

The high frequency current oscillation pattern for predominant radial expansion of plasma flow may comprise repeating 5 regions, where the total duration may be T=10 μs to 50 μs. In a first region, the current maintained at the base current. Base current level $I_{BASE}$ may be defined by the required type of action. For example, a ratio of base current to a heating channel diameter $I_{BASE}/d_H$ may be set to relatively low level (e.g., about 7 A/mm to about 10 A/mm) for controlled heating of object without vaporization and sublimation of treated surface boundary and to a relatively higher level of about 25 A/mm to about 35 A/mm for controlled speed of vaporization of surface boundary. In a second region, the current rapidly rises to top pulse current during time interval (0.01-0.1)·T. In a third region, the current may be slightly reduced to bottom pulse current. In a fourth region, the current may be rapidly reduced to intermediate value $I_{FALL}$ during time interval (0.01-0.1)·T. In a fifth region, the current may be reduced to initial base temperature during time interval (0.2-0.4)·T. A ratio of sound speed of the base plasma flow at the base current to sound speed of pulse plasma flow at top pulse current may be equal to about 0.5.

$$\left(\frac{a(I_{base})}{a(I_{t\_pulse})} = 0.5\right).$$

A ratio of sound speed of the base plasma flow at the base current to sound speed of pulse plasma flow at bottom pulse current may be equal to about 0.6.

$$\left(\frac{a(I_{base})}{a(I_{b\_pulse})} = 0.6\right).$$

An intermediate current $T_{FALL}=(0.2-0.4)\cdot(I_{PULSE}^b-I_{BASE})$.

The high frequency current oscillation pattern may deviate from these parameters if a desired degree of radial expansion is lower or the desired shape of plasma flow may not be uniform. The following examples demonstrates how the plasma jet shape may be adjusted by varying the following parameters: increase the total duration T from about 25 μs to about 50 μs may result in elongation of plasma jet shape; varying the pulse current values may result in non-equal volumes of base and pulse plasma flows and correspond to radially expanded plasma jet shape with a small portion of laminar flow at the end; increasing the duration ratio of pulse to base plasma flow may result in a smaller degree of radial expansion; varying the current pattern shape may result in a different distribution of degree of radial expansion along the plasma jet axis; the low and high frequency current oscillation pattern may be defined based on a type of procedure. Generalized low and high frequency current pattern may be expressed in the following way: low-frequency modulation defines the set of the desired plasma jet shapes and duration of each of the shape. The typical period of these modulations may be in the range of between about 0.5 ms and about 10 ms, that allow to avoid affecting the conditions for each plasma jet shape to cover variations in thermal procedures; high-frequency modulation defines the temporal plasma jet shape; the low-frequency modulation may typically form at least two plasma jet shapes with two corresponding base currents. For example, plasma flow with lower base current may control the heating transfer inside the treated specimen, and plasma flow with relatively high base current may control the evaporation rate of the treated specimen.

A current pattern may have the following structure: the base current switches between at least two levels, such as low and high base current ($I_{BL}$ and $I_{BH}$). The frequency of these switches may have a period in a range of between about 0.5 ms and about 10 ms (or a frequency between about 100 Hz and about 2000 Hz). Each of these base currents may correspond to a plasma flow of low and high intensity of energy. Plasma flow of low intensity may be used for controlled heat transfer inside the treated specimen, and plasma flow of high intensity may be used for controlled vaporization/sublimation of the treated specimen. A duration ratio of high to low base current (duty of low frequency current modulation) may be used for a precise tuning heat transfer and vaporization/sublimation rates. For each base current, there may be a synchronized high frequency current modulation. For maximum degree of radial expansion, high frequency current modulation may follow the high frequency current oscillation pattern for predominant radial expansion. For a specific shape of the plasma flow, the high frequency current modulation may deviate from the parameters as described above. If application requires laminar plasma flow for the particular base current high frequency modulation may be suppressed to achieve constant base current. Each high frequency modulation can be characterized by period which may be in a range of between about 10 μs to about 50 μs and high frequency duty.

The parameters for generating predominantly radially expanded flows can be set according to predetermined ranges, as set forth in Table 6, described in the section above.

For some applications of current pattern, it can be desirable to increase the working pressure inside the active chamber of a plasma-generating device and keep plasma flow of high intensity with the same duration. This may be achieved by adding to low frequency modulation a small oscillation of low base current. For example, the low base current may additionally oscillate with a period of about 0.5 ms to about 1 ms. Alternatively, a number of base currents with various duration may correspond with high frequency modulation for each base current.

The current control generator may dynamically control a plasma jet shape. The dynamic control may comprise additional slow modulation to a temperature-time profile: the current control generator may be configured to operate for a set of procedures based on the method to generate radially expanded plasma flow with dynamic control of plasma jet shape. The generalized current pattern may be adjusted to the desired procedure by changing appropriate parameters, and allow for the generation of a dynamically controlled plasms flow with independent control over the plasma flow shape and average energy of plasma particles. The freedom of controlling the key parameters allows to design and tune the treatment procedure to achieve unique effects by thermal interaction with the specimen, that may not possible with any other instruments. For example, the following procedures can be achieved with the proposed embodiment of current pattern: vaporization/sublimation of the object surface without heat transfer inside the object; controlled heating of the material avoiding potential damage of the object due to local overheating; combined simultaneous vaporization/sublimation and controlled heating treatment with precise control of vaporization rate and heat diffusion rate; current pattern adjustment to tune the procedure to more specific effect. Some examples of such procedures for surgical applications may include lympho-sealing, tissue coagulation, tissue dissection, and tissue cutting.

Embodiment 5—System for Generating Predominantly Radially Expanded Plasma Flows

A system for generating and discharging a plasma flow with dynamic control of plasma jet shape may comprise: a plasma-generating device configured to generate a dynamically controlled plasma flow, and a gas flow controller configured to supply a plasma-generating gas to the plasma-generating device at a flow rate.

The inlet pressure may be maintained constant. This can be achieved by storing sufficient amount of gas in the expansion chamber, so the pressure may not drop when the base plasma flow drains the considerable amount of gas. The volume of expansion chamber may be at least $V_{EXP}=N \cdot G_B \cdot T(1-D)$, where factor N—is number that needs to be equal to at least 2-5 to preserve the inlet pressure fluctuation.

A current control generator may be configured to supply a current to the plasma that meet the following criteria for current modulation: provide low frequency current oscillation with current pulse resolution in range of between about 0.1 ms to about 0.2 ms; provide high frequency current oscillation with current pulse resolution in a range of between about 0.1 µs to about 1 µs; provide synchronization of the high and low frequency current oscillation; provide RMS current that corresponds to maximum RMS current that can be used in plasma-generating device.

Embodiment 6—Method of Generating Radially Expanded Plasma Flow

Embodiment 6: A method of generating radially expanded plasma flow may comprise applying, to plasma-generating gas supplied to a plasma-generating device, energy that alternates between being at a base level for a first duration and at a pulse level for a second duration according to a controlled pattern; generating, in response to applying the energy, a plasma flow having a directional axis; discharging, from the outlet of the plasma-generating device, the plasma flow alternating between a base configuration and a pulse configuration according to the controlled pattern, the plasma flow in the base configuration having (1) a first temperature at the outlet and (2) a first flow front that advances along the directional axis; the plasma flow in the pulse configuration having (1) a second temperature at the outlet that is greater than the first temperature and (2) a second flow front that advances along the directional axis at a speed greater than the first flow front such that a distance traversed by the second flow front during the second duration is substantially the same as a distance traversed by the first flow front during the first duration and the second duration.

The method of Embodiment 6, wherein the plasma flow in the base configuration includes plasma having a first density at the first temperature, and the plasma flow in the pulse configuration includes plasma having a second density at the second temperature, the first density being at least twice the second density.

The method of Embodiment 6, wherein the plasma flow in the base configuration includes plasma having a first speed of sound at the first temperature and the plasma flow in the pulse configuration includes plasma having a second speed of sound at the second temperature, the second speed of sound being at most four times the first speed of sound.

The method of Embodiment 6, wherein the first temperature is between about 2,000 K and about 4,000 K.

The method of Embodiment 6, wherein the second temperature is less than or equal to 15,000 K, a ratio of a flow rate G (L/min) of the plasma-generating gas to a diameter d (mm) of the outlet is less than or equal to 100, and a sum of the first and second durations is less than $100{,}000*d^4/G^2$.

The method of Embodiment 6, wherein the second temperature is less than or equal to 15,000 K, a ratio of a flow rate G (L/min) of the plasma-generating gas to a diameter d (mm) of the outlet is greater than 100, and a sum of the first and second durations is less than 5 ms.

The method of Embodiment 6, wherein the second temperature is greater than 15,000 K, a ratio of a flow rate G (L/min) of the plasma-generating gas to a diameter d (mm) of the outlet is less than or equal to 100, and a sum of the first and second durations is less than $5{,}000*d^4/G^2$.

The method of Embodiment 6, wherein the second temperature is greater than 15,000 K, a ratio of a flow rate G (L/min) of the plasma-generating gas to a diameter d (mm) of the outlet is greater than 100, and a sum of the first and second durations is less than 500 µs.

Embodiment 7—System for Generating Radially Expanded Plasma Flow

Embodiment 7: A system for generating radially expanded plasma flow may comprise a current generator configured to generate a current having a controlled pattern, the controlled pattern including: a first set of oscillations between a first base level and a first pulse level, the first pulse level being higher than the first base level; and a second set of oscillations between a second base level and a second pulse level, the second pulse level being higher than the second base level; and a plasma-generating device configured to: heat, in response to the current being applied to a heating portion of the plasma-generating device, a plasma-generating gas to generate a plasma flow within the plasma-generating device; and discharge, from an outlet of the plasma-generating device, the plasma flow alternating between a first configuration having a first degree of radial expansion and a second configuration having a second degree of radial expansion, according to the controlled pattern of the current.

The system of Embodiment 7, wherein second base level is greater than the first base level, and the second pulse level is greater than the first pulse level.

The system of Embodiment 7, wherein the heating portion includes a heating channel, and a diameter of the heating channel is no more than about 0.4 mm.

The system of Embodiment 7, wherein a diameter of the outlet is greater than a diameter of the heating channel.

The system of Embodiment 7, wherein the first degree of radial expansion is greater than the second degree of radial expansion.

The system of Embodiment 7, wherein the plasma flow includes an active zone defined by plasma having a temperature above 1,000 K, the active zone having a diameter that is at least ten times greater than a diameter of the outlet.

Embodiment 8—Plasma-Generating Device for Generating Radially Expanded Plasma Flows Embodiment 8: A plasma-generating device for generating radially expanded plasma flow may comprise a cathode including a tapered distal portion; an anode disposed downstream from the cathode and being electrically insulated from the cathode, the anode defining an opening therethrough; a plurality of intermediate electrodes disposed between the cathode and the anode, the plurality of intermediate electrodes electrically insulated from each other and from the anode and the cathode, each intermediate electrode from the plurality of intermediate electrodes defining an opening therethrough such that the openings in the plurality of intermediate electrodes and the anode collectively define a plasma channel for discharging a plasma flow, the plasma channel including: a first portion having a first cross-sectional diameter; and a second portion having a second cross-sectional diameter, the first cross-sectional diameter being at least four times the second cross-sectional diameter; and an insulator sleeve extending along a surrounding a portion of the cathode.

The plasma-generating device of Embodiment 8, wherein a distance from a distal end of the cathode to the second portion of the plasma channel is at least 1.5 times the second cross-sectional diameter.

The plasma-generating device of Embodiment 8, wherein the opening in the anode has a cross-sectional diameter at a proximal end of the anode that is less than a cross-sectional diameter at a distal end of the anode.

The plasma-generating device of Embodiment 8, further comprising an outer sleeve coupled to the anode; and a divider disposed between the outer sleeve and the plurality of intermediate electrodes, the divider with outside surfaces of the plurality of intermediate electrode, an outside surface of the anode, and an inside surface of the outer sleeve collectively defining a cooling channel for cooling the plasma channel.

The plasma-generating device of Embodiment 8, wherein the cathode is disposed in a cathode chamber having a diameter $d_{CC}$, the diameter $d_{CC}$ being at least four times the second cross-sectional diameter.

The plasma-generating device of Embodiment 8, wherein a distance between a distal end of the insulator sleeve and a distal end of the cathode is at least a diameter of the cathode and less than 1.6 times the diameter of the cathode.

The plasma-generating device of Embodiment 8, wherein a length of the anode is between two times to eight times a diameter of the anode.

Embodiment 9—Method of Treatment

Embodiment 9: A method of treatment may comprise discharging, from an outlet of a plasma-generating device, a plasma flow having a directional axis, the plasma flow alternating between: a first configuration including plasma having a first temperature higher than 1,000 K between first and second points along the directional axis, the first point being closer to the outlet than the second point; and a second configuration including plasma having a second temperature higher than 1,000 K between third and fourth points along the directional axis, the third point being closer to the outlet than the fourth point and the fourth point being closer to the outlet than the second point; and directing the plasma flow at a treatment surface disposed between the second point and the fourth point.

The method of Embodiment 9, wherein discharging the plasma flow alternating between the first and second configurations includes discharging the plasma flow in the first configuration for a first duration and discharging the plasma flow in the second configuration for a second duration, the first duration being greater than the second duration.

The method of Embodiment 9, wherein the discharging the plasma flow in the first configuration for the first duration causes evaporation of liquid from the treatment surface and does not cause substantial damage to the treatment surface.

The method of Embodiment 9, wherein the first duration is about five times the second duration.

The method of Embodiment 9, wherein the first temperature alternates between first and second values, the first value being lower than the second value, and the second temperature alternates between third and fourth values, the third value being lower than the fourth value and higher than the second value.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto; inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

As used herein, the terms "about" and/or "approximately" when used in conjunction with numerical values and/or ranges generally refer to those numerical values and/or ranges near to a recited numerical value and/or range. In some instances, the terms "about" and "approximately" may mean within ±10% of the recited value. For example, in some instances, "about 100 [units]" may mean within ±10% of 100 (e.g., from 90 to 110). The terms "about" and "approximately" may be used interchangeably.

The specific examples and descriptions herein are exemplary in nature and embodiments may be developed by those skilled in the art based on the material taught herein without departing from the scope of the present invention.

Unless otherwise specified, the illustrated embodiments can be understood as providing exemplary features of varying detail of certain embodiments, and therefore, unless otherwise specified, features, components, modules, and/or aspects of the illustrations can be otherwise combined, separated, interchanged, and/or rearranged without departing from the disclosed systems or methods. Additionally, the shapes and sizes of components are also exemplary and unless otherwise specified, can be altered without affecting the scope of the disclosed and exemplary systems, apparatuses, or methods of the present disclosure.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

The invention claimed is:

1. A method, comprising:
supplying a plasma-generating gas to a plasma generating device having an outlet;
applying energy to the plasma-generating gas according to a predetermined energy pattern; and
discharging, in response to applying the energy, a plasma flow from the outlet of the plasma generating device, the plasma flow having a periodic pattern including a base plasma flow and a pulse plasma flow,
the base plasma flow having a first temperature at the outlet of the device, and the pulse plasma flow having a second temperature at the outlet of the device that is greater than the first temperature, the first temperature at the outlet being no greater than 10,000K and the second temperature at the outlet of the device being no greater than 20,000K,
the plasma flow having a first density at the first temperature, and the pulse plasma flow having a second density at the second temperature, the first density being at least two times the second density,
the base plasma flow having a first speed of sound, and the pulse plasma flow having a second speed of sound that is at most four times greater than the first speed of sound.

2. The method of claim 1, wherein the first temperature at the outlet is equal to or greater than 2,000K.

3. The method of claim 1, wherein the pattern includes alternating between discharging the base plasma flow for a base duration and discharging the pulse plasma flow for a pulse duration, the pulse duration being less than the base duration.

4. The method of claim 3, wherein the plasma-generating gas is supplied at a predetermined flow rate, and
the sum of the base duration and the pulse duration is based at least in part on the flow rate.

5. The method of claim 4, wherein the sum of the base duration and the pulse duration is further based on the second temperature.

6. The method of claim 3, wherein a frequency of the alternating between the base plasma flow and the pulse plasma flow is greater than 1 kHz.

7. A method, comprising:
supplying a plasma-generating gas to a plasma generating device having an outlet;
applying energy to the plasma-generating gas according to a predetermined energy pattern; and
discharging, in response to applying the energy, a plasma flow from the outlet of the plasma generating device, the plasma flow having a periodic pattern including a base plasma flow and a pulse plasma flow,
the base plasma flow having a first temperature at the outlet of the device, and the pulse plasma flow having a second temperature at the outlet of the device that is greater than the first temperature, the second temperature at the outlet of the device being no greater than 20,000K,
wherein a ratio of a speed of sound of the base plasma flow to a speed of sound of the pulse plasma flow is between 0.25 to 0.60.

8. The method of claim 7, wherein the first temperature at the outlet is no greater than 10,000K.

9. The method of claim 7, wherein the first temperature at the outlet is equal to or greater than 2,000K.

10. The method of claim 7, wherein the pattern includes alternating between discharging the base plasma flow for a base duration and discharging the pulse plasma flow for a pulse duration, the pulse duration being less than the base duration.

11. The method of claim 10, wherein the plasma-generating gas is supplied at a predetermined flow rate, and
the sum of the base duration and the pulse duration is based at least in part on the flow rate.

12. The method of claim 11, wherein the sum of the base duration and the pulse duration is further based on the second temperature.

13. The method of claim 10, wherein a frequency of the alternating between the base plasma flow and the pulse plasma flow is greater than 1 kHz.

14. A system, comprising:
a power supply for a current control generator configured to generate a current wave having a low current level and pulses reaching a high current level according to a controlled pattern; and
a plasma-generating device operatively coupled to the current control generator, the plasma-generating device configured to:

heat a plasma-generating gas to a first temperature for a first duration of time $t_1$ with the current wave at the low current level;

heat the plasma-generating gas to a second temperature for a second duration of time $t_2$ with the current wave at the high current level;

discharge from an outlet of the plasma-generating device, after heating the plasma-generating gas at the first and second temperatures, a base plasma flow and a pulse plasma flow that interact to form a radially expanded plasma flow, wherein a length of the base plasma flow equals a length of the pulse plasma flow at a time equal to $t_1+t_2$.

15. The system of claim 14, wherein the plasma flow includes an active zone defined by plasma having a temperature above 1,000 K, the active zone having a diameter that is at least ten times greater than a diameter of the outlet.

16. The system of claim 14, wherein the plasma-generating device is configured to iteratively perform the heating the plasma-generating gas to the first temperature, the heating the plasma-generating gas to the second temperature, and the discharging the base plasma flow and the pulse plasma flow.

17. The system of claim 16, wherein the plasma-generating device is configured to alternate between discharging the base plasma flow and the pulse plasma flow.

18. The system of claim 14, wherein the base plasma flow has a temperature at the outlet that is no greater than 10,000K, and the pulse plasma flow has a temperature at the outlet being no greater than 20,000K.

19. The system of claim 14, wherein the base plasma flow has a temperature at the outlet of between 2,000K and 10,000K.

20. The system of claim 14, wherein a ratio of a speed of sound of the base plasma flow to a speed of sound of the pulse plasma flow is between 0.25 to 0.60.

\* \* \* \* \*